US012558220B2

(12) United States Patent
Subramanian et al.

(10) Patent No.: US 12,558,220 B2
(45) Date of Patent: Feb. 24, 2026

(54) TRANSVALVULAR INTRAANNULAR IMPLANT FOR VALVE REPAIR

(71) Applicant: Heart Repair Technologies, Inc., San Jose, CA (US)

(72) Inventors: Valavanur A. Subramanian, New York, NY (US); Gene Reis, San Jose, CA (US); Maurice Buchbinder, La Jolla, CA (US); Tim MacNeil, Nashville, TN (US)

(73) Assignee: Heart Repair Technologies, Inc., San Jose, CA (US)

( * ) Notice: Subject to any disclaimer, the term of this patent is extended or adjusted under 35 U.S.C. 154(b) by 143 days.

(21) Appl. No.: 17/592,856

(22) Filed: Feb. 4, 2022

(65) Prior Publication Data

US 2022/0273432 A1 Sep. 1, 2022

Related U.S. Application Data

(60) Provisional application No. 63/162,174, filed on Mar. 17, 2021, provisional application No. 63/154,268, filed on Feb. 26, 2021.

(51) Int. Cl.
*A61F 2/24* (2006.01)

(52) U.S. Cl.
CPC .... *A61F 2/2454* (2013.01); *A61F 2210/0014* (2013.01); *A61F 2220/0008* (2013.01); *A61F 2230/0017* (2013.01)

(58) Field of Classification Search
CPC ...... A61F 2/2454; A61F 2/246; A61F 2/2487; A61F 2210/0014; A61F 2220/0008;
(Continued)

(56) References Cited

U.S. PATENT DOCUMENTS

| | | |
|---|---|---|
| 3,789,851 A | 2/1974 | LeVeen |
| 4,056,854 A | 11/1977 | Boretos et al. |
| | (Continued) | |

FOREIGN PATENT DOCUMENTS

| | | |
|---|---|---|
| AU | 2016339984 | 4/2018 |
| DE | 29618925 | 1/1997 |
| | (Continued) | |

OTHER PUBLICATIONS

Non-Final Office Action for U.S. Appl. No. 16/786,580 mailed Mar. 28, 2022, in 31 pages.
(Continued)

*Primary Examiner* — Suzette J Gherbi
(74) *Attorney, Agent, or Firm* — Knobbe, Martens, Olson & Bear, LLP

(57) ABSTRACT

Mitral valve prolapse and mitral regurgitation can be treating by implanting in the mitral annulus a transvalvular implant. The transvalvular implant has a first end, a first anchoring portion located proximate the first end, a second end, a second anchoring portion located proximate the second end, and a central portion. The transvalvular implant can include a wire form curved body The transvalvular implant can include eyelets and the center of the transvalvular implant can include an opening. The central portion can be positioned so that it extends transversely across a coaptive edge formed by the closure of the mitral valve leaflets. Tricuspid regurgitation can be treated by implanting in the tricuspid annulus a transvalvular bridge. The transvalvular bridge can have a first anchoring portion and a second anchoring portion. The transvalvular bridge can positioned so that the bridge extends transversely across a coaptive edges formed by the closure of the leaflets. The transvalvular bridge can be positioned between a midpoint of the anterior annulus and straddling the commissure
(Continued)

between the posterior annulus and the septal annulus. The transvalvular bridge can be anchored to the anterior annulus, the posterior annulus, and the septal annulus.

20 Claims, 71 Drawing Sheets

(58) Field of Classification Search
CPC ........... A61F 2230/0017; A61F 2/2466; A61B 2017/00243; A61B 2017/0409; A61B 2017/0441; A61B 2017/0464; A61B 17/0401
See application file for complete search history.

(56) References Cited

U.S. PATENT DOCUMENTS

| | | | |
|---|---|---|---|
| 4,270,143 A | 5/1981 | Morris | |
| 5,181,513 A | 1/1993 | Touboul et al. | |
| 5,291,889 A | 3/1994 | Kenet et al. | |
| 5,360,444 A | 11/1994 | Kusuhara | |
| 5,381,791 A | 1/1995 | Qian | |
| 5,398,691 A | 3/1995 | Martin et al. | |
| 5,400,771 A | 3/1995 | Pirak et al. | |
| 5,434,617 A | 7/1995 | Bianchi | |
| 5,572,999 A | 11/1996 | Funda et al. | |
| 5,593,424 A | 1/1997 | Northrup, III | |
| 5,631,970 A | 5/1997 | Hsu | |
| 5,631,981 A | 5/1997 | Rao | |
| 5,638,819 A | 6/1997 | Manwaring et al. | |
| 5,690,108 A | 11/1997 | Chakeres | |
| 5,765,561 A | 6/1998 | Chen et al. | |
| 5,792,155 A | 8/1998 | Van Cleef | |
| 5,906,578 A | 5/1999 | Rajan et al. | |
| 5,961,440 A | 10/1999 | Schweich, Jr. et al. | |
| 6,001,127 A | 12/1999 | Schoon et al. | |
| 6,019,791 A | 2/2000 | Wood | |
| 6,045,497 A | 4/2000 | Schweich, Jr. et al. | |
| 6,050,936 A | 4/2000 | Schweich, Jr. et al. | |
| 6,117,162 A | 9/2000 | Schmieding et al. | |
| 6,332,893 B1 | 12/2001 | Mortier et al. | |
| 6,416,522 B1 | 7/2002 | Strecker | |
| 6,419,695 B1 | 7/2002 | Gabbay | |
| 6,626,899 B2 | 9/2003 | Houser et al. | |
| 6,723,038 B1 | 4/2004 | Schroeder et al. | |
| 6,726,717 B2 | 4/2004 | Alfieri et al. | |
| 6,752,813 B2 | 6/2004 | Goldfarb et al. | |
| 6,764,510 B2 | 7/2004 | Vidlund et al. | |
| 6,797,002 B2 | 9/2004 | Spence et al. | |
| 6,805,710 B2 | 10/2004 | Bolling et al. | |
| 6,869,444 B2 | 3/2005 | Gabbay | |
| 6,913,608 B2 | 7/2005 | Liddicoat et al. | |
| 7,070,618 B2 | 7/2006 | Streeter | |
| 7,077,862 B2 | 7/2006 | Vidlund et al. | |
| 7,087,064 B1 | 8/2006 | Hyde | |
| 7,101,395 B2 | 9/2006 | Tremulis et al. | |
| 7,125,421 B2 | 10/2006 | Tremulis et al. | |
| 7,160,322 B2 | 1/2007 | Gabbay | |
| 7,291,168 B2 | 11/2007 | Macoviak et al. | |
| 7,381,220 B2 | 6/2008 | Macoviak et al. | |
| 7,455,690 B2 | 11/2008 | Cartledge | |
| 7,527,646 B2 | 5/2009 | Rahdert et al. | |
| 7,691,144 B2 | 4/2010 | Chang et al. | |
| 7,704,277 B2 | 4/2010 | Zakay et al. | |
| 8,262,725 B2 | 9/2012 | Subramanian | |
| 8,333,777 B2 | 12/2012 | Schaller et al. | |
| 8,348,963 B2 | 1/2013 | Wilson | |
| 8,382,829 B1 | 2/2013 | Call et al. | |
| 8,480,732 B2 | 7/2013 | Subramanian | |
| 8,845,717 B2 | 9/2014 | Khairkhahan et al. | |
| 8,956,406 B2 | 2/2015 | Subramanian et al. | |
| 8,961,597 B2 | 2/2015 | Subramanian et al. | |
| 9,168,137 B2 | 10/2015 | Subramanian et al. | |
| 9,180,005 B1 | 11/2015 | Lashinski et al. | |
| 9,468,526 B2 | 10/2016 | Subramanian et al. | |
| 9,554,903 B2 | 1/2017 | Rowe et al. | |
| 9,585,753 B2 | 3/2017 | Subramanian et al. | |
| 9,615,925 B2 | 4/2017 | Subramanian et al. | |
| 9,968,451 B2 | 5/2018 | Marquez et al. | |
| 10,143,553 B2 | 12/2018 | Alon et al. | |
| 10,219,903 B2 | 3/2019 | Subramanian et al. | |
| 10,238,488 B2 | 3/2019 | Subramanian et al. | |
| 10,456,259 B2 | 10/2019 | Subramanian et al. | |
| 11,013,599 B2 | 5/2021 | Subramanian et al. | |
| 11,033,391 B2* | 6/2021 | Subramanian ..... A61B 17/0401 | |
| 11,083,579 B2 | 8/2021 | Subramanian et al. | |
| 11,123,542 B1* | 9/2021 | Mitchell ............... A61B 17/11 | |
| 11,986,391 B2 | 5/2024 | Subramanian et al. | |
| 12,201,526 B2 | 1/2025 | Subramanian et al. | |
| 12,364,604 B2 | 7/2025 | Subramanian et al. | |
| 2002/0013571 A1 | 1/2002 | Goldfarb et al. | |
| 2002/0065554 A1 | 5/2002 | Streeter | |
| 2003/0033009 A1 | 2/2003 | Gabbay | |
| 2003/0083742 A1 | 5/2003 | Spence et al. | |
| 2003/0093148 A1 | 5/2003 | Bolling et al. | |
| 2003/0120340 A1 | 6/2003 | Liska et al. | |
| 2003/0199974 A1 | 10/2003 | Lee et al. | |
| 2003/0233022 A1 | 12/2003 | Vidlund et al. | |
| 2004/0049211 A1 | 3/2004 | Tremulis et al. | |
| 2004/0088047 A1 | 5/2004 | Spence et al. | |
| 2004/0106989 A1 | 6/2004 | Wilson et al. | |
| 2004/0127981 A1 | 7/2004 | Rahdert et al. | |
| 2004/0127982 A1 | 7/2004 | Machold et al. | |
| 2004/0138745 A1 | 7/2004 | Macoviak et al. | |
| 2004/0148021 A1 | 7/2004 | Cartledge et al. | |
| 2004/0152947 A1 | 8/2004 | Schroeder et al. | |
| 2004/0162610 A1 | 8/2004 | Liska et al. | |
| 2004/0225300 A1 | 11/2004 | Goldfarb et al. | |
| 2004/0260393 A1 | 12/2004 | Rahdert et al. | |
| 2005/0004665 A1 | 1/2005 | Aklog et al. | |
| 2005/0004666 A1 | 1/2005 | Alfieri et al. | |
| 2005/0004668 A1 | 1/2005 | Aklog et al. | |
| 2005/0010287 A1 | 1/2005 | Macoviak et al. | |
| 2005/0038505 A1 | 2/2005 | Shulze et al. | |
| 2005/0038508 A1 | 2/2005 | Gabbay | |
| 2005/0070999 A1 | 3/2005 | Spence | |
| 2005/0075723 A1 | 4/2005 | Schroeder et al. | |
| 2005/0107871 A1 | 5/2005 | Realyvasquez et al. | |
| 2005/0143811 A1 | 6/2005 | Realyvasquez | |
| 2005/0216039 A1 | 9/2005 | Lederman | |
| 2005/0256568 A1 | 11/2005 | Lim et al. | |
| 2005/0267572 A1 | 12/2005 | Schoon et al. | |
| 2005/0267573 A9 | 12/2005 | Macoviak et al. | |
| 2005/0288776 A1 | 12/2005 | Shaoulian et al. | |
| 2006/0004443 A1 | 1/2006 | Liddicoat et al. | |
| 2006/0020336 A1 | 1/2006 | Liddicoat | |
| 2006/0030885 A1 | 2/2006 | Hyde | |
| 2006/0058871 A1 | 3/2006 | Zakay et al. | |
| 2006/0069430 A9 | 3/2006 | Rahdert et al. | |
| 2006/0106456 A9 | 5/2006 | Machold et al. | |
| 2006/0135967 A1 | 6/2006 | Realyvasquez | |
| 2006/0149368 A1 | 7/2006 | Spence | |
| 2006/0161040 A1 | 7/2006 | McCarthy et al. | |
| 2006/0195012 A1 | 8/2006 | Mortier et al. | |
| 2006/0229708 A1 | 10/2006 | Powell et al. | |
| 2006/0247492 A1 | 11/2006 | Streeter | |
| 2006/0259135 A1 | 11/2006 | Navia et al. | |
| 2006/0287661 A1 | 12/2006 | Bolduc et al. | |
| 2007/0015957 A1* | 1/2007 | Li ......................... A61F 2/0045 600/37 | |
| 2007/0118151 A1 | 5/2007 | Davidson | |
| 2007/0173930 A1 | 7/2007 | Sogard et al. | |
| 2007/0213810 A1 | 9/2007 | Newhauser | |
| 2007/0250161 A1 | 10/2007 | Dolan | |
| 2007/0270943 A1 | 11/2007 | Solem et al. | |
| 2008/0243245 A1 | 10/2008 | Thambar et al. | |
| 2008/0306586 A1 | 12/2008 | Cartledge et al. | |
| 2009/0163934 A1 | 6/2009 | Raschdorf et al. | |
| 2009/0177277 A1 | 7/2009 | Milo | |
| 2009/0228099 A1 | 9/2009 | Rahdert et al. | |
| 2009/0259304 A1* | 10/2009 | O'Beirne .............. A61F 2/2466 606/228 | |
| 2009/0264995 A1* | 10/2009 | Subramanian ........ A61F 2/2454 623/2.36 | |

(56) References Cited

U.S. PATENT DOCUMENTS

| | | | |
|---|---|---|---|
| 2009/0276055 A1 | 11/2009 | Harris et al. | |
| 2009/0292353 A1 | 11/2009 | Yoganathan et al. | |
| 2010/0076550 A1 | 3/2010 | Subramanian | |
| 2010/0121435 A1* | 5/2010 | Subramanian | A61F 2/2427 |
| | | | 623/2.11 |
| 2010/0121437 A1 | 5/2010 | Subramanian et al. | |
| 2010/0131057 A1* | 5/2010 | Subramanian | A61F 2/2445 |
| | | | 623/2.36 |
| 2010/0262233 A1* | 10/2010 | He | A61F 2/2454 |
| | | | 623/2.41 |
| 2011/0082538 A1 | 4/2011 | Dahlgren et al. | |
| 2012/0101489 A1 | 4/2012 | Bloom et al. | |
| 2012/0209375 A1 | 8/2012 | Madrid et al. | |
| 2013/0090724 A1 | 4/2013 | Subramanian et al. | |
| 2013/0103140 A1 | 4/2013 | Subramanian et al. | |
| 2013/0103142 A1 | 4/2013 | Subramanian et al. | |
| 2013/0226289 A1 | 8/2013 | Shaolian et al. | |
| 2013/0331930 A1 | 12/2013 | Rowe et al. | |
| 2014/0039607 A1 | 2/2014 | Kovach | |
| 2014/0039615 A1* | 2/2014 | Padala | A61F 2/246 |
| | | | 623/2.37 |
| 2014/0275757 A1 | 9/2014 | Goodwin et al. | |
| 2014/0343601 A1 | 11/2014 | Abbott et al. | |
| 2015/0223793 A1 | 8/2015 | Goldfarb et al. | |
| 2015/0223935 A1 | 8/2015 | Subramanian et al. | |
| 2015/0257884 A1 | 9/2015 | Subramanian et al. | |
| 2015/0366556 A1 | 12/2015 | Khairkhahan et al. | |
| 2016/0045314 A1 | 2/2016 | Keren et al. | |
| 2016/0143735 A1 | 5/2016 | Subramanian et al. | |
| 2016/0324636 A1 | 11/2016 | Rourke et al. | |
| 2017/0100245 A1 | 4/2017 | Subramanian et al. | |
| 2017/0105839 A1* | 4/2017 | Subramanian | A61F 2/2454 |
| 2017/0172741 A1 | 6/2017 | Subramanian et al. | |
| 2017/0224477 A1* | 8/2017 | Seguin | A61F 2/246 |
| 2017/0354500 A1* | 12/2017 | Martinez | A61F 2/2454 |
| 2018/0055638 A1 | 3/2018 | Subramanian et al. | |
| 2018/0126119 A1 | 5/2018 | McNiven et al. | |
| 2018/0214270 A1 | 8/2018 | Subramanian et al. | |
| 2018/0256153 A1 | 9/2018 | Stone et al. | |
| 2018/0318083 A1 | 11/2018 | Bolling et al. | |
| 2019/0183648 A1* | 6/2019 | Trapp | A61F 2/2463 |
| 2019/0282361 A1 | 9/2019 | Subramanian et al. | |
| 2019/0298521 A1 | 10/2019 | Rafiee et al. | |
| 2019/0298522 A1 | 10/2019 | Subramanian et al. | |
| 2019/0336284 A1 | 11/2019 | Genovese et al. | |
| 2020/0030096 A1* | 1/2020 | Zeitani | A61F 2/2445 |
| 2020/0188109 A1* | 6/2020 | Fatemi Far | A61F 2/246 |
| 2020/0253733 A1 | 8/2020 | Subramanian et al. | |
| 2020/0276017 A1 | 9/2020 | Subramanian et al. | |
| 2021/0290388 A1 | 9/2021 | Subramanian et al. | |
| 2021/0290391 A1 | 9/2021 | Subramanian et al. | |
| 2021/0386546 A1 | 12/2021 | Subramanian et al. | |
| 2022/0151783 A1 | 5/2022 | Subramanian et al. | |
| 2022/0249831 A1* | 8/2022 | Mitchell | A61M 60/117 |
| 2022/0273432 A1 | 9/2022 | Subramanian et al. | |
| 2024/0058127 A1* | 2/2024 | Subramanian | A61B 17/0401 |
| 2024/0261102 A1 | 8/2024 | Subramanian et al. | |
| 2025/0017733 A1* | 1/2025 | Sheps | A61F 2/2463 |

FOREIGN PATENT DOCUMENTS

| | | |
|---|---|---|
| EP | 1 059 893 | 9/2005 |
| FR | 3027212 | 4/2016 |
| GB | 2 254 254 | 7/1992 |
| JP | 05-184611 | 7/1993 |
| JP | 2008-523886 | 7/2008 |
| WO | WO 1998/18411 | 5/1998 |
| WO | WO 2000/60995 | 10/2000 |
| WO | WO 2006/052687 | 5/2006 |
| WO | WO 2006/065212 | 6/2006 |
| WO | WO 2007/029252 | 3/2007 |
| WO | WO 2007/136468 | 11/2007 |
| WO | WO 2009/129189 | 10/2009 |
| WO | WO 2011/047168 | 4/2011 |
| WO | WO 2011/086401 | 7/2011 |
| WO | WO 2017/066480 | 4/2017 |
| WO | WO 2018/119304 | 6/2018 |
| WO | WO 2019/241777 | 12/2019 |
| WO | WO 2020/167672 | 8/2020 |
| WO | WO 2022/183159 | 9/2022 |
| WO | WO 2024/044110 | 2/2024 |

OTHER PUBLICATIONS

International Search Report for PCT/US2022/070534 mailed May 19, 2022, in 9 pages.

Extended European Search Report for Application No. EP 20756481.6 dated Oct. 11, 2022 in 6 pages.

Final Office Action for U.S. Appl. No. 16/786,580 mailed Sep. 19, 2022, in 10 pages.

Final Office Action for U.S. Appl. No. 12/104,011, mailed Nov. 15, 2010, in 9 pages.

Final Office Action for U.S. Appl. No. 12/104,011 mailed Mar. 30, 2012, in 8 pages.

Non-Final Office Action for U.S. Appl. No. 12/104,011 mailed Jul. 12, 2011, in 9 pages.

Non-Final Office Action for U.S. Appl. No. 12/104,011 mailed Feb. 23, 2010, in 12 pages.

Non-Final Office Action for U.S. Appl. No. 12/104,011 mailed Feb. 3, 2011, in 9 pages.

Notice of Allowance for U.S. Appl. No. 12/104,011 mailed Jun. 25, 2012, in 7 pages.

Australian 1st Office Action for App. No. 2009/236358, issued Nov. 26, 2013, in 4 pages.

Australian Notice of Acceptance for Application No. 2009/236358, issued Aug. 17, 2015 in 5 pages.

Australian 1st Office Action for App. No. 2015/261696, issued Feb. 10, 2017, in 5 pages.

Australian 1st Office Action for App. No. 2018200859, issued Sep. 21, 2018, in 3 pages.

Canadian 1st Office Action for Application No. 2,721,450, issued Feb. 1, 2016, in 4 pages.

Canadian Notice of Allowance for Application No. 2,721,450, issued Oct. 27, 2016, in 4 pages.

Canadian Notice of Abandonment for Application No. 2,965,632, issued Oct. 30, 2017, in 1 page.

Non-Final Office Action for U.S. Appl. No. 12/579,330 mailed Jul. 13, 2012, in 13 pages.

Non-Final Office Action for U.S. Appl. No. 12/579,331 mailed Jun. 26, 2012, in 14 pages.

Non-Final Office Action for U.S. Appl. No. 12/579,364 mailed Jul. 18, 2012, in 18 pages.

Non-Final Office Action for U.S. Appl. No. 12/626,272 mailed Apr. 29, 2010, in 10 pages.

Non-Final Office Action for U.S. Appl. No. 12/626,272 mailed Jan. 6, 2012, in 8 pages.

Final Office Action for U.S. Appl. No. 12/626,272 mailed Jan. 24, 2011, in 9 pages.

Notice of Allowance for U.S. Appl. No. 12/626,272 mailed May 13, 2013, in 6 pages.

Extended European Search Report for Application No. EP 09732605 dated Jul. 31, 2013, in 6 pages.

EPO Communcaiton for Application No. EP 09732605 dated May 9, 2014, in 4 pages.

EPO Communcaiton for Application No. EP 09732605 dated Aug. 13, 2015, in 4 pages.

EPO Communcaiton for Application No. EP 09732605 dated Aug. 22, 2016, in 4 pages.

Japanese First Office Action for Application No. 2011/505117 issued May 28, 2013, in 4 pages.

Japanese Office Action for Application No. 2011-505117 dated Nov. 26, 2013, in 3 pages.

Japanese Notice of Allowance for Application No. 2011/505117 issued May 26, 2014, in 3 pages.

International Search Report for PCT/US2009/040386 mailed Jun. 4, 2009, in 7 pages.

(56) References Cited

OTHER PUBLICATIONS

Australian 1st Office Action for Application No. 2010/306762 issued Jan. 9, 2014, in 6 pages.
Australian Notice of Acceptance for Application No. 2010/306762 issued Sep. 29, 2015, in 3 pages.
Canadian 1st Office Action for Application No. 2,777,067 issued Sep. 1, 2016, in 4 pages.
Canadian 2nd Office Action for Application No. 2,777,067 issued May 17, 2017, in 4 pages.
Canadian Notice of Abandonment for Application No. 2,777,067, issued Nov. 17, 2017, in 1 page.
Office Action for Application No. 10824103.5 dated Nov. 12, 2018, in 4 pages.
Notice of Allowance for U.S. Appl. No. 13/650,998 mailed Oct. 10, 2014, in 7 pages.
Non-Final Office Action for U.S. Appl. No. 14/628,114 mailed Oct. 7, 2015, in 13 pages.
Notice of Allowance for U.S. Appl. No. 13/650,998 mailed Jun. 15, 2016, in 5 pages.
Non-Final Office Action for U.S. Appl. No. 15/295,204 mailed Apr. 20, 2018, in 13 pages.
Notice of Allowance for U.S. Appl. No. 15/295,204 mailed Nov. 6, 2018, in 6 pages.
Extended European Search Report for Application No. 10824103.5 dated Sep. 16, 2013, in 9 pages.
EPO Communication for Application No. EP 10824103 dated Jan. 12, 2017, in 4 pages.
Japanese First Office Action for Application No. 2012-534360 issued Aug. 25, 2014, in 3 pages.
Japanese Notice of Allowance for Application No. 2012-534360 issued Jun. 1, 2015, in 3 pages.
International Search Report and Written Opinion for PCT/US2010/052695 mailed Dec. 6, 2010, in 18 pages.
Non-Final Office Action for U.S. Appl. No. 13/630,197 mailed Sep. 12, 2013, in 12 pages.
Notice of Allowance for U.S. Appl. No. 13/630,197 mailed Oct. 10, 2014, in 5 pages.
Non-Final Office Action for U.S. Appl. No. 14/622,611 mailed Nov. 6, 2015, in 9 pages.
Final Office Action for U.S. Appl. No. 14/622,611 mailed Jun. 3, 2016, in 6 pages.
Notice of Allowance for U.S. Appl. No. 14/622,611 mailed Nov. 9, 2016, in 5 pages.
Non-Final Office Action for U.S. Appl. No. 15/482,650 mailed Mar. 27, 2018, in 15 pages.
Notice of Allowance for U.S. Appl. No. 15/482,650 mailed Oct. 24, 2018, in 8 pages.
Non-Final Office Action for U.S. Appl. No. 13/653,783 mailed Oct. 24, 2014, in 11 pages.
Notice of Allowance for U.S. Appl. No. 13/653,783 mailed Aug. 14, 2015, in 5 pages.
Non-Final Office Action for U.S. Appl. No. 14/919,525 mailed Apr. 4, 2016, in 5 pages.
Notice of Allowance for U.S. Appl. No. 14/919,525 mailed Oct. 17, 2016, in 5 pages.
Non-Final Office Action for U.S. Appl. No. 15/450,971 mailed Oct. 20, 2017, in 4 pages.
Final Office Action for U.S. Appl. No. 15/450,971 mailed Oct. 5, 2018, in 18 pages.
International Search Report and Written Opinion for PCT/US2016/056900 mailed Jan. 12, 2017, in 7 pages.

International Search Report and Written Opinion for PCT/US2017/068011 mailed Mar. 29, 2018, in 11 pages.
EPO Communication for Application No. EP 09732605 dated Jan. 15, 2019, in 4 pages.
Canadian 3nd Office Action for Application No. 2,777,067 issued Feb. 11, 2019, in 4 pages.
Non-Final Office Action for U.S. Appl. No. 15/293,111 mailed Apr. 25, 2018, in 26 pages.
Notice of Allowance for U.S. Appl. No. 15/293,111 mailed Oct. 11, 2018, in 7 pages.
Extended European Search Report for Application No. EP 16856213.0 dated Apr. 9, 2019 in 8 pages.
Non-Final Office Action for U.S. Appl. No. 15/450,971 mailed Jul. 18, 2019, in 11 pages.
EPO Communcaiton for Application No. EP 09732605 dated Sep. 3, 2019, in 44 pages.
Australian Notice of Acceptance for App. No. 2018200859, issued Sep. 9, 2019, in 4 pages.
Non-Final Office Action for U.S. Appl. No. 15/851,577 mailed Dec. 9, 2019, in 26 pages.
Non-Final Office Action for U.S. Appl. No. 16/290,195 mailed Nov. 18, 2019, in 15 pages.
Notice of Acceptance for U.S. Pat. No. 2,965,632, issued Sep. 25, 2019, in 1 page.
Final Office Action for U.S. Appl. No. 15/450,971 mailed Apr. 9, 2020 in 11 pages.
International Search Report and Written Opinion for PCT/US2020/017526 mailed May 21, 2020, in 7 pages.
Non-Final Office Action for U.S. Appl. No. 16/361,694 mailed Jun. 25, 2020, in 16 pages.
Non-Final Office Action for U.S. Appl. No. 16/290,195 mailed Aug. 18, 2020, in 6 pages.
Office Action for Application No. 10824103.5 dated Mar. 15, 2021, in 4 pages.
Notice of Allowance for U.S. Appl. No. 16/361,694 mailed Jan. 27, 2021, in 10 pages.
Notice of Allowance for U.S. Appl. No. 16/290,195 mailed Mar. 30, 2021, in 10 pages.
Notice of Allowance for U.S. Appl. No. 15/851,577 mailed Jan. 11, 2021, in 10 pages.
Notice of Allowance for U.S. Appl. No. 15/851,577 mailed Sep. 8, 2020, in 10 pages.
Notice of Allowance for U.S. Appl. No. 15/851,577 mailed May 18, 2020, in 8 pages.
Extended European Search Report for Application No. EP 17883051.9 dated Mar. 1, 2021, in 11 pages.
Non-Final Office Action for U.S. Appl. No. 16/665,786 mailed May 14, 2021, in 25 pages.
Final Office Action for U.S. Appl. No. 16/665,786 mailed Aug. 31, 2021, in 21 pages.
Medical Carbon Research Institute, LLC, "Summary of Safety and Effectiveness Data On-X Prosthetic Heart Valve, Models ONXM and ONXMC," Mar. 6, 2002; 16 pages.
Examination Report No. 1 for AU Application No. 2020222892, dated Sep. 13, 2024; 5 pages.
Extended European Search Report for Application No. EP 22760600.1 dated Dec. 23, 2024 in 9 pages.
Office Action for CA Application No. 3, 129,819 dated Jun. 13, 2025 in 4 pages.
Invitation to Pay Additional Fees for PCT/US2023/030608 mailed Oct. 31, 2023.
International Search Report for PCT/US2023/030608 mailed Jan. 11, 2024, in 17 pages.

* cited by examiner

Clinical surgical Tricuspid Annulus

Posterior annulus

Septal annulus

Anterior annulus

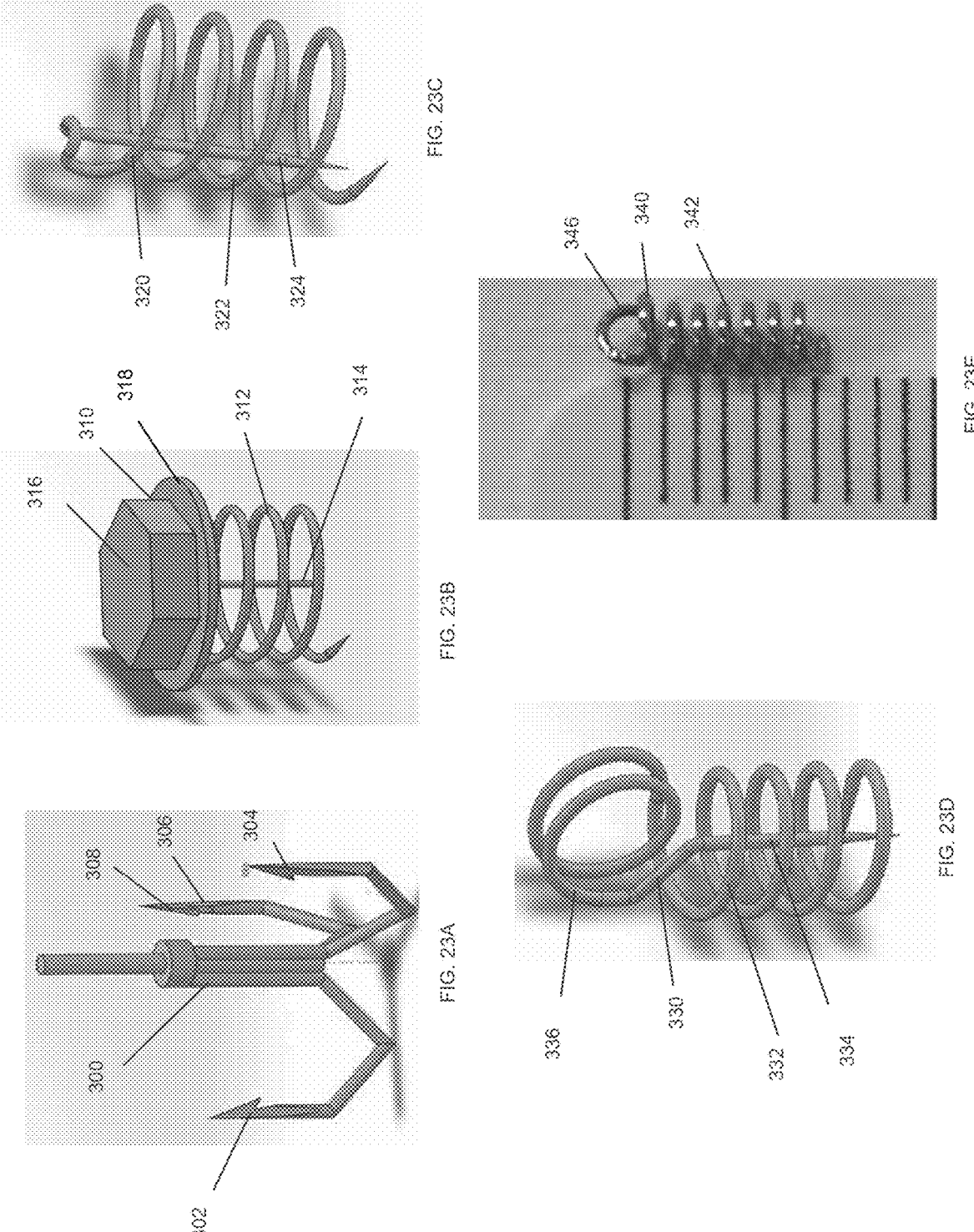

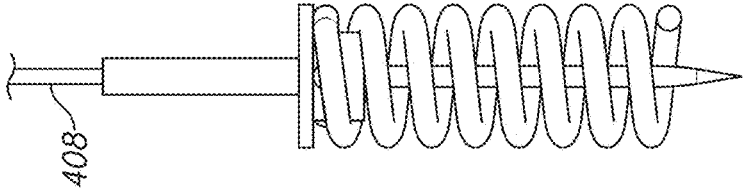
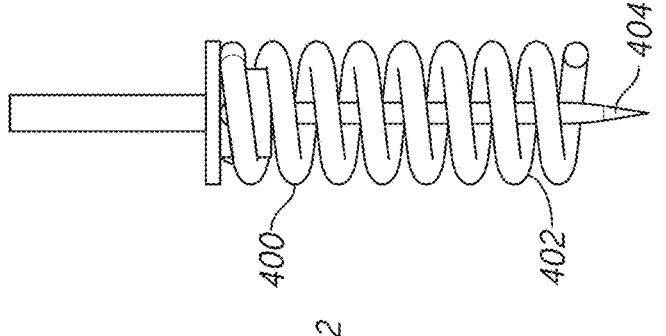
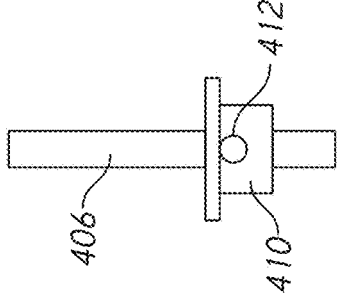
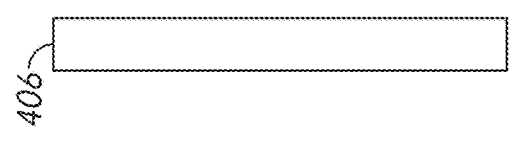
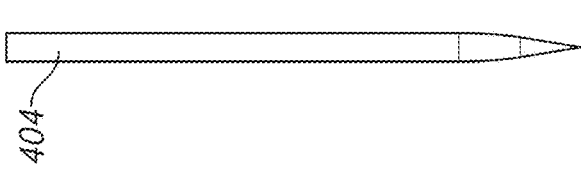
FIG. 26B
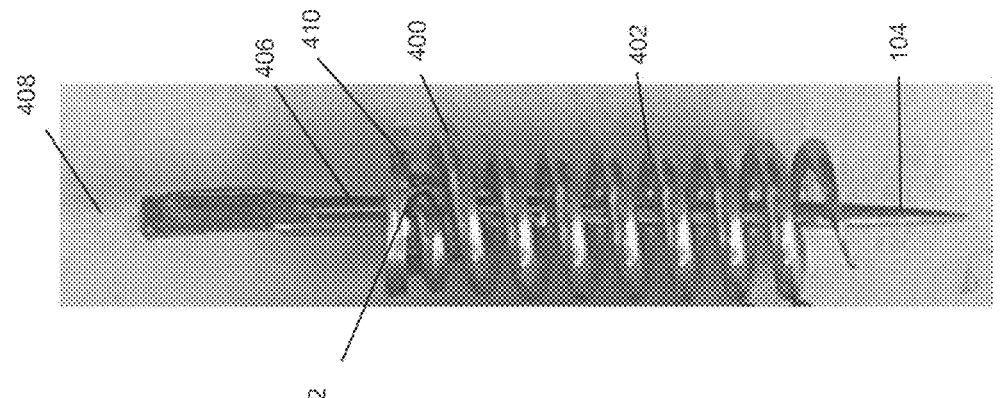
FIG. 26A 390,450

390,450

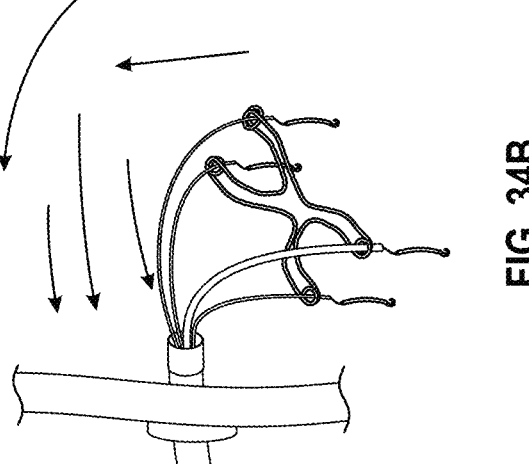
FIG. 34B
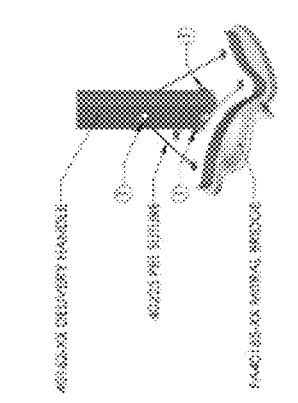
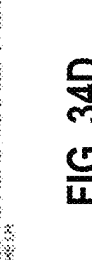
FIG. 34D
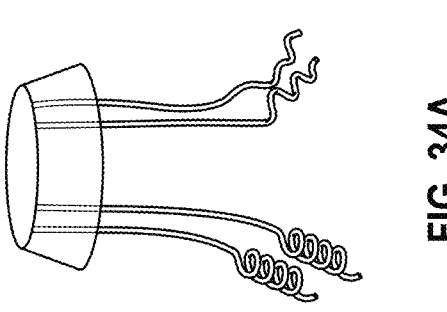
FIG. 34A
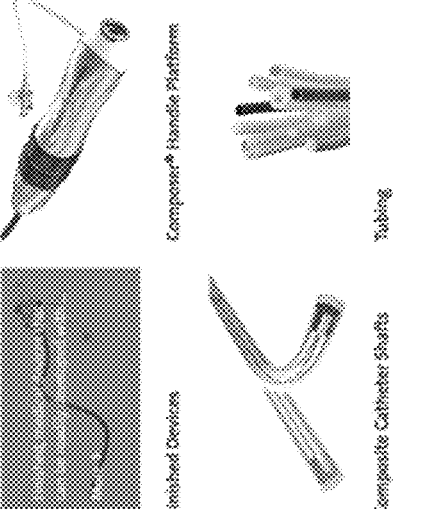
FIG. 34C

580

582

584

582

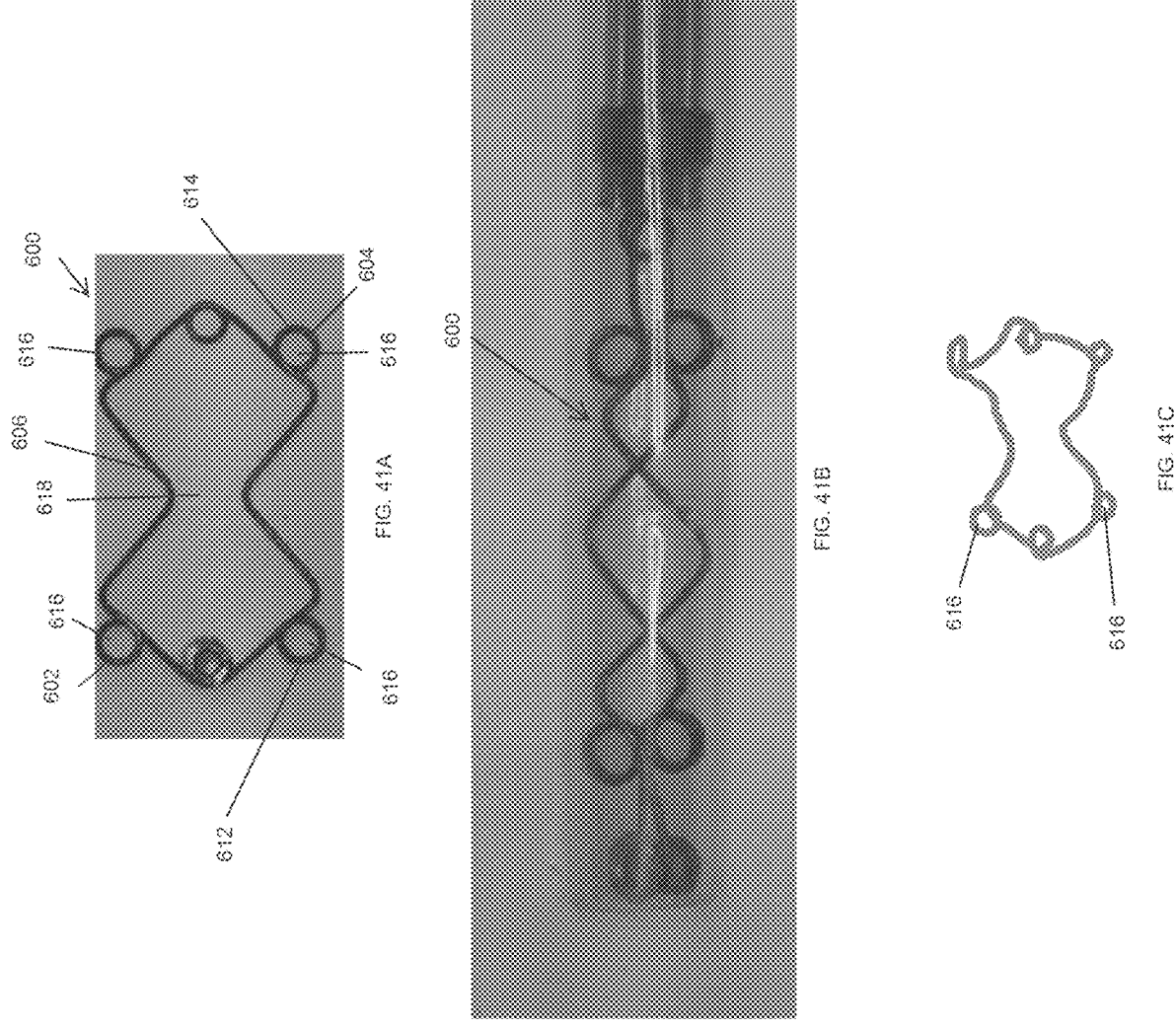

1300

1350

600

1350

1408

1400

1400

1300

TRANSVALVULAR INTRAANNULAR IMPLANT FOR VALVE REPAIR

CROSS-REFERENCE TO RELATED APPLICATIONS

This application claims priority benefit to U.S. Provisional Patent Application No. 63/154,268, filed Feb. 26, 2021, and U.S. Provisional Patent Application No. 63/162, 174, filed Mar. 17, 2021, each of which is incorporated herein by reference in its entirety for all purposes.

BACKGROUND

Field of the Invention

Embodiments of the present invention relate generally to treatment of valve prolapse and regurgitation, and more specifically, relate to the use of a transvalvular implant to treat mitral valve prolapse and mitral regurgitation and relate to the use of a transvalvular implant to treat the tricuspid valve prolapse and tricuspid regurgitation.

Description of the Related Art

The heart is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenated ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

Various disease processes can impair the proper functioning of one or more of these valves. These include degenerative processes (e.g., Barlow's Disease, fibroelastic deficiency, congenital heart defects, Ebstein's anomaly, Marfan syndrome), inflammatory processes (e.g., Rheumatic Heart Disease) and infectious processes (e.g., endocarditis, infective endocarditis). In addition, damage to the ventricle from prior heart attacks or diseases (i.e., myocardial infarction secondary to coronary artery disease, coronary artery disease, cardiomyopath) or other heart diseases or trauma (e.g., cardiomyopathy, blunt chest trauma), or procedures (e.g., pacemaker or implantable device leads, endomyocardial biopsy, radiation) can distort the valve's geometry causing it to dysfunction.

The mitral valve is comprised of an anterior leaflet and a posterior leaflet. The bases of the leaflets are fixed to a circumferential partly fibrous structure, the annulus, preventing dehiscence of the valve. A subvalvular apparatus of chordae and papillary muscles prevents the valve from prolapsing into the left atrium. Mitral valve disease can be expressed as a complex variety of pathological lesions of either valve or subvalvular structures, but can also be related to the functional status of the valve. Functionally the mitral valve disease can be categorized into two anomalies, increased leaflet motion i.e. leaflet prolapse leading to regurgitation, or diminished leaflet motion i.e. restricted leaflet motion leading to obstruction and/or regurgitation of blood flow.

Leaflet prolapse is defined as when a portion of the leaflet overrides the plane of the orifice during ventricular contraction. The mitral regurgitation can also develop secondary to alteration in the annular ventricular apparatus and altered ventricular geometry, followed by incomplete leaflet coaptation. In ischemic heart failure this can be attributed to papillary or lateral wall muscle dysfunction, and in non-ischemic heart failure it can be ascribed to annular dilation and chordal tethering, all as a result of dysfunctional remodeling.

The predominant cause of dysfunction of the mitral valve is regurgitation which produces an ineffective cardiac pump function resulting in several deleterious conditions such as ventricular and atrial enlargement, pulmonary hypertension and heart-failure and ultimately death.

The main objective for the surgical correction is to restore normal function and not necessarily anatomical correction. This is accomplished by replacing the valve or by reconstructing the valve. Both of the procedures require the use of cardiopulmonary bypass and is a major surgical operation carrying a non-negligible early morbidity and mortality risk, and a postoperative rehabilitation for months with substantial postoperative pain. Historically, the surgical approach to patients with functional mitral regurgitation was mitral valve replacement, however with certain adverse consequences such as thromboembolic complications, the need for anti-coagulation, insufficient durability of the valve, loss of ventricular function and geometry.

Reconstruction of the mitral valve is therefore the preferred treatment for the correction of mitral valve regurgitation and typically consists of a quadrangular resection of the posterior valve (valvuloplasty) in combination with a reduction of the mitral valve annulus (annuloplasty) by the means of suturing a ring onto the annulus. These procedures are surgically demanding and require a bloodless and well-exposed operating field for an optimal surgical result. The technique has virtually not been changed for more than three decades.

More recently, prolapse of the valve has been repaired by anchoring the free edge of the prolapsing leaflet to the corresponding free edge of the opposing leaflet and thereby restoring apposition but not necessarily coaptation. In this procedure a ring annuloplasty is also required to attain complete coaptation.

This method commonly referred to as an edge-to-edge or "Alfieri" repair also has certain drawbacks such as the creation of a double orifice valve and thereby reducing the effective orifice area. Several less invasive approaches related to the edge-to-edge technique has been suggested, for repairing mitral valve regurgitation by placing a clip through a catheter to suture the valve edges. However, it still remains to conduct an annuloplasty procedure, which has not yet been resolved by a catheter technique and therefore is to be performed by conventional surgery, which makes the method impractical.

Notwithstanding the presence of a variety of presently available surgical techniques and promising catheter based procedures for the future, there remains a need for a simple but effective device and corresponding surgical, minimally invasive or transvascular procedure to treat the mitral or tricuspid valve.

SUMMARY

Further features and advantages of the present invention will become apparent to those of skill in the art in view of the detailed description of preferred embodiments which follows, when considered together with the attached drawings and claims.

Some embodiments of this invention are directed to a transvalvular intraannular implant to treat mitral valve prolapse and mitral regurgitation. The terminology "transvalvular" as used herein encompasses "across", "over", or "through" the valve surfaces by any means, and "intraannular" provides an axial spatial reference to within the native valve annulus or an annular implant that serves to function within the valve annulus. Axial with respect to the valve axis means along the axis of the valve and can describe position relative to the atrium, "supra", or relative to the ventricle, "infra". Specifically, it creates an axis through which a plane is pierced by the aforementioned axis, and encompasses an embodiment that is intraannular to address coaptation at the valvular plane or series of valvular planes created during each cardiac cycle, but does not obviate other salient features of the invention that may be clearly infraannular or supraannular during the cardiac cycle. Further, the terminology in the following descriptions may use "transannular implant" or "implant" and it means to include all features that may be infraannular, intraannular, or suprannular without or with stating each axially descriptive term. As well "offset" refers to directionally displaced from a frame of reference.

In some embodiments, a transvalvular implant is provided. The transvalvular implant can include an elongate body having a first end, a first anchoring portion located proximate the first end, a second end, a second anchoring portion located proximate the second end, and a central portion connected to the first end and the second end. In some embodiments, the central portion comprises an arcuate shape. In some embodiments, the elongate body comprises a wire form curved body. In some embodiments, the first anchoring portion comprises two eyelets and the second anchoring portion comprises two eyelets. In some embodiments, the center of the elongate body comprises an opening.

In some embodiments, the central portion is configured to be displaced transversely from the intraannular plane which includes the valve annulus and is transverse to the direction of blood flow when the elongate body is attached to the annulus. In some embodiments, the first end and the second end are configured to be attached to the mitral valve annulus within the intraannular plane and the central portion is configured to be convex in the direction of outflow to support the valve leaflets at a point displaced toward the ventricle from the intraannular plane. In some embodiments, the first end and the second end are configured to reside on a generally septal-lateral axis transverse to the coaptive edges of the valve leaflets when the elongate body is attached to the valve annulus. In some embodiments, the transvalvular implant does not comprise an annuloplasty ring. In some embodiments, the transvalvular implant is configured to be implanted onto a cardiac valve annulus for treatment of valve leak. In some embodiments, the transvalvular implant is configured for a mitral valve or a tricuspid valve. In some embodiments, the transvalvular implant is configured for straddling the mitral valve orifice in a septal lateral diameter of mitral valve annulus. In some embodiments, the transvalvular implant is configured for the treatment of mitral valve regurgitation caused by dilatation of mitral valve annulus and deformation of mitral valve leaflets. In some embodiments, the first end and the second end are configured to be anchored to the annulus. In some embodiments, sutures coupled to anchors are threaded through the first anchoring portion and the second anchoring portion. In some embodiments, caps are configured to hold the transvalvular implant to the annulus. In some embodiments, the elongate body is made of single wire. In some embodiments, the elongate body is made of a plurality of wires. In some embodiments, the elongate body comprises stainless steel or nitinol.

In some embodiments, a method is provided. The method can include delivering one or more anchors to a valve annulus of a heart valve. The method can include delivering the transvalvular implant to the valve annulus.

In some embodiments, the heart valve is a mitral valve. In some embodiments, the method can include treating functional mitral regurgitation by reducing the septal lateral diameter sufficiently to bring the posterior annulus towards the anterior annulus to achieve full closure of leaflets and competent mitral valve during systole preventing mitral regurgitation. In some embodiments, the transvalvular implant straddles the valve orifice in an annular horizontal plane in a septal lateral dimension of the annulus. In some embodiments, the central portion is curved towards the left ventricular cavity. In some embodiments, the central portion is curved left atrial cavity. In some embodiments, the one or more anchors comprise a helical screw. In some embodiments, the one or more anchors comprise a center pin. In some embodiments, the one or more anchors comprise a center post. In some embodiments, the one or more anchors comprise a quadrangular helix top mount.

In some embodiments, a transvalvular implant is provided. The transvalvular implant can include an elongate body having a first end, a first anchoring portion located proximate the first end, a second end, a second anchoring portion located proximate the second end, and a central portion connected to the first end and the second end. In some embodiments, the central portion comprises an arcuate shape. In some embodiments, the elongate body comprises a wire form curved body. In some embodiments, the first anchoring portion comprises one or more eyelets and the second anchoring portion comprises one or more eyelets. In some embodiments, the center of the elongate body comprises an opening.

In some embodiments, the first anchoring portion comprises two or more eyelets. In some embodiments, the second anchoring portion comprises two or more eyelets. In some embodiments, the first anchoring portion comprises one or more eyelets and the second anchoring portion comprises two or more eyelets. In some embodiments, the first anchoring portion comprises a single eyelet. In some embodiments, the second anchoring portion comprises a single eyelet. In some embodiments, the central portion is configured to be displaced transversely from the intraannular plane which includes the valve annulus and is transverse to the direction of blood flow when the elongate body is attached to the annulus. In some embodiments, the first end and the second end are configured to be attached to the mitral valve annulus within the intraannular plane and the central portion is configured to be convex in the direction of outflow to support the valve leaflets at a point displaced toward the ventricle from the intraannular plane. In some embodiments, the first end and the second end are configured to be attached to the tricuspid valve annulus within the intraannular plane and the central portion is configured to be convex. In some embodiments, the first end and the second end are configured to reside on an axis generally transverse to the coaptive edges of the valve leaflets when the elongate body is attached to the valve annulus. In some embodiments, the first end and the second end are configured to reside on a generally septal-lateral axis in the mitral annulus. In some embodiments, the first end and the second end are configured to reside on a generally septal-lateral axis transverse to the coaptive edges of the valve leaflets when the elongate body is attached to the valve annulus. In some embodiments, the first end and the second end are configured to reside on a generally anterior-posterior axis in the tricuspid annulus. In some embodiments, the first end and the second end are configured to reside on a generally anterior-posterior axis transverse to the coaptive edges of the valve leaflets when the elongate body is attached to the valve annulus. In some embodiments, the transvalvular implant does not comprise an annuloplasty ring. In some embodiments, the transvalvular implant is configured to be implanted onto a cardiac valve annulus for treatment of valve leak. In some embodiments, the transvalvular implant is configured for a mitral valve or a tricuspid valve. In some embodiments, the transvalvular implant is configured for straddling the valve orifice. In some embodiments, the transvalvular implant is configured for straddling the mitral valve orifice in a septal lateral diameter of mitral valve annulus. In some embodiments, the transvalvular implant is configured for straddling the tricuspid valve orifice in an anterior-posterior diameter of tricuspid valve annulus. In some embodiments, the transvalvular implant is configured for the treatment of mitral valve regurgitation caused by dilatation of mitral valve annulus and deformation of mitral valve leaflets. In some embodiments, the first end and the second end are configured to be anchored to the annulus. In some embodiments, tethers coupled to anchors are threaded through the one or more eyelets of the first anchoring portion and the second anchoring portion. In some embodiments, caps or clips are configured to secure the transvalvular implant to anchors. In some embodiments, the elongate body is made of single wire. In some embodiments, the elongate body is made of a plurality of wires. In some embodiments, the elongate body comprises stainless steel or nitinol. In some embodiments, the first anchoring portion comprises three eyelets. In some embodiments, the second anchoring portion comprises three eyelets. In some embodiments, at least one eyelet comprises a rivet. In some embodiments, at least one eyelet facilitates compression of the implant. In some embodiments, the second anchoring portion comprises adjacent eyelets. In some embodiments, the second anchoring portion comprises a figure eight eyelet. In some embodiments, the first anchoring portion comprises two or more eyelets. In some embodiments, the implant is generally triangular. In some embodiments, the implant is generally X-shaped. In some embodiments, the implant tapers inward toward the central portion. In some embodiments, the implant is generally diamond shaped. In some embodiments, the implant tapers outward the central portion.

In some embodiments, a method is provided. The method can include delivering one or more anchors to a valve annulus of a heart valve. The method can include delivering the transvalvular implant described herein to the valve annulus.

In some embodiments, the method can include providing a guide catheter and an annular steering catheter. In some embodiments, the method can include providing an anchor delivery catheter and a multi-lumen bridge delivery catheter. In some embodiments, the heart valve is a mitral valve. In some embodiments, the heart valve is a tricuspid valve. In some embodiments, the method can include treating functional mitral regurgitation by reducing the septal lateral diameter sufficiently to bring the posterior annulus towards the anterior annulus to achieve full closure of leaflets and competent mitral valve during systole preventing mitral regurgitation. In some embodiments, the method can include treating functional tricuspid regurgitation by reducing the anterior-posterior diameter of the tricuspid valve annulus sufficiently to bring the anterior annulus to the septal and or posterior annulus to achieve full closure of the tricuspid leaflets and competent tricuspid valve preventing tricuspid valve regurgitation. In some embodiments, the transvalvular implant straddles the valve orifice in an annular horizontal plane of the annulus. In some embodiments, the transvalvular implant straddles the mitral valve orifice in an annular horizontal plane in a septal lateral dimension of the mitral annulus. In some embodiments, the transvalvular implant straddles the tricuspid valve orifice in an annular horizontal plane in an anterior-posterior dimension of the tricuspid valve annulus. In some embodiments, the central portion is curved towards the left ventricular cavity. In some embodiments, the central portion is curved towards the right ventricular cavity, as in the tricuspid valve. In some embodiments, the central portion is curved towards the left atrial cavity. In some embodiments, the one or more anchors comprise a helical screw. In some embodiments, the one or more anchors comprise a center pin. In some embodiments, the one or more anchors comprise a center post. In some embodiments, the one or more anchors comprise a quadrangular helix top mount. In some embodiments, the method can include advancing a pusher rod to deliver the transvalvular implant. In some embodiments, the method can include advancing a pusher rod to deliver a clip. In some embodiments, the clip comprises one or more flanges and a central opening, wherein the pusher rod advances the clip onto a central post of an anchor. In some embodiments, the method can include positioning at least one catheter in a sled holder. In some embodiments, the method can include inserting the one or more anchors at a 45 degree angle.

In some embodiments, a method of treating a tricuspid valve is provided. The method can include positioning a transvalvular bridge comprising an elongate body having a first anchoring portion, a second anchoring portion, and a central portion. The method can include anchoring the transvalvular bridge only on the annulus. The method can include anchoring the transvalvular bridge at the anterior annulus. The method can include anchoring the transvalvular bridge only on the anterior annulus and the posterior annulus. The method can include anchoring the transvalvular bridge at the posterior annulus. The method can include anchoring the transvalvular bridge between an anterior annulus and straddling the commissure between the septal annulus and the posterior annulus. The method can include anchoring the transvalvular bridge only on the posterior annulus beyond the septal-posterior commissure.

In some embodiments, anchoring the transvalvular bridge comprises anchoring the transvalvular bridge to two anchors attached to the anterior annulus. In some embodiments, anchoring the transvalvular bridge comprises anchoring the transvalvular bridge to two anchors near a midpoint of the anterior annulus. In some embodiments, anchoring the transvalvular bridge comprises anchoring the transvalvular bridge to an anchor attached to the posterior annulus. In some embodiments, anchoring the transvalvular bridge comprises anchoring the transvalvular bridge to an anchor attached to the septal annulus. In some embodiments, anchoring the transvalvular bridge comprises anchoring the transvalvular bridge to span the coaptive edge between the anterior leaflets and both the posterior and septal leaflets. In some embodiments, positioning a transvalvular bridge comprises positioning the transvalvular bridge to extend transversely across coaptive edge formed by the closure of the anterior leaflet during systole. In some embodiments, positioning a transvalvular bridge comprises positioning the central portion convex in the direction of the right ventricle. In some embodiments, the method can include elevating the position of the coaptive edges during valve closure to thereby cause early coaption relative to the cardiac cycle. In some embodiments, anchoring the transvalvular bridge does not affect the size and shape of the tricuspid annulus.

In some embodiments, a method of treating a tricuspid valve is provided. The method can include positioning a transvalvular bridge comprising an elongate body having a first anchoring portion, a second anchoring portion, and a longitudinal axis. The method can include anchoring the transvalvular bridge, wherein the longitudinal axis resides generally on an anterior-septal-posterior diameter extending from the anterior annulus along the coaptive edge between the septal annulus and posterior annulus.

In some embodiments, anchoring the transvalvular bridge comprises anchoring to the anterior annulus, the posterior annulus, and the septal annulus. In some embodiments, anchoring the transvalvular bridge comprises anchoring the transvalvular bridge to straddle the posteroseptal commissure. In some embodiments, anchoring the transvalvular bridge comprises positioning a post of an anchor relative to an aperture of the first anchoring portion. In some embodiments, anchoring the transvalvular bridge comprises lowering the transvalvular bridge relative to anchors. In some embodiments, anchoring the transvalvular bridge comprises anchoring the transvalvular bridge to span the valve opening. In some embodiments, anchoring the transvalvular bridge comprises anchoring the transvalvular bridge on both sides of a midpoint of the anterior annulus. In some embodiments, anchoring the transvalvular bridge comprises anchoring the transvalvular bridge more toward the posterior annulus than the septal annulus.

In some embodiments, a method of treating a tricuspid valve is provided. The method can include positioning a transvalvular bridge comprising an elongate body having a plurality of apertures and a longitudinal axis. The method can include anchoring the transvalvular bridge to the anterior annulus, the posterior annulus, and the septal annulus.

In some embodiments, anchoring the transvalvular bridge comprises anchoring the transvalvular bridge to straddle the commissure between the posterior annulus and the septal annulus.

BRIEF DESCRIPTION OF THE DRAWINGS

FIGS. 23A-23E are views of embodiments of anchors.

FIGS. 26A-26B are views of embodiments of anchors and mounts.

FIGS. 34A-34D are views of an embodiment of delivery systems.

FIGS. 41A-41C are views of embodiments of a transvalvular implant.

DETAILED DESCRIPTION

Figure 1:
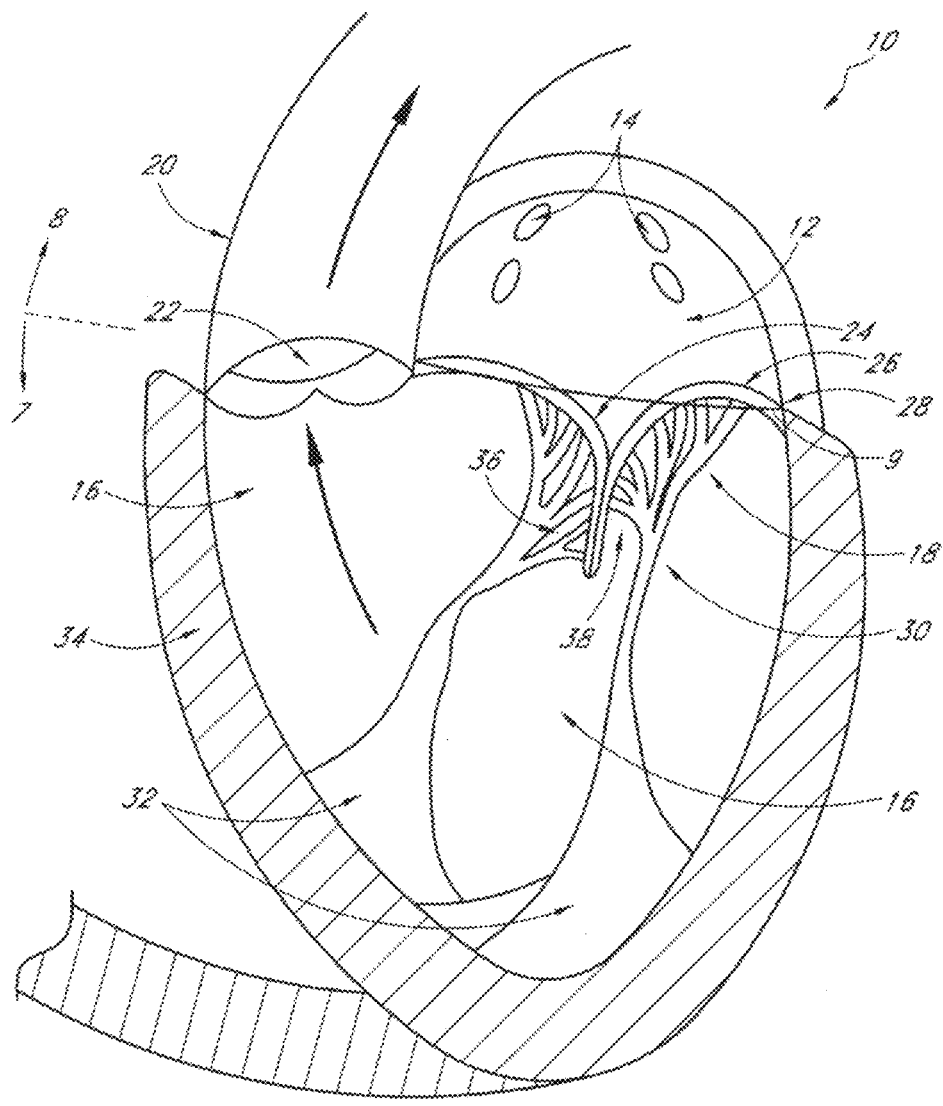
FIG. 1 is a simplified cross-sectional view of the heart with a normal mitral valve during systole. The intraannular plane is illustrated relative to supraannular and infrannular.

FIG. 1 illustrates a cross-sectional view of the heart 10 with a normal mitral valve 18 in systole. As illustrated, the heart 10 comprises the left atrium 12 which receives oxygenated blood from the pulmonary veins 14 and the left ventricle 16 which receives blood from the left atrium 12. The mitral valve 18 is located between the left atrium 12 and left ventricle 16 and functions to regulate the flow of blood from the left atrium 12 to the left ventricle 16. During ventricular diastole, the mitral valve 18 is open which allows blood to fill the left ventricle 16. During ventricular systole, the left ventricle 16 contracts, which results in an increase in pressure inside the left ventricle 16. The mitral valve 18 closes when the pressure inside the left ventricle 16 increases above the pressure within the left atrium 12. The pressure within the left ventricle 16 continues increasing until the pressure within the left ventricle 16 exceeds the pressure within the aorta 20, which causes the aortic valve 22 to open and blood to be ejected from the left ventricle and into the aorta 20.

The mitral valve 18 comprises an anterior leaflet 24 and a posterior leaflet 26 that have base portions that are attached to a fibrous ring called the mitral valve annulus 28. Each of the leaflets 24 and 26 has respective free edges 36 and 38. Attached to the ventricular side of the leaflets 24 and 26 are relatively inelastic chordae tendineae 30. The chordae tendineae 30 are anchored to papillary muscles 32 that extend from the intraventricular septum 34. The chordae tendineae 30 and papillary muscle 32 function to prevent the leaflets 24 and 26 from prolapsing and enable proper coaptation of the leaflets 24 and 26 during mitral valve 18 closure. Also shown schematically is line 9 through the valve annulus 28 representing the intraannular plane. Arrow 8 points supraannularly, toward the left atrium 12, while arrow 7 points infraannularly, toward the left ventricle 16.

Figure 2:
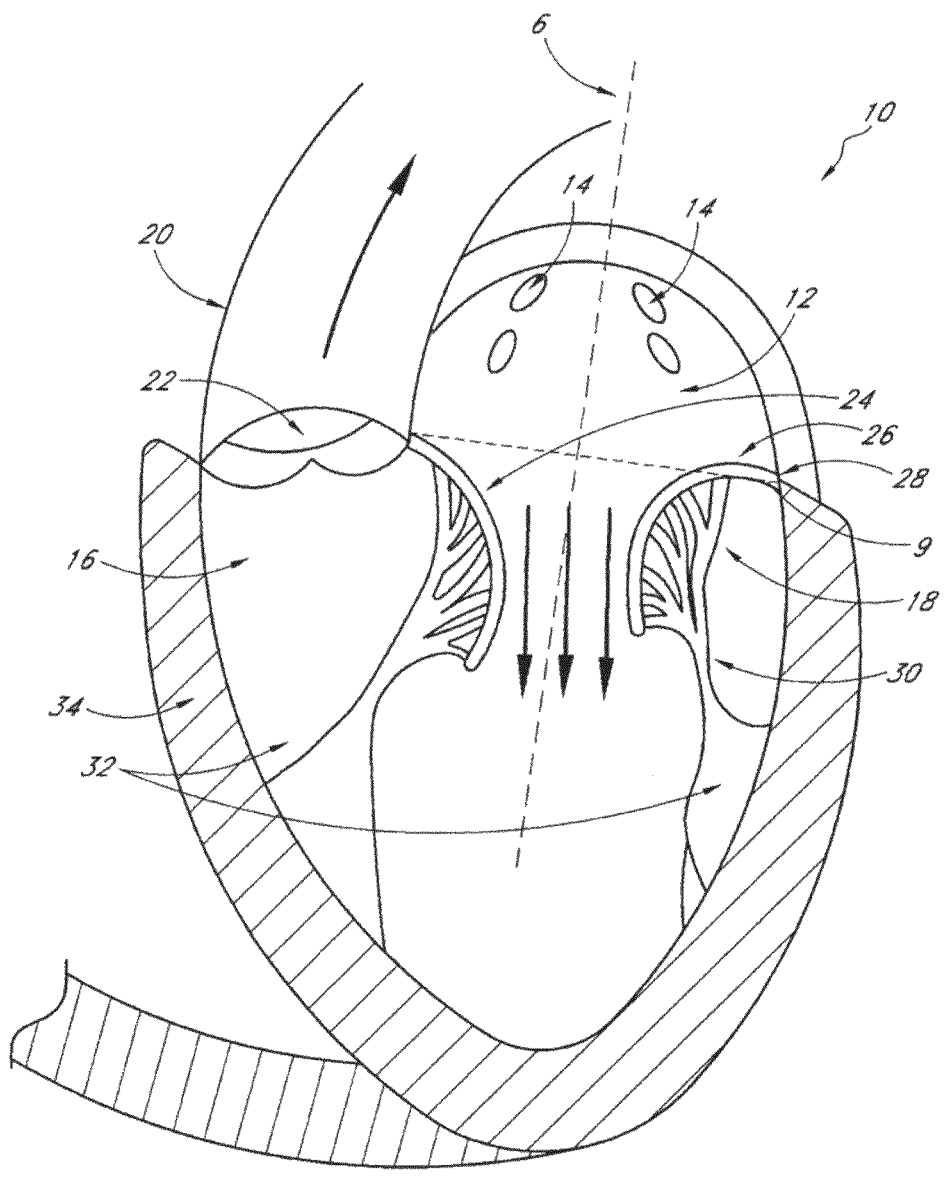
FIG. 2 is a cross-sectional view of the heart with a normal mitral valve during diastole. The axis of the mitral valve is illustrated, and shown piercing the intraannular plane.

FIG. 2 illustrates a cross-sectional view of the heart 10 with a normal mitral valve 18 in diastole. After the left ventricle 16 has ejected the blood into the aorta, the left ventricle relaxes, which results in a drop in pressure within the left ventricle 16. When the pressure in the left ventricle 16 drops below the pressure in the aorta 20, the aortic valve 22 closes. The pressure within the left ventricle 16 continues dropping until the pressure in the left ventricle 16 is less than the pressure in the left atrium 12, at which point the mitral valve 18 opens, as shown in FIG. 2. During the early filling phase, blood passively fills the left ventricle 16 and this accounts for most of the filling of the left ventricle 16 in an individual at rest. At the end of the filling phase, the left atrium 12 contracts and provides a final kick that ejects additional blood into the left ventricle. Also shown is intraannular plane 9 as described above, and line 6 representing the longitudinal axis 6 of the valve 18.

Figures 3, 4:
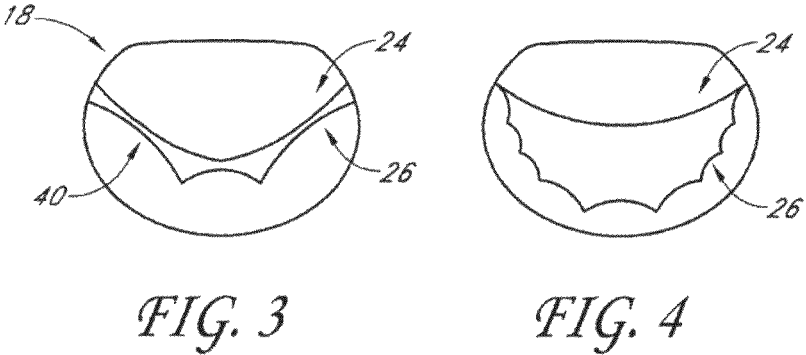
FIG. 3 is a bottom view of the normal mitral valve of FIG. 1 during systole looking from the left atrium to the left ventricle.
FIG. 4 is a bottom view of the normal mitral valve of FIG. 2 during diastole looking from the left atrium to the left ventricle.
Figures 5, 6:
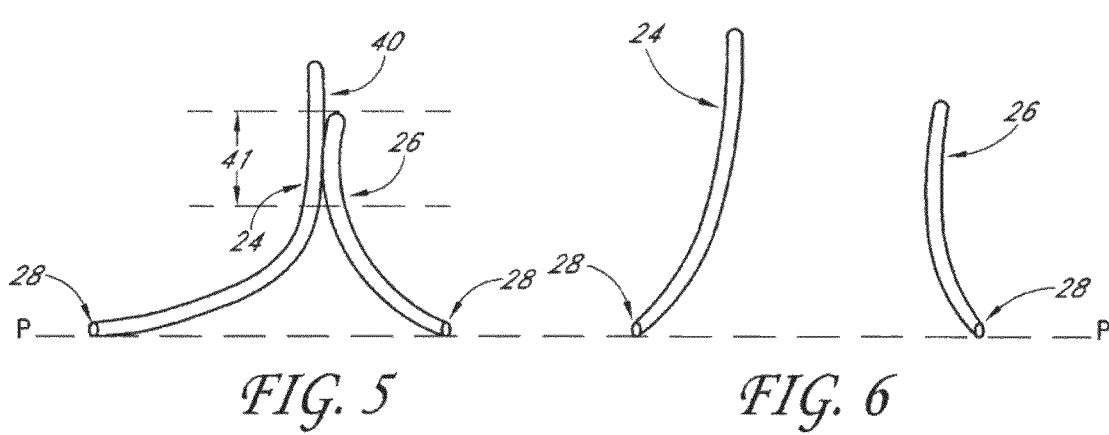
FIG. 5 is a cross-sectional schematic view of the normal mitral valve of FIG. 1 during systole, illustrating the depth of the coaption zone.
FIG. 6 is a cross-sectional schematic view of the normal mitral valve of FIG. 2 during diastole.

FIG. 3 illustrates a bottom view of normal mitral valve 18 in systole, looking from the left atrium and to the left ventricle. As shown, the anterior leaflet 24 and posterior leaflet 26 are properly coapted, thereby forming a coaptive edge 40 that forms a seal that prevents retrograde flow of blood through the mitral valve 18, which is known as mitral regurgitation. FIG. 4 illustrates a bottom view of normal mitral valve 18 in diastole. FIG. 5 provides a side cross-sectional view of a normal mitral valve 18 in systole. As shown in FIG. 5, the valve leaflets 24 and 26 do not normally cross the plane P defined by the annulus and the free edges 36 and 38 coapt together to form a coaptive edge 40.

FIG. 5 also illustrates a coaption zone 41. Preferably the depth of coaption (length of zone 41 in the direction of blood flow, in which the leaflets 24 and 26 are in contact) is at least about 2 mm or 5 mm, and is preferably within the range of from about 7 mm to about 10 mm for the mitral valve.

Thus, implantation of the devices in accordance with the present invention preferably achieves an increase in the depth of coaption. At increase of at least about 1 mm, preferably at least about 2 mm, and in some instances an increase of at least about 3 mm to 5 mm or more may be accomplished.

In addition to improving coaption depth, implantation of devices in accordance with the present invention preferably also increase the width of coaptation along the coaption plane. This may be accomplished, for example, by utilizing an implant having a widened portion for contacting the leaflets in the area of coaption such as is illustrated in connection with FIGS. 19A and 19B below. A further modification of the coaptive action of the leaflets which is accomplished in accordance with the present invention is to achieve early coaption. This is accomplished by the curvature or other elevation of the implant in the ventricle direction. This allows the present invention to achieve early coaption relative to the cardiac cycle, relative to the coaption point prior to implantation of devices in accordance with the present invention.

FIGS. 4 and 6 illustrate normal mitral valve 18 in diastole. As shown, the anterior leaflet 24 and posterior leaflet 26 are in a fully opened configuration which allows blood to flow from the left atrium to the left ventricle.

Figure 7:
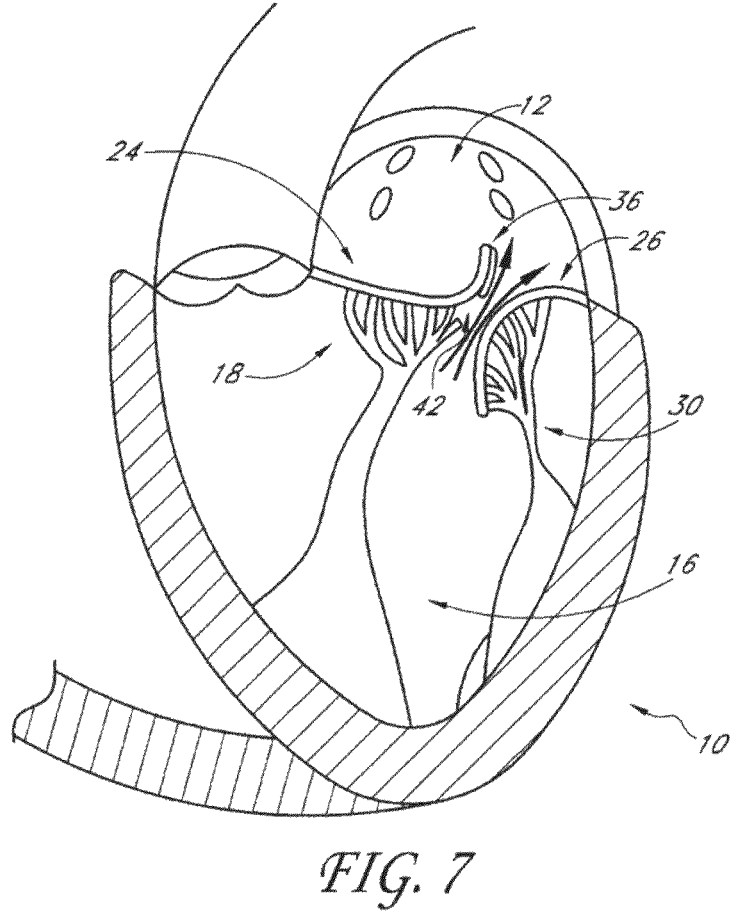
FIG. 7 is a cross-sectional view of the heart during systole showing a mitral valve with a prolapsed anterior leaflet caused by the rupture of the chordae tendineae attached to the anterior leaflet.
Figure 8:
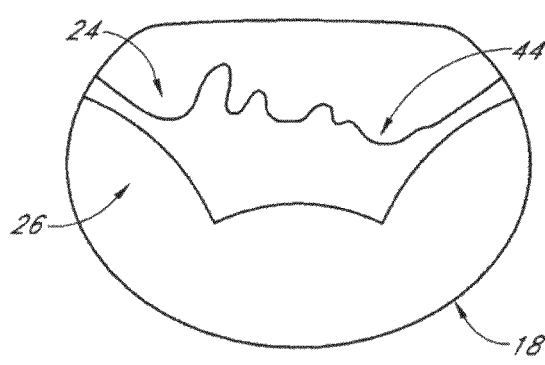
FIG. 8 is a bottom view of the mitral valve of FIG. 7 having a prolapsed anterior leaflet looking from the left atrium to the left ventricle.

FIGS. 7 and 8 illustrate a heart 10 in systole where the anterior leaflet 24 of the mitral valve 18 is in prolapse. Anterior leaflet 24 prolapse can be caused by a variety of mechanisms. For example, as illustrated in FIG. 7, rupture 42 of a portion of the chordae tendineae 30 attached to the anterior leaflet 24 can cause the free edge 36 of the anterior leaflet 24 to invert during mitral valve 18 closure. As shown in FIG. 8, inversion 44 of the anterior leaflet 24 can prevent the mitral valve leaflets 24 and 26 from properly coapting and forming a seal. This situation where the free edge 36 of the anterior leaflet 24 crosses into the left atrium 12 during mitral valve 18 closure can lead to mitral regurgitation.

Figure 9:
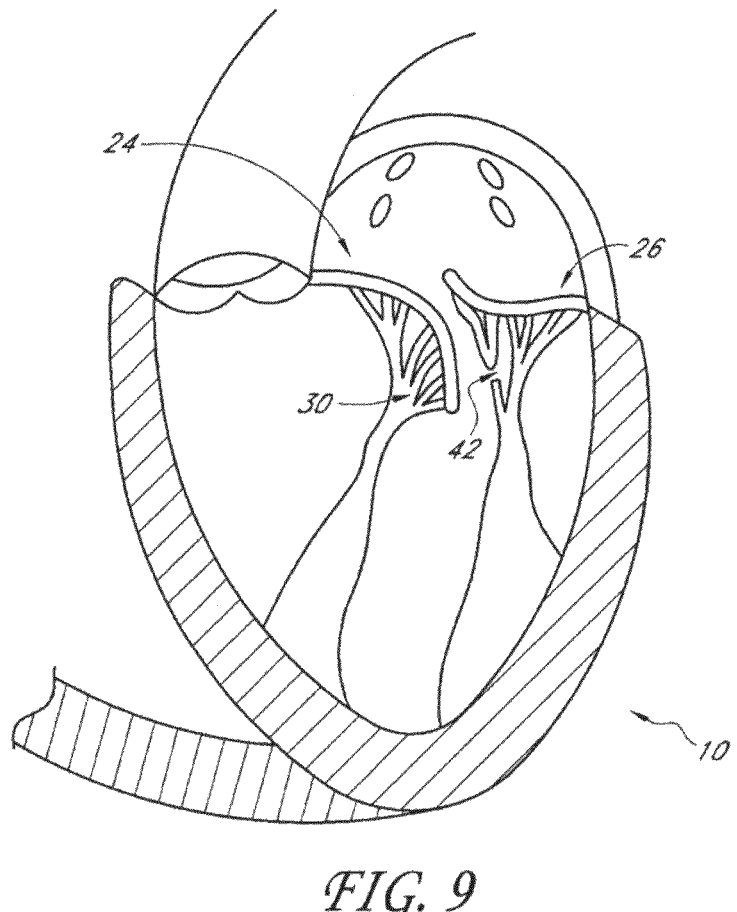
FIG. 9 is a cross-sectional view of the heart during systole showing a mitral valve with a prolapsed posterior leaflet caused by the rupture of the chordae tendineae attached to the posterior leaflet.
Figure 10:
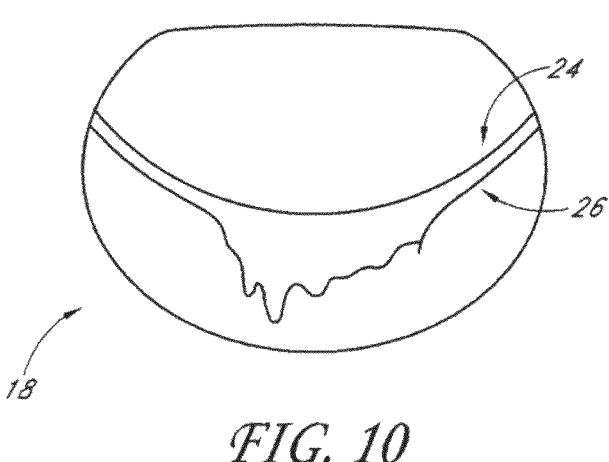
FIG. 10 is a bottom view of the mitral valve of FIG. 9 having a prolapsed posterior leaflet looking from the left atrium to the left ventricle.

Similarly, FIGS. 9 and 10 illustrate posterior leaflet 26 prolapse caused by a rupture of the chordae tendineae 30 attached to the posterior leaflet 26. In this case, the posterior leaflet 26 can invert and cross into the left atrium 12 during mitral valve 18 closure. The inversion of the posterior leaflet 26 prevents the mitral valve leaflets 24 and 26 from properly coapting and forming a seal, which can lead to mitral regurgitation.

Figure 11:
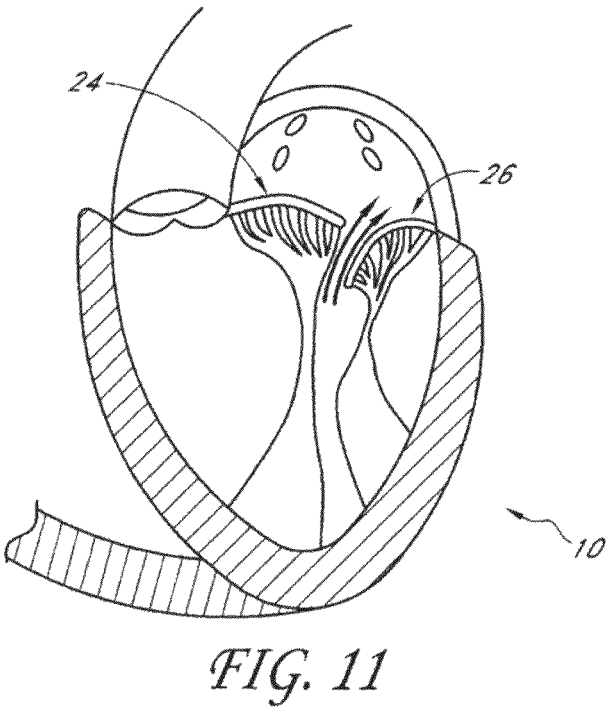
FIG. 11 is a cross-sectional view of the heart during systole showing a mitral valve with anterior leaflet prolapse.
Figure 11A:
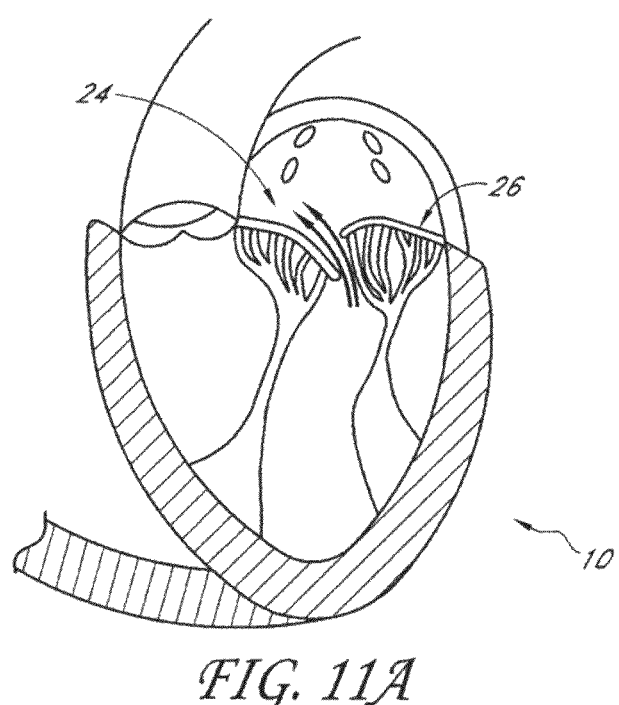
FIG. 11A is a cross sectional view as in FIG. 11, showing posterior leaflet prolapse.
Figure 11B:
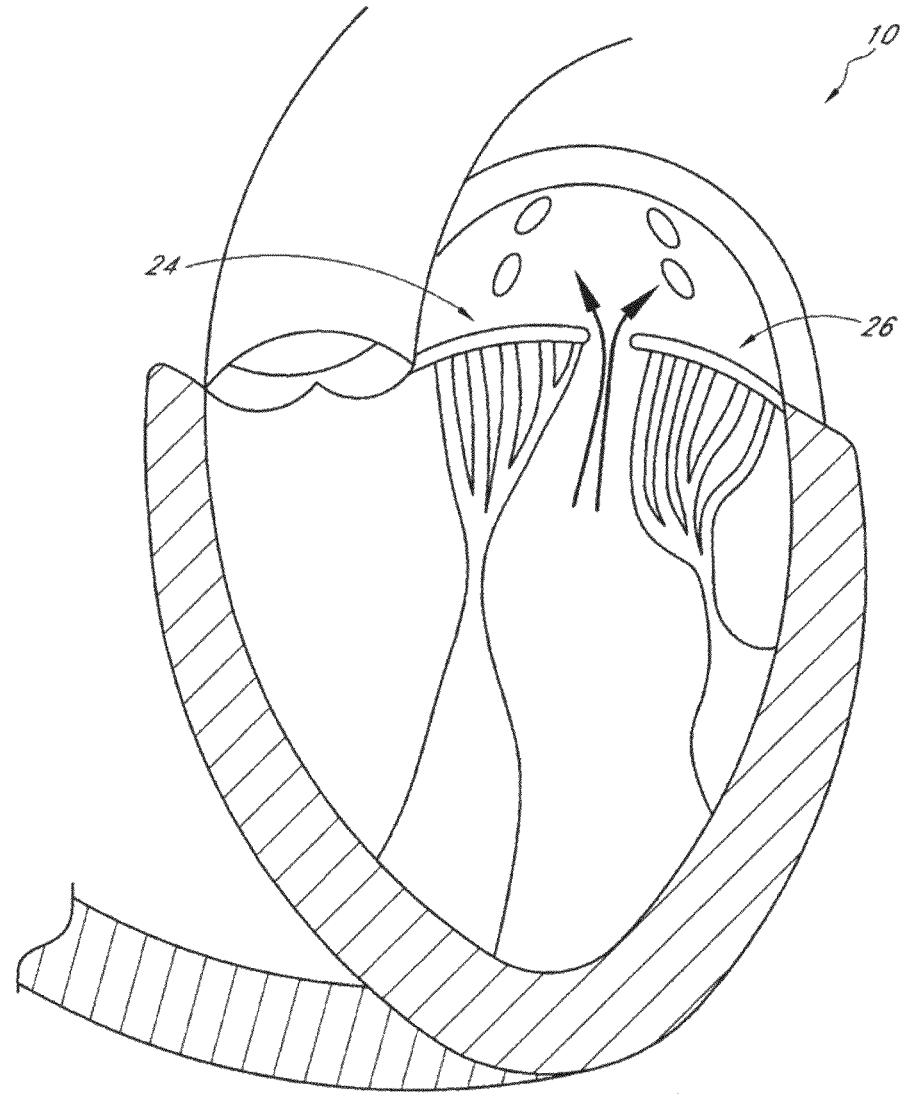
FIG. 11B is a cross sectional view as in FIG. 11, showing bileaflet prolapse with mitral regurgitation.
Figure 11C:
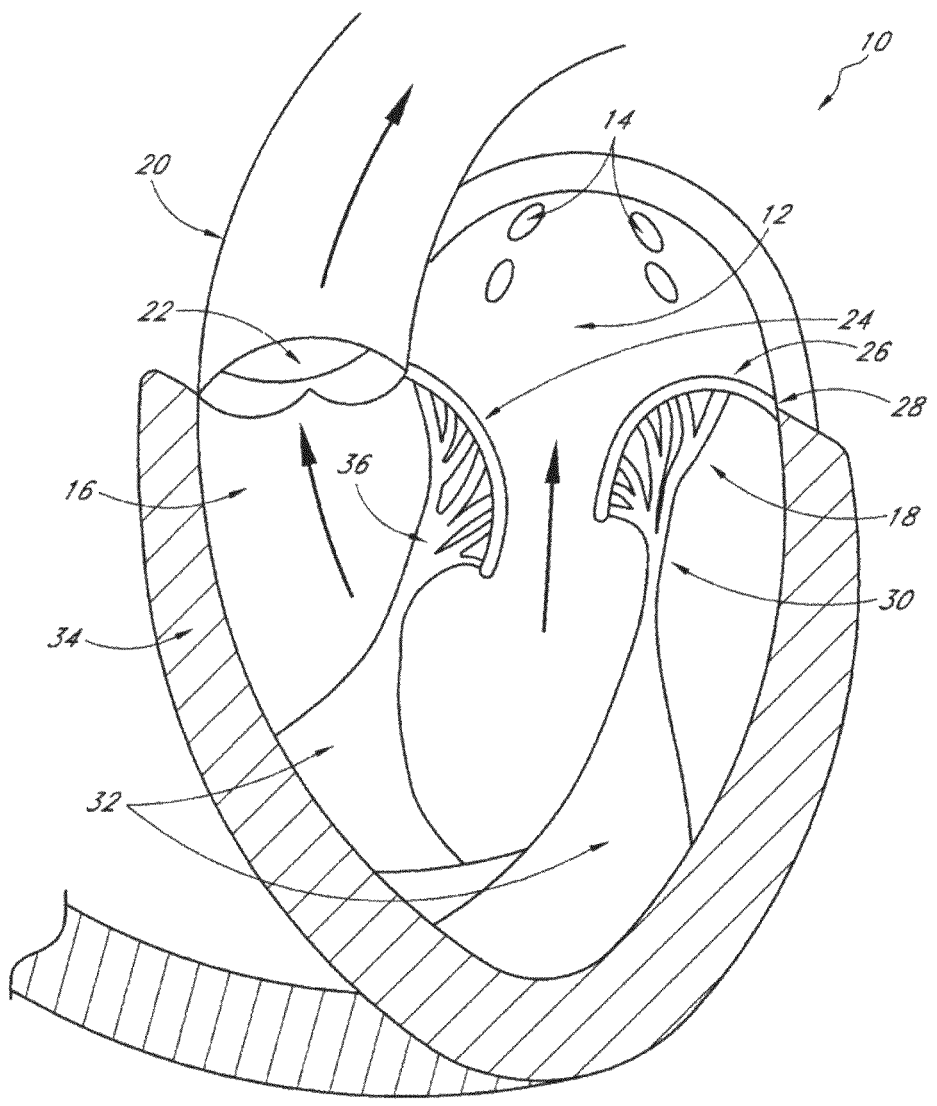
FIG. 11C illustrates a dilated mitral annulus with little or no coaption of both leaflets causing central mitral regurgitation in ischemic cardiomyopathy.

Mitral regurgitation can also be caused by an elongated valve leaflet 24 and 26. For example, an elongated anterior leaflet 24, as shown in FIG. 11, can prevent the valve leaflets 24 and 26 from properly coapting during mitral valve 18 closure. This can lead to excessive bulging of the anterior leaflet 24 into the left atrium 12 and misalignment of the free edges 36 and 38 during coaptation, which can lead to mitral regurgitation.

Figure 12A:
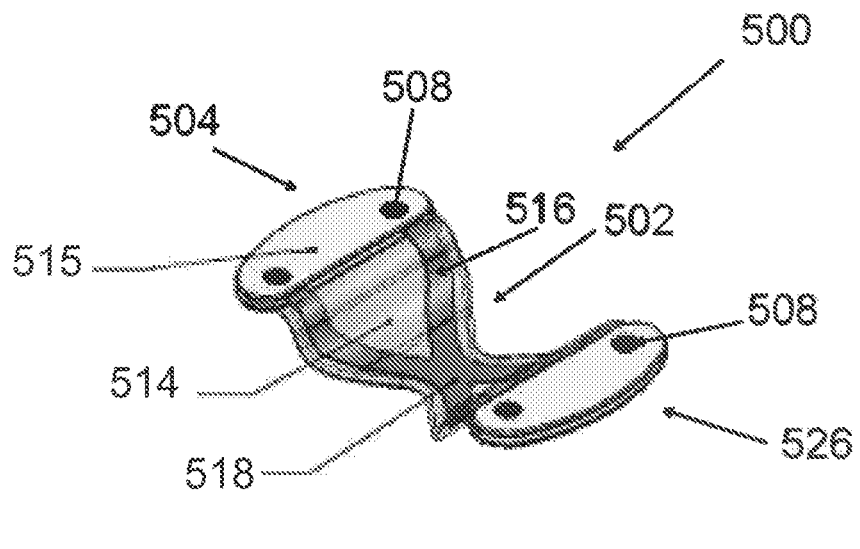
FIGS. 12A-12D illustrate an embodiment of a transvalvular bridge.

FIGS. 12A-12D illustrate another embodiment of a transvalvular bridge 500. FIG. 12A is a perspective view of the transvalvular bridge 500. The transvalvular bridge 500 can include a first attachment structure 504 at a first end of the bridge 500 and a second attachment structure 526 at a second end of the bridge 500. Both attachment structures 504, 526 can include a variety of structures for anchoring to the valve annulus. As illustrated, the attachment structures 504, 526 can have one or more layers 515. The material can be a mesh and having an underlying frame for supporting the mesh. The material can be a velour such as a 6111 Polyester Double Velour Fabric. The mesh material can advantageously promote tissue ingrowth in some embodiments. The attachment structures 504, 526 can also include one or a plurality of apertures 508 that can be configured to allow an anchor to attach the transvalvular bridge 500 to the valve annulus. Each attachment structures 504, 526 can include two apertures 508. Each attachment structures 504, 526 can include a plurality of apertures 508. The apertures 508 of the first attachment structure 504 can be aligned. The apertures 508 of the first attachment structure 504 can be a predetermined distance apart. The apertures 508 of the second attachment structure 526 can be aligned. The apertures 508 of the second attachment structure 526 can be a predetermined distance apart. In some methods, the distance can be determined based on the anatomy of the tricuspid valve of the patient.

Still referring to FIG. 12A, the transvalvular bridge 500 can also include an arcuate central portion 502 which can be generally convex in the direction of the ventricle. As illustrated, the central portion 502 can include a plurality of struts 516 that form a generally "X" shape. The plurality of struts 516 can be monolithically formed. The plurality of struts 516 can cross at intersection zone or junction 518. The struts 516 can be made of any appropriate material, such as a metal. The struts 516 can be made of a shape memory metal such as Nitinol. The struts 516 can be treated or coated. The struts 516 can be encapsulated with silicone or another appropriate material, in order to eliminate untoward effects such as thrombosis or corrosion. The spaces 514 in between the struts 516 can be treated or coated. The spaces 514 in between the struts 516 can be encapsulated with silicone or another appropriate material. The spaces 514 in between the struts 516 can be open. The transvalvular bridge 500 can have one or more open spaces between the struts 516.

Figure 12B:
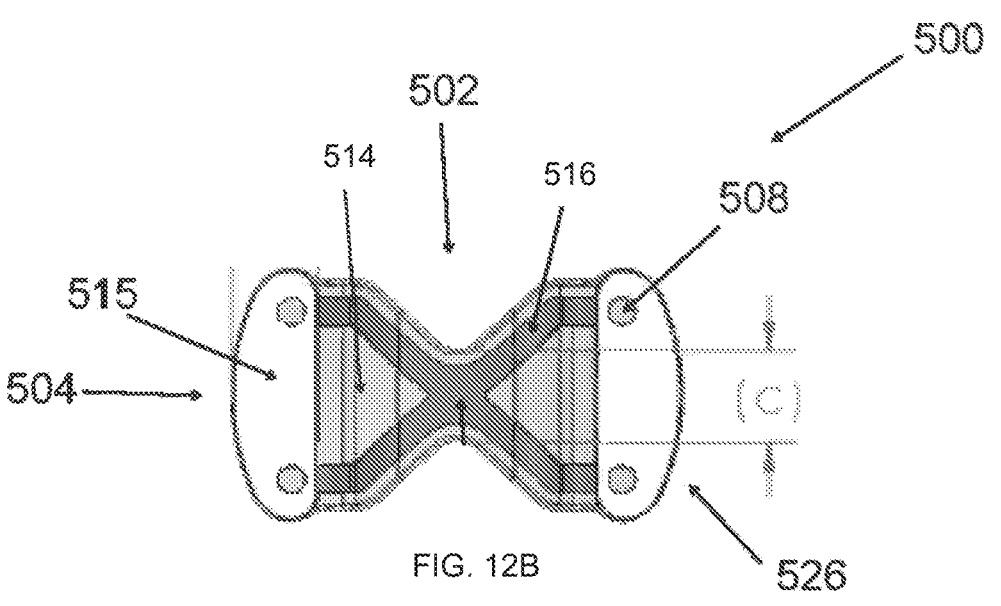

FIG. 12B is a top view of the transvalvular bridge 500 of FIG. 1A. As shown, the central portion 502 spans between the first attachment portion 504 and the second attachment portion 526, and can have a transverse width laterally that is substantially the same as that of the attachment portions 504, 526, but can become narrower toward the center toward intersection zone 518. In some embodiments, the width C in the central intersection zone 518 (measured perpendicular to blood flow) is between about 20% and about 80%, such as between about 25% and about 50%, or about 20%, 25%, 30%, 35%, 40%, 45%, 50%, 55%, 60%, 65%, 70%, or 75% of the width of the central portion 502 just proximate to the attachment portions 504, 526, and can gradually narrow toward the center as illustrated. In some embodiments, the width C in the central intersection zone 518 can be between about 4 mm and about 7 mm, such as between about 5 mm and about 6 mm, or about 5 mm, about 5.2 mm, about 5.4 mm, about 5.6 mm, about 5.8 mm, or about 6 mm. By narrowing the central portion 502, the resistance to blood flow can advantageously be reduced.

Figure 12C:
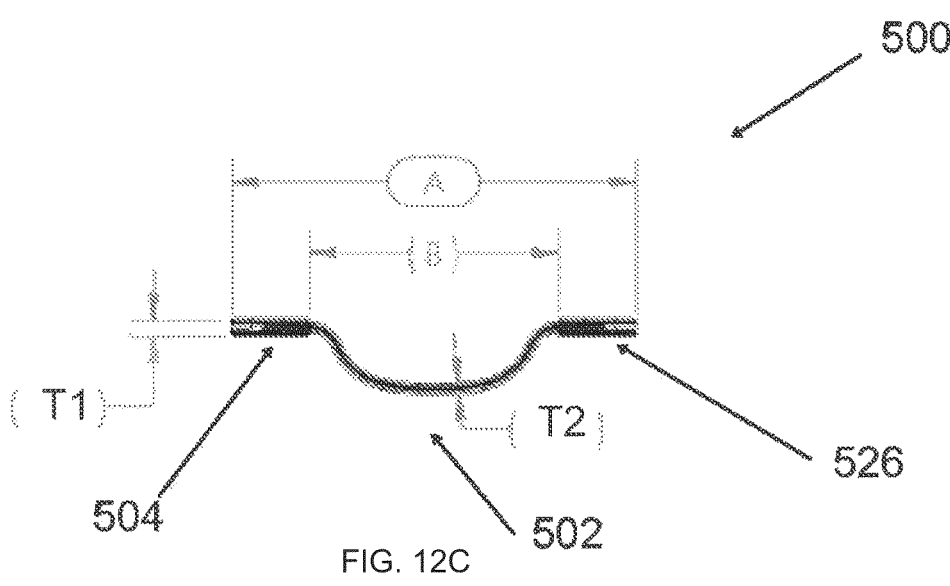

FIG. 12C is a side view of the transvalvular bridge 500 illustrated and described in connection with FIGS. 12A-12B. In some embodiments, the thickness T2 of the central portion 502 can be defined by the strut 516 and any encapsulation layer or coating surrounding the strut, if present. In some embodiments, the thickness T1 of the attachment portions 504, 526 can be defined by the ends of the struts 516, any encapsulation layer or coating surrounding the strut 516, if present, and/or one or more the material layers 515. The attachment portions 504, 526 can have a relatively greater thickness than the thickness of the central portion 502. In some embodiments, the attachment portions 504, 526 can have a thickness that is between about 25% and about 75% greater than that of the central portion 502, such as between about 40% and about 60% greater, or about 25%, 30%, 40%, 45%, 50%, 55%, 60%, 65%, 70%, or 75% greater than the thickness of the central portion 502. In some embodiments, the central portion 502 can have a thickness T1 of between about 0.5 mm and about 1.0 mm, such as about 0.6 mm, 0.7 mm, or 0.8 mm. In some embodiments, the attachment portions 504, 526 can have a thickness of between about 0.8 mm and about 1.3 mm, such as about 0.9 mm, 1.0 mm, 1.05 mm, 1.07 mm, 1.1 mm, or 1.2 mm.

Still referring to FIG. 12C, the transvalvular bridge 500 can have an entire axial length A in some embodiments of between about 15 mm and about 40 mm, such as between about 20 mm and about 32 mm depending on the patient's anatomy. The central portion 502 of the transvalvular bridge 500 can have an axial length in some embodiments of between about 8 mm and about 24 mm, such as between about 12 mm and about 20 mm in some embodiments.

Figure 12D:
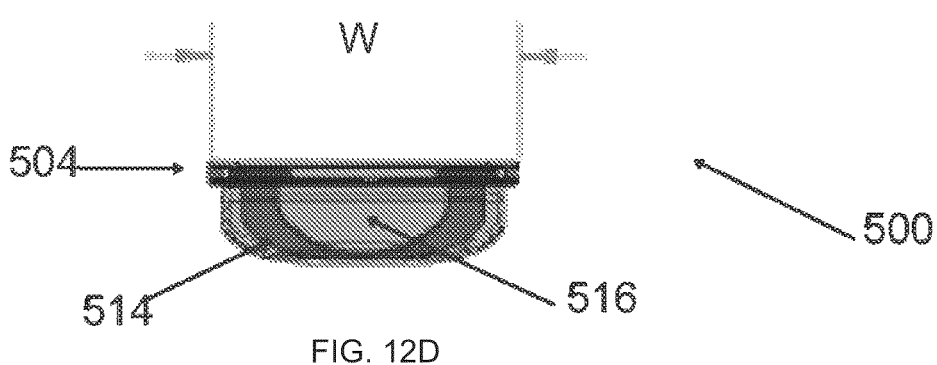

FIG. 12D illustrates an end view of the transvalvular bridge 500 illustrated and described in connection with FIGS. 12A-12C above, showing the struts 516, the encapsulation layer, and attachment portion 504. In some embodiments, the width W of the attachment structures 504, 526 can be between about 10 mm and about 20 mm, and about 15 mm in some embodiments.

Figure 12E:
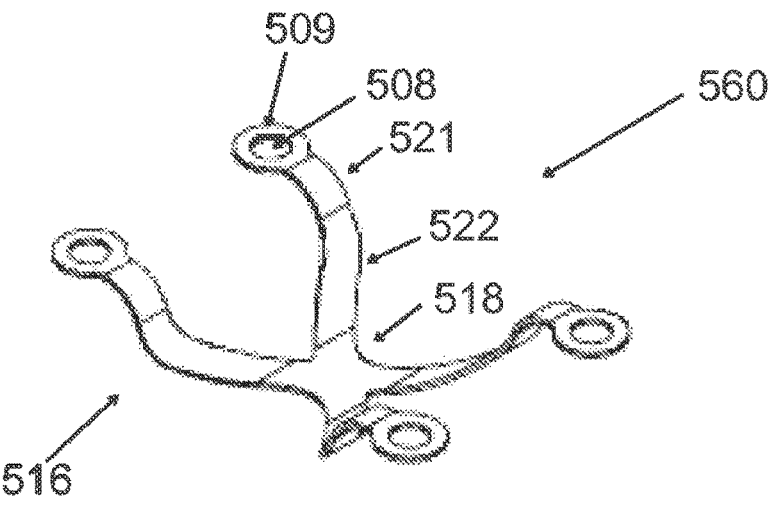
FIGS. 12E-12H illustrate views of the underlying skeleton layer of the transvalvular bridge.
Figure 12F:
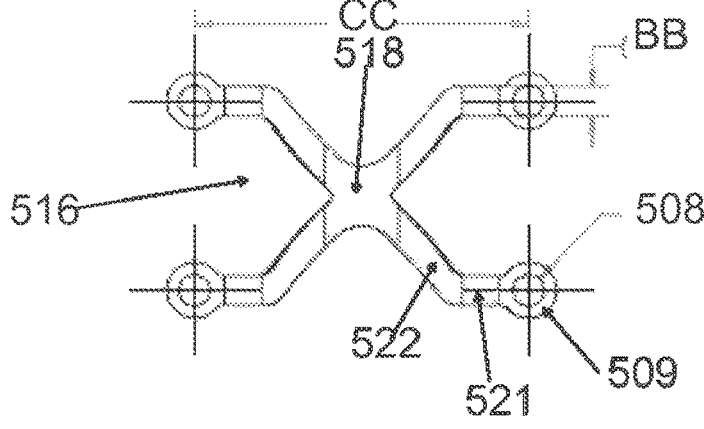
Figure 12G:
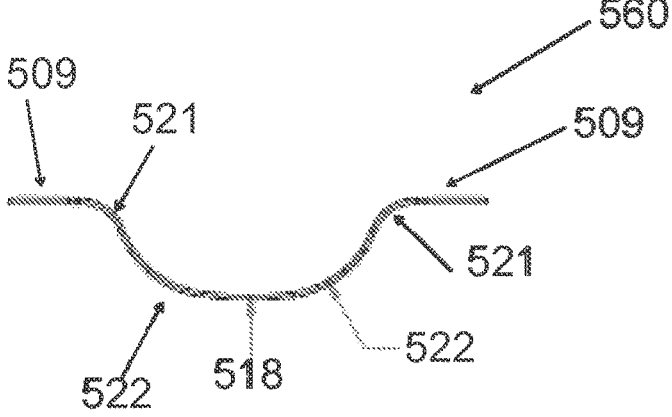
Figure 12H:
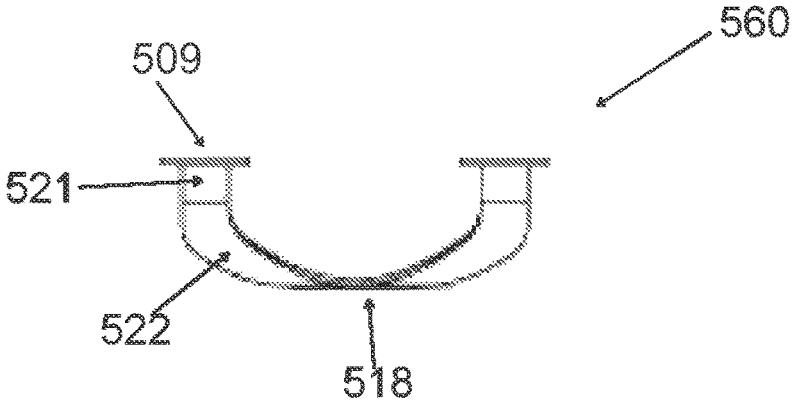

FIGS. 12E-12H illustrate views of the skeleton layer 560 of the transvalvular bridge 500. In some embodiments, the encapsulation layer is not present. The struts 516 are uncoated. In some embodiments, the material layers 515 are not present. In some embodiments, the transvalvular bridge 500 consists of a wire frame. In some embodiments, the transvalvular bridge 500 can include the plurality of apertures 508 for anchoring. In some embodiments, the transvalvular bridge 500 does not include additional material 515 connecting the plurality of apertures 508. The skeleton layer 560 can be formed of a shape set Nitinol that can be convex in the direction of the ventricle as previously described. FIG. 12E is a perspective view of the shape memory skeleton 560 of the transvalvular bridge 500, which can include struts 516. The struts 516 can be monolithically formed from a single piece of material. The struts 516 can be separately formed and cross at intersection zone 518. The lateral ends of the skeleton 560 can include eyelets 509 defining apertures 508 that can be utilized for anchoring. The skeleton layer 560 near the central portion 502 of the transvalvular band 500 can include lateral curved transition zone 521 of the struts 516, which has a first curvature, which is in turn connected to medial curved transition zone 522 of the strut 516 which has a second curvature different from the first curvature, which is in turn connected to the intersection zone 518 which includes the vertex of the arcuate central portion 502. The skeleton layer 560 can have one or more curvatures. The skeleton layer 560 can have one or more radius of curvature. FIG. 12F is a top view of the skeleton layer 560 of FIG. 12E. As illustrated, in some embodiments the lateral curved transition zones 521 of the struts 516, while configured to slope downwardly as shown, can run substantially parallel to the longitudinal axis of the transvalvular bridge 500, while the medial curved transition zone 522 can be oblique to the longitudinal axis of the transvalvular bridge 500. In some embodiments, the axial length CC of the skeleton layer 560 can be between about 13 mm and about 25 mm, and the width BB of each strut 516 can be between about 1 mm and about 2 mm, such as between about 1.3 mm and about 2.0 mm. FIG. 12G is a side view, and FIG. 12H is an end view of the skeleton of FIGS. 12E-12F.

Figure 13B:
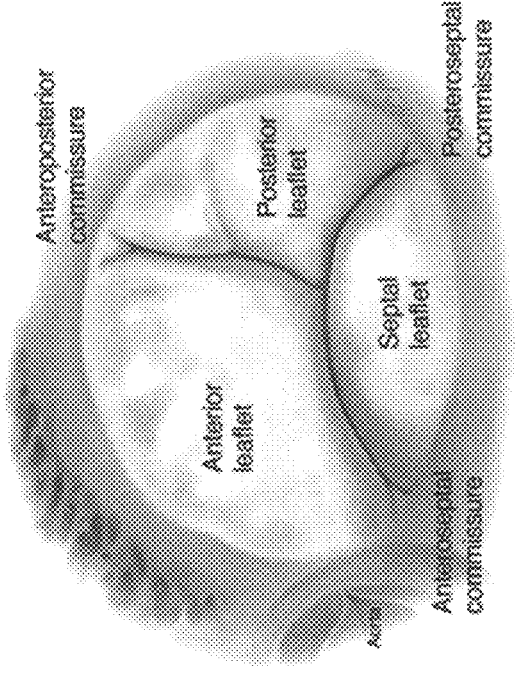
FIG. 13A-13B are diagrammatic representations of a tricuspid valve.
Figure 13A:
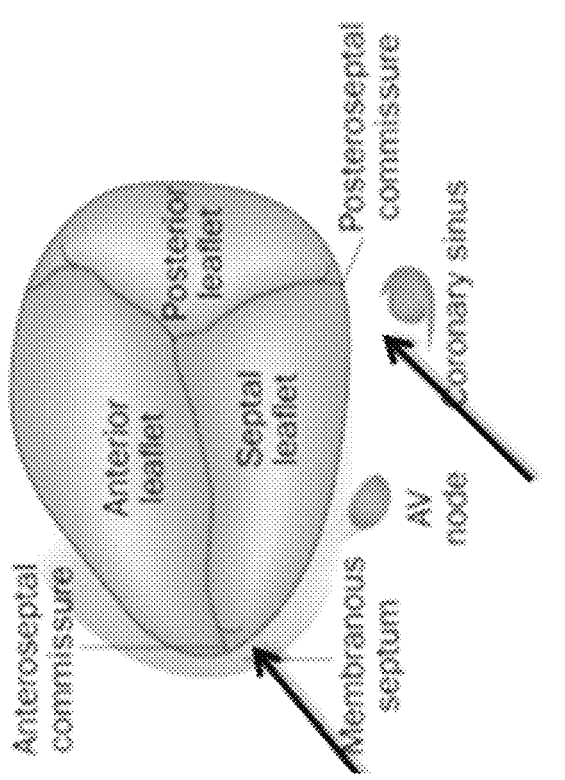

FIG. 13A-13B are diagrammatic representations of a tricuspid valve. The tricuspid valve is the right atrioventricular valve. The tricuspid valve separates the right atrium from the right ventricle. The tricuspid valve has three leaflets. The tricuspid valve includes an anterior leaflet, a posterior leaflet, and a septal leaflet. The anterior leaflet is the largest leaflet. The posterior leaflet is typically the smallest leaflet. The leaflets are connected via chordae tendineae to the papillary muscles of the right ventricle.

The tricuspid valve includes an anteroseptal commissure between the anterior leaflet and the septal leaflet. The tricuspid valve includes a posteroseptal commissure between the posterior leaflet and the septal leaflet. The tricuspid valve includes an anteroposterior commissure between the anterior leaflet and the posterior leaflet. The mitral valve and the tricuspid valve are disposed relative to the aorta. The mitral valve is located posteriorly and to the left. The tricuspid valves is located inferiorly and to the right. The mitral valve and the tricuspid valve are generally adjacent to the aortic root. The tricuspid valve includes an annulus. The tricuspid annulus can include one or more planes. The tricuspid valve can be a saddle-shaped valve.

The tricuspid valve closes during systole to prevent blood flow from the right atrium to the right ventricle. The tricuspid valve opens during diastole allowing blood to flow from the right atrium to the right ventricle The healthy tricuspid valve prevents regurgitation of blood when the valve is closed. Tricuspid regurgitation is the backflow of blood from the right ventricle to the right atrium during systole. The tricuspid valve fails to close properly or tightly allowing blood to flow back into the right atrium. The failure can interfere with the proper direction of blood flow and force the ventricles to work harder to eject blood. The function of the tricuspid valve depends on interactions between many structures of the heart including the tricuspid annulus, the tricuspid leaflets, the papillary muscles, the chordae tendinae, and the right atrial and right ventricular muscular tissue.

Figure 14:
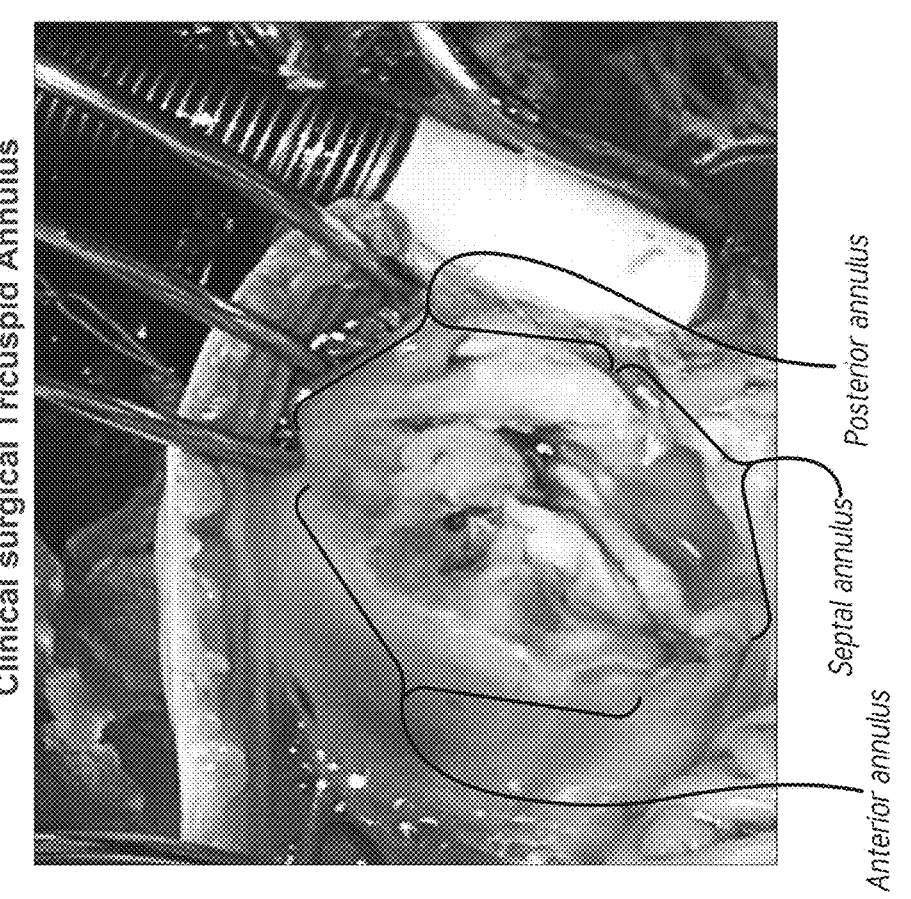
FIG. 14 is a view of a tricuspid valve.

FIG. 14 is a view of a tricuspid valve. FIG. 14 illustrates the clinical surgical tricuspid annulus. The annulus can be divided into three segments. The tricuspid annulus can include the anterior annulus, the posterior annulus, and the septal annulus. The three segments of the annulus are shown.

Figure 15:
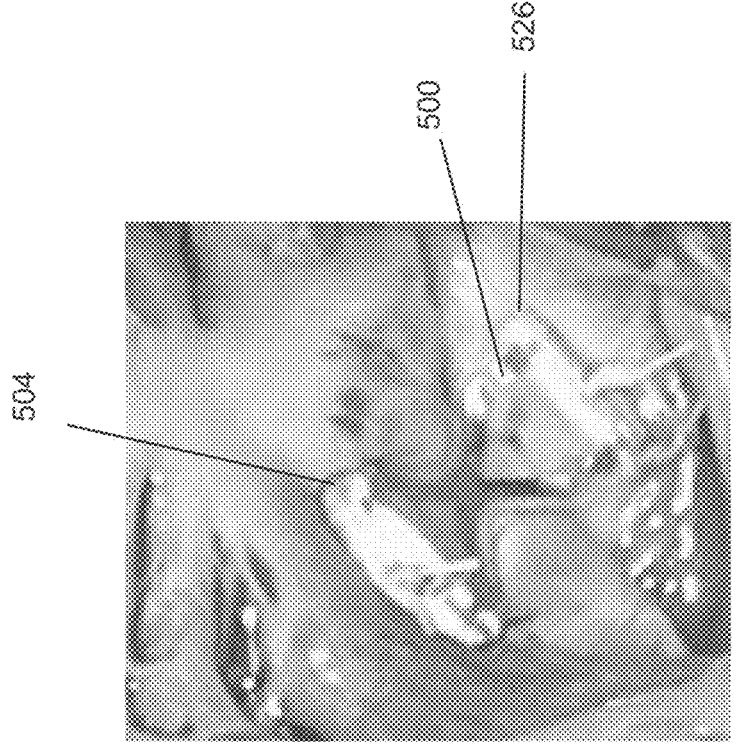
FIG. 15 is a view of a transvalvular bridge positioned on a tricuspid valve.

FIG. 15 illustrates the transvalvular bridge 500 positioned relative to the tricuspid valve. The location of the transvalvular bridge 500 on the tricuspid valve can be relative to anchoring positions. The transvalvular bridge 500 can be located on the annulus. The transvalvular bridge 500 can be located on the anterior annulus. The transvalvular bridge 500 can be located on the posterior annulus. The transvalvular bridge 500 can be straddling the commissure between the septal and posterior annulus. The method can include anchoring the transvalvular bridge between an anterior annulus and the posterior annulus. The transvalvular bridge 500 can be located between the midpoints of anterior annulus and the annulus straddling the commissure between septal and posterior annulus. The transvalvular bridge 500 can include the first attachment structure 504 at a first end of the bridge 500 and the second attachment structure 526 at a second end of the bridge 500. The first attachment structure 504 can be located on the anterior annulus. The second attachment structure 526 can be located on the septal annulus and the posterior annulus. The transvalvular bridge 500 can include the plurality of apertures 508. The plurality of apertures 508 can align with anchoring locations on the anterior annulus, posterior annulus, and the septal annulus. The transvalvular bridge 500 alignment contacts all three segments of the tricuspid annulus.

The transvalvular bridge 500 can include a narrowed central portion to reduce resistance to blood. The narrowed central portion is separated from the first attachment structure 504 and second attachment structure 526. The length of the central portion can be less than about 50% of the overall length of the device. The length of the central portion can be less than about 30% of the overall length of the device. The length of the central portion can minimize the obstruction to the flow path. The transvalvular bridge 500 can include a wider transverse surface for supporting the leaflets when the valve is closed. The narrowed central portion can extend out of a reference plane. The narrowed central portion extends transversely across a coaptive edge formed by two or three valve leaflets when the transvalvular bridge is positioned.

The transvalvular bridge 500 can oriented in the annulus so that the transvalvular bridge 500 is positioned approximately transversely to the coaptive edge formed by the closure of the leaflets. The transvalvular bridge 500 is positioned approximately transversely to the coaptive edge extending from the anteroposterior commissure to the anteroseptal commissure. The transvalvular bridge 500 is positioned approximately transversely to the coaptive edge extending between the anterior leaflet and both the posterior leaflet and the septal leaflet. The transvalvular bridge 500 is positioned toward the posteroseptal commissure. The transvalvular bridge 500 is positioned approximately parallel to the coaptive edge between the posterior leaflet and the septal leaflet.

The transvalvular bridge 500 can function to reduce the anterior posterior diameter of the tricuspid annulus in functional regurgitation. The transvalvular bridge 500 can be positioned over a portion of the anterior leaflet, a portion of the posterior leaflet, and a portion of the septal leaflet. The transvalvular bridge 500 can directly support a portion of the anterior leaflet, a portion of the posterior leaflet, and a portion of the septal leaflet. The transvalvular bridge 500 can be anchored to the annulus and span the coaptive edges formed by the leaflets. The transvalvular bridge 500 can directly reduce the anterior posterior diameter to reduce annular enlargement and dysfunction. The transvalvular bridge 500 can reshape the anterior posterior diameter. The transvalvular bridge 500 can correct a geometric distortion of the tricuspid valve. The transvalvular bridge 500 can keep the anterior leaflet, the posterior leaflet, and the septal leaflet in a more normal spatial relationship relative to each other. The transvalvular bridge 500 can keep the anterior leaflet, the posterior leaflet, and the septal leaflet in a more normal spatial relationship relative to the tricuspid annulus. The transvalvular bridge 500 can position the anterior leaflet, the posterior leaflet, and the septal leaflet preventing or reducing regurgitation.

The transvalvular bridge 500 can have an effect on the tricuspid valve during systole. The anterior leaflet, the posterior leaflet, and the septal leaflet are supported by the transvalvular bridge 500 during closure of the tricuspid valve. The transvalvular bridge 500 can function to maintain the anterior posterior diameter of the tricuspid annulus. The transvalvular bridge 500 can function to maintain the relationship between leaflets. The transvalvular bridge 500 can function to enable the anterior leaflet, the posterior leaflet, and the septal leaflet to form coaptive edges. The transvalvular bridge 500 can function to improve the tricuspid valve seal. In some embodiments, the leaflets rest upon the transvalvular bridge 500 during closure. In some embodiments, the leaflets rest upon each other during closure. The pressure exerted by the blood upon the distal portion of the leaflets can form the coaptive edge. The leaflets close to prevent blood from flowing from the right atrium to the right ventricle during systole.

The performance of the tricuspid valve during diastole is not substantially affected by the transvalvular bridge 500. The transvalvular bridge 500 allows the valve to open. The leaflets open to allow blood to flow from the right atrium to the right ventricle. The transvalvular bridge 500 can include a narrowed or tapered central portion. The transvalvular bridge 500 can include one or more central openings. The transvalvular bridge 500 can include one or more pathways for blood to flow therethrough during diastole.

In some methods, a single transvalvular bridge 500 is implanted. The transvalvular bridge 500 can provide support to the tricuspid valve leaflets. The transvalvular bridge 500 can support all three leaflets. The transvalvular bridge 500 can be attached to anchors located at the annulus. The transvalvular bridge 500 can be characterized by a longitudinal axis. The transvalvular bridge 500 is oriented in the tricuspid valve such that the longitudinal axis of the transvalvular bridge 500 is oriented substantially transversely to the coaptive edge formed between the anterior leaflet and both the posterior and septal leaflets. The transvalvular bridge 500 is oriented in the tricuspid valve such that the longitudinal axis of the transvalvular bridge 500 is oriented toward the posteroseptal commissure. The transvalvular bridge 500 can be convex or inclined in the direction of the ventricle. The transvalvular bridge 500 can be convex or inclined to advance the coaptation of the valve leaflets in the direction of the ventricle.

In some embodiments, the transvalvular bridge 500 can be oriented in a particular fashion to enhance performance of the transvalvular bridge 500. The configuration of the transvalvular bridge 500 allows a larger surface area to make contact with and support the valve leaflets. The configuration of the transvalvular bridge 500 allows a larger surface area near the apertures 508. The configuration of the transvalvular bridge 500 allows a larger surface area for anchoring on the annulus. The configuration of the transvalvular bridge 500 allows for reinforcement of apertures for anchoring. The configuration of the transvalvular bridge 500 presents a streamlined shape over the valve opening. The configuration of the transvalvular bridge 500 provides less resistance to blood flowing from the right atrium to the right ventricle when the tricuspid valve is open. In some methods, decreasing the resistance to blood flow is desirable because it can reduce turbulence and reduce the impedance of the transvalvular bridge 500 on the filling of the right ventricle.

In some embodiments, the transvalvular bridge 500 is formed from a single length of material. The skeleton frame of the transvalvular bridge 500 can be unitarily formed. The transvalvular bridge 500 can be monolithic. In some embodiments, the transvalvular bridge 500 is formed or several lengths of material. The transvalvular bridge 500 can include two or more struts. The transvalvular bridge 500 can include crossing or overlapping struts. The transvalvular bridge 500 can include a shape memory material. In some embodiments, the bend angles and orientation of the struts can be readily altered, to accommodate the desired axes of compression which may be desirable for a particular deployment procedure.

The transvalvular bridge 500 can include an elongate body having a first end, a first anchoring portion located proximate the first end, a second end, a second anchoring portion located proximate the second end, and a central portion connected to the first end and the second end. The first anchoring portion and the second anchoring portion are configured to be attached to the annulus. In some embodiments, the first anchoring portion and the first anchoring portion reside on an anterior-septal-posterior diameter. The A-S-P diameter spans the valve opening. The A-S-P diameter extends from the anterior annulus along the coaptive edge between the septal annulus and posterior annulus. This anterior-septal-posterior alignment of the transvalvular bridge 500 on tricuspid is illustrated in FIG. 3B. This anterior-septal-posterior alignment of the transvalvular bridge 500 is transverse to coaptive edge formed by the anterior leaflet. This anterior-septal-posterior alignment of the transvalvular bridge 500 is along to coaptive edge formed by the posterior and septal leaflets.

In some embodiments, transvalvular bridge 500 can include a plurality of crossing struts. The struts can comprise Nitinol. The struts can form an X shape. The struts can comprise a shape memory material. In some embodiments, transvalvular bridge 500 can include a plurality of crossing struts encapsulated by a material. The transvalvular bridge 500 does not comprise an annuloplasty ring. The transvalvular bridge 500 can be configured for trileaflet valves.

In some embodiments, the central portion comprises a convex arcuate shape. In some embodiments the central portion is configured to be displaced transversely from an intraannular plane when the transvalvular bridge 500 is attached to an annulus. In some embodiments, the central portion is configured to be convex in a direction of outflow to support valve leaflets at a point displaced toward a ventricle from the intraannular plane. In some embodiments, the central portion is curved downward toward the right ventricle. In some embodiments, the central portion lowers the leaflets toward the right ventricle. In some embodiments, the central portion lowers the point of coaptation.

Tricuspid regurgitation is prevalent in patients with heart disease. However, treatment has been lagging behind treatment for the mitral valve. Surgical treatment is increasing. The transvalvular bridge 500, as well as the alignment of the transvalvular bridge 500, can be advantageous.

Figure 16B:
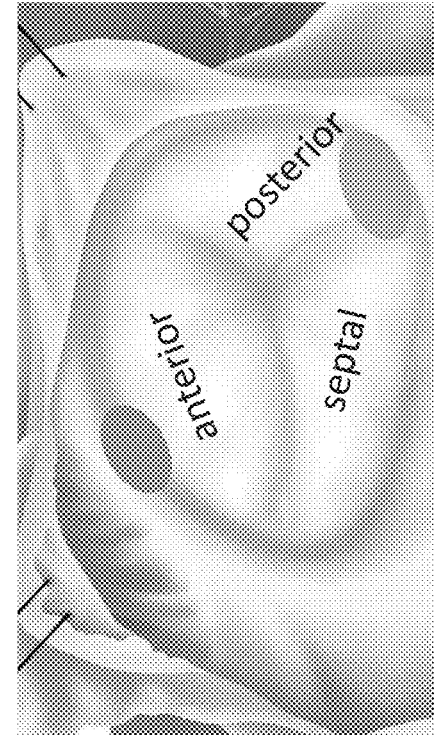
FIG. 16A-16B are view of alignments of a transvalvular bridge on tricuspid annulus.
Figure 16A:
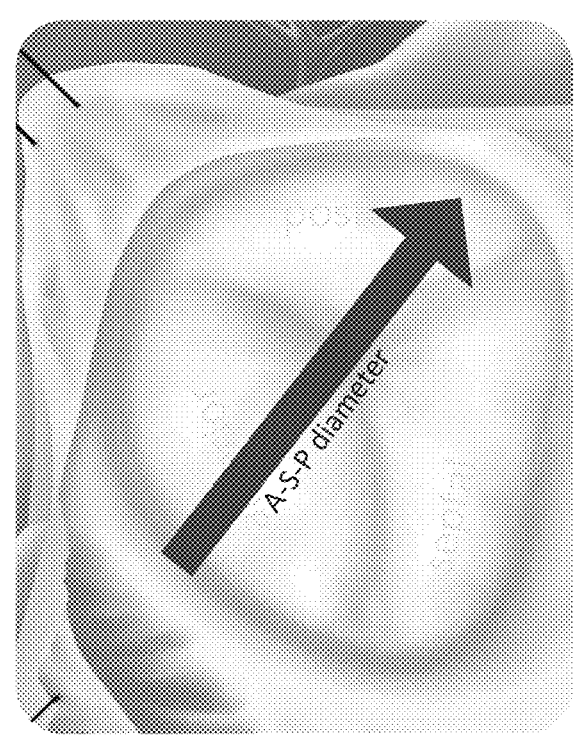

FIG. 16A-16B are view of alignments of the transvalvular bridge 500 relative to the tricuspid annulus. The transvalvular bridge 500 alignment has no known predicate either in surgical or transcatheter tricuspid repair. The transvalvular bridge 500 can be positioned along the A-S-P diameter. The transvalvular bridge 500 can be anchored on the anterior annulus on the A-S-P diameter. The transvalvular bridge 500 can be anchored on the posterior annulus on the A-S-P diameter. The transvalvular bridge 500 can be anchored on the septal annulus on the A-S-P diameter. The A-S-P diameter extends between the anterior annulus and both the septal annulus and posterior annulus. The transvalvular bridge 500 can extend across one or more leaflets on the A-S-P diameter. The A-S-P diameter can extend through a midpoint of the anterior leaflet. The A-S-P diameter can extend over the anterior leaflet. The A-S-P diameter can extend along the coaptive edge formed from the posterior leaflet and the septal leaflet. The A-S-P diameter can extend along the posterior leaflet. The A-S-P diameter can extend along the septal leaflet. The A-S-P diameter can extend over all three leaflets. The A-S-P diameter can position the transvalvular bridge 500 relative to all three leaflets. The longitudinal axis of the transvalvular bridge 500 can align along the A-S-P diameter. The A-S-P diameter can allow for anchoring of the transvalvular bridge 500 on the annulus. FIG. 16A illustrates this alignment with a blue arrow.

FIG. 16B illustrates the location of anchors for the transvalvular bridge 500 implantation. The blue area represents the anterior anchors. The green area represents the septal posterior anchors. The blue area can correspond to the first attachment structure 504 at the first end of the transvalvular bridge 500. The green area can correspond to the second attachment structure 526 at the second end of the transvalvular bridge 500. The attachment structures 504, 526 can include one or more apertures 508 which can anchor the transvalvular bridge 500 to the annuluses. The first attachment structure 504 can include two apertures 508. The first attachment structure 504 can couple to two anchors coupled to the anterior annulus. The second attachment structure 526 can include two apertures 508. The second attachment structure 526 can couple to two anchors. In some embodiments, the second attachment structure 526 can couple to one anchor coupled to the posterior annulus and one anchor coupled to the septal annulus. In some embodiments, the second attachment structure 526 can couple one or more anchors coupled to the posterior annulus. In some embodiments, the second attachment structure 526 can couple one or more anchors coupled to the septal annulus. In some embodiments, the second attachment structure 526 can couple to the posterior annulus beyond the septal-posterior commissure. In some embodiments, the second attachment structure 526 can couple to the septal annulus beyond the septal-posterior commissure.

Figure 17:
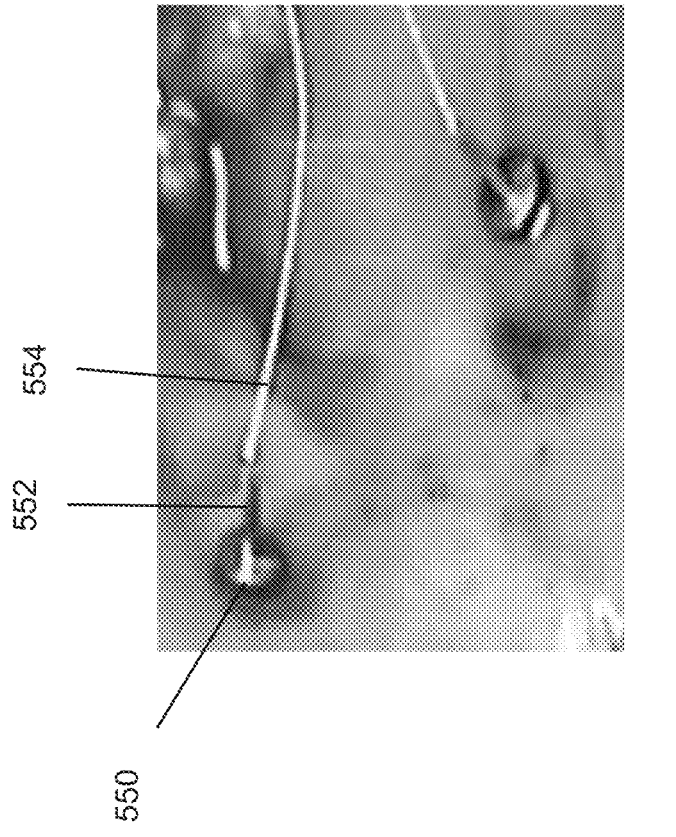
FIG. 17 is a view of anchors.

FIG. 17 illustrates an embodiment of an anchor 550 for anchoring the transvalvular bridge 500. The anchors can engage the annulus. The valve annulus can be a fibrous ring or structure which provides support. In some embodiments, the anchors engage the more robust tissue of the annulus than the leaflets. The anchors can be subannular anchors. The anchors can be expanding anchors. The anchors can be helical anchors. The anchors can include a central post 552 configured to engage the transvalvular bridge 500. The central post 552 can extend through the aperture of the transvalvular bridge 500. The anchors can include sutures 554 that act as guide rails for delivery of the transvalvular bridge 500. In some methods, the anchors 550 are inserted into tissue before the transvalvular bridge 500 is positioned. The suture 554 can be threaded through the aperture 508 of the first attachment structure 504. The transvalvular bridge 500 can include two or more aperture 508 of the first attachment structure 504. The transvalvular bridge 500 can include two or more aperture 508 of the second anchoring portion 526.

The anchor 550 can be positioned on the anterior annulus. In some methods, two or more anchors can be positioned on the anterior annulus. The two or more anchors can be aligned. The two or more anchors can be parallel. The two or more anchors can be spaced apart a predetermined distance. The two or more anchors can be positioned on either side of a midpoint of the anterior annulus. The two or more anchors can be positioned through the anterior annulus to a subannular space.

The anchor 550 can be positioned on the posterior annulus. In some methods, one or more anchors can be positioned on the posterior annulus. The anchor 550 can be positioned on the septal annulus. In some methods, one or more anchors can be positioned on the septal annulus. The two or more anchors can be positioned beyond the posteroseptal commissure. The two or more anchors can be positioned beyond and on either side of the posteroseptal commissure.

The anchor 550 on the posterior annulus and the anchor 550 on the septal annulus can be aligned. The anchor 550 on the posterior annulus and the anchor 550 on the septal annulus can be parallel. The anchor 550 on the posterior annulus and the anchor 550 on the septal annulus can be spaced apart a predetermined distance. The anchor 550 can be positioned on the annulus beyond the beyond the septal-posterior commissure. The anchor 550 on the posterior annulus and the anchor 550 on the septal annulus can be positioned beyond and on either side of the coaptive edge of the septal leaflet and the posterior leaflet. The anchor 550 on the posterior annulus and the anchor 550 on the septal annulus can be positioned through the posterior annulus and the septal annulus.

Figure 18:
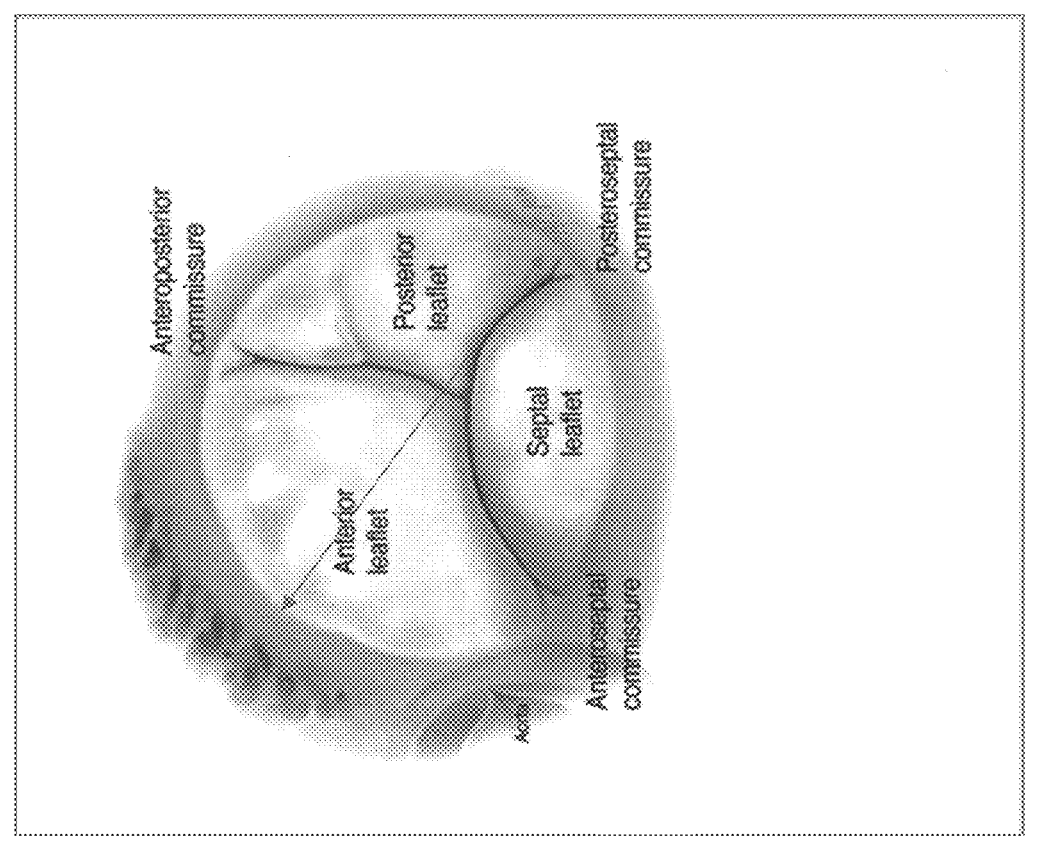
FIG. 18 is a view of an alignment on a tricuspid annulus.

FIG. 18 is a view of an alignment of the transvalvular bridge 500 on tricuspid annulus. The transvalvular bridge 500 alignment has no known predicate. The transvalvular bridge 500 can be anchored to the tricuspid annulus on the A-S-P diameter. The A-S-P diameter provides advantages to anchoring the transvalvular bridge 500. The transvalvular bridge 500 can be anchored to the anterior annulus. The transvalvular bridge 500 can be anchored to the posterior annulus, the septal annulus, or both the posterior annulus and the septal annulus. In some embodiments, the transvalvular bridge 500 can be anchored to all three annuluses. The transvalvular bridge 500 can span across the valve along a midpoint of the valve. In some embodiments, the transvalvular bridge 500 can be anchored to the anterior and septal annulus of the tricuspid valve. In some embodiments, the transvalvular bridge 500 can be anchored to the anterior and posterior annulus of the tricuspid valve. In some embodiments, the transvalvular bridge 500 can be anchored to the anterior, posterior, and septal posterior annulus of the tricuspid valve. The transvalvular bridge 500 can span across the tricuspid valve. In some embodiments, the transvalvular bridge 500 can couple all three annuluses. The annulus can provide more robust anchoring than the leaflet. The transvalvular bridge 500 couples spans across all three leaflets. In some embodiments, the transvalvular bridge 500 can be anchored to all three annuluses. In some embodiments, the transvalvular bridge 500 can be anchored to at least two annuluses of the tricuspid valve.

The transvalvular bridge 500 alignment is shown in red. In some embodiments, the transvalvular bridge 500 alignment can extend from a midpoint of the anterior leaflet. In some embodiments, the transvalvular bridge 500 alignment is centered on the anterior leaflet. In some embodiments, the transvalvular bridge 500 alignment passes toward the posterior septal commissure. In some embodiments, the transvalvular bridge 500 alignment passes between the posterior annulus and the septal annulus. In some embodiments, the transvalvular bridge 500 alignment positions the bridge on the posterior leaflet and the septal leaflet. In some embodiments, the transvalvular bridge 500 alignment is anchored to all three annuluses. In some embodiments, the transvalvular bridge 500 alignment is anchored to the anterior annulus, the posterior annulus, and the septal annulus with a single device. In some embodiments, the transvalvular bridge 500 alignment spans the coaptive edge formed by the anterior leaflet and both the septal leaflet and the posterior leaflet.

Figure 19:
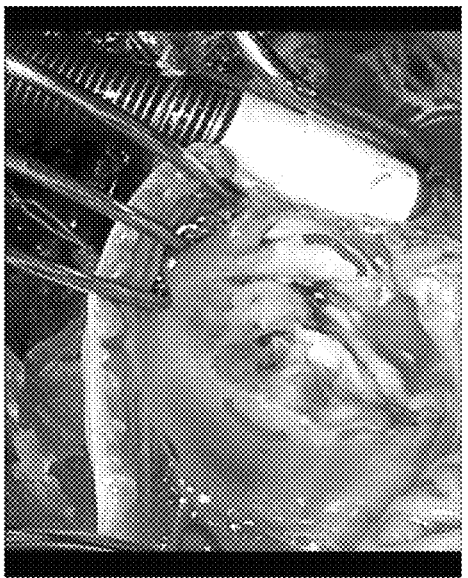
FIG. 19 illustrates the position of the anchors for the transvalvular bridge.

FIG. 19 illustrates the position of the anchors for the transvalvular bridge 500 alignment. The anchors can be on both sides of the midpoint of the anterior annulus. The anchors can straddle the commissure between the posterior and septal annulus. The anchors can be deployed at the red marks. In some embodiments, transvalvular bridge 500 alignment can be more toward the posterior annulus than the septal annulus. In some embodiments, transvalvular bridge 500 alignment can be more toward the septal annulus than the posterior annulus. In some embodiments, transvalvular bridge 500 alignment is located at a midpoint between the posterior annulus and the septal annulus. In some embodiments, transvalvular bridge 500 alignment straddles the posteroseptal commissure.

Any of a wide variety of specific tissue anchor constructions may be utilized in combination with the transvalvular bridge 500. In addition, a variety of features have been described as illustrative in connection with a variety of implementations of the transvalvular bridge 500. Any of the features described above, may be recombined with any other of the embodiments disclosed herein, without departing from the present invention, as should be apparent to those of skill in the art. In some embodiments, the transvalvular bridge 500 does not include a complete or partial annuloplasty ring, and/or does not affect or substantially affect the size and/or shape of the valve annulus when operably attached to the valve annulus.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological conduit within the body.

Figure 20B:
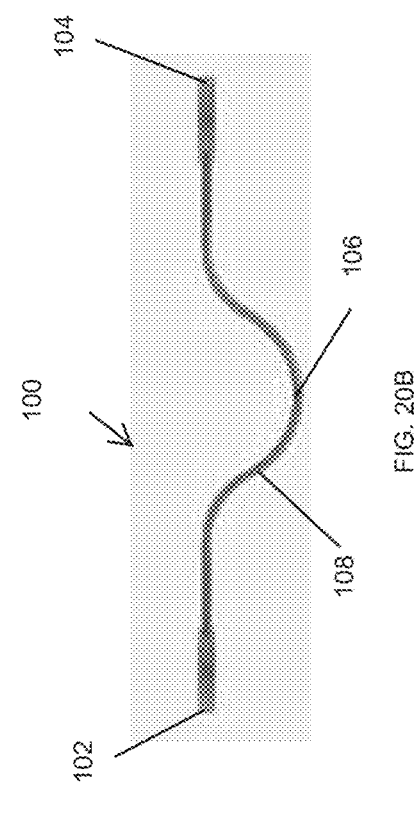
FIGS. 20A-20C are views of an embodiment of a transvalvular implant.
Figure 20A:
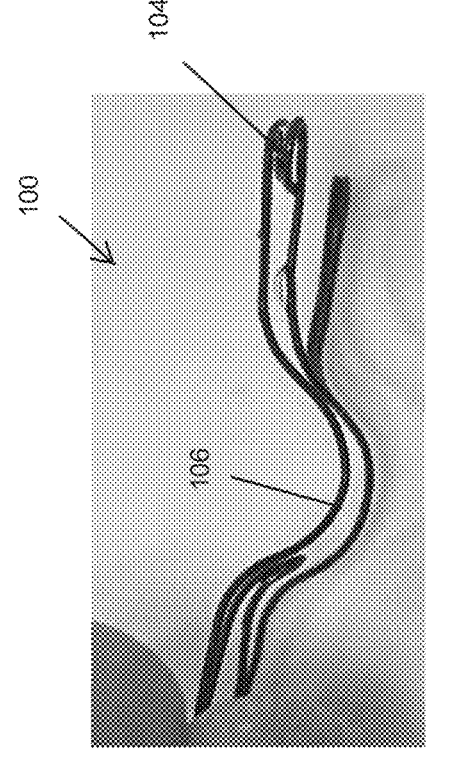
Figure 20C:
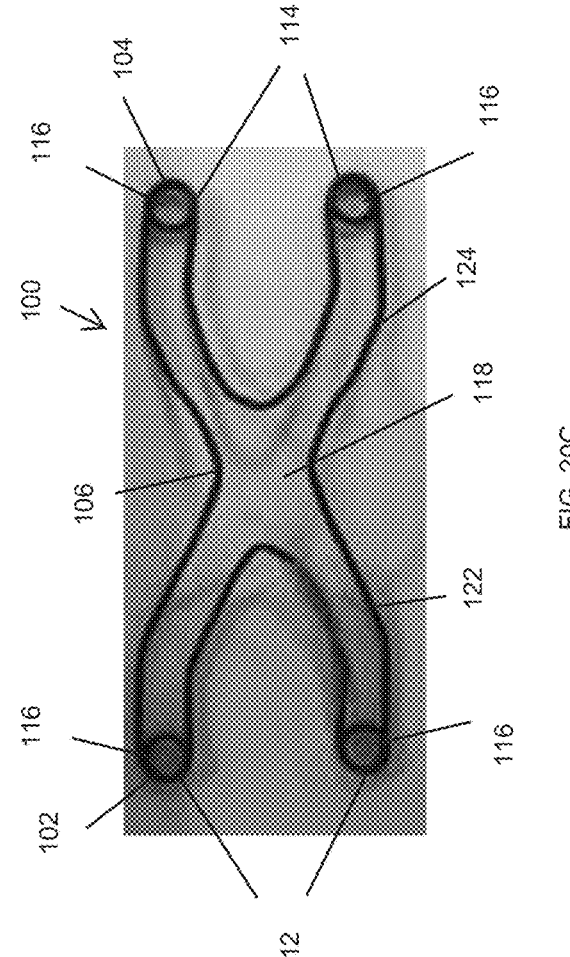

FIGS. 20A-20C illustrate an embodiment of a transvalvular implant 100. The transvalvular implant 100 can improve valve leaflet coaptation and prevent or reduce mitral regurgitation. The transvalvular implant 100 can also be referred to herein as a transvalvular bridge. FIG. 20A is a perspective view of the transvalvular implant 100. FIG. 20B is a side view of the transvalvular implant 100. FIG. 20C is a top view of the transvalvular implant 100.

In some embodiments, the transvalvular implant 100 comprises an elongate and curved structure. The transvalvular implant 100 can include a first end 102 and a second end 104. The second end 104 can be opposite the first end 102. The transvalvular implant 100 can have a length between the first end 102 and the second end 104 to span the valve as described herein. The transvalvular implant 100 can have a length between the first end 102 and the second end 104 that is capable of extending across the annulus. The transvalvular implant 100 can include a central portion 106. The central portion 106 can be located between the first end 102 and the second end 104.

The transvalvular implant 100 can be symmetrical. The transvalvular implant 100 can be symmetrical about the central portion 106. The transvalvular implant 100 can be symmetrical vertically. The transvalvular implant 100 can be symmetrical horizontally. Features described in relation to the first end 102 can apply to features of the second end 104. The first end 102 and the second end 104 can be identical. The first end 102 and the second end 104 can be substantially similar. In some embodiments, the first end 102 has different features than the second end 104. The first end 102 and the second end 104 can have different dimensions. The first end 102 and the second end 104 can have different attachment structures.

The transvalvular implant 100 can include a lower surface 106 disposed toward the annulus and an upper surface disposed away from the annulus. The transvalvular implant 100 can include a leaflet contact surface 108. The leaflet contact surface 108 can be convex along the longitudinal axis. The leaflet contact surface 108 can be configured to contact one or both leaflets, as described herein. In other embodiments, the leaflet contact surface 108 can have a different shape and profile. The leaflet contact surface 108 can be concave. The leaflet contact surface 108 straight. The leaflet contact surface 108 can be a combination of convex, concave and/or straight. The leaflet contact surface 108 can include two concave or straight portions joined together at an apex.

The transvalvular implant 100 can have a substantially maximum width at the first end 102. The transvalvular implant 100 can have a substantially maximum width at the second end 104. The transvalvular implant 100 can have a substantially maximum width at either end 102, 104 or both ends 102, 104. The transvalvular implant 100 can have a substantially minimum width at the central portion 106. The transvalvular implant 100 can taper along a portion of the length of the transvalvular implant 100. The transvalvular implant 100 can taper from the maximum width at the ends 102, 104 to the minimum width at the central portion 106. The transvalvular implant 100 can form a generally X shape. The sides of the transvalvular implant 100 can include in an indent toward the central portion 106. The sides of the transvalvular implant 100 can form a generally V shape. The sides of the transvalvular implant 100 can be pinched inward.

The transvalvular implant 100 can include a first anchoring portion 112. The transvalvular implant 100 can include a second anchoring portion 114. The first anchoring portion 112 can be disposed toward the first end 102. The second anchoring portion 114 can be disposed toward the second end 104. In some embodiments, the first end 102 can include the first anchoring portion 112 and the second end 104 can include the second anchoring portion 114.

The anchoring portions 112, 114 can have eyelets 116. The first anchoring portion 112 can include one or more eyelets 116. The first anchoring portion 112 can include two eyelets 116. The two eyelets 116 of the first anchoring portion 112 can be aligned. The two eyelets 116 of the first anchoring portion 112 can be offset. The two eyelets 116 of the first anchoring portion 112 can be spaced apart. The second anchoring portion 114 can include one or more eyelets 116. The second anchoring portion 114 can include two eyelets 116. The two eyelets 116 of the second anchoring portion 114 can be aligned. The two eyelets 116 of the second anchoring portion 114 can be offset. The two eyelets of the second anchoring portion 114 can be spaced apart.

The eyelets 116 can be for accepting anchors. The eyelets 116 can be for accepting sutures. The eyelets 116 can be for accepting tethers than extend from a portion of the anchors, as described herein. The eyelets 116 can be for accepting a central post of the anchors, as described herein. The eyelets 116 can be for accepting any device that allow the transvalvular implant 100 to be secured to the annulus. In some embodiments, the anchors are implanted before the transvalvular implant 100 is positioned relative to the annulus. The eyelets 116 can serve as guides as the transvalvular implant 100 is lowered toward the annulus. The transvalvular implant 100 can slide along a guide tether that extends through the eyelets 116. Alternatively, in other embodiments the anchoring portions 112 and 114 can have other means for securing the transvalvular implant 100 to the annulus.

The transvalvular implant 100 can have a central opening 118. The central opening 118 can be enclosed by the transvalvular implant 100. The central opening 118 can have a length and width. The transvalvular implants can become narrower toward the center. In some embodiments, the width of the central opening 118 is between about 5% and about 80% of the maximum width of the transvalvular implant 100, such as between about 25% and about 50%, or about 5%, 10%, 15%, 20%, 25%, 30%, 35%, 40%, 45%, 50%, 55%, 60%, 65%, 70%, 75% or 80% of the width of the first end 102 and the second end 104. In some embodiments, the length of the central opening 118 is between about 5% and about 80% of the maximum length of the transvalvular implant 100, such as between about 25% and about 50%, or about 5%, 10%, 15%, 20%, 25%, 30%, 35%, 40%, 45%, 50%, 55%, 60%, 65%, 70%, 75% or 80% of the length between the first end 102 and the second end 104.

The central opening 118 can be any shape. The central opening 118 can be X shaped. The central opening 118 can be completely open to allow blood to flow through. The central opening 118 can be completely open to allow tools or other implants to be passed through. The central opening 118 can be separated and distinct from the holes of the anchoring portions 112, 114. The central opening 118 can be uncoated. The c transvalvular implant 100 does not obstruct the flow of blood during use due to the central opening 118. The outline of the transvalvular implant 100 can form the central opening 118. The central opening 118 can extend through the central portion 106.

The central portion 106 can have a variety of shapes. For example, the shape of the central portion 106 can be substantially X shaped, rectangular, circular, oblong or triangular. The edges of the transvalvular implant 100 can be rounded or otherwise configured so that the transvalvular implant 100 presents an atraumatic surface to the valve leaflets. In some embodiments, the shape can be oriented in a particular fashion to enhance performance of the transvalvular implant 100. The transvalvular implant 100 can include generally two shaped ends which can be designed so that a relatively larger surface is toward the ends while a smaller surface is towards the middle. This configuration allows a larger surface area to make contact with the annulus. This configuration allows a smaller surface area to be in the direction of flow. This design can be a more streamlined shape that provides less resistance to blood flowing from the left atrium to the left ventricle. Decreasing the resistance to blood flow is desirable because it can reduce turbulence and reduce the impedance of the transvalvular implant 100 on the filling of the left ventricle. The transvalvular implant 100 can have any shape that increases the surface area for contact with the valve leaflets and/or reduces the resistance to blood flow.

The dimensions of the transvalvular implant 100 will vary, depending upon the specific configuration of the transvalvular implant 100 as well as the intended patient. In general, the transvalvular implant 100 will have an axial length from first end 102 to second end 104 within the range of from about 20 mm to about 32 mm. In one embodiment, intended for a typical male adult, the axial length of the transvalvular implant 100 is about 24 mm to 26 mm. The width of the transvalvular implant 100 in the central zone 106 may be varied depending upon the desired performance, as will be discussed herein. In general, the leaflet contact surface 108 is preferably large enough to minimize the risk of erosion resulting from repeated contact between the closed leaflets and the transvalvular implant 100. The width of the leaflet contact surface 108 is preferably minimized to minimize flow turbulence and flow obstruction. In general, widths of the leaflet contact surface 108 measured perpendicular to the flow of blood are presently contemplated to be less than about 5 mm, and often within the range of from about 5 mm to about 10 mm in the zone of coaptation.

The central portion 106 of the transvalvular implant 100 can be narrower in width, measured perpendicular to blood flow than the first and second anchoring portions 112 and 114. By narrowing the central portion 106, the resistance to blood flow can be reduced. In some embodiments, narrowing the central portion 106 reduces the surface area of the leaflet contact surface 108 that supports the valve leaflets. In some embodiments, the narrowed central portion 106 is separated from the first anchoring portion 112 and the second anchoring portion 114 by a first shoulder 122 and a second shoulder 124. The length of the central portion 106, between first shoulder 122 and second shoulder 124, can be less than about 50% of the overall length of the transvalvular implant 100. The length of the central portion 106 can be less than about 30% of the overall length of the transvalvular implant 100. The length of the central portion 106 can be less than about 10% of the overall length of the transvalvular implant 100. The length of the central portion 106 can be designed to minimize the obstruction in the center of the flow path. Alternatively, the length of the central portion 106 may be greater than 50%, and in some embodiments greater than 75% of the overall length of the transvalvular implant 100. The transvalvular implant 100 can present a wider transverse surface for supporting the leaflets when the valve is closed. In some embodiments, the central portion 106 can be generally convex in the direction of the ventricle. In some embodiments, the central portion 106 can be generally concave.

The transvalvular implant 100 can be formed from a single length of wire. The transvalvular implant 100 can be formed form several lengths of wire. The transvalvular implant 100 can be formed from a continuous wire. The transvalvular implant 100 can be formed from separate pieces of wire joined together. The transvalvular implant 100 can be formed from flexible wire. The bend angles and orientation of the wire can be readily altered to accommodate the desired axes of compression which may be desirable for a particular deployment procedure. The transvalvular implant 100 can be formed from any biocompatible material. The transvalvular implant 100 can be formed from stainless steel. The transvalvular implant 100 can be formed metal. The transvalvular implant 100 can be formed shape memory material. The transvalvular implant 100 can be formed from Nitinol. In some embodiments, a portion of the transvalvular implant 100 is coated. In some embodiments, the transvalvular implant 100 is uncoated. In some embodiments, at least the central opening 118 of the transvalvular implant 100 is uncoated. In some embodiments, the transvalvular implant 100 is not encased with a material. In some embodiments, at least the central opening 118 of the transvalvular implant 100 is not encased with a material.

The transvalvular implant 100 can include a shaped body. The transvalvular implant 100 comprises an elongate flexible wire formed into a X shaped pattern. The transvalvular implant 100 can includes four legs forming the X shape. The transvalvular implant 100 can include open spaces between the legs. The transvalvular implant 100 can include an outline of the X shaped pattern. The transvalvular implant 100 can be any shape for providing a support for the valve leaflets as discussed herein. The transvalvular implant 100 can include a wire which may be formed such that it bows or inclines in the direction of the ventricle to achieve early closure as discussed herein. The wire may extend to form the first end 102 and the second end 104. The wire may form a complete circle to enclose the eyelet 116 of the first anchoring portion 112. The wire may form a complete circle to enclose the eyelet 116 of the second anchoring portion 114. The wire may form two eyelets 116 of the first anchoring portion 112. The wire may form two eyelets 116 of the second anchoring portion 114. The wire may enclose the central opening 118.

The transvalvular implant 100 can form a continuous shape. The wire can extend from a starting point, form an coil or eyelet 116 of the first anchoring portion 112, extend along the side of the implant forming a pinched in shape near the central portion 106, form an coil or eyelet 116 of the second anchoring portion 114, form a bowed inward shape, form an coil or eyelet 116 of the second anchoring portion 114, extend along the side of the implant forming a pinched in shape near the central portion 106, form an coil or eyelet 116 of the first anchoring portion 112, form a bowed inward shape to the starting point. The transvalvular implant 100 can form an outlined shape. The transvalvular implant 100 can include two legs of the first anchoring portion 112 separated by a bowed inward shape. The transvalvular implant 100 can include two legs of the second anchoring portion 114 separated by a bowed inward shape. The transvalvular implant 100 can include a leg of the first anchoring portion 112 and a leg of the second anchoring portion 114 pinched inward near the central portion 106. The transvalvular implant 100 can include the other leg of the first anchoring portion 112 and the other leg of the second anchoring portion 114 pinched inward near the central portion 106. The transvalvular implant 100 can include a continuous outline. The transvalvular implant 100 can include a X shaped enclosed space. The transvalvular implant 100 can include one or more coils that form each eyelet 116. The transvalvular implant 100 can form an closed shape. The transvalvular implant 100 can connect the starting point and the ending point.

This design can provide a relatively large support footprint against the valve leaflets, while at the same time optimizing the area of open space to permit maximum blood flow therethrough. The transvalvular implant 100 can be made of any appropriate material, such as a metal. The transvalvular implant 100 can be made of a shape memory metal such as Nitinol. The transvalvular implant 100 may be formed from any of a variety of flexible materials, including various polymers described elsewhere herein as well as titanium, titanium alloy, Nitinol, stainless steel, elgiloy, MP35N, or other metals known in the art. The transvalvular implant 100 can be treated or coated. The transvalvular implant 100 can be encapsulated with silicone or another appropriate material, in order to eliminate untoward effects such as thrombosis or corrosion. The design may be treated or coated with silicone or other suitable material to eliminate untoward effects such as thrombosis or corrosion. Treatments may be sequential and include more than one listed but not limited to electropolishing, harperization, tumbling, pickling, plating, encapsulation or physical vapor deposition of appropriate materials. The transvalvular implant 100 can be free from a coating.

The transvalvular implant 100 can be made of single Nitinol wire. The transvalvular implant 100 can be free of any silicone central implant. The transvalvular implant 100 can include the central opening 118 in the center of the implant. The central opening 118 can be completely open, allowing blood to flow through the implant. The transvalvular implant 100 can allow potential for future transcatheter intervention with other transcatheter devices. The transvalvular implant 100 can be generally X shaped. The transvalvular implant 100 can include attachment points. The transvalvular implant 100 can include two eyelets 116 at each end 102, 104. The transvalvular implant 100 can include the arcuate central portion 106. The transvalvular implant 100 can be curved downward into left ventricle cavity or into left atrium. The transvalvular implant 100 can from an arch. The transvalvular implant 100 can from a mitral arch. The transvalvular implant 100 can from a tricuspid arch. The transvalvular implant 100 can form a mitral straddle. The transvalvular implant 100 can form a tricuspid straddle. The transvalvular implant 100 can straddle the valve.

Figures 21A, 21B, 21C:
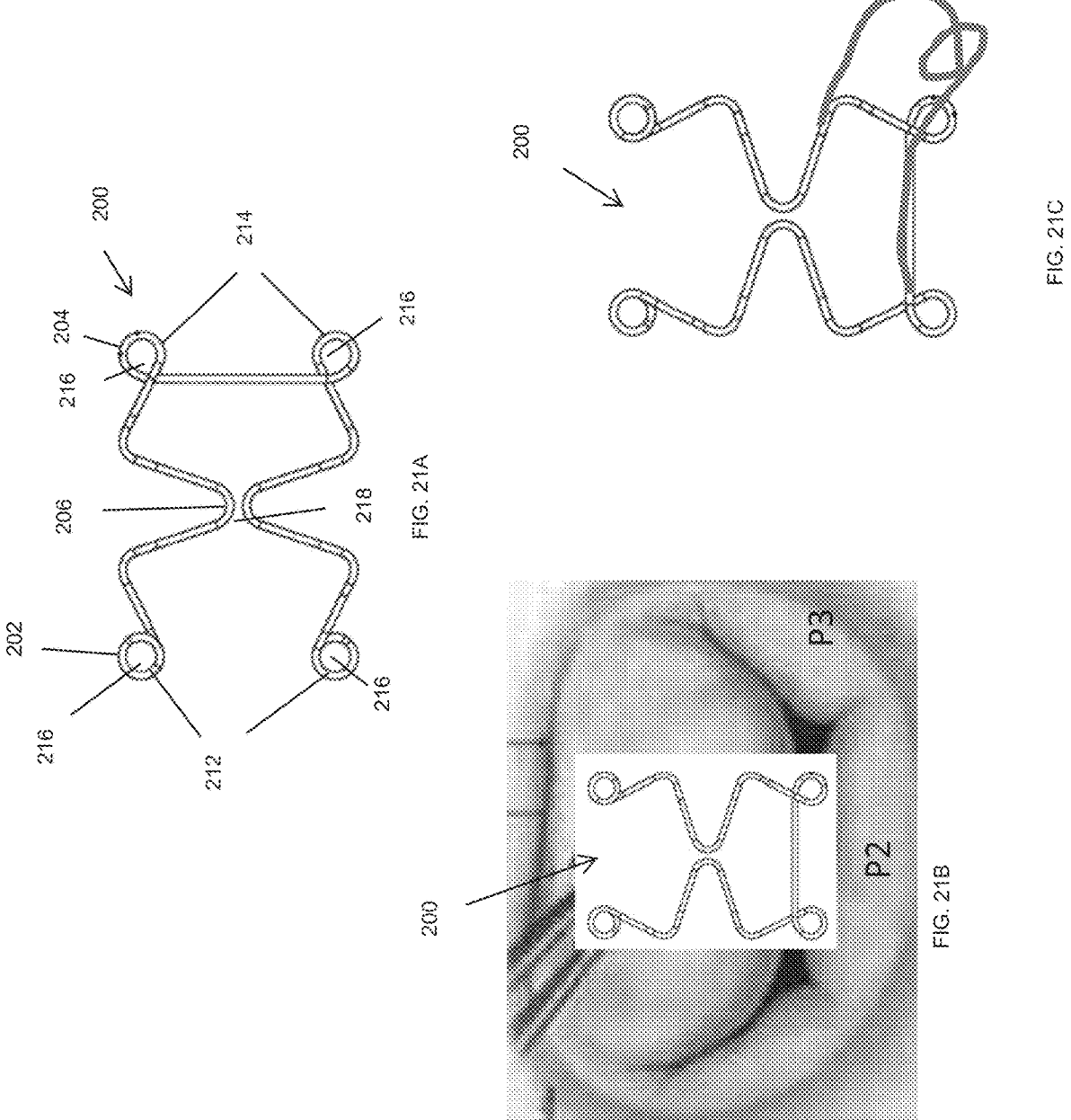
FIGS. 21A-21C are views of an embodiment of a transvalvular implant.

FIGS. 21A-21C illustrate an embodiment of a transvalvular implant 200. The transvalvular implant 200 can improve valve leaflet coaptation and prevent or reduce regurgitation. The transvalvular implant 200 can improve mitral valve leaflet 24 and 26 coaptation and prevent or reduce mitral regurgitation. The transvalvular implant 200 can improve tricuspid valve leaflet coaptation and prevent or reduce tricuspid regurgitation. The transvalvular implant 200 can include any features of the transvalvular implant 100 described herein. The transvalvular implant 200 can also be referred to herein as a transvalvular bridge or a mitral bridge. FIG. 21A is a top view of the transvalvular implant 200. FIG. 21B is a view of the transvalvular implant 200 positioned relative to the anatomy. FIG. 21C is a top view of the transvalvular implant 200 with an additional feature. The transvalvular implant 200 can include a first end 202 and a second end 204. The transvalvular implant 200 can include a central portion 206. The transvalvular implant 200 can include a leaflet contact surface 208. The transvalvular implant 200 can include a first anchoring portion 212 and a second anchoring portion 214. The transvalvular implant 200 can have eyelets 216 and a central opening 218.

The transvalvular implant 200 comprises an elongate flexible wire formed into a shaped pattern. The transvalvular implant 200 can be formed from a single length of wire. The transvalvular implant 200 can be formed form several lengths of wire. The transvalvular implant 200 can be formed from shape set wire. The bend angles and orientation of the wire can be altered before implantation to accommodate the desired axes of compression. The transvalvular implant 200 can be formed of a single nitinol wire.

The transvalvular implant 200 comprises an elongate flexible wire formed into a shaped pattern. The transvalvular implant 200 can be any shape for providing a support for the valve leaflets as has been discussed herein. The transvalvular implant 200 can include a shape which can be planar. The transvalvular implant 200 can include a shape which can be non-planar. The wire may extend to from the first end 202 and the second end 204. The wire may form a complete circle to enclose the eyelet 216 of the first anchoring portion 212. The wire may form a complete circle to enclose the eyelet 216 of the second anchoring portion 214. The wire may form two eyelets 216 of the first anchoring portion 212. The wire may form two eyelets 216 of the second anchoring portion 214.

The transvalvular implant 200 can form a continuous shape. The wire can form an coil or eyelet 116 of the first anchoring portion 212, extend along the side of the implant forming a pinched in shape near the central portion 206, form an coil or eyelet 116 of the second anchoring portion 214, extend generally straight across the second anchoring portion 214, form an coil or eyelet 116 of the second anchoring portion 214, extend along the side of the implant forming a pinched in shape near the central portion 206, form an coil or eyelet 116 of the first anchoring portion 212. The coils or eyelets of the first anchoring portion 212 can be not directly connected. The transvalvular implant 200 can form an open shape. The starting point and the ending point of the transvalvular implant 200 can be disconnected.

The transvalvular implant 200 can include two eyelets 216 of the first anchoring portion 212 separated and unconnected. The transvalvular implant 200 can include two eyelets 216 of the second anchoring portion 214 separated and connected by the wire. The transvalvular implant 200 can include a leg of the first anchoring portion 212 and a leg of the second anchoring portion 214 pinched inward near the central portion 206. The transvalvular implant 200 can include the other leg of the first anchoring portion 212 and the other leg of the second anchoring portion 214 pinched inward near the central portion 206. The transvalvular implant 200 can include a discontinuous outline. The transvalvular implant 200 can include any shape. The transvalvular implant 200 can include one or more coils that form each eyelet 216. The transvalvular implant 100, 200 can have any shape to cover any anatomical area.

In ischemic mitral regurgitation, the MR jet is pointed between the P2 and P3 junction. Other current surgical and transcatheter mitral bridge designs may not cover this area, leading to recurrences in extreme cases of IMR. The transvalvular implant 100, 200 can have any shape to cover any anatomical area.

The transvalvular implant 200 can be symmetrical. The transvalvular implant 200 can be symmetrical about one axis extending across the valve. The transvalvular implant 200 can be asymmetrical about another axis. The transvalvular implant 200 can be asymmetrical about the central portion 206. The first end 202 and the second end 204 can be different. FIG. 21C illustrates the transvalvular implant 200 with an additional feature. The transvalvular implant 200 can have one or more additional strands of wire. The transvalvular implant 200 can include a wire connecting the second end 204 or a portion thereof to a side. The transvalvular implant 200 can include an expanded posterior part. The transvalvular implant 200 can include can include an asymmetric feature. The transvalvular implant 200 can include an expanded part that is non-planar with the single wire that forms the shape. The additional feature can provide support to the transvalvular implant 200. The additional feature can act as a spring.

Figures 22A, 22B, 22C, 22D:
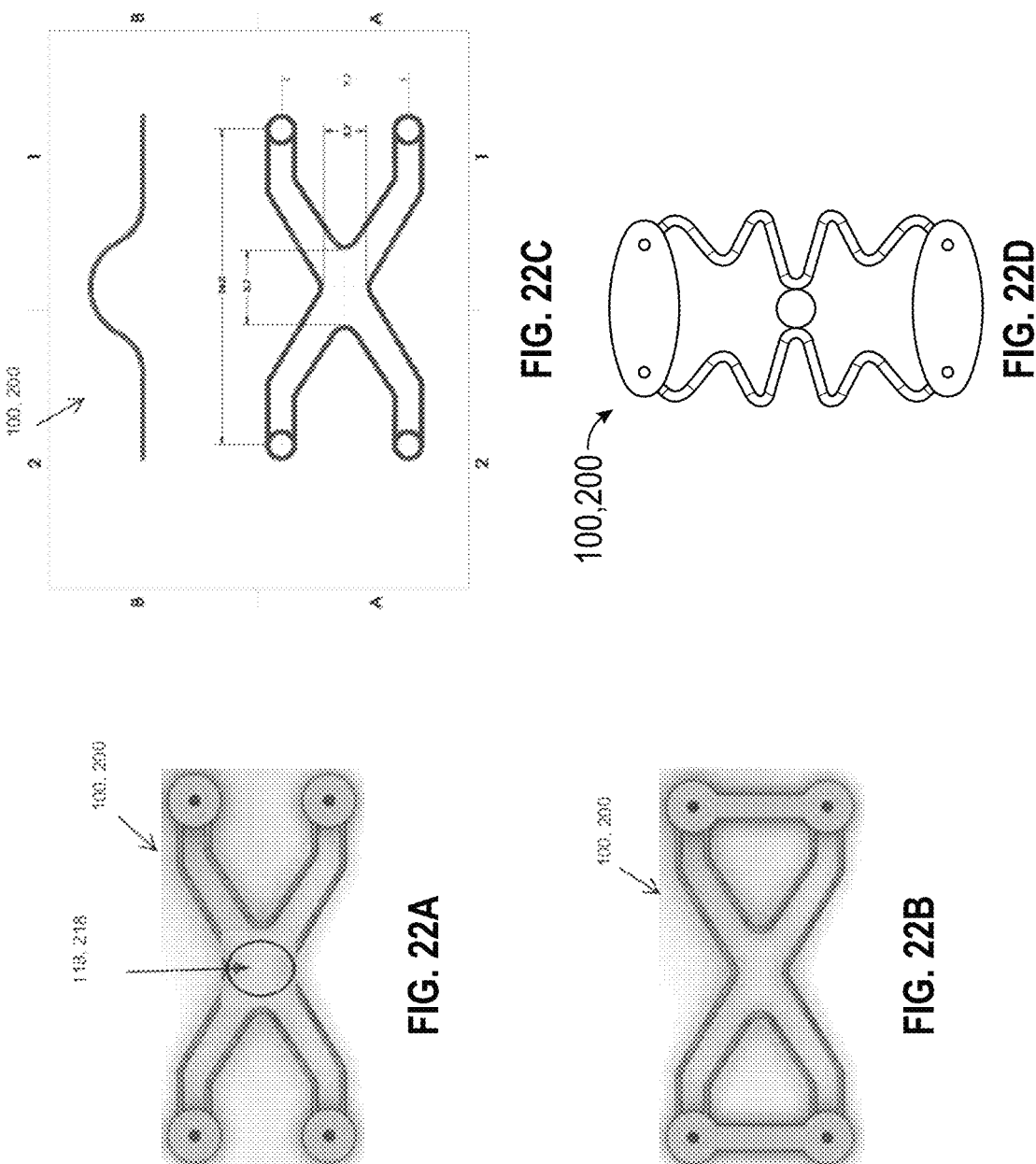
FIGS. 22A-22F are views of an embodiment of a transvalvular implant.

FIGS. 22A-22F illustrate additional features of transvalvular implants described herein. FIG. 22A illustrates a central opening. The central opening 118, 218 can be designed to have a bigger opening. The central opening 118, 218 can have any size. The central opening 118, 218 can be a 9 Fr. central opening 118, 218. The central opening 118, 218 can be 1 Fr., 2 Fr., 3 Fr., 4 Fr., 5 Fr., 6 Fr., 7 Fr., 8 Fr., 9 Fr., 10 Fr., 11 Fr., 12 Fr., 13 Fr., 14 Fr., 15 Fr., 16 Fr., 17 Fr., 18 Fr., 19 Fr., 20 Fr., or any range of two of the foregoing values. The transvalvular implants can include floating anchor attachment points. The transvalvular implants can include eyelets that are separate and distinct. The transvalvular implants can include eyelets are that are not directly and longitudinally connected. The transvalvular implants can include eyelets that are on the ends of each leg. FIG. 22A illustrates floating anchor attachment points.

The transvalvular implants can include fixed anchor attachment points. The transvalvular implants can include eyelets that are linked. The transvalvular implants can include eyelets are that are directly and longitudinally connected. The transvalvular implants can include eyelets that are on the ends of each leg, wherein each leg further connected. FIG. 22B illustrates fixed anchor attachment points. The transvalvular implants can include a felt pad attachment at the anchor point. The transvalvular implants can include additional structures at the anchor points. For example, the anchoring portions can be made of a membrane or other fabric-like material such as Dacron or ePTFE. Sutures can be threaded directly through the fabric and through the eyelets. The fabric can be attached to the other portions of the transvalvular implants by a variety of techniques. For example, the fabric can be attached to the other portions of the transvalvular implants with the use of an adhesive, by suturing, by tying, by clamping or by fusing the parts together. The transvalvular implants can include silicone over mold over nitinol wire frame. The central opening 118, 218 can remain open.

FIG. 22C illustrates some dimensions of the transvalvular implants. The dimensions of the transvalvular implants will vary, depending upon the specific configuration of the trans-valvular implants as well as the intended patient. In the illustrated embodiment, the transvalvular implant has a length of 24 mm. The transvalvular implant has a central opening with a length of 5.7 mm. The transvalvular implant has a central opening with a width of 3.2 mm. The transvalvular implant has a width of 9.7 mm from eyelet to eyelet. FIG. 22D illustrates that the transvalvular implants can form a serpentine shape. The transvalvular implants can expand to annulus bridge.

Figure 22F:
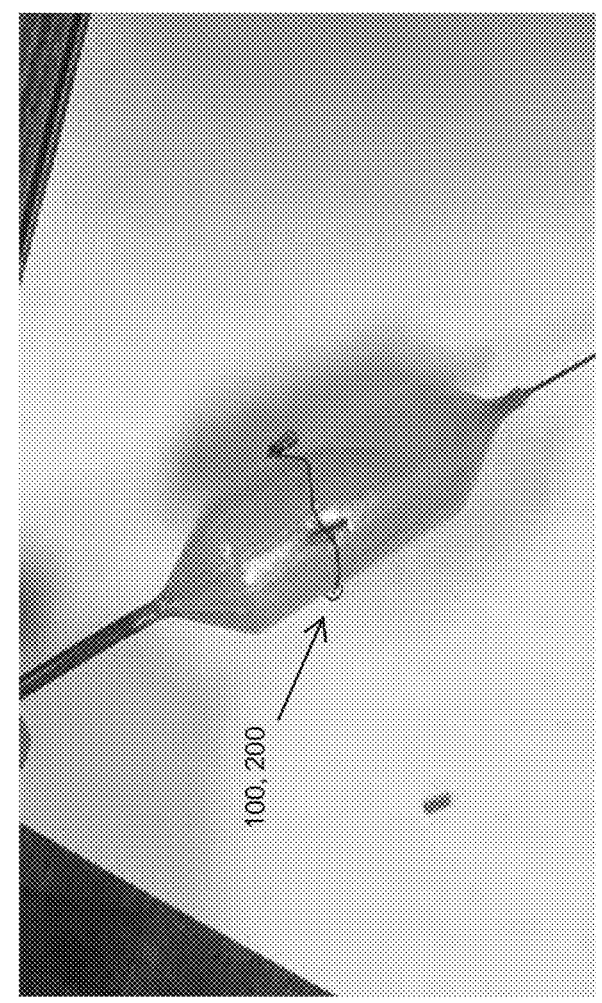
Figure 22E:
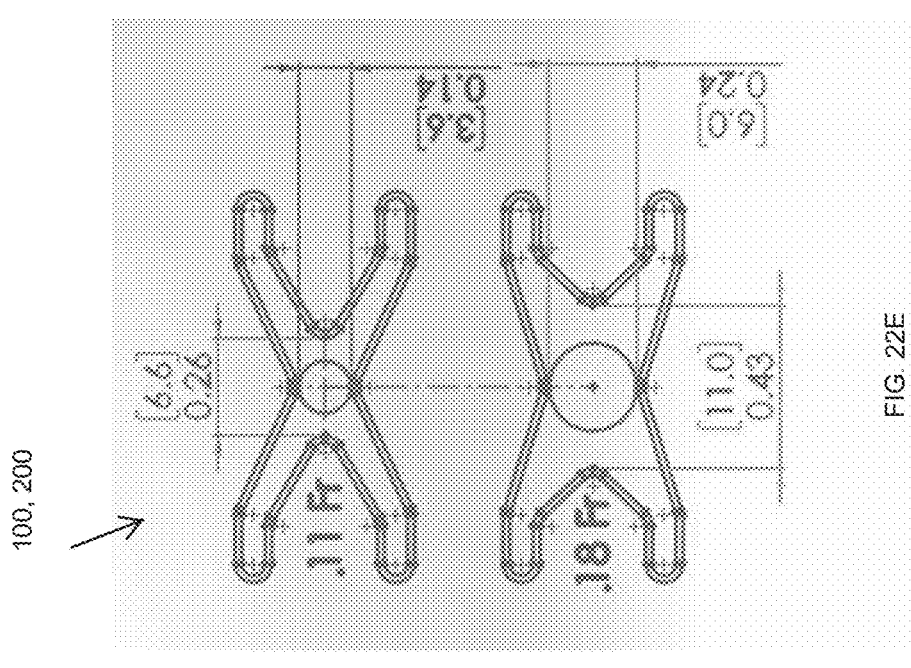

FIG. 22E illustrates two designs. The top design has a central opening and the bottom design has a larger central opening. In the illustrated top embodiment, the transvalvular implant has a 0.11 Fr dimension. The transvalvular implant has a central opening with a length of 6.6 mm. The transvalvular implant has a central opening with a width of 3.6 mm. In the illustrated bottom embodiment, the transvalvular implant has a 0.18 Fr dimension. The transvalvular implant has a central opening with a length of 11 mm. The transvalvular implant has a central opening with a width of 6 mm. In the illustrated bottom embodiment, the central orifice is opened up. The central opening can be enlarged to facilitate MitraClip® deployment. The MitraClip® can be deployed in addition to the transvalvular implants. The MitraClip® can be deployed in case of failure the transvalvular implants.

FIG. 22F illustrates deployment of the transvalvular implants. The key attributes can include reducing the annular diameter. The key attributes can include reducing the septo-lateral mitral annular diameter. The key attributes can include promoting early coaptation of the valve leaflets. The key attributes can include that it does not constrain future interventions. The key attributes can include transcatheter delivery. The transvalvular implants can be considered an arch or straddle. The transvalvular implants can be for functional regurgitation. The transvalvular implants can be considered a mitral arch or mitral straddle. The transvalvular implants can be for function mitral regurgitation. The transvalvular implants can be considered a tricuspid arch or tricuspid straddle. The transvalvular implants can be for function tricuspid regurgitation. The transvalvular implants can include a first anchoring portion and a second anchoring portion. The transvalvular implants can include a skeleton.

The transvalvular implants can include an elongate body having a first end, a second end, and a central portion connected to the first end and the second end. The central portion can include a convex arcuate shape. The elongate body can form a generally X shape skeleton comprising Nitinol. The transvalvular implants can include a first anchoring portion of the skeleton which includes two rings, each ring defining an aperture. The first anchoring portion can be located proximate the first end. The transvalvular implants can include a second anchoring portion of the skeleton which includes two rings, each ring defining an aperture. The second anchoring portion can be located proximate the second end. The central portion can be configured to be displaced transversely from an intraannular plane when the implant is attached to an annulus. The first anchoring portion and the second anchoring portion can be configured to be attached to the annulus within the intraannular plane. The central portion can be configured to be convex in a direction of outflow to support valve leaflets at a point displaced toward a ventricle from the intraannular plane. The first end and the second end reside on a septal-lateral axis transverse to coaptive edges of the valve leaflets when the transvalvular implant is attached to the annulus. The transvalvular implants do not comprise an annuloplasty ring.

The transvalvular implants can become narrower toward the center. In some embodiments, the width in the central portion is between about 20% and about 80%, such as between about 25% and about 50%, or about 20%, 25%, 30%, 35%, 40%, 45%, 50%, 55%, 60%, 65%, 70%, or 75% of the width of the first end and the second end. The transvalvular implants can gradually narrow toward the center as illustrated. In some embodiments, the width in the central portion can be between about 4 mm and about 7 mm, such as between about 5 mm and about 6 mm, or about 5 mm, about 5.2 mm, about 5.4 mm, about 5.6 mm, about 5.8 mm, or about 6 mm. By narrowing the central portion, the resistance to blood flow can advantageously be reduced.

The transvalvular implants can include a thickness. The thickness can correspond to the diameter of the wire. The thickness can correspond to the coils of wire at the eyelets. The thickness can be defined by any layers added to the anchoring portions. The transvalvular implants can omit an encapsulation layer. The transvalvular implants can omit an encapsulation layer to form the central opening. The transvalvular implants can include one or more additional layers near the anchoring portions. The anchoring portions can have a relatively greater thickness than the thickness of the central portion. In some embodiments, the anchoring portions can have a thickness that is between about 25% and about 75% greater than that of the central portion, such as between about 40% and about 60% greater, or about 25%, 30%, 40%, 45%, 50%, 55%, 60%, 65%, 70%, or 75% greater than the thickness of the central portion. In some embodiments, the central portion can have a thickness of between about 0.5 mm and about 1.0 mm, such as about 0.6 mm, 0.7 mm, or 0.8 mm. In some embodiments, the anchoring portions can have a thickness of between about 0.8 mm and about 1.3 mm, such as about 0.9 mm, 1.0 mm, 1.05 mm, 1.07 mm, 1.1 mm, or 1.2 mm.

The transvalvular implants can have an axial length of between about 15 mm and about 40 mm, such as between about 20 mm and about 32 mm depending on the patient's anatomy. The central portion of the transvalvular implants can have an axial length in some embodiments of between about 8 mm and about 24 mm, such as between about 12 mm and about 20 mm in some embodiments. In some embodiments, the width of the anchoring portions can be between about 10 mm and about 20 mm, and about 15 mm in some embodiments.

The transvalvular implants can include a wire which forms a skeleton layer. The transvalvular implants be formed of a shape set Nitinol skeleton. The transvalvular implants can be convex in the direction of the ventricle. The lateral ends of the skeleton can include eyelets defining apertures that can be utilized for anchoring. The skeleton can include a lateral curved transition zone, which has a first curvature. The skeleton can include a medial curved transition zone which has a second curvature different from the first curvature. The skeleton can include any curvature. The skeleton can include a planar surface. The skeleton can the vertex of the arcuate central portion.

As described above, the mitral valve and supporting structures are composed of the valve annulus, two leaflets, chordae tendineae, and papillary muscles. The anterior and posterior leaflets, oriented in the septal-lateral direction, provide for closing the valve opening during systole. During systole, the annulus and valvular surface create a saddle shape optimizing forces during closure by arching. The chordae and papillary muscles work together to limit the leaflet coaptation to the intraannular plane. The mitral valve has a saddle shape. As the saddle gets deeper, the commissures drop, and the anteroposterior diameter contracts. This contraction results in a compressive load on the transvalvular implant. During this contraction, the pressure behind the leaflets causes them to contact the transvalvular implant. In some embodiments, the transvalvular implant is configured to withstand a total circumferential or compressive force applied to the transvalvular implant of at about or at least about 0.35N, 0.40N, 0.45N, 0.50N, or about 0.368N per cardiac cycle in some embodiments. In some embodiments, the transvalvular implant can be configured to tolerate a septal-lateral displacement of about or at least about 0.4 mm, 0.5 mm, or 0.6 mm during the cardiac cycle. As such, the transvalvular implant can be configured to withstand load in cyclic fatigue without damage allowing long term function; maintain an AP diameter or septal-lateral diameter for early coaptation eliminating regurgitation; and/or maintain an AP diameter facilitating LV remodeling. In some embodiments the transvalvular implant can be configured to tolerate a displacement of about 0.5 mm in compression and tension. The average force to displace a device ±0.5 mm is between about 0.80N and about 0.85N, such as about 0.8358N in tension; and between about 0.60N and about 0.70N, such as about 0.63808N in compression. The forces found are over double the circumferential forces. The transvalvular implant can be configured, when implanted, to withstand such forces and continue to stably function to improve valve coaptation without being damaged, displaced, or substantially displaced as noted above. The transvalvular implant can thus be configured to tolerate, in some embodiments, a tension force of about or at least about 0.75N, 0.80N, 0.85N, 0.90N, 0.95N, 1.00N, or more. The transvalvular implant can thus be configured to tolerate, in some embodiments, a compression force of about or at least about 0.55N, 0.60N, 0.65N, 0.70N, 0.75N, 0.80N, or more.

One of the objectives of the present invention is to not merely provide support to the leaflets during systole, but to elevate the plane of coaption in the direction of the ventricle, to cause early coaption (closure) relative to the cardiac cycle, as is discussed elsewhere herein. The variation in conditions, and other patient to patient variations may warrant production of the transvalvular implant of the present invention in an array of sizes and/or configurations, so that clinical judgment may be exercised to select the appropriate implant for a given case. Alternatively, the transvalvular implant may be provided in an adjustable form or a modular form so that an implant of the desired configuration can be constructed or modified intraoperatively at the clinical site.

The transvalvular implants can be made of any of a variety of materials that are compatible with implantation within a patient's body and which has the requisite structural integrity to support the valve leaflets. The transvalvular implants can be made of any of a variety of materials that are compatible with implantation within a patient's body and which has the requisite structural integrity to support the mitral valve leaflets. The transvalvular implants can be made of any of a variety of materials that are compatible with implantation within a patient's body and which has the requisite structural integrity to support the tricuspid valve leaflets. For example, suitable materials include titanium, titanium alloys, stainless steel, stainless steel alloys, nitinol, elgiloy, MP35N, other metals and alloys, ceramics, and polymers such as PTFE, polycarbonate, polypropylene, UHMWPE, HDPE, PEEK, PEBAX and the like.

In order to reduce the thrombogenicity of the transvalvular implants, the transvalvular implants can be provided with a smooth surface or appropriately micro-texture the surface in some embodiments, such as via a porous or microporous structure. Other factors such as surface chemistry, energy, morphology, macrofeatures, and general material properties matching the in situ needs can also be considered in tailoring the surface of the implant. In addition, the transvalvular implants can be coated with a variety of substances to reduce thrombogenicity. For example, the transvalvular implants can be coated with a antithrombogenic agent such as heparin, a polymer such as PTFE, or a polymer conjugated with heparin or another antithrombogenic agent. Heparin coatings can be achieved in a variety of methods, one of which may be to coat or drip the prosthesis in TDMAC-heparin (Tridodecylmethylammonium heparinate).

The transvalvular implant can be implanted in the plane of the valve annulus. The transvalvular implant can be implanted in the plane of the mitral valve annulus 28 in a patient. The transvalvular implant can be implanted in the plane of the tricuspid valve annulus in a patient. The transvalvular implant can be attached to the annulus 28 by a variety of techniques, such as sutures, anchors, barbs, stapes, self-expanding stents, or other techniques that are known or are apparent to those of skill in the art. The transvalvular implant is oriented in the annulus so that the transvalvular implant is positioned approximately transversely to a coaptive edge formed by the closure of valve leaflets. The transvalvular implant is oriented in the annulus 28 so that the transvalvular implant is positioned approximately transversely to the coaptive edge 42 formed by the closure of the mitral valve leaflets 24 and 26. The transvalvular implant is oriented in the annulus so that the transvalvular implant is positioned as described herein relative to the tricuspid leaflets. The transvalvular implant in accordance with the present invention can be implanted via an open surgical procedure, via thoracotomy (e.g. transapically) or alternatively, via a percutaneous procedure using a transluminally implantable embodiment.

FIGS. 23A-23E illustrate anchoring design concepts. In some embodiments, disclosed herein is a system for delivering and anchoring an implant to a valve annulus. The system can include an anchor catheter configured to deliver an annular anchor to a valve annulus of a heart of a patient. The annular anchor can have a variety of configurations. In some embodiments, the annular anchor comprises barbs to engage tissue. In some embodiments, the annular anchor is a coil or helix. In some embodiments, the annular anchor comprises a suture. Also disclosed herein is a method for delivering and anchoring an implant to a valve annulus of a valve. The transvalvular implant can be utilized with any anchor described herein.

FIG. 23A illustrates an embodiment of an annular anchor. The annular anchor can be a treble hook anchor 300. The treble hook anchor 300 uses multiple hooks to avoid dehiscence. The treble hook anchor 300 can include three hooks 302, 304, 306. The annular anchor can include any number of hooks, including one hook, two hooks, three hooks, four hooks, five hooks, six hooks, or any range of two of the forgoing values. The hooks 302, 304, 306 can curve upward forming a J shape. The hooks 302, 304, 306 can include barbs 308. The barbs 308 can face inward. The treble hook anchor 300 can be delivered in a compressed configuration through a hole in the annulus. The treble hook anchor 300 can expand in a subannular space. The treble hook anchor 300 can be pulled to engage tissue. The treble hook anchor 300 can be located in the subannular space.

FIG. 23B illustrates an embodiment of an annular anchor. The annular anchor can be a hex screw 310. The hex screw 310 can be twist type anchor. The hex screw 310 can have a spring 312. The spring 312 can be flexible. The spring 312 can be rigid. The spring 312 can have a sharpened tip to engage tissue. The hex screw 310 can have a needle 314. The needle 314 can have a sharpened tip. The spring 312 can drive the needle 314. In some methods, the hex screw 310 is rotated to drive the spring 312 into tissue. As the hex screw 310 is rotated, the needle 314 passes further into tissue. The hex screw 310 can include a hub 316. The needle 314 can be centrally located on the hub 316. The hub 316 can be rotated by a driver. In some embodiments, the hub 316 is a hex and the driver has a hex socket. The hub 316 can include a washer 318 to distribute pressure of the hub 316.

FIG. 23C illustrates an embodiment of an annular anchor. The annular anchor can be a locking screw 320. The locking screw 320 can be twist type anchor. The locking screw 320 can have a spring 322. The spring 322 can be flexible or rigid. The spring 322 can have a sharpened tip to engage tissue. The locking screw 320 can have an off center pin 324. The off center pin 324 can have a sharpened tip. The off center pin 324 can stop rotation. In some embodiments, the spring 322 is rotated to be driven into tissue. After the spring 322 is in position, the off center pin 324 can be released to prevent further rotation of the spring 322. Other methods of use are contemplated.

FIG. 23D illustrates an embodiment of an annular anchor. The annular anchor can be a single piece wire screw 330. The single piece wire screw 330 can be twist type anchor. The single piece wire screw 330 can be formed from a single piece of wire. The single piece wire screw 330 can have a spring 332. The spring 332 can have one or more coils. The spring 332 can have a sharpened tip to engage tissue. The single piece wire screw 330 can have a needle 334. The needle 334 can have a sharpened tip. The spring 332 can drive the needle 334. In some methods, the single piece wire screw 330 is rotated to drive the spring 332 into tissue. As the single piece wire screw 330 is rotated, the needle 334 passes further into tissue. The single piece wire screw 330 can include a hub 336. The needle 334 can be centrally located on the hub 336. The hub 336 can include one or more coils. The one or more coils of the hub 336 can be perpendicular to one or more coils of the spring 332. The hub 336 can be rotated by a driver. The single piece wire screw 330 can be turned by a flathead screwdriver. The flathead screwdriver can be inserted between the one or more coils and then rotated.

FIG. 23E illustrates an embodiment of an annular anchor. The annular anchor can be a single piece wire screw 340. The single piece wire screw 340 can have a spring 342. The spring 342 can have one or more coils. The single piece wire screw 340 can include a hub 346. The hub 346 can include an eyelet. The eyelet of the hub 346 can be perpendicular to one or more coils of the spring 342. The eyelet of the hub 346 can be rotated by a driver. The single piece wire screw 340 can omit a needle or offset locking pin.

The anchors 300, 310, 320, 330, 340 can be a radially symmetrical embedded anchors. The anchor 300, 310, 320, 330, 340 can embed itself in tissue by expanding after entry. In some embodiments, the anchor 300, 310, 320, 330, 340 is rigid and has a fixed shape. In some embodiments, the anchor 310, 320, 330, 340 can be rotated to engage tissue. In some embodiments, the anchor 300, 310, 320, 330, 340 can comprise a shape memory shape. In some embodiments, the anchor 300, 310, 320, 330, 340 can comprise a shape memory material that assumes a preformed shape. In some embodiments, the anchor 300, 310, 320, 330, 340 can comprise a shape that expands after implantation. For instance, the spring 312, 322, 332, 342 can expand after entry to embed into tissue. For instance, the hooks 302, 304, 306 can expand after entry to embed into tissue. The anchor 300, 310, 320, 330, 340 can be radially symmetrical. The anchor 300, 310, 320, 330, 340 can radially expand.

The annular anchor can include one or more barbs. The annular anchor can include one or more hooks. The annular anchor can include can include a helix. The annular anchor can include a needle. The annular anchor can include a head. The annular anchor can include an interface to be engaged by a driver. The annular anchor can include a washer. The annular anchor can include a hub. The annular anchor can include a single piece construction. The annular anchor can include a multiple piece construction. The annular anchor can include an off center pin. The annular anchor can include a central needle. The annular anchor can include one or more coils. The annular anchor can be expandable. The annular anchor can be self-expandable. The annular anchor can prevent retraction. The annular anchor can have any combination of features of annular anchors described herein. The annular anchor can have any engagement portion to engage tissue. The annular anchor can have any hub. The annular anchor can have any secondary feature such as barbs, needles, or pins to further engage tissue.

The annular anchor can include one or more key attributes. The annular anchor can require minimal insertion force. The annular anchor can be repositionable. The annular anchor can be simple to deploy. The annular anchor can have excellent retention force. The annular anchor can be delivered via transcatheter delivery.

Figure 24B:
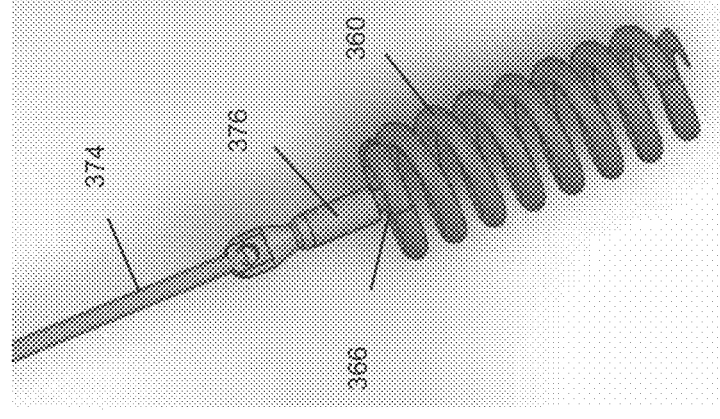
FIGS. 24A-24B are views of embodiments of anchors and tethers.
Figure 24A:
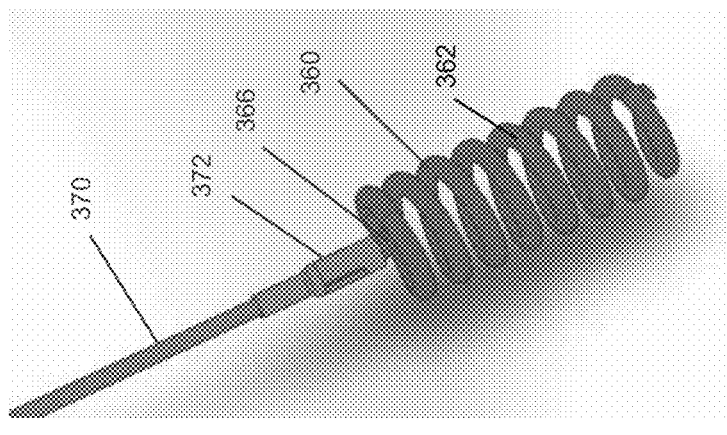

FIGS. 24A-24B illustrate anchor and tether designs. In some embodiments, the annular anchor 360 can be coupled to a tether 370. The tether 370 can be a monofilament tether as shown in FIG. 24A. The annular anchor 360 can have any feature of the annular anchors described herein. The annular anchor 360 can include a spring 362. The annular anchor 360 can include a hub 366. The hub 366 can be bent upward. The hub 366 can be a top portion of the spring 362. The system can include an anchor crimp 372. The anchor crimp 372 can crimp the tether 370 to the hub 366 of the anchor 360. In some embodiments, the anchor crimp 372 is a tubular structure that surrounds the hub 366 and the tether 370. The anchor crimp 372 can have pressure applied to secure the hub 366 and the tether 370 together.

In some embodiments, the annular anchor 360 can be coupled to a tether 374. The tether 374 can be a looped monofilament fiber or braided suture as shown in FIG. 24B. The tether 374 can be made of polyester. The system can include an anchor crimp 376 shown in FIG. 24B. The anchor crimp 376 can crimp the tether 374 to the hub 366 of the anchor 360. In some embodiments, the anchor crimp 376 is a tubular structure that surrounds the hub 366. The anchor crimp 376 can include an opening to accept the tether 374. The tether 374 can be looped through the anchor crimp 376.

The anchor crimp 372, 376 can be in an offset position. The anchor crimp 372 can be offset relative to the center of the spring 362. The anchor crimp 372, 376 can be stainless steel. The anchor crimp 372, 376 can be titanium. The outer diameter of the annular anchor 360 can be 0.095". The height of the annular anchor 360 can be 6 mm. The anchor can have a different wire diameter. The anchor can have a different pitch. The anchor can have a different anchor diameter.

Figure 25B:
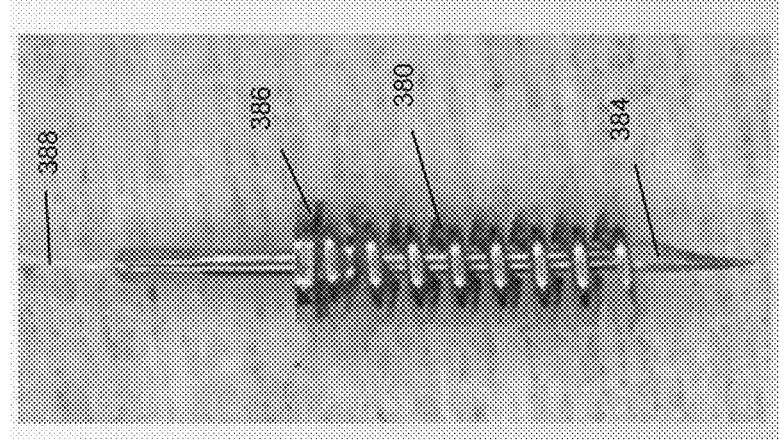
FIGS. 25A-25B are views of embodiments of anchors and delivery catheters.
Figure 25A:
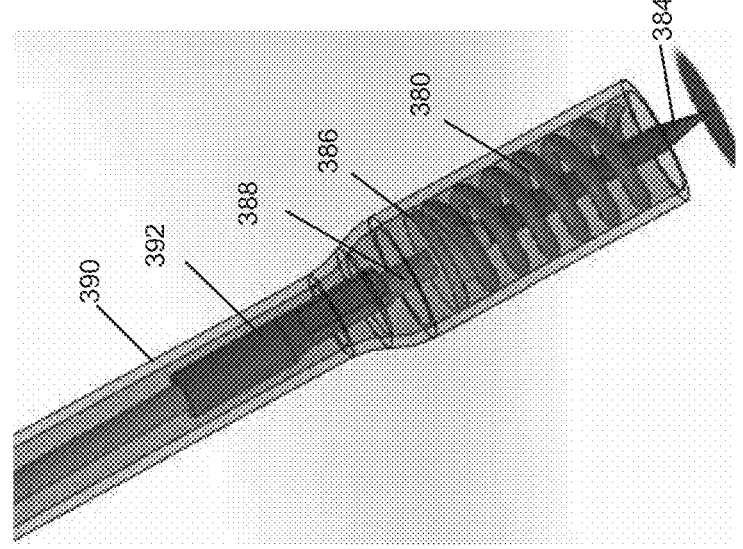

FIGS. 25A-25B illustrate anchor and tether designs. The annular anchor can be an anchor with center point 380. The anchor with center point 380 can have a spring 382. The anchor with center point 380 can have a center point 384. The center point 384 can have a sharpened tip. The center point 384 can hold the position during deployment. The center point 384 can be centrally disposed within the spring 382. The central point 384 can be centrally located on the anchor. The spring 382 can drive the needle 384.

The anchor with center point 380 can include a hub 386. In some embodiments, the hub 386 can include a central post. The central post of the hub 386 can extend proximally. The central post can be centrally located on the anchor. The center post can be centrally located on the hub 386. The center post can be rotated by a driver. The center post can be keyed and the corresponding driver can have a keyed socket. The anchor with center point 380 can include a tether 388. The tether 388 can be coupled to the central post of the hub 386. The tether 388 can be crimped to the center post. The anchor with center point 380 can include an anchor crimp and tether 388 all in central position. In some embodiments, the center point 384 and the central post of the hub 386 are continuous. In some embodiments, the center point 384 and the central post of the hub 386 are axially aligned.

The anchor with center point 380 can include an outside diameter of 0.092". The anchor with center point 380 can have a length of 6 mm. The anchor with center point 380 can be made stainless steel 316L. The anchor with center point 380 can be made of titanium.

The anchor with center point 380 can be delivered with a delivery catheter 390. The delivery catheter 390 can include a Pebax outer sheath. The delivery catheter 390 can include 35D Pebax at an articulation section of the delivery catheter 390. The delivery catheter 390 can have an enlarged distal section to accommodate the anchor with center point 380. The delivery catheter 390 can accommodate a driver 392. The driver 392 can engage the central post of the hub 386. The driver 392 can rotate the anchor with center point 380. The driver 392 can slide along the tether 388. In some embodiments, the tether 388 can have tension applied during delivery to facilitate coupling the driver 392 to the anchor with center point 380.

FIGS. 26A-26B illustrate anchor and mount designs. In some embodiments, the annular anchor 400 can be coupled to a mount 410. The annular anchor 400 can have any feature of annular anchors described herein. The annular anchor 400 can include a spring 402. The annular anchor 400 can include a needle 404. The annular anchor 400 can include a hub 406. The hub 406 can include a central post. The needle 404 and the central post of the hub 406 can be separately formed. The annular anchor 400 can include a tether 408 coupled to the central post of the hub 406. The tether 408 can be crimped onto the central post of the hub 406.

The spring 402 can include a portion that is bent. The spring 402 can include a cross-pin at the top of the coil. The top coil can be turned inward. The mount 410 can include an opening 412. The opening 412 can be sized to accept the cross-pin of the spring 402. The top of the spring 402 can be inserted into the drilled hole. The coil of the anchor extends through the mount 410. The mount 410 can include a flange 414. The flange 414 can extend to the diameter of the coil.

The needle 404 can have a length of 7 mm. The central post of the hub 406 can have a length of 5.5 mm. The needle 404 and the central post of the hub 406 can be separately formed. These features can be cut to length. The mount 410 can be positioned on the central post. The length of 3.3 mm of the center post can extend above the flange 414. The opening 412 can extend through the mount 410. The opening 412 can extend through the central post of the hub 406. The mount 410 can include a hypotube. The hypotube can form the opening 412. The annular anchor 400 can include the spring 402. The top of the spring 402 can be passed through the opening 412. The spring 402 can be 6.66 mm. The needle 404 can extend beyond the spring 402.

Figure 27B:
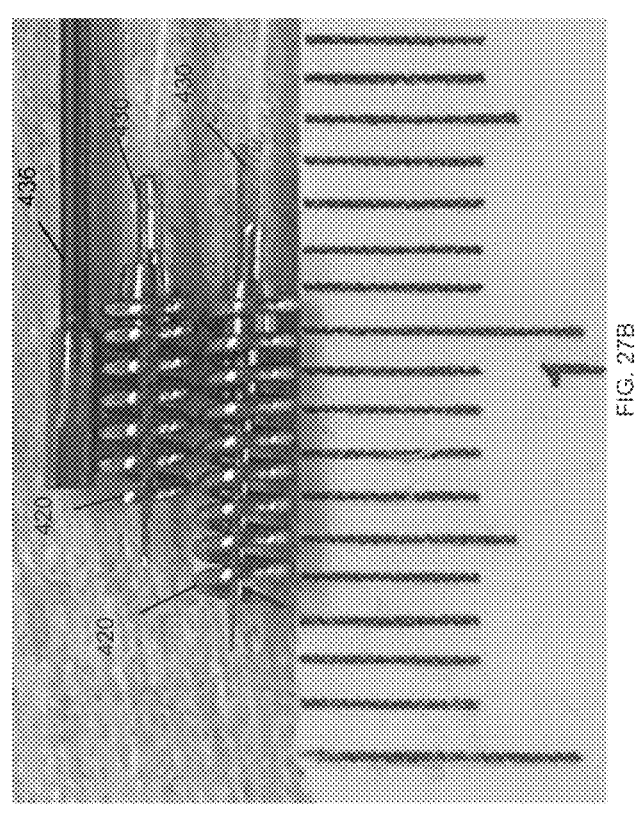
FIGS. 27A-27D are views of embodiments of anchors and mounts.
Figure 27D:
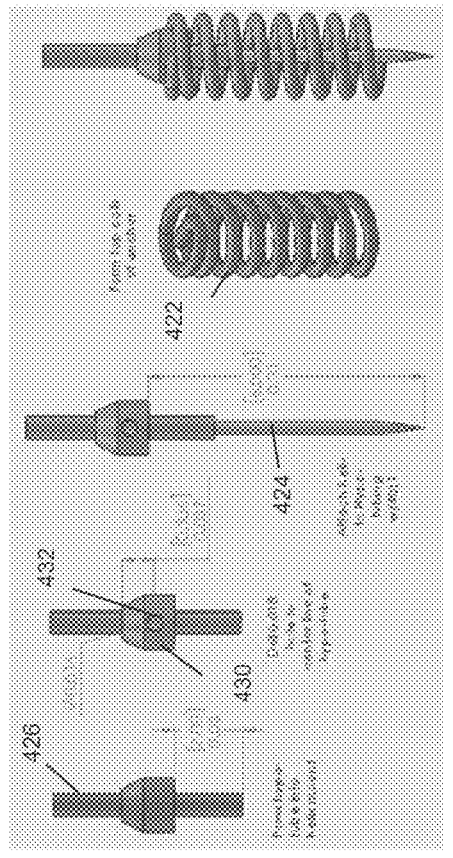
Figure 27A:
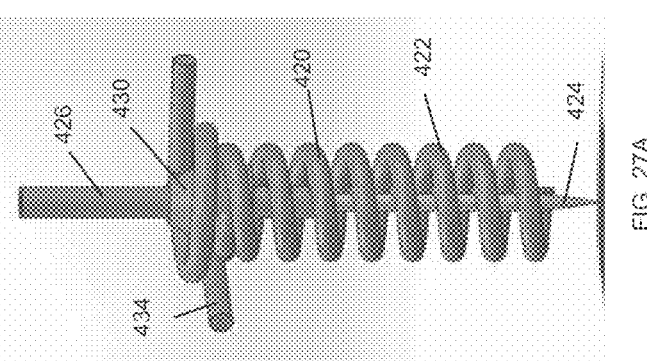
Figure 27C:
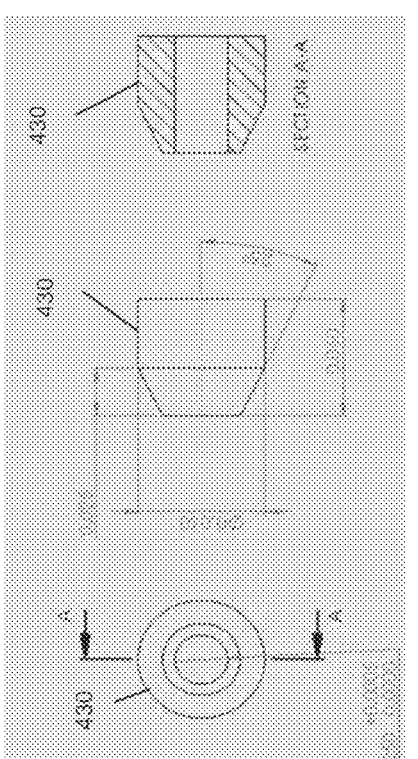

FIGS. 27A-27D illustrate anchor and mount designs. In some embodiments, an annular anchor 420 can be coupled to a mount 430. The annular anchor 420 can have any feature of annular anchors described herein. The annular anchor 420 can include a spring 422. The spring 422 can include a cross-pin at the top coil. FIG. 27A illustrates an extra coil 434. The extra coil 434 can be proximal to the spring 422. The annular anchor 420 can include a needle 424. The annular anchor 420 can include a hub 426. The hub 426 can have a quadrangular luer-lock type of fit. The annular anchor 420 can include a quadrangular mounting structure. The annular anchor 420 can include the extra coil 434 coupled to the quadrangular mounting structure.

The hub 426 can include a central post. The needle 424 and the central post of the hub 426 can be separately formed. The annular anchor 420 can include a tether 428 coupled to the central post of the hub 426. FIG. 27B illustrates two lengths from tip of the needle 424 to the top of the helix of the spring 422. The two lengths are 6 mm and 8 mm. The anchor can include a driver 436. The driver 436 can couple to the central post of the hub 426. The driver 436 can include a socket to engage the central post of the hub 426.

The mount 430 can include a diameter of 0.060". The mount 430 can include a taper with a length of 0.025". The mount 430 can include a length of 0.060". The taper can have a 25 degree angle. The mount 430 can include an opening 432. The opening 432 can be sized to accept the cross-pin of the spring 422. The mount 430 can be less than the diameter of the spring 422.

The central post of the hub 426 can include a hypotube. The hypotube can be pressed into the mount 430. The central post of the hub 426 can have a length of 2 mm below the mount 430. The opening 432 can be drilled into the mount 430. The opening 432 can be drilled into the central post of the hub 426. The opening 432 can be 0.018". The opening 432 can be 0.037" below the top of the mount 430. The needle 424 can have a length of 8 mm. The needle 424 can be inserted into the hypotube of the central post of the hub 426. The spring 422 can have a cross-pin formed from the top coil. The top coils of the spring 422 are shown. The spring 422 can be attached to the mount 430. The top of the spring 422 can be inserted into the opening 412 in the mount 430.

Figure 28:
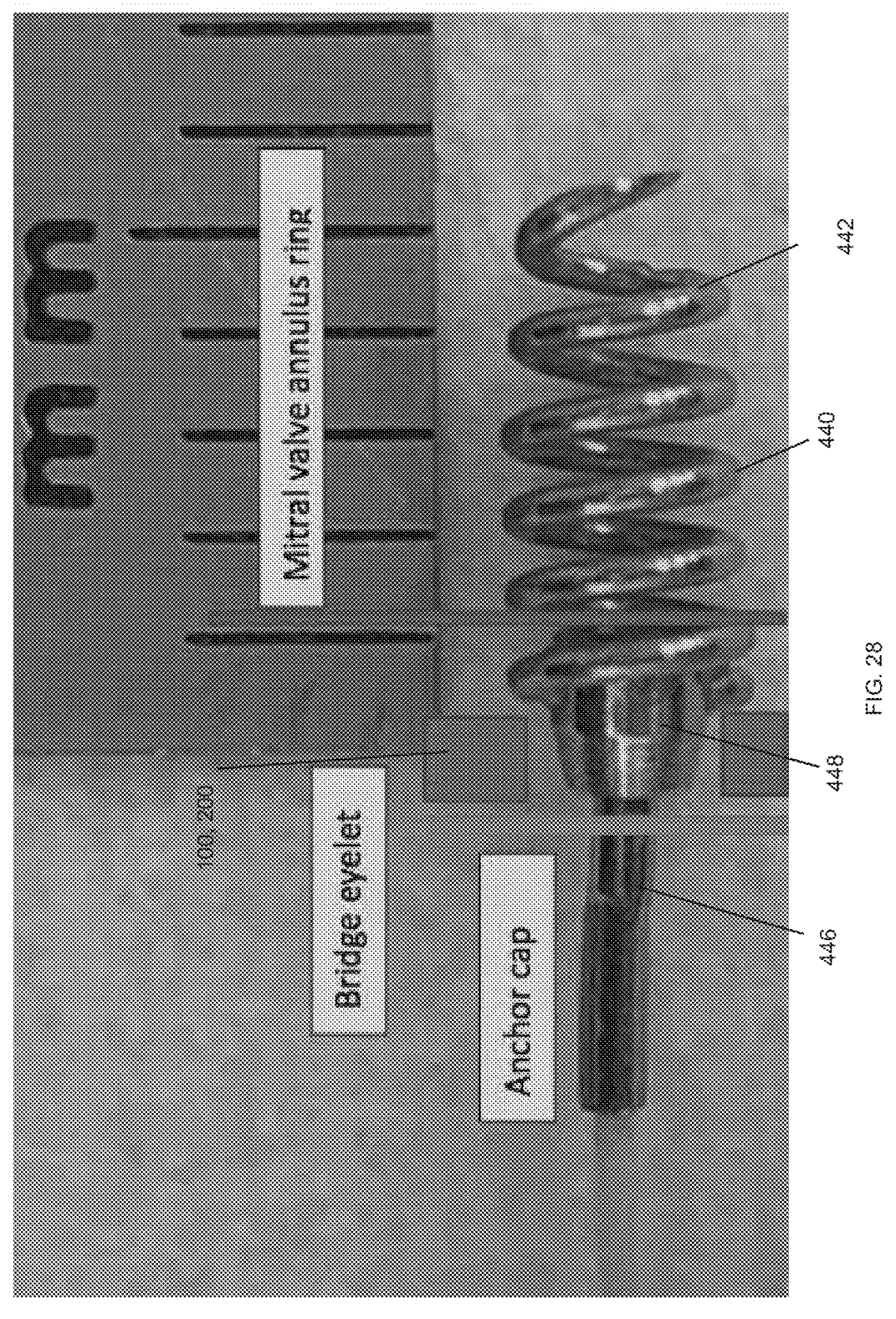
FIG. 28 is a view of an embodiment of an anchor.

FIG. 28 illustrates an annular anchor 440. The annular anchor 440 can have any feature described herein. The annular anchor 440 can be an optimized anchor with tapered anchoring end. The annular anchor 440 can omit the central pin. The annular anchor 440 can include a spring 442. The annular anchor 440 can include a hub 446. The annular anchor 440 can include a mount 448. FIG. 28 schematically illustrates the position of the annular anchor 440 relative to the transvalvular implant 100, 200. The annular anchor 440 can be positioned relative to the mitral valve annulus ring. The annular anchor 440 can be positioned relative to the anchoring portion of the transvalvular implant 100, 200. The mount 448 can be positioned within the eyelet of the transvalvular implant 100, 200. The system can include an anchor cap as described herein. The mount 448 of the annular anchor 440 can be distal to the anchor cap.

Figure 29C:
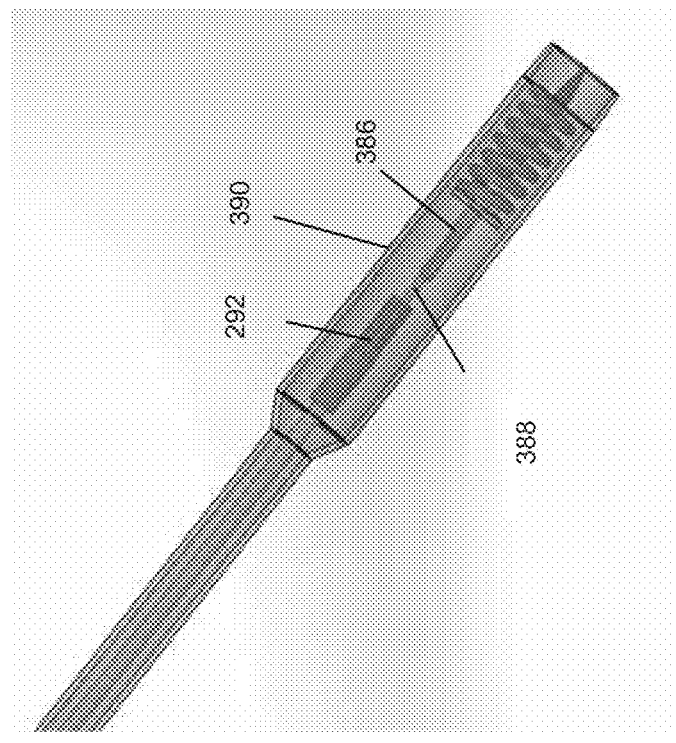
FIGS. 29A-29C ire views of an embodiment of an anchor and driver.
Figure 29B:
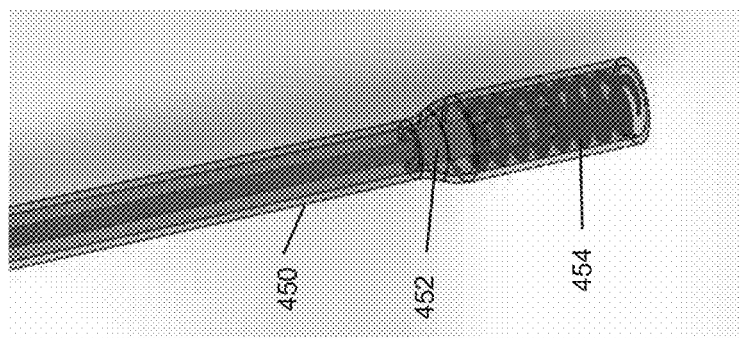
Figure 29A:
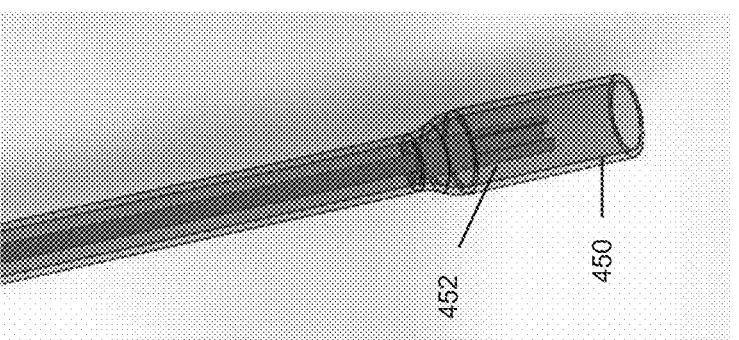

FIGS. 29A-29C illustrate a delivery catheter 450. The delivery catheter 450 can be an anchor therapy catheter. The delivery catheter 450 can be utilized with any anchor described herein. The delivery catheter 450 can have an inner diameter. The delivery catheter 450 can be 12 Fr (0.205" 5.2 mm) inner diameter compatible. FIG. 29A illustrates a keyed driver 452. The keyed driver 452 can include a hypotube shaft. The keyed driver 452 can include a keyed slot. The keyed slot can accept a cross-pin of an anchor 454. The cross-pin of an anchor 454 can slide distally within the slot as the keyed driver 452 is rotated. The keyed driver 452 for anchor attachment is shown in FIG. 29A. FIG. 29B illustrates the anchor 454 preloaded. The anchor 454 can be inserted into the distal end of the delivery catheter 450. The keyed driver 452 can rotate thereby deploying the anchor 454. The system can include a hemostatic flush line. The system can be configured for single use deployment. The anchor 454 can omit the tether.

FIG. 29C illustrates the delivery catheter 390 described herein. The delivery catheter 390 can accommodate the driver 392. The driver 392 can engage the central post of the hub 386. The driver 392 can include a keyed socket to engage a keyed portion of the central post. In some embodiments, the tether 388 can be coupled to the annular anchor 380. The tether 388 can facilitate engagement of the driver 392 with the annular anchor 380 after deployment to reposition the annular anchor 380. The system can be configured for deployment and redeployment.

Figures 30A, 30B:
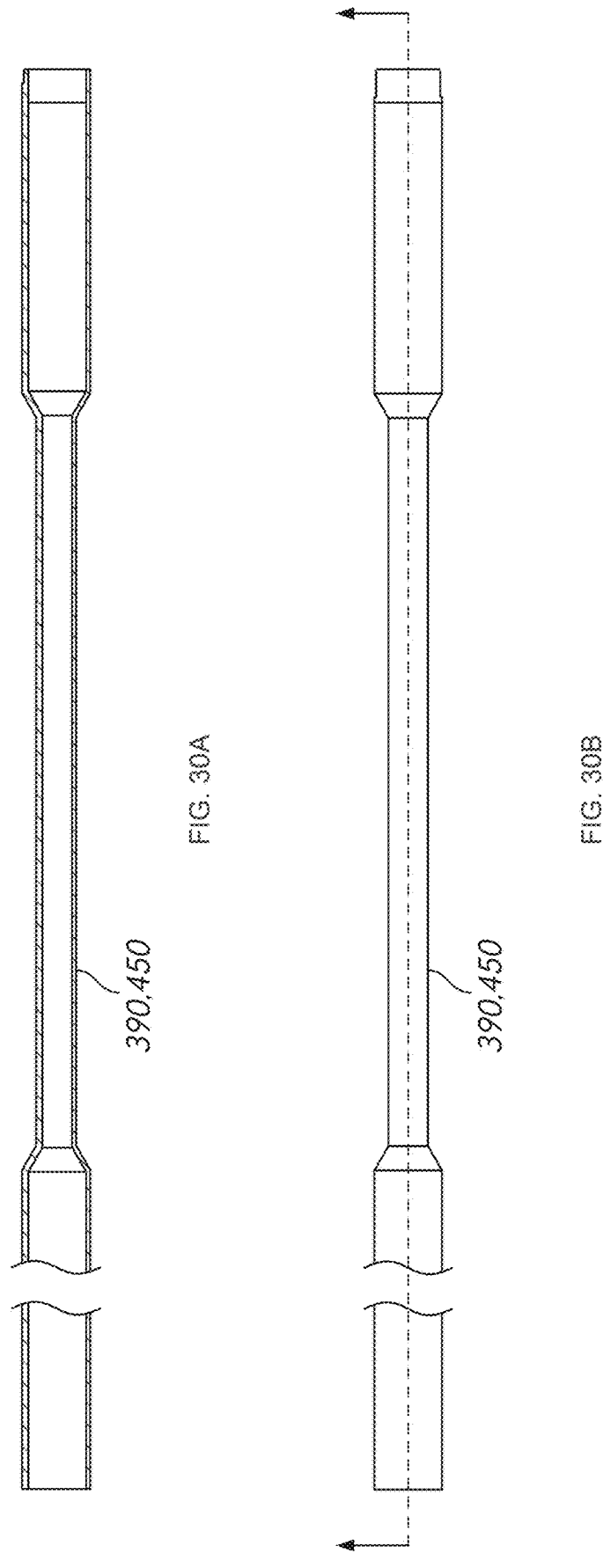
FIGS. 30A-30B are views of an embodiment of a delivery catheter.

FIGS. 30A-30B illustrate a sheath for the delivery catheter 390, 450. The material can be 0.0050" 30 x-series stainless steel. The parts can be delivered still attached to the sheet of raw material by connector sprues. The orientation and number of sprues to be determined by the laser cutting vendor. The sprues that attach the laser cut component to the sheet of raw material can be made as narrow as possible while still maintaining part quality to facilitate ease of detachment and to minimize the amount of secondary operations including filing needed to remove evidence of sprue. The sheath can have a length of 72.3". The wall thickness can be 0.010". The diameter can be 0.078" in a middle section. The diameter can be 0.137" in an end section. The first end section can have a length of 70". The first end section can be 72D Pebax. The middle section can have a length of 1.6". The middle section can be 35D Pebax. The second end section can have a length of 0.60". The second end section can be 72D Pebax. The second end section can include a tip. The tip can be 35D Pebax. The tip can have a length of 0.065".

Figure 31B:
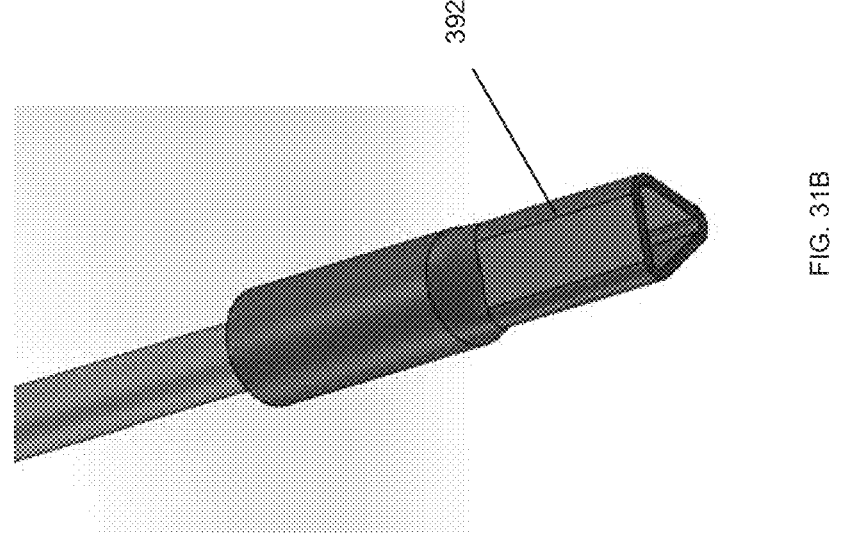
FIGS. 31A-31B are views of an embodiment of an anchor and driver.
Figure 31A:
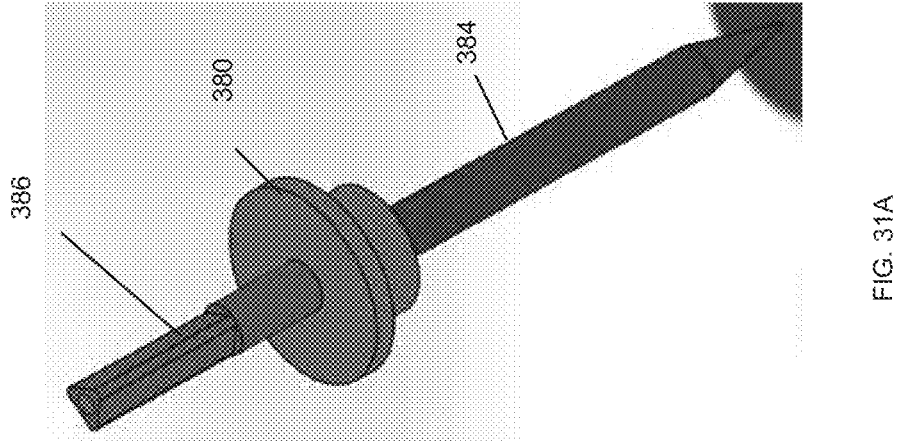

FIGS. 31A-31B illustrate the driver 392 and the central post of the hub 386. The driver 392 can include a keyed socket to engage a keyed portion of the central post of the hub 386. The annular anchor 380 can include an anchor triangle drive. The annular anchor 380 can have the center point 384. The central point 384 can be centrally located on the annular anchor 380. The central post of the hub 386 can be centrally located on the annular anchor 380. The tether 388 can be crimped to the center post. The anchor to tether crimping process can create a triangle shaped feature. This feature is used to couple to a matching feature of the driver 392. The annular anchor 380 can include a crimp. The crimp can be triangular. The driver 392 can include a triangular recess to mate with the crimp.

Figures 32A, 32B:
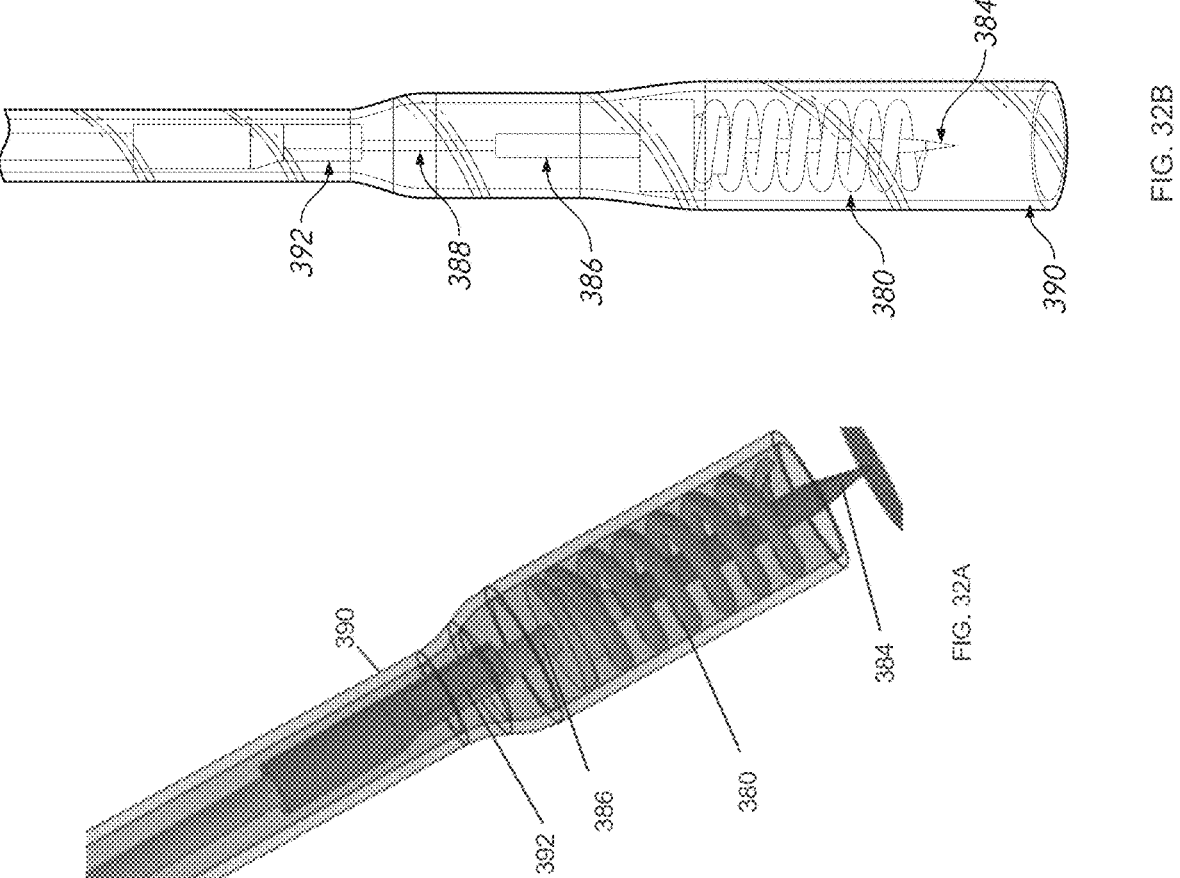
FIGS. 32A-32B are views of an embodiment of an anchor and delivery catheter.

FIGS. 32A-32B illustrate the delivery catheter 390 described herein. The system can include the annular anchor 380. The annular anchor 380 can include the center point 384. The center point 384 can be a stabilizing center pin. The system can include the driver 392. The driver 392 can include a triangular drive mechanism. The annular anchor 380 can include the tether 388. The tether 388 can extend from the annular anchor 380. The annular anchor 380 can include the central post of the hub 386. The central post of the hub 386 can be an anchoring post for the transvalvular implant 100, 200. The system can include the delivery catheter 390.

Figure 33B:
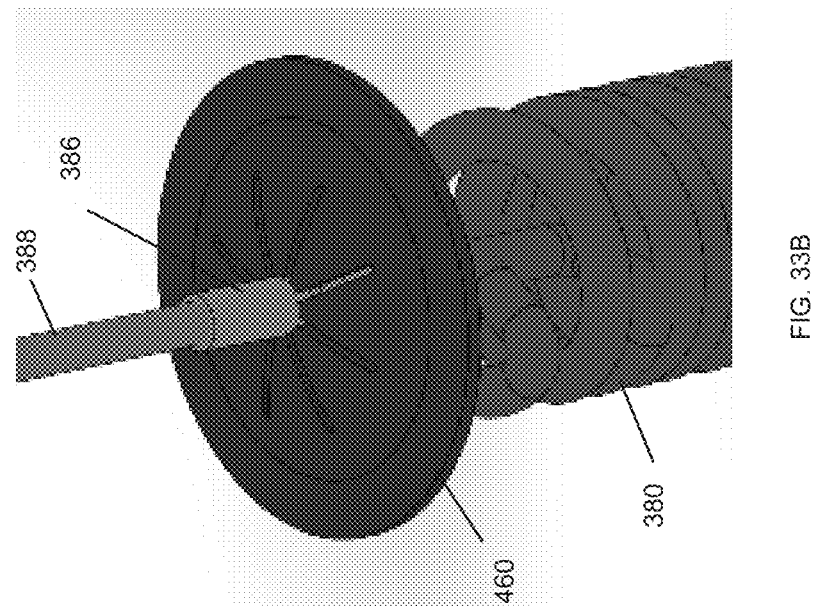
FIGS. 33A-33B are views of an embodiment of an anchor and cap.
Figure 33A:
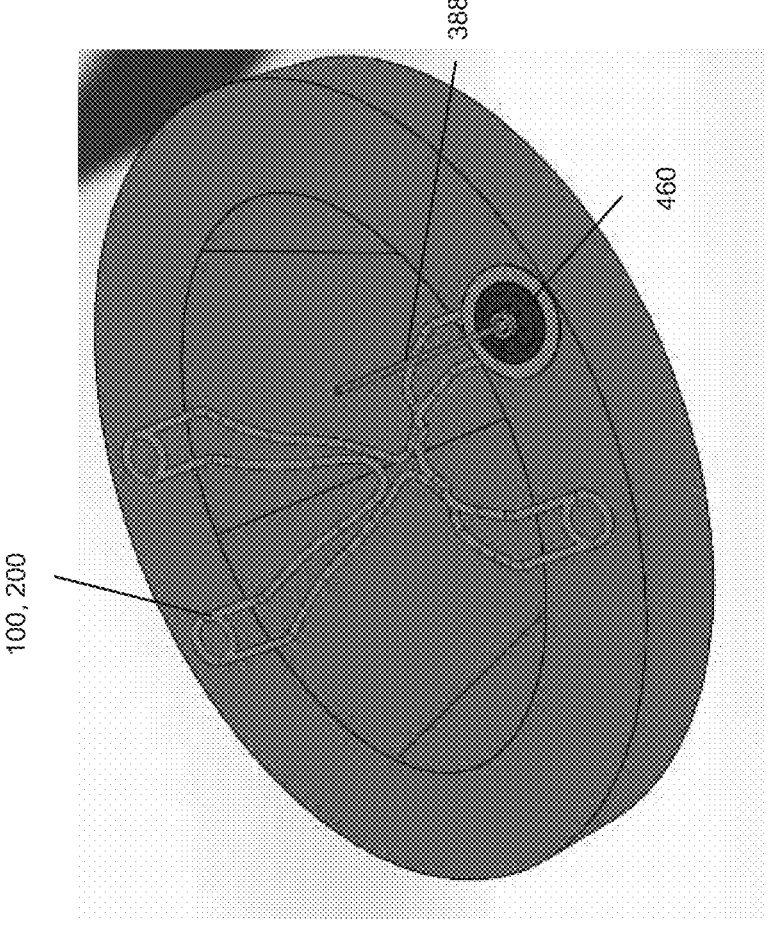

FIGS. 33A-33B illustrate bridge to anchor attachment concepts. The system can include the transvalvular implant 100, 200. The transvalvular implant 100, 200 can be disposed relative to the valve. The system can include any anchor described herein. FIG. 33B illustrates the anchor 380. The system can include a cap 460. The cap 460 can be a push-on cap. The cap 460 can be round. The cap 460 can function as a locking clip to hold the transvalvular implant 100 in position. The cap 460 can be positioned over the central post of the hub 386 of the anchor 380. The cap 460 can be pushed on the central post of the hub 386. In some embodiments, the cap 460 is not attached to a suture. In some embodiments, the tether 388 can be cut to release the annular anchor 380 after deployment. In some embodiments, the anchor is not reversible after release of the tether 388. In some embodiments, the cap 460 can be photo etched titanium or stainless steel. The cap 460 remains in place after the transvalvular implant 100, 200 is deployed. The cap 460 can securely lock the transvalvular implant 100, 200 in position.

FIG. 34A-34D illustrates delivery design concepts. The delivery can include one or more key attributes. The systems can be configured for transcatheter delivery. The systems can be configured for a trans-septal approach. The systems can include custom guide catheters. The systems can be a custom steerable delivery system. In some embodiments, the systems can be configured to place the anchors and then the transvalvular implant. In some embodiments, the systems can be configured to place the anchors and transvalvular implant together.

FIGS. 34A-34D illustrates a method of delivery. In some embodiments, one or more anchors are delivered. The anchors can be any anchors described herein. In some embodiments, four anchors are delivered. In some embodiments, the anchors can be delivered individually. In some embodiments, the anchors can be delivered in pairs. In some embodiments, the anchors can be delivered together. FIG. 34A illustrates a delivery method. The anchors are seated within the tissue. The anchors can include tethers as described herein. In some embodiments, a sleeve is advanced relative to the tethers. The advancing sleeve can tighten the tethers. The transvalvular implant can then be positioned. The transvalvular implant can slide along the tethers into positon relative to the valve. FIG. 34B illustrates a delivery method. A first anchor set is seated within tissue. The first anchor set can include two anchors. The two anchors can correspond to the first anchoring portion of the transvalvular implant. The method can include seating the transvalvular implant relative to the first anchor set. The method can include pulling against the septum. Then a second anchor set is seated within tissue. The second anchor set can include two anchors. The two anchors can correspond to the second anchoring portion of the transvalvular implant. The method can include seating the transvalvular implant relative to the second anchor set.

FIG. 34C illustrates the Freudenberg modular systems. The systems can include a handle platform. The systems can include composite catheter shafts. The systems can include tubing. FIG. 34D illustrates the surgical design. The system can include a delivery handle. The systems can include a suture or tether. The suture can wrap around the delivery handle. The suture can include one more suture knots. The system can include the transvalvular implant.

Figure 35:
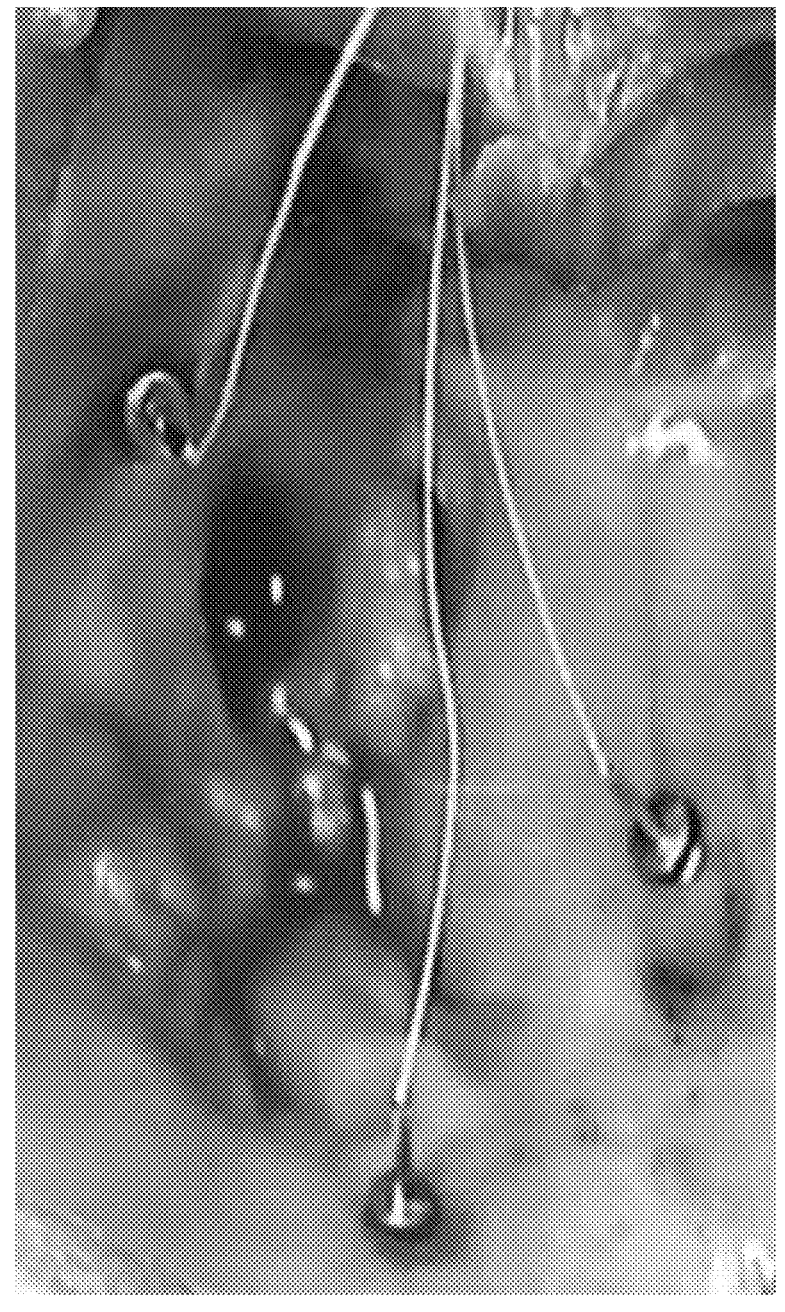
FIG. 35 is an embodiment of anchors deployed.

FIG. 35 illustrates the annular anchors deployed in a heart of a pig. The anchors are embedded in the annulus. The tethers extend from the anchors. While three anchors are shown, any number of anchors can be deployed. In some methods, the tethers can serve as a means to deliver the transvalvular implant to the annulus. In some methods, the tethers can serve as a means to cinch the annulus before delivery of the implant.

Figure 36:
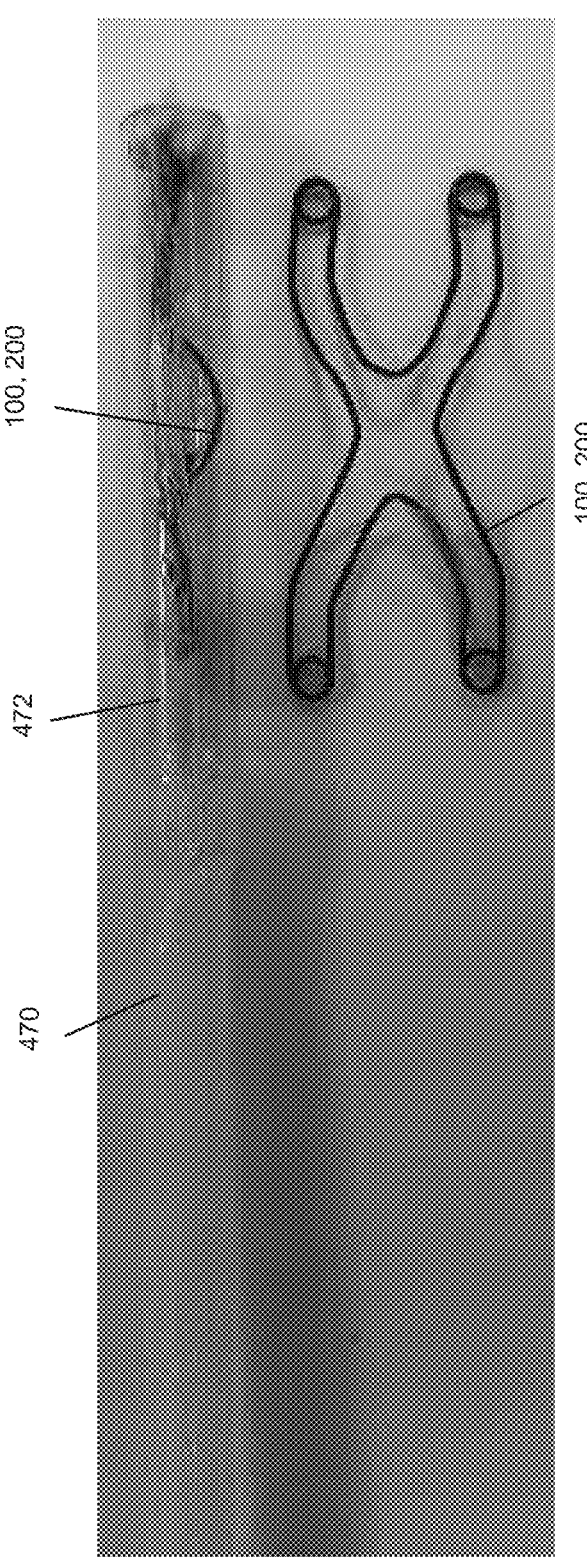
FIG. 36 is a view of an embodiment of a transvalvular implant and delivery catheter.

FIG. 36 illustrates an embodiment of the transvalvular implant delivery catheter 470. The transvalvular implant 100 can be delivered via the delivery catheter 470. The delivery catheter 470 can be 12 Fr (0.320″ 8.2 mm) inner diameter compatible. The delivery catheter 470 can be configured for single use deployment. The delivery catheter 470 can include a Pebax sheath with PTFE liner. The delivery catheter 470 can include any features described herein. The delivery catheter 470 can be configured for hemostasis with flush line. The delivery catheter 470 can include a pushrod 472. The pushrod 472 can facilitate delivery of the transvalvular implant 100. Other delivery catheter and systems are contemplated for transvalvular implants described herein.

Figures 37A, 37B, 37C, 37D:
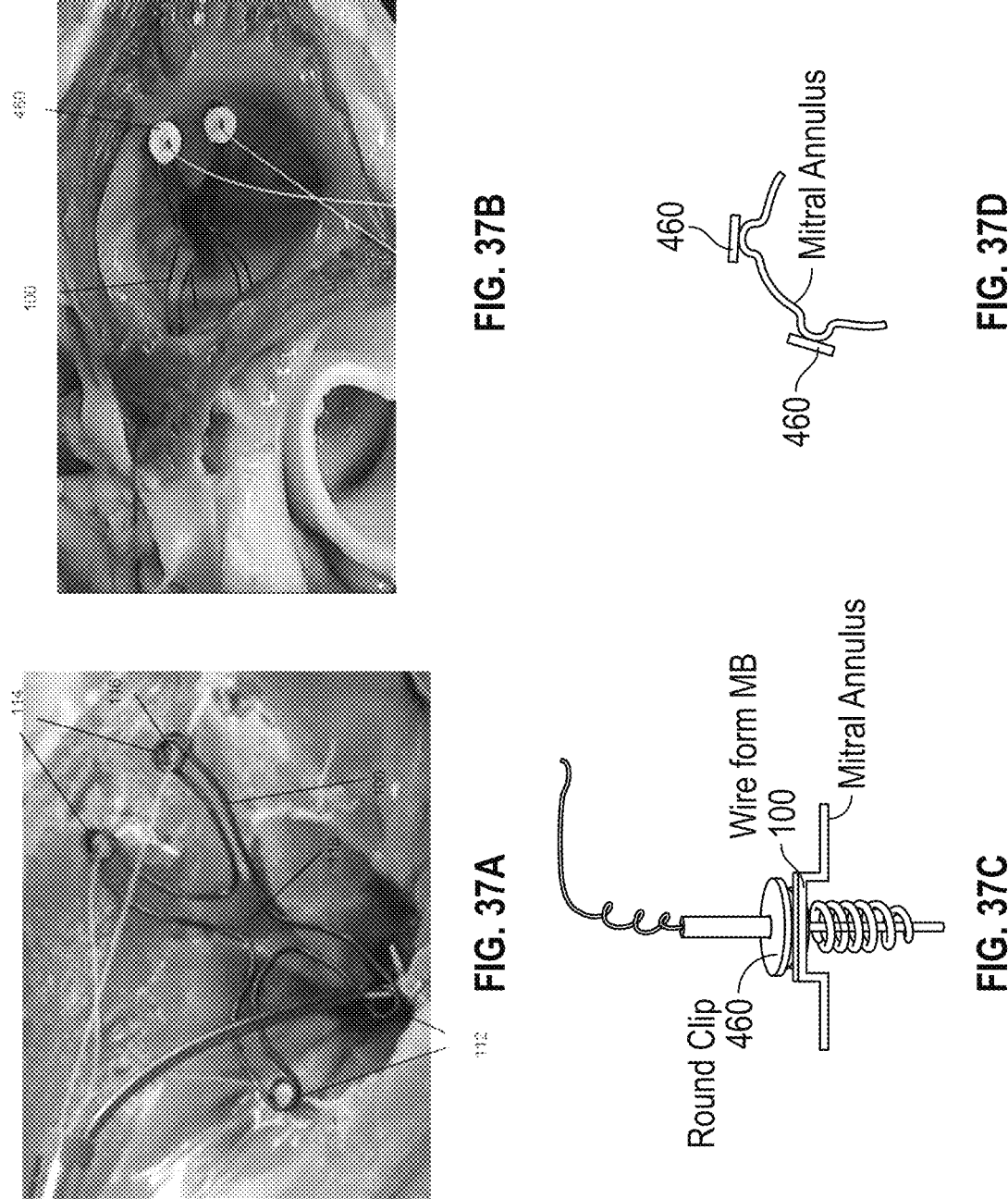
FIGS. 37A-37D are views of an embodiment of a transvalvular implant deployed.

FIGS. 37A-37D illustrates the transvalvular implant 100 in place. FIG. 37A illustrates the four deployed annular anchors. The anchors can include tethers extending proximally. The transvalvular implant 100 can include the first anchoring portion 112 and the second anchoring portion 114. The anchoring portions 112, 114 can have eyelets 116. In some methods, the eyelets 116 can accept the tethers. In some methods, the transvalvular implant 100 can be delivered with the anchors. In some methods, the tethers are threaded through the eyelets 116 of transvalvular implant 100 in situ. In some methods, the tethers are threaded through the eyelets 116 of transvalvular implant 100 outside the body. The tethers can act as guides as the transvalvular implant 100 is positioned. In some methods, the transvalvular implant 100 can be delivered after the anchors. The transvalvular implant 100 can have a central opening 118. The transvalvular implant 100 can be very low profile. The transvalvular implant 100 can straddle the valve. The transvalvular implant 100 can form an arch over the valve.

FIG. 37B illustrates the cap 460. The cap 460 can be positioned over the transvalvular implant 100. The cap 460 can couple to the central post of the hub of the anchor. In some methods, the cap 460 does not couple to the tether. The cap 460 can lock the position of the transvalvular implant 100 relative to the valve. FIGS. 37C-37D illustrates the deployment schematically. The anchor is deployed in the annulus. The anchor is deployed in the mitral annulus. The anchor is deployed in the tricuspid annulus. The central post of the hub of the anchor extends from the annulus. The central post of the hub of the anchor is coupled to the tether. The transvalvular implant 100 is positioned over the annulus. The cap 460 is positioned over the transvalvular implant 100. The cap 460 is coupled to the central post of the hub of the anchor. The cap 460 maintains the position of the transvalvular implant 100 relative to the annulus. The cap 460 maintains the position of the transvalvular implant 100 relative to the anchor. FIG. 37D illustrates two caps 460 relative to the annulus.

Figure 38:
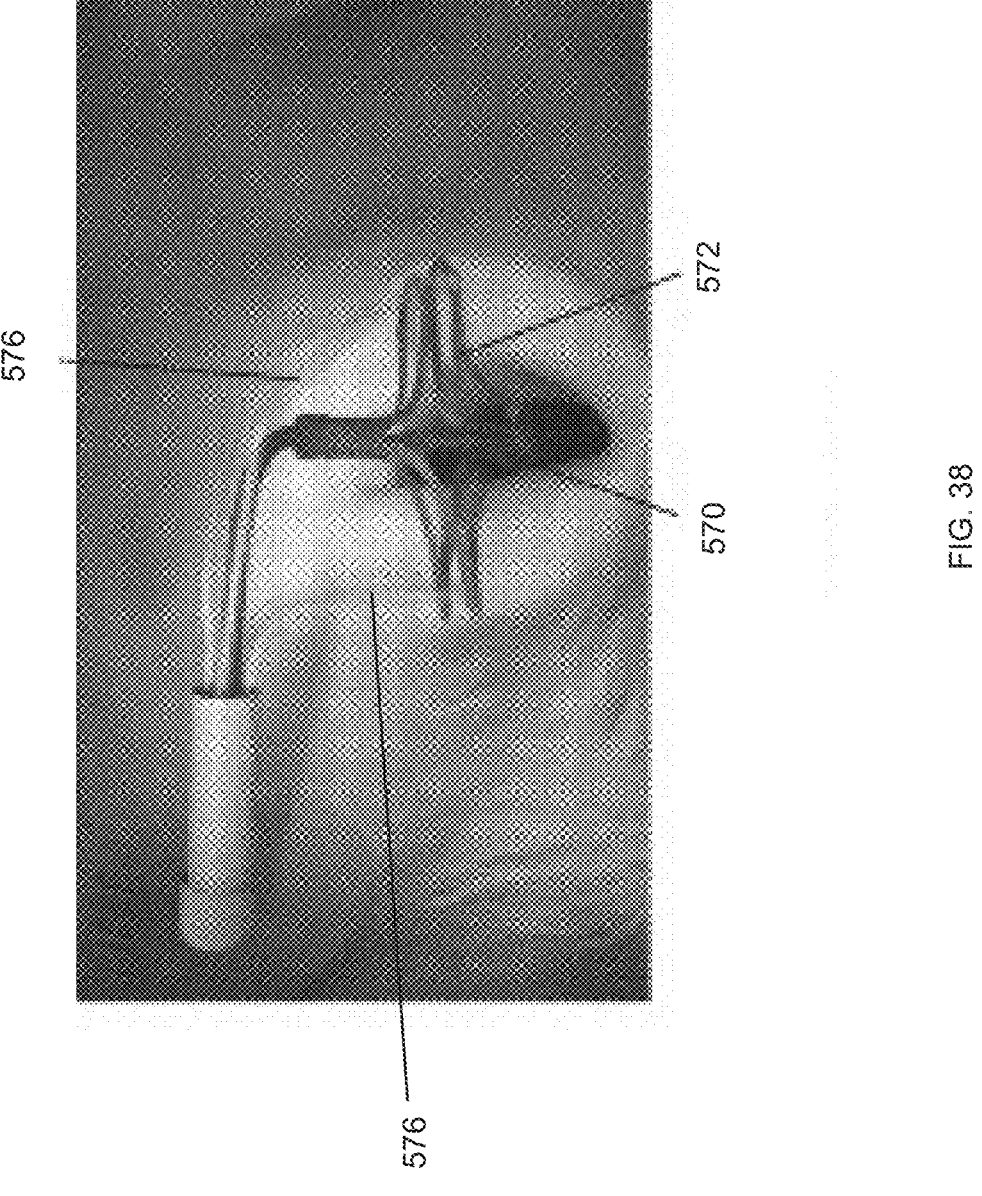
FIG. 38 is a view of an embodiment of a template catheter.

FIG. 38 illustrates an embodiment of a transcatheter system. The system can include a guide catheter to provide a transseptal conduit to, for example, the left atrium. The guide catheter can be placed in the left atrium through the transseptal access. The system can include a guide wire. The guide wire can span between the right atrium and the left atrium. The guide wire can extend from the left atrium, through the valve annulus and toward the left ventricle. While some embodiments are described in the context of the transvalvular implant, other implants that span the annulus can be utilized, and the method adapted to other valve annuli including the tricuspid, aortic, and/or pulmonic valve annuli depending on the desired clinical result.

In some embodiments, a template catheter 570 can be utilized after the guide catheter is placed. The template catheter 570 can be delivered in a compressed configuration. The template catheter 570 can be deployed in an atrium to direct the system appropriately to the valve. The template catheter 570 can be deployed in the left atrium to direct the system appropriately to the mitral valve. The template catheter 570 can be deployed in the right atrium to direct the system appropriately to the tricuspid valve. FIG. 38 illustrates the template catheter 570 being deployed according to some embodiments. The template catheter 570 can slide along the guide wire toward the valve. The template catheter 570 can slide along the guide wire toward the mitral valve. The template catheter 570 can slide along the guide wire toward the tricuspid valve. The template catheter 570 can include one or more struts 572 that fold outward as shown. In some embodiments, each strut can comprise a pair of apertures through which an anchor catheter conduit 576 passes. In the illustrated embodiment, the template catheter 570 can include four struts 572 with four corresponding anchor catheter conduits 576. The anchor catheter conduit 576 can be a flexible tube.

The template catheter 570 can be positioned across the anterior and posterior leaflets. The template catheter 570 can provide the appropriate spacing for the anchors via anchor catheter conduits 576. The anchor catheter conduits 576 can be positioned at or near the 5 o'clock, 7 o'clock, 11 o'clock, and 1 o'clock positions. In some embodiments, two anchors can be spaced apart from another two anchors along an axis of symmetry. The 5 o'clock and 7 o'clock positions can be the locations of the anchors on the posterior annulus. The 11 o'clock and 1 o'clock positions can be the locations of the anchors on the anterior annulus. Other positions are contemplated (e.g., 1 o'clock, 2 o'clock, 3 o'clock, 4 o'clock, 5 o'clock, 6 o'clock, 7 o'clock, 8 o'clock, 9 o'clock, 10 o'clock, 11 o'clock, 12 o'clock, or any range including two or more values). The template catheter 570 can be rotated relative to the guide wire to position the anchor catheter conduits 576. FIG. 38 illustrates the position of the template catheter 570 against the leaflets and the annulus, according to some embodiments. A portion of the template catheter 570 can extend toward the left ventricle and between the leaflets. The struts 572, or a portion thereof, can be positioned against the annulus. The anchor catheter conduits 576 can extend in an appropriate direction such as downward toward the annulus.

The template catheter 570 can be utilized with any anchor disclosed herein. The template catheter 570 can be utilized with any driver disclosed herein. The driver can be sized to pass through the anchor catheter conduit 576 toward the annulus. In some embodiments, the anchors can be delivered sequentially such that the driver can be removed from one anchor catheter conduit 506 after anchor delivery, and can be inserted into a second anchor catheter conduit 576 for delivery of a second anchor, until all four anchors are sequentially delivered. In other embodiments, two or more of the anchors can be delivered simultaneously. There can be four tethers extending from the four anchors according to some embodiments. In some embodiments, after all four anchors are delivered, the template catheter 570 can be removed. In some embodiments, the template catheter 570 including the anchor catheter conduit 576 can provide tether management. Each tether can extend through the anchor catheter conduit 576 such that the tethers are prevented from tangling or tangling is reduced.

In some embodiments, the annulus is cinched. In some embodiments, with the anchors in place and the tethers extending from the anchors, the annulus can be cinched, in other words, the opposing sides of the annulus can be brought closer together along part of the annulus. The cinching can confirm securement of the annular anchors. The cinching can reduce any slack in the teethers. The cinching can confirm the correct size of the transvalvular implant. The cinching can confirm the desired spacing or length between the pair of tethers associated with the posterior leaflet and the pair of tethers associated with the anterior leaflet. The length of the transvalvular implant can be selected to maintain the cinched position of the annulus. In some embodiments, tension is applied to the tethers to cinch the tethers and thus the underlying anatomy. The cinching can increase the engagement between the posterior and anterior leaflet to enhance coaptation, as described herein.

The transvalvular implant 100, 200 can be deployed after the anchors are deployed. The transvalvular implant 100, 200 can be guided into place through the guide catheter via the tethers which are permanently attached to the anchors. The transvalvular implant 100, 200 can include apertures or eyelets through which the tethers can pass. In some embodiments, each aperture can be designed to accept one tether. The first end of the transvalvular implant 100, 200 can include two apertures 116 designed to accept two tethers, respectively. The second end of the transvalvular implant 100, 200 can include two apertures 116 designed to accept two tethers, respectively. Once positioned, the transvalvular implant 100, 200 can be used in conjunction with the anchored tethers to cinch the posterior annulus toward the anterior annulus to facilitate proper leaflet coaptation. Each cap 460 can slide along the corresponding tether during delivery. The cap 460 can secure transvalvular implant 100, 200 to the anchor.

The systems and methods can include the template catheter 570. The template catheter 570 can have key attributes. The template catheter 570 can facilitates center alignment from midpoint A2 to P2. In some methods of use, the transvalvular implant 100, 200 is placed between midpoints of A2-P2. The template catheter 570 can properly position the transvalvular implant 100, 200 relative the annulus. The template catheter 570 can be scaled to fit any annular dimensions. The template catheter 570 can be scaled to fit any septal-lateral diameter (SLD). The template catheter 570 can be available in a range of sizes depending on the anatomy to be treated. The template catheter 570 can include an inter-commissural diameter. The template catheter 570 can be scaled to fit any inter-commissural diameter. The template catheter 570 can add another dimension, an inter-commissural diameter, in the template for more stability, perfect center lining alignment. The template catheter 570 can also be set in an offset diameter to cover the P #-P@ area in ischaemic mitral regurgitation (IMR) with retracted posterior leaflet. The template catheter 570 can include specificity for anchor delivery at 1, 5, 7, and 11 clock positions on the annulus. The template catheter 570 can provide stabilization of annulus during anchor delivery. The template catheter 570 can provide a counter force during anchor delivery into the annulus by holding the template. The template catheter 570 can facilitate the angle of anchor entry into the annulus. By matching the apertures on the expanded template, the angle of entry into the annulus is maintained.

The systems and methods can include system for delivering and anchoring an implant to a valve annulus. The system can include a template catheter configured to deliver an anchor to a valve annulus of a heart of a patient. The template catheter can include a pathway through which the anchor is delivered. The system can include the anchor. The system can include a driver. The system can include an implant configured to be delivered to the valve annulus. The implant can include a first anchoring portion aligned with the pathway.

Figures 39A, 39B:
FIGS. 39A-39B are views of an embodiment of a template catheter.

FIGS. 39A-39B illustrate embodiments of transcatheter systems. FIGS. 39A-39B illustrate rail road concepts for the template. The template catheter 580 can include rails 582. The template catheter 580 can include open ended annular circumference at the ends 584. The template catheter 580 can extend ¾ of the circumference at the ends 584. The template catheter 580 can include a central coaxial guide wire. The template catheter 580 can include thin blades. The template catheter 580 can have ¼ circle rails for anchor catheters or drivers. The template catheter 580 can be positioned between A2 and P2. The ends 584 can have slots for anchor catheters or drivers. The tether can be pulled to the side. FIG. 39B illustrates the compressed configuration. The template catheter 580 can include the rails 582. The template catheter 580 can include a removable collar. The template catheter 580 can have an anchor catheter entrance near the ends 514.

Figure 40B:
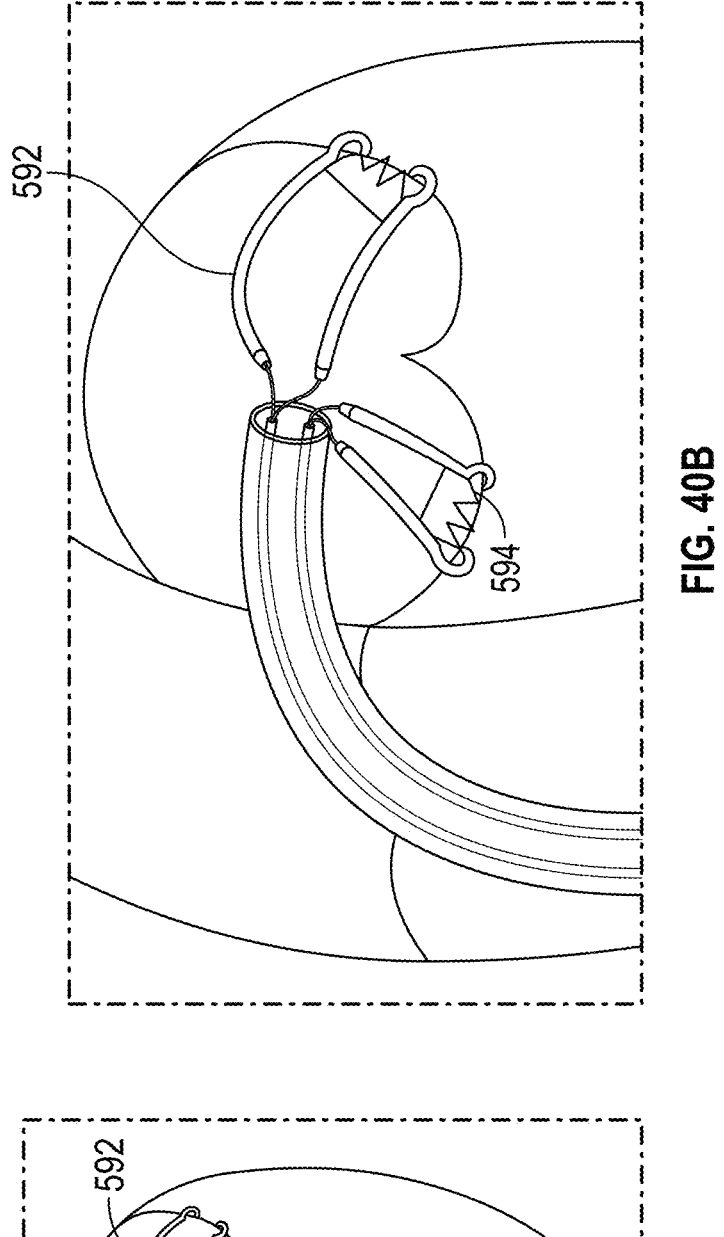
FIGS. 40A-40B are views of an embodiment of a template catheter.
Figure 40A:
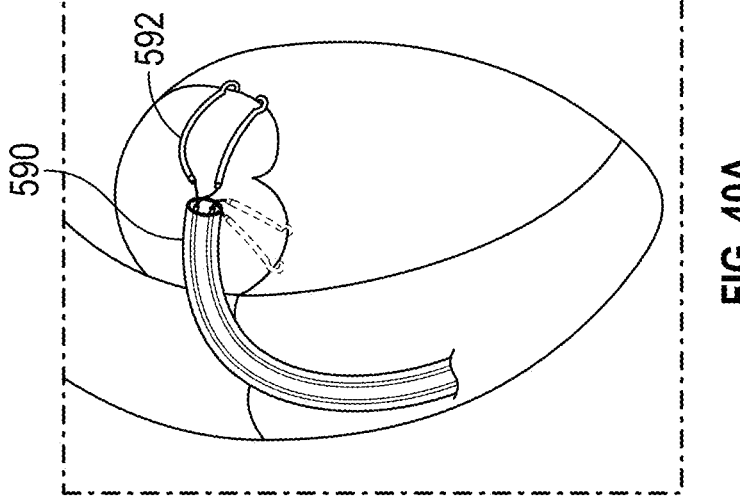

FIGS. 40A-40B illustrate embodiments of transcatheter systems. The template catheter 590 can include delivery catheters 592. All four delivery catheters 592 can expand. All four delivery catheters 592 can sit on the annulus. The template catheter 590 can include a collapsible element between the anchor points. The template catheter 590 can include feet 594. The template catheter 590 can include features to give stability.

The systems and methods can include any features or combination of features described herein. The systems and methods can include trans catheter delivery systems for implanting an arching or straddling implant on to a cardiac valve annulus for treatment of valve leak. The systems and methods can be for mitral or tricuspid valves. Methods, devices and systems can be used for implanting an arch implant straddling the valve orifice. Methods, devices and systems can be used for implanting an arch implant straddling the mitral valve orifice in a septal lateral diameter of mitral valve annulus for the treatment of mitral valve regurgitation caused by dilatation of mitral valve annulus and deformation of mitral valve leaflets. Methods, devices and systems can be used for implanting an arch implant straddling the tricuspid for the treatment of valve regurgitation caused by dilatation of valve annulus and deformation of valve leaflets. The arch implant can be made of wire form curved body with an opening in its center and the implant can straddle across the mitral valve orifice in a septal lateral diameter. The arch implant can be made of wire form curved body with an opening in its center and the implant can straddle across the tricuspid valve orifice.

Both ends of the wire implant can be anchored to the annulus by delivering it to the annulus with two anchors or more in the front and back part of the mitral annulus. The different sizes of the implant can help to reduce the septal lateral diameter of the annulus to varying degree to facilitate the closure of mitral valve leaflets. The implant can be delivered to the annulus via percutaneous access through a vein in the leg after delivering the anchors with long tethers on to the annulus and threading the implant through the tethers of the anchors outside the body and delivered via the percutaneous delivery catheters on to the mitral annulus. Locking clips can be delivered through the percutaneous catheters to hold the implant onto the anchors on the annulus.

FIGS. 41A-41C illustrate an embodiment of a transvalvular implant 600. The transvalvular implant 600 can have any feature of any implant describe herein. The transvalvular implant 600 can improve coaptation of the mitral valve leaflets and prevent or reduce mitral regurgitation. FIG. 41A is a top view of the transvalvular implant 600. FIG. 41B is a view of the transvalvular implant 600 positioned in a delivery catheter. FIG. 41C is a schematic view of the transvalvular implant 600. The transvalvular implant 600 can include a first end 602 and a second end 604. The transvalvular implant 600 can include a central portion 606. The transvalvular implant 600 can include a first anchoring portion 612 and a second anchoring portion 614. The transvalvular implant 600 can have eyelets 616. The transvalvular implant 600 can have a central opening 618. The central opening 618 can allows later trans catheter intervention with another device through the central opening 618.

The transvalvular implant 600 can include a central eyelet 616. The transvalvular implant 600 can include a pair of central eyelets 616. The first anchoring portion 612 can include a central eyelet 616. The eyelets 616 of the first anchoring portion 612 can be aligned along an axis. The eyelets 616 of the first anchoring portion 612 can be on opposite sides of the wire. The first eyelet 616 of the first anchoring portion 612 can be outwardly disposed, the central eyelet 616 of the first anchoring portion 612 can be inwardly disposed, and the third eyelet 616 of the first anchoring portion 612 can be outwardly disposed. The central eyelet 616 can be an additional anchor point if needed. The central eyelet 616 of the first anchoring portion 612 can be a rivet.

The second anchoring portion 614 can include a central eyelet 616. The transvalvular implant 600 can be symmetrical. The first anchoring portion 612 can mirror the second anchoring portion 614. The eyelets 616 of the second anchoring portion 614 can be aligned along an axis. The eyelets 616 of the second anchoring portion 614 can be on opposite sides of the wire. The first eyelet 616 of the second anchoring portion 614 can be outwardly disposed, the central eyelet 616 of the second anchoring portion 614 can be inwardly disposed, and the third eyelet 616 of second anchoring portion 614 can be outwardly disposed.

The transvalvular implant 600 comprises an elongate flexible wire formed into a shaped pattern. The transvalvular implant 600 can be formed from a single length of wire. The transvalvular implant 600 can be formed from several lengths of wire. The wire may extend from the first end 602 and the second end 604. The wire may form a complete coil to enclose the one or more eyelets 616 of the first anchoring portion 612. The wire may form a complete coil to enclose the one or more eyelets 616 of the second anchoring portion 614. The wire may form three eyelets 616 of the first anchoring portion 612. The wire may form three eyelets 616 of the second anchoring portion 614. The transvalvular implant 600 can form a continuous shape. The transvalvular implant 600 can form a closed shape.

The transvalvular implant 600 can have advantageous features. The central folds on either sides are removed. The transvalvular implant 600 can be shaped to avoid LVOT obstruction. The infra annular curvature is maintained. The eyelets 616 are enlarged to have a tight fit on anchor posts. The transvalvular implant 600 can be more robust with central rivets.

The transvalvular implant 600 can be easily folded inside the delivery catheter as shown in FIG. 41B. The transvalvular implant 600 can be easily deployed from the delivery catheter. The central eyelets 616 can be points about which the transvalvular implant 600 folds for compression within a delivery catheter. The upper and lower portions can be brought toward each other. The first and third eyelets 616 of the first anchoring portion 612 can be positioned near or adjacent to each other. The first and third eyelets 616 of the second anchoring portion 614 can be positioned near or adjacent to each other. The narrowed central portion 606 can be brought together to overlap. The transvalvular implant 600 can lengthen. The transvalvular implant 600 can be pinched together for delivery.

FIG. 41C illustrates the transvalvular implant 600 schematically. The transvalvular implant 600 can have an inter anchor distance. The distance can be measured between first and third eyelets 616 of the first anchoring portion 612. The distance can be measured between the first and third eyelets 616 of the second anchoring portion. The frame of the transvalvular implant 600 can be extended. The inter anchor distance can be 14 mm, 16 mm, 18 mm or any range of two of the foregoing values. The inter anchor distance can be extended to account for varying degrees of ischaemic mitral regurgitation (IMR) and restriction at the P3 scallop.

The wire can form a first coil or eyelet 616 of the first anchoring portion 612, extend along the side of the implant forming a pinched in shape near the central portion 606, form a first coil or eyelet 616 of the second anchoring portion 614, form the central coil or eyelet 616 of the second anchoring portion 614, form a third coil or eyelet 616 of the second anchoring portion 614, extend along the side of the implant forming a pinched in shape near the central portion 606, form a third coil or eyelet 616 of the first anchoring portion 612, form the central coil or eyelet 616 of the first anchoring portion 612, and connect with the first coil or eyelet 616 of the first anchoring portion 612. The coils or eyelets of the first anchoring portion 612 can be directly connected. The starting point and the ending point of the transvalvular implant 600 can be connected. In some embodiments, the central coil or eyelet 616 of the first anchoring portion 612 can be reinforced.

Figure 42B:
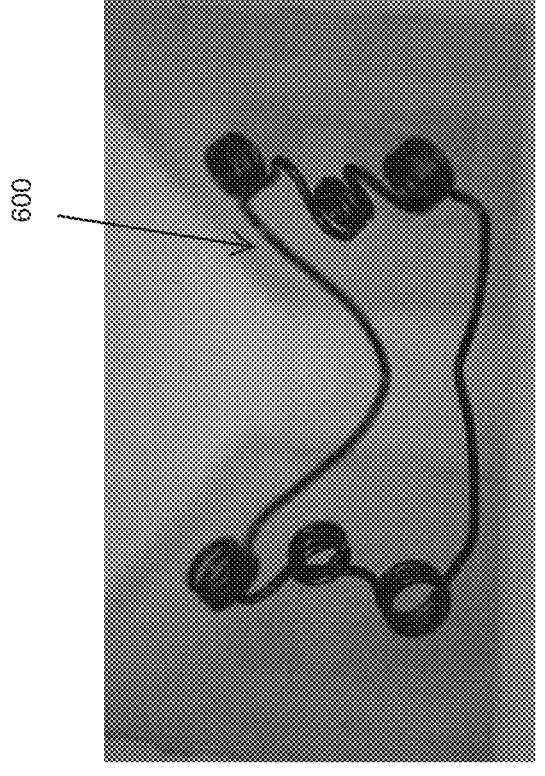
FIGS. 42A-42B are views of embodiments of a transvalvular implant.
Figure 42A:
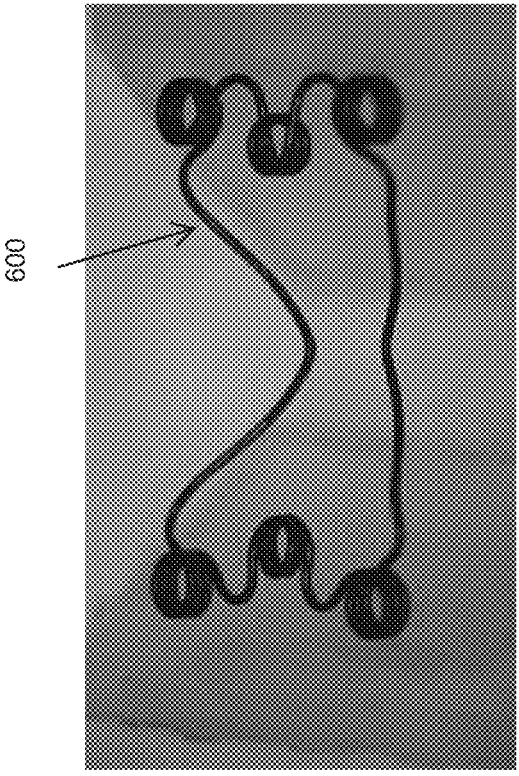

FIGS. 42A-42B illustrate an embodiment of the transvalvular implant 600. The transvalvular implant 600 can be positioned relative to the anatomy. The eyelets 616 can be in a horizontal plane in FIG. 42A. The eyelets 616 of the first anchoring portion 612 can be generally axially aligned. The eyelets 616 of the second anchoring portion 614 can be generally axially aligned. The transvalvular implant 600 can span the valve.

The eyelets 616 can be at a 45 degree angle in FIG. 42B. The transvalvular implant 600 can flex to accommodate different angles of the eyelets. The transvalvular implant 600 is aligned well to the saddle shaped mitral annulus. The transvalvular implant 600 is aligned well to the angled anchor posts. The transvalvular implant 600 can allow for changes in the eyelet angle. The angle can be 30 degrees, 35 degrees, 40 degrees, 45 degrees, 50 degrees, 55 degrees, 60 degrees, or any range of two of the foregoing values. In some embodiments, the angle is approximately 45 degrees.

Figure 43A:
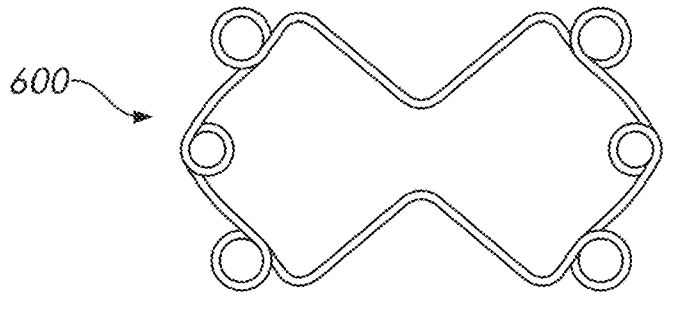
FIGS. 43A-43D are views of embodiments of a transvalvular implant.
Figure 43B:
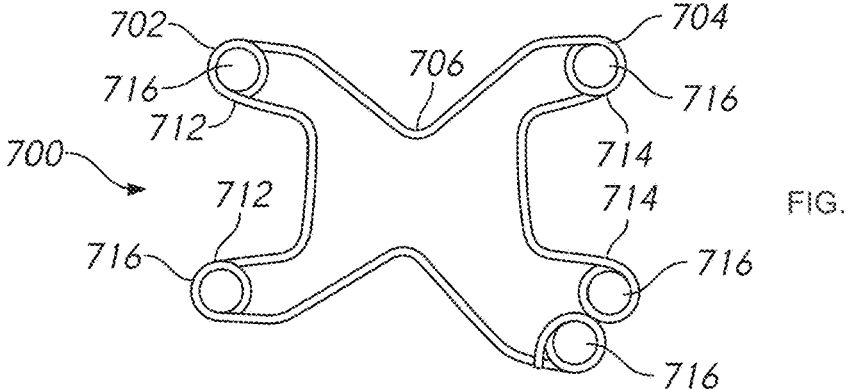
Figure 43C:
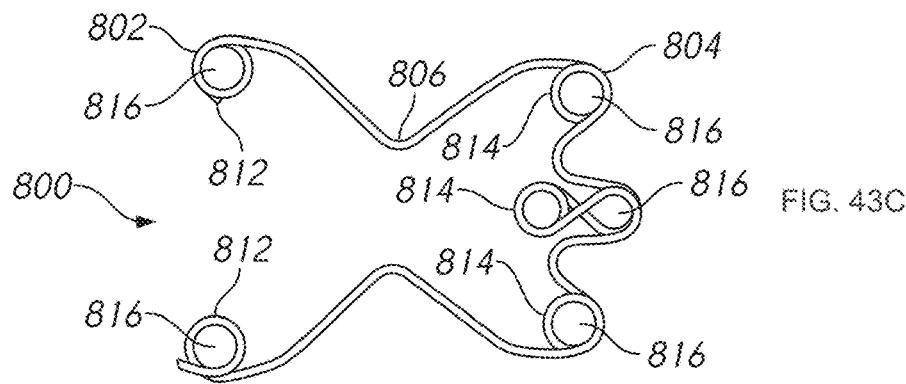
Figure 43D:
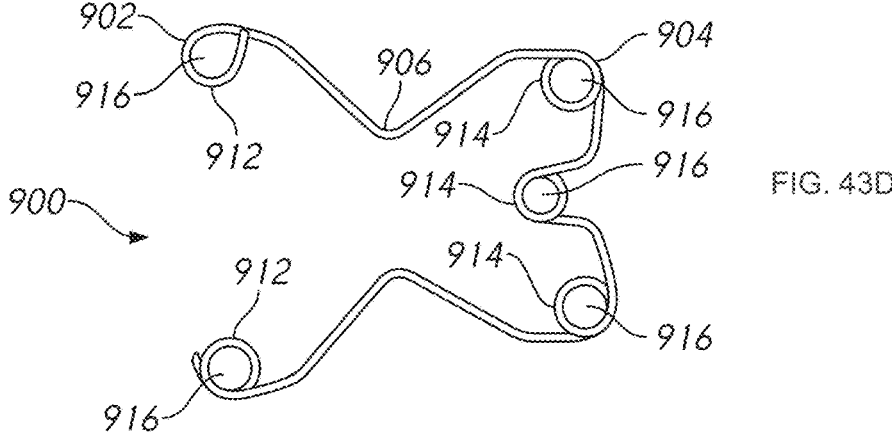

FIGS. 43A-43D illustrate embodiments of the transvalvular implant. FIG. 43A illustrates the transvalvular implant 600. FIG. 43B-43D illustrate variations to the transvalvular implant. The transvalvular implant comprises an elongate flexible wire formed into a shaped pattern. The transvalvular implant can be any shape for providing a support for the valve leaflets as discussed herein. The wire may form a coil to enclose the eyelet. The transvalvular implant can be shaped to facilitate collapsing of the implant. The transvalvular implant can encourage the sides to come toward each other. The transvalvular implant can form a continuous or discontinuous shape.

FIG. 43B illustrates a transvalvular implant 700. FIG. 43C illustrates a transvalvular implant 800. FIG. 43D illustrates a transvalvular implant 900. The transvalvular implants 700, 800, 900 can have any feature of any implant describe herein. The transvalvular implant 700, 800, 900 can include a first end 702, 802, 902 and a second end 704, 804, 904. The transvalvular implant 700, 800, 900 can include a central portion 706, 806, 906. The transvalvular implant 700, 800, 900 can include a first anchoring portion 712, 812, 912 and a second anchoring portion 714, 814, 914. The transvalvular implant 600 can have eyelets 716, 816, 916.

The transvalvular implant 700 can have two eyelets 716 for one anchoring portion. The transvalvular implant 700 can have three eyelets 716 for another anchoring portion. The additional eyelet can be utilized for anchoring to the anatomy. The wire can form a first coil or eyelet of the first anchoring portion 712, extend along the side of the implant forming a pinched in shape near the central portion 706, form a first coil or eyelet 716 of the second anchoring portion 714, extend inward and to a second coil or eyelet 716 of the second anchoring portion 714, form a third coil or eyelet 716 of the second anchoring portion 714, extend along the side of the implant forming a pinched in shape near the central portion 706, form a second coil or eyelet 716 of the first anchoring portion 712, and extend inward and connect with the first coil or eyelet 716 of the first anchoring portion 712. The coils or eyelets of the first anchoring portion 712 can be directly connected. The coils or eyelets of the second anchoring portion 714 can be directly connected. The starting point and the ending point of the transvalvular implant 700 can be connected to form a closed shape.

The transvalvular implant 800 can have two eyelets 816 for one anchoring portion. The transvalvular implant 800 can have two or more eyelets 816 for another anchoring portion. The transvalvular implant 800 can have one more central eyelets 816. The central eyelet 816 can facilitate folding of the implant. The central eyelet 816 can be for anchoring if needed. The central eyelet 816 can form a figure eight. The central eyelet 816 can include two adjacent eyelets. The wire can form a first coil or eyelet 816 of the first anchoring portion 812, extend along the side of the implant forming a pinched in shape near the central portion 806, form a first coil or eyelet 816 of the second anchoring portion 814, form the central eyelet 816 which can be a figure eight, form a third coil or eyelet 816 of the second anchoring portion 814, extend along the side of the implant forming a pinched in shape near the central portion 806, and form a second coil or eyelet 816 of the first anchoring portion 812. The coils or eyelets of the first anchoring portion 812 can be disconnected. The coils or eyelets of the second anchoring portion 814 can be directly connected. The starting point and the ending point of the transvalvular implant 800 can form an open shape.

The transvalvular implant 900 can have two eyelets 916 for one anchoring portion. The transvalvular implant 900 can have three eyelets 916 for another anchoring portion. The central eyelet can be positioned inward. The central eyelet 916 can anchor to a third location on the anatomy. The transvalvular implant 900 can have a central eyelet 916. The wire can form a first coil or eyelet 916 of the first anchoring portion 912, extend along the side of the implant forming a pinched in shape near the central portion 906, form a first coil or eyelet 916 of the second anchoring portion 914, form the central eyelet 916 of the second anchoring portion 914, form a third coil or eyelet 916 of the second anchoring portion 914, extend along the side of the implant forming a pinched in shape near the central portion 906, and form a second coil or eyelet 916 of the first anchoring portion 912. The coils or eyelets of the first anchoring portion 912 can be disconnected. The first coil or eyelet 916 of the second anchoring portion 914 can be inward. The central eyelet 916 can be outward. The third coil or eyelet 916 of the second anchoring portion 914 can be inward. The coils or eyelets of the second anchoring portion 914 can be directly connected. The starting point and the ending point of the transvalvular implant 900 can form an open shape.

Figure 44A:
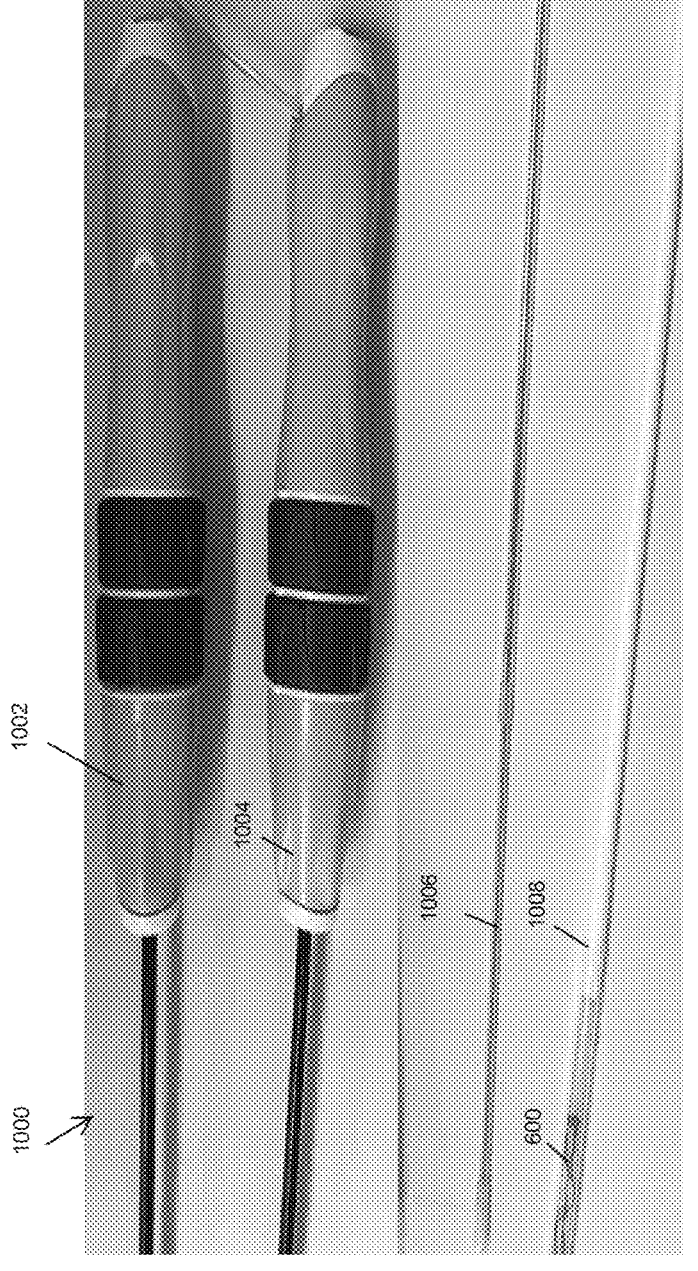
FIG. 44A is a view of an embodiment of a catheter delivery system.
Figure 44B:
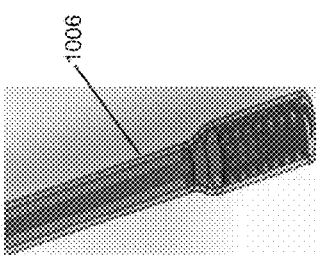
FIG. 44B is a view of an embodiment of an anchor and delivery catheter.

FIG. 44A illustrates a catheter delivery system 1000 for the transvalvular implant. A guide catheter 1002 can be provided. The guide catheter 1002 can be 24 Fr. Other sizes are contemplated. The guide catheter 1002 can be utilized as a trans septal conduit to the left atrial cavity. An annular steering catheter 1004 can be provided. The annular steering catheter 1004 can be 16 Fr. Other sizes are contemplated. The annular steering catheter 1004 can be steerable to the annulus. The annular steering catheter 1004 can be steerable to the mitral annulus. The annular steering catheter 1004 can be steerable to the tricuspid annulus. An anchor delivery catheter 1006 can be provided. The anchor delivery catheter 1006 can be 12 Fr. Other sizes are contemplated. The anchor delivery catheter 1006 can deliver the anchors to the annulus. The anchor delivery catheter 1006 can have any features of the anchor delivery catheters described herein. The anchor can be preloaded inside the anchor delivery catheter 1006, as shown in FIG. 44B. A multi-lumen bridge delivery catheter 1008 can be provided. The multi-lumen bridge delivery catheter 1008 can be 18 Fr. Other sizes are contemplated. The multi-lumen bridge delivery catheter 1008 can deliver the transvalvular implant. The transvalvular implant 600 is illustrated in FIG. 44A but the catheter delivery system 1000 can deliver any implant described herein The multi-lumen bridge delivery catheter 1008 can secure the transvalvular implant. The catheters can be removed and the procedure finished after the transvalvular implant is secured. The catheter delivery system 1000 can be ergonomically easy to use. The catheter delivery system 1000 can simplify and reduce procedure times. The catheter delivery system 1000 can include catheter sizes and additional functionality of commercial systems.

Figure 45:
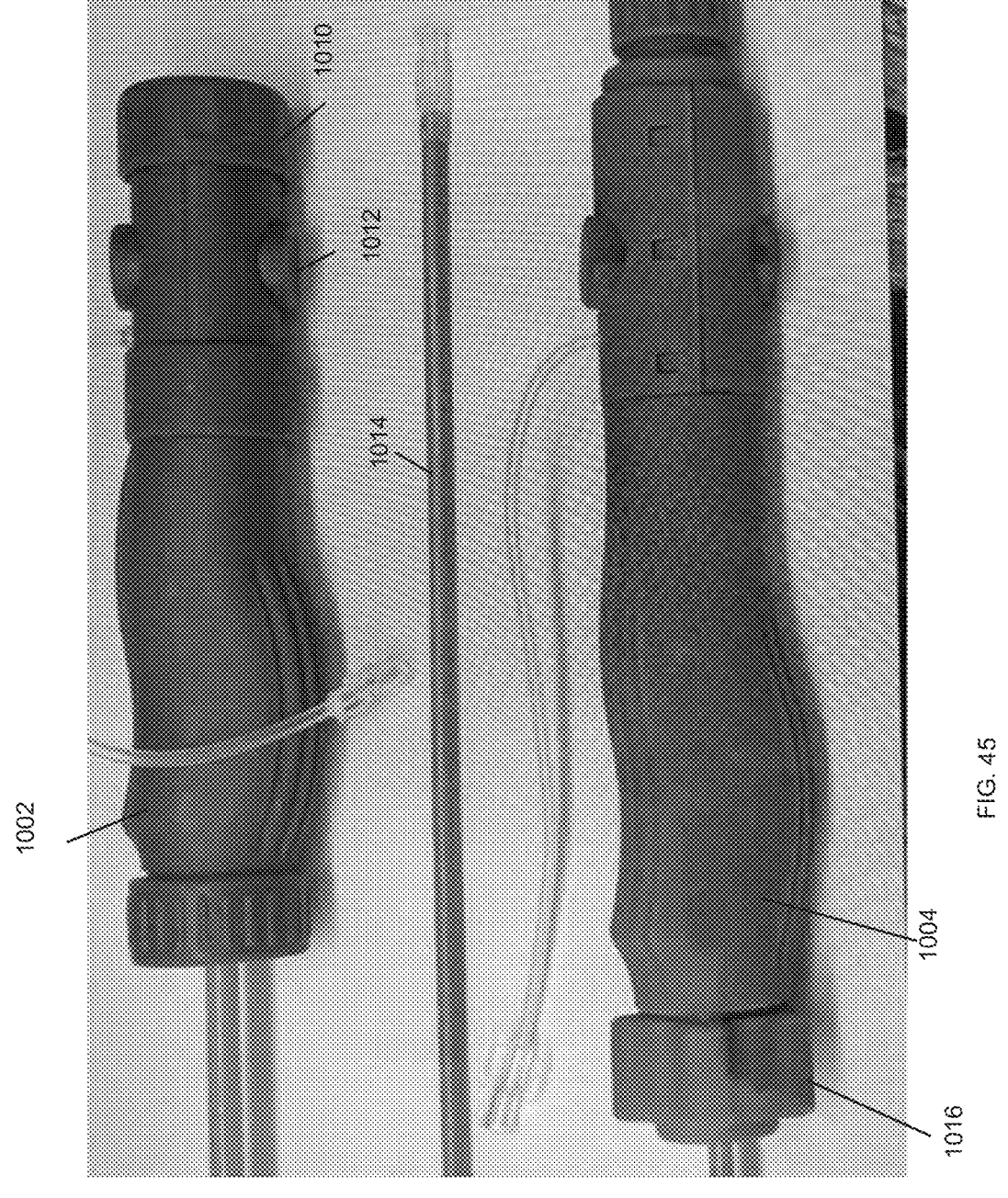
FIG. 45 is a view of an embodiment of catheters.

FIG. 45 illustrates the guide catheter 1002 and the annular steering catheter 1004. The catheter can include a hemostasis valve 1010. The catheter can include a pinch valve for hemostasis 1012. The catheter can include a guide catheter dilator 1014. The catheter can include a control knob 1016.

Figure 46:
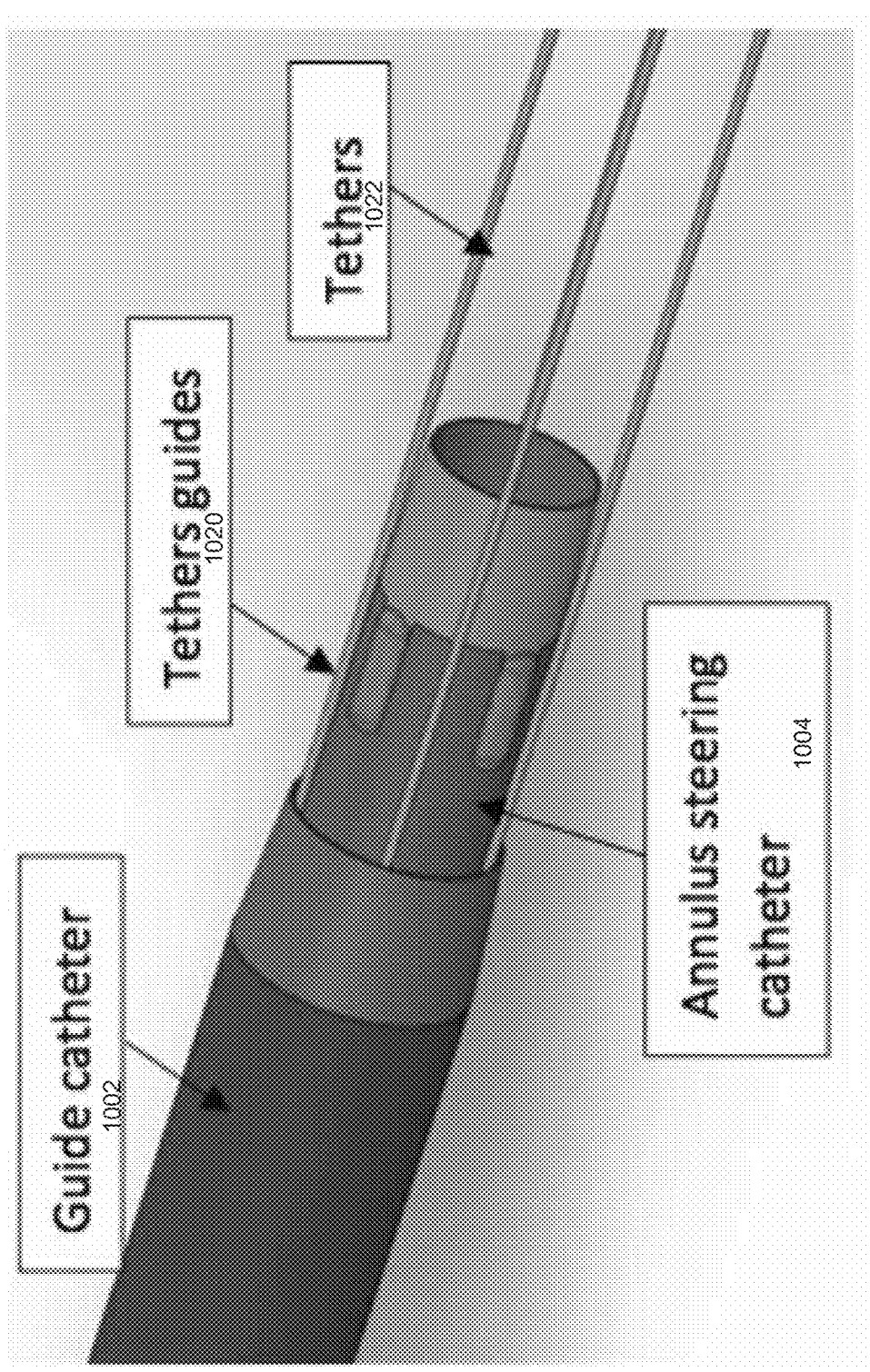
FIG. 46 is a view of an embodiment of catheters.

FIG. 46 illustrates the guide catheter 1002 and the annular steering catheter 1004. The catheter delivery system 1000 can include tether guards or guides 1020. The tether guards 1020 can prevent tangling of tethers 1022 during anchor delivery. The annular steering catheter 1004 can include the tether guards or guides 1020. The tether guards or guides 1020 can be on an outer surface of the annular steering catheter 1004. The guide catheter 1002 an include the tether guards or guides 1020. The tether guards or guides 1020 can be on an inner surface of the guide catheter 1002. The tether guards or guides 1020 can be grooves or channels that separate the tethers 1022.

Figure 47:
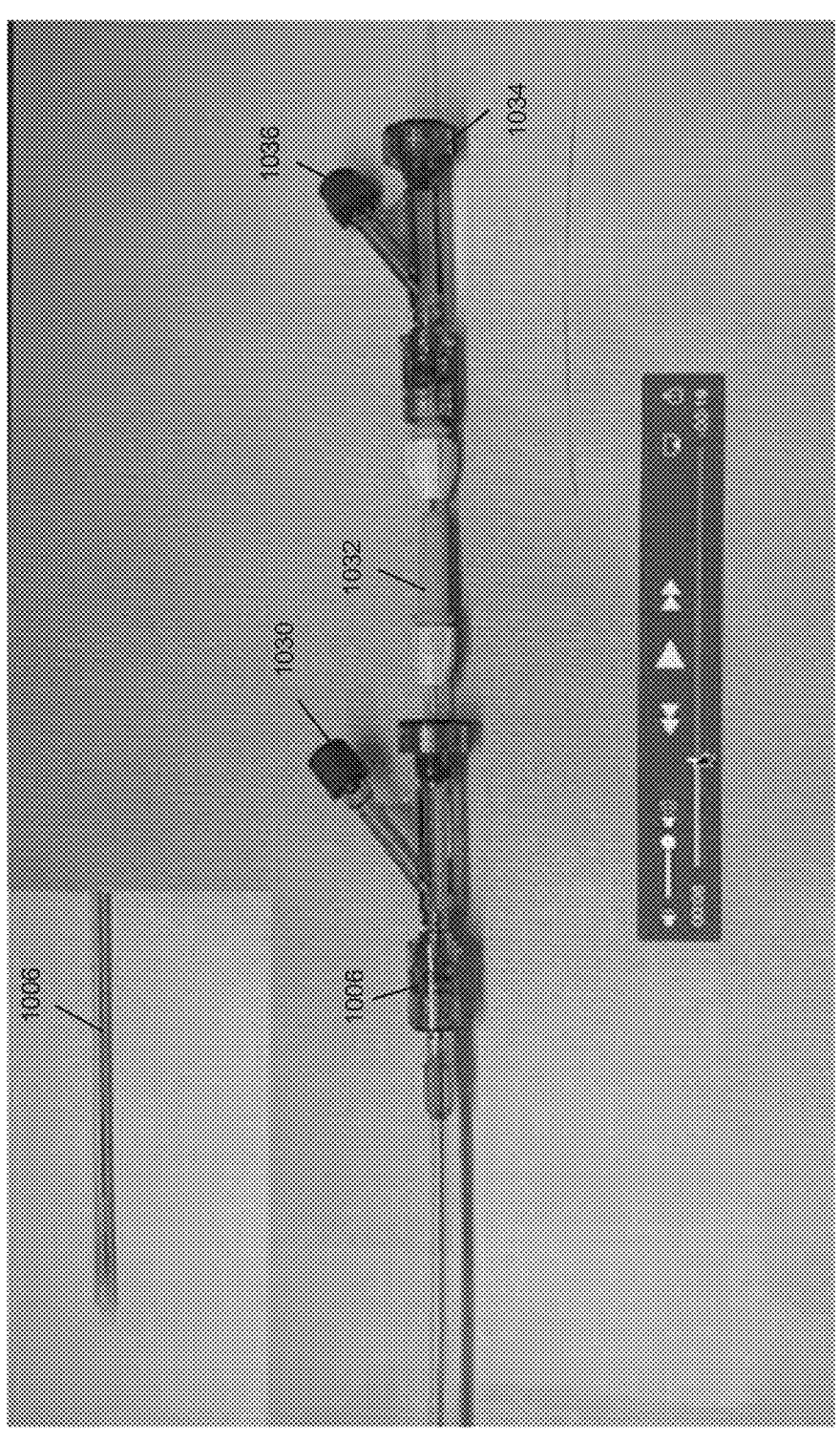
FIG. 47 is a view of an embodiment of a catheter.

FIG. 47 illustrate the anchor deployment system. The anchor delivery catheter 1006 can deliver an anchor to the annulus. The anchor can be disposed inside the anchor delivery catheter 1006. The distal end of the anchor delivery catheter 1006 is shown in the top left corner. The proximal end of the anchor delivery catheter 1006 is also shown. The anchor delivery catheter 1006 can include a hemostatic valve 1030. The anchor delivery catheter 1006 can include an anchor deployment travel indicator 1032. The anchor deployment travel indicator 1032 can provide a visual representation of how deep the anchor has traveled relative to the anchor delivery catheter 1006. The anchor delivery catheter 1006 can include anchor tension lock 1034. The anchor delivery catheter 1006 can include a hemostatic valve 1036.

Figure 48:
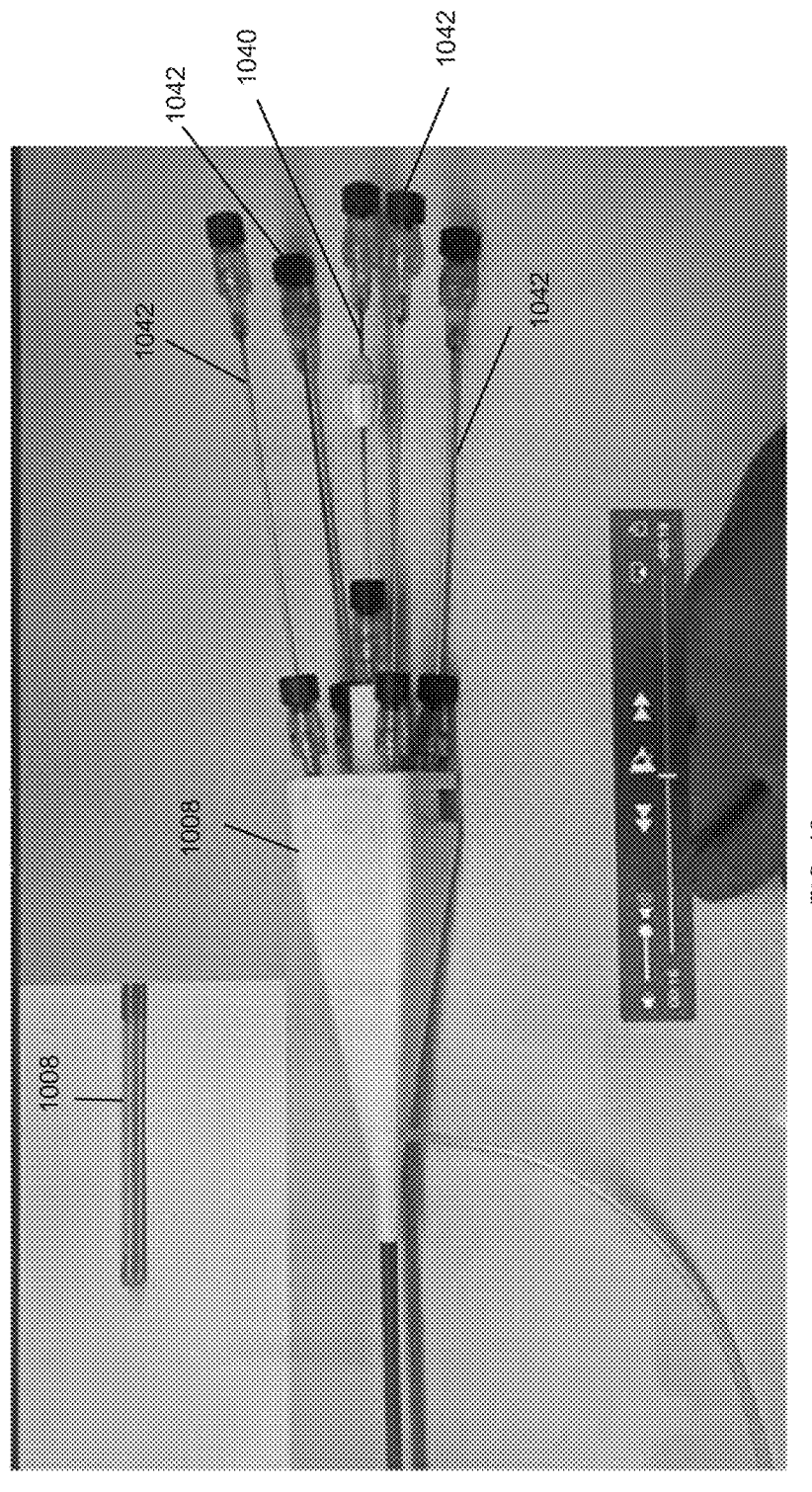
FIG. 48 is a view of an embodiment of a catheter.

FIG. 48 illustrates the bridge deployment system. The multi-lumen bridge delivery catheter 1008 can be provided. The transvalvular implant can be disposed inside the multi-lumen bridge delivery catheter 1008. The distal end of the multi-lumen bridge delivery catheter 1008 is shown in the top left corner. The proximal end of the multi-lumen bridge delivery catheter 1008 is also shown. A pusher rod 1040 can be provided. The pusher rod 1040 can be for transvalvular implant deployment. The pusher rod 1040 can push the transvalvular implant from the catheter. A plurality of pusher rods 1042 can be provided. In some embodiments, four pusher rods 1042 can be provided. The pusher rods 1042 can be for bridge and clip anchor attachments. Each pusher rod 1042 can push a clip toward the transvalvular implant. The clip can slide along the tether of an anchor. The clip can secure the transvalvular implant to the anchor. The clip, the tether, and/or the anchor can have any of the features described herein. The multi-lumen bridge delivery catheter 1008 can include a lumen for the pusher rod 1040. The multi-lumen bridge delivery catheter 1008 can include a lumen each pusher rod 1042.

Figure 49:
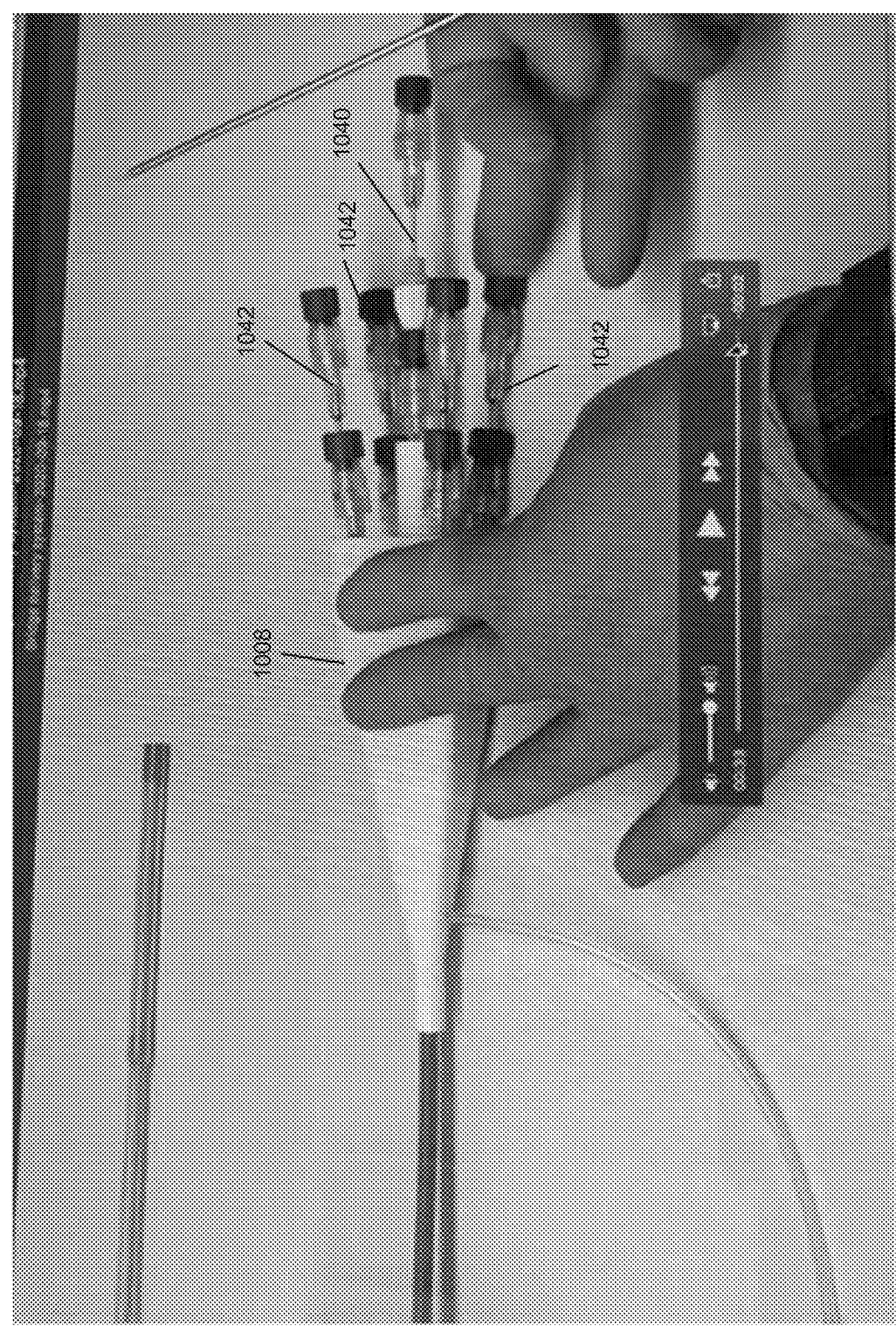
FIG. 49 is a view of an embodiment of a catheter.

FIG. 49 illustrates the fully deployed transvalvular implant. The pusher rod 1040 can be pushed toward the distal end of the catheter. Each pusher rod 1042 can be pushed toward the distal end of the catheter. In this positon, the transvalvular implant is deployed and positioned relative to the anchors. In this positon, the clips are deployed and positioned relative to the transvalvular implant. The clips secure the transvalvular implant.

Figure 50A:
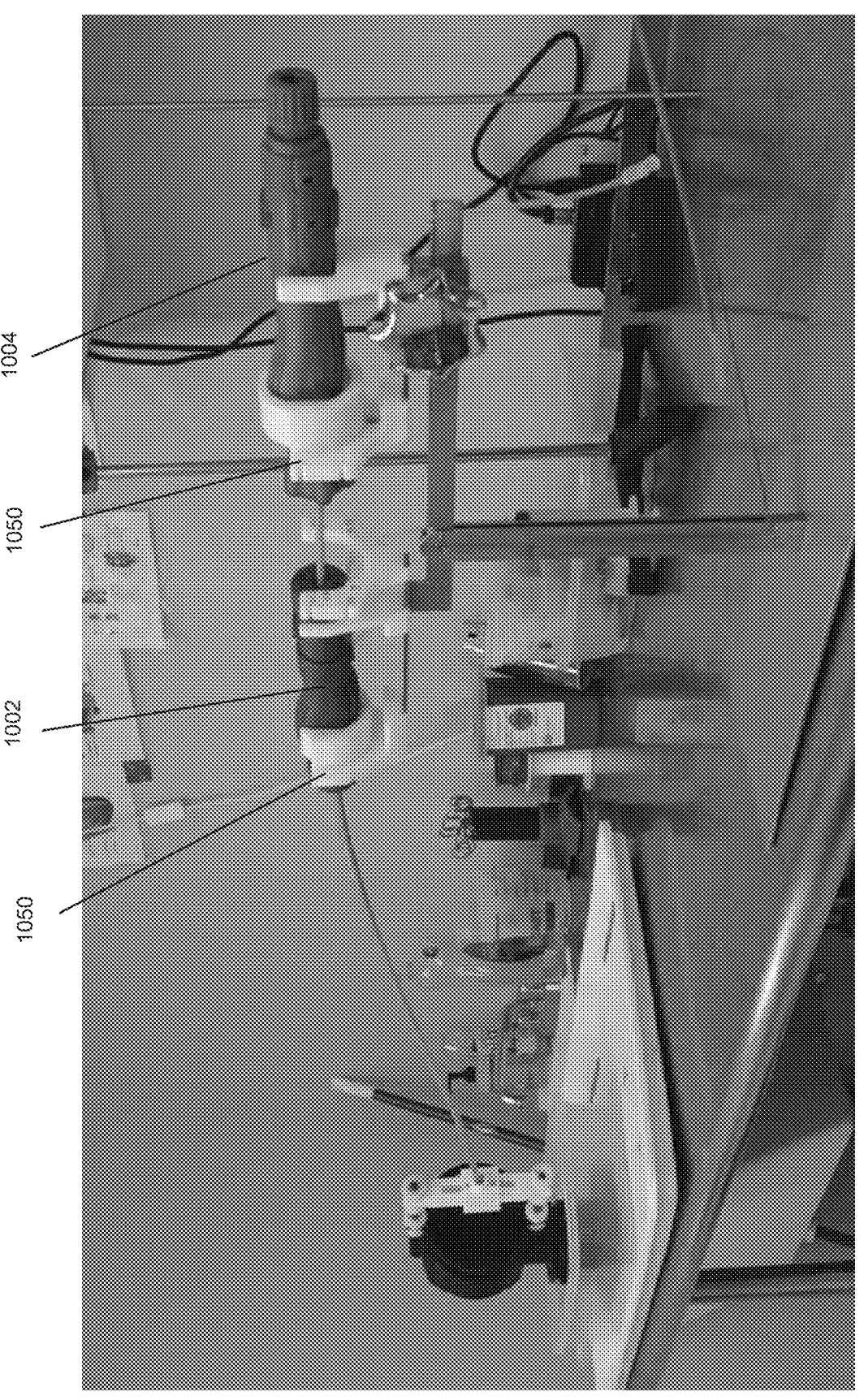
FIGS. 50A-50B is a view of additional components of an embodiment of a catheter delivery system.
Figure 50B:
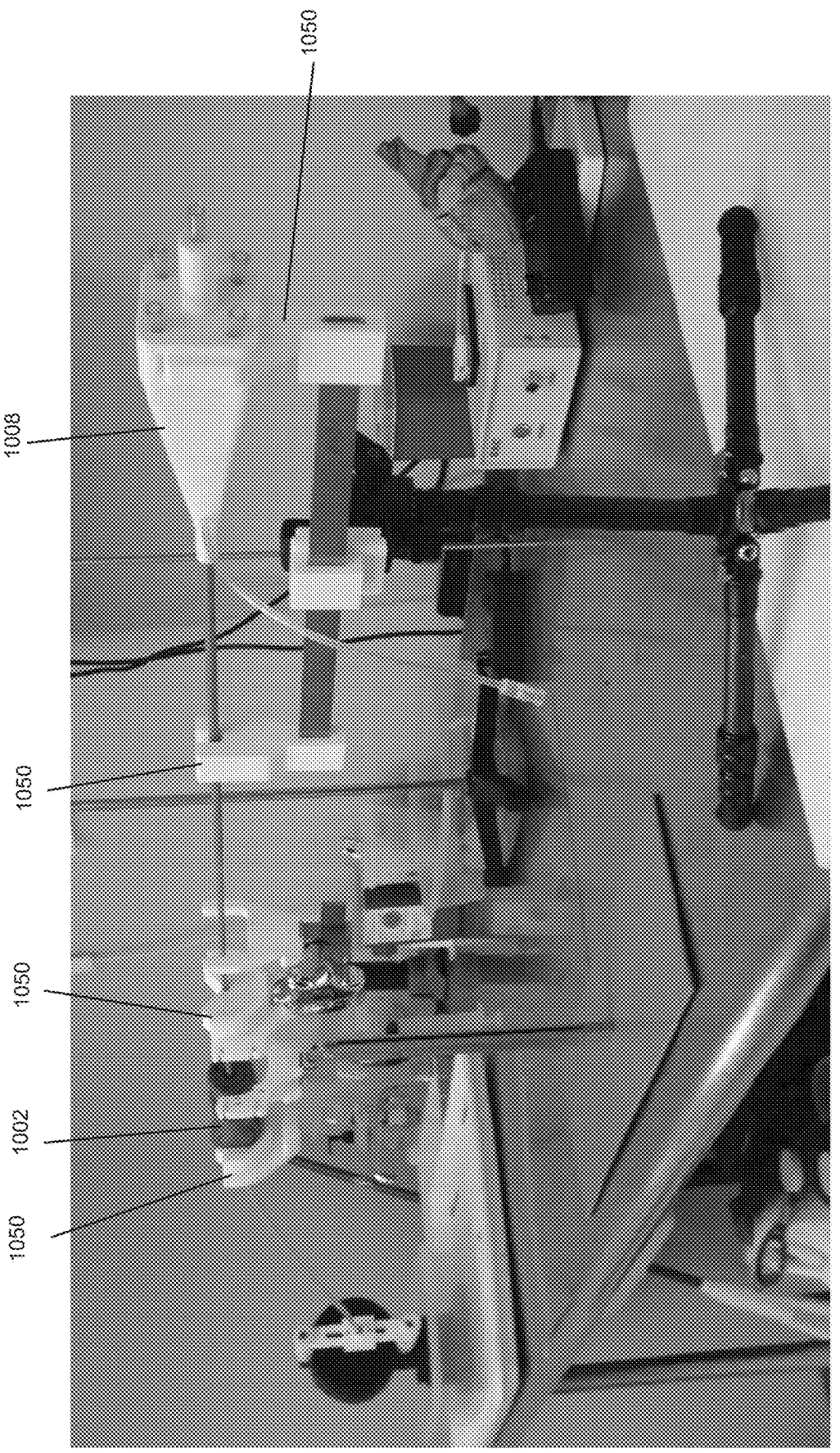

FIGS. 50A-50B illustrates additional components of the catheter delivery system 1000. The catheter delivery system 1000 can include sled holders 1050. The sled holders 1050 can support the guide catheter 1002. The sled holders 1050 can support the annular steering catheter 1004. The sled holders 1050 can support the anchor delivery catheter 1006. The sled holders 1050 can support the multi-lumen bridge delivery catheter 1008.

FIG. 51A-51G illustrate embodiments of clips. The clips can have any features of the caps or clips described herein. The system can include a clip. The clip can be a push-on cap. The clip can be round. The clip can function as a locking clip to hold the transvalvular implant in position. The clip can be positioned over the central post of a hub of an anchor. The clip can be pushed on the central post of the hub. The clip can be guided by a suture coupled to the anchor.

Figures 51A, 51B, 51C:
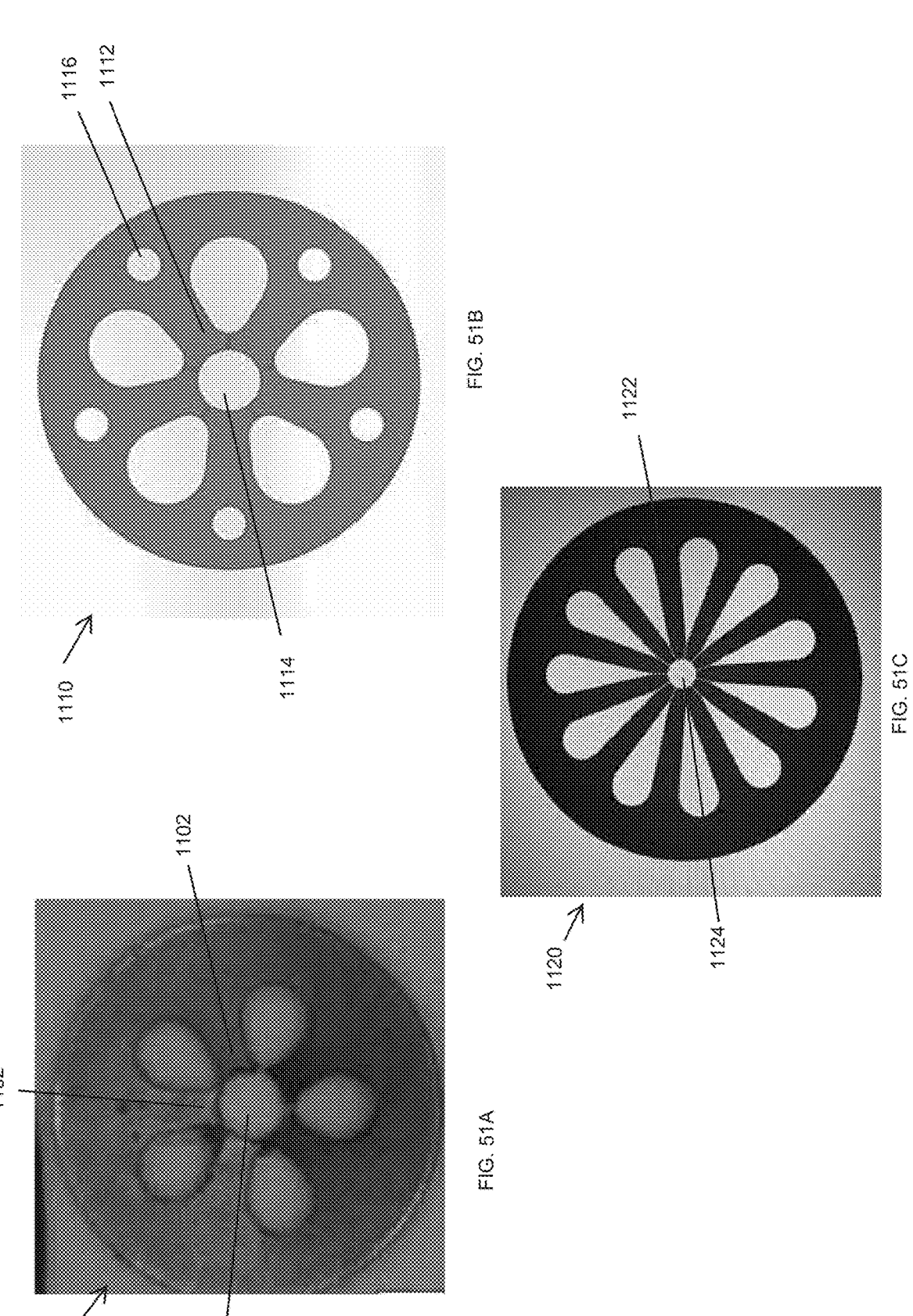
FIG. 51A-51G are views of embodiments of clips.

FIG. 51A illustrates an embodiment of a clip 1100. The clip 1100 can be an uncoated clip. The clip 1100 can have five point contact. The clip 1100 can have a round anchor contact point. The clip 1100 can have five flanges 1102 which surround a central opening 1104. The five flanges 1102 contact the anchor post to couple the clip 1100 to the anchor. The central opening 1104 can include a shape and size complementary to the central post of the anchor. The central opening 1104 can be circular, oval or rounded. The central opening 1104 can be polygonal such as triangular, square or rectangular. Other shapes are contemplated.

FIG. 51B illustrates an embodiment of a clip 1110. The clip 1110 can include can have five flanges 1112 which surround a central opening 1114. The clip can have additional cutouts or openings 1116. The additional cutouts or openings can change the flexibility of the clip. The additional cutouts or openings can reduce the weight of the clip.

FIG. 51C illustrates an embodiment of a clip 1120. The clip 1120 can include a plurality of flanges 1122 which surround a central opening 1124. The clip 1120 can have eleven flanges 1122. The clip 1120 can have any number of flanges including three, four, five, six, seven, eight, nine, ten, eleven, twelve, thirteen, fourteen, fifteen, or any range of two of the foregoing values.

Figures 51D, 51E:
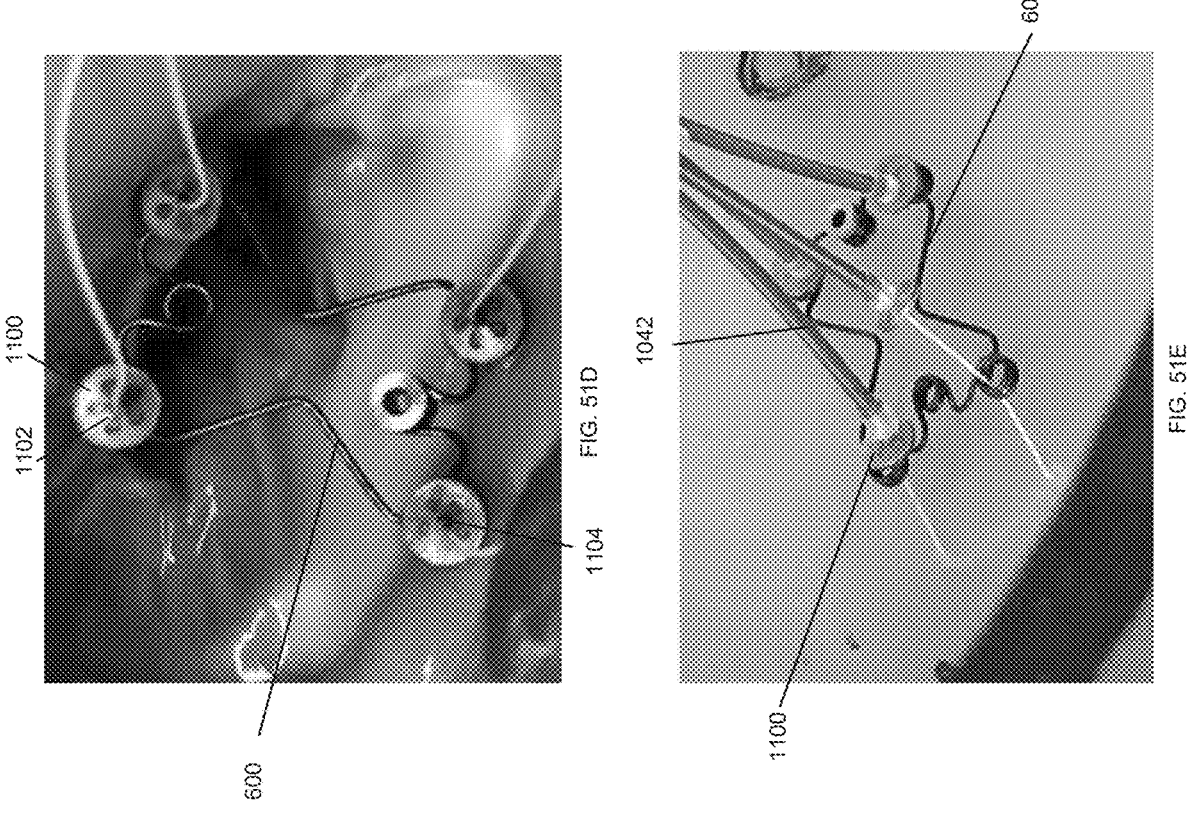

FIG. 51D illustrates the clip 1100 positioned relative to the transvalvular implant 600. The transvalvular implant 600 can be locked in by the round contact point clip. In the illustrated embodiment, four anchors are implanted in the heart. The sutures extend from the anchors. The transvalvular implant 600 is slid along the sutures toward the anchors. The central posts of the anchors extend through the corresponding eyelets. Each clip 1100 is slid along a respective suture toward an anchor. The flanges 1102 form the central opening 1104. The central opening 1104 tightly fits onto the central post of the anchor, thereby securing the transvalvular implant 600. The clips can provide permanent securement for the transvalvular implant 600.

FIG. 51E illustrates the clip 1100 positioned relative to the transvalvular implant 600 during deployment of the clip 1100. Each pusher rod 1042 can push the clip 1100 toward the transvalvular implant 600. The pusher rod 1042 slides the clip 1100 toward the anchor. The pusher rod 1042 provides force to snap the clip 1100 onto the post of the anchor. Each pusher rod 1042 slides along a respective suture or tether. Each pusher rod 1042 can prevent tangling of the sutures.

Figures 51F, 51G:
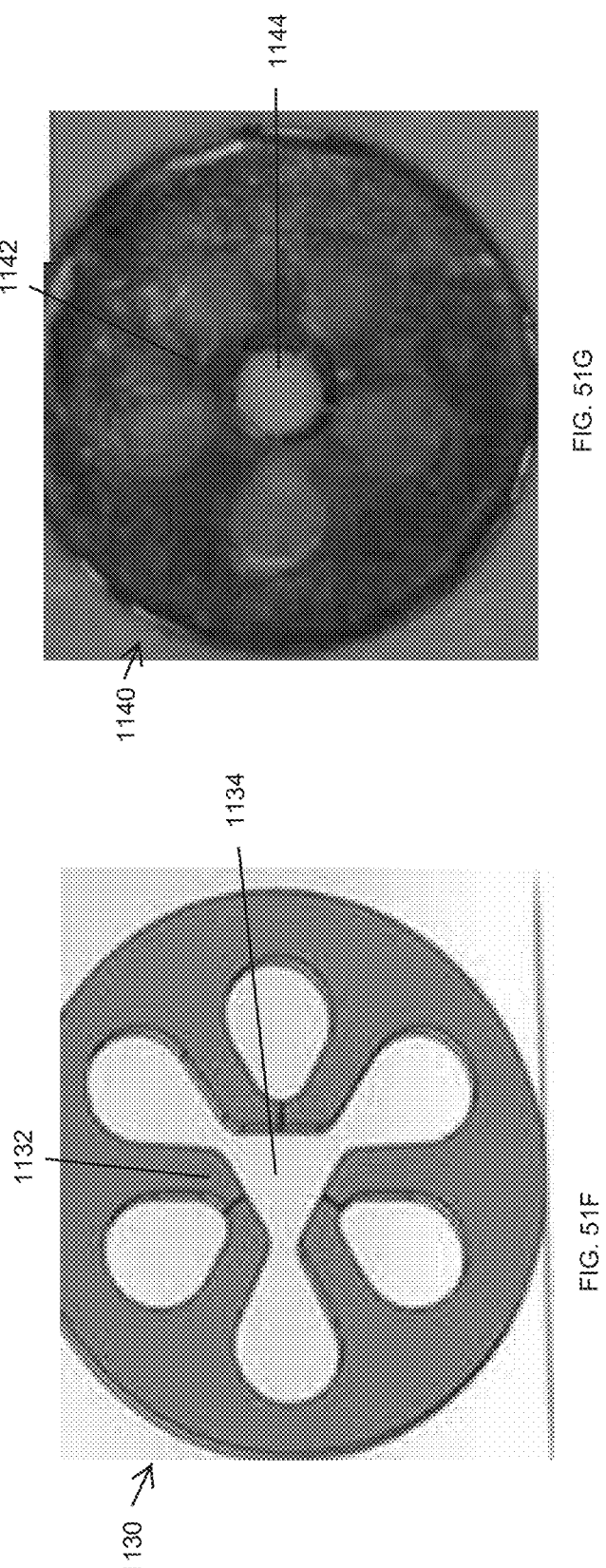

FIG. 51F illustrates an embodiment of a clip 1130. The clip 1130 can have a plurality of flanges 1132 which surround a central opening 1134. The opening 1134 can be generally triangular. The opening 1134 can have three flat edges. The triangular shape can be formed by the flanges 1132. The flanges 1132 can have an irregular shape. The clip 1130 can have six flanges 1132. The clip 1130 can have any number of flanges. A pair of flanges forms a triangular contact point. The triangular contact point can maximize holding force. The triangular contact point can decrease push force in some embodiments.

FIG. 51G illustrates an embodiment of a clip 1140. The clip 1140 can include a plurality of flanges 1142 which surround a central opening 1144. The clip 1140 can include lamination on both sides of clip 1140. The lamination can prevents tether snagging during deployment. The clips described herein can be uncoated, coated or laminated on one side, or coated or laminated on both sides.

Figure 52:
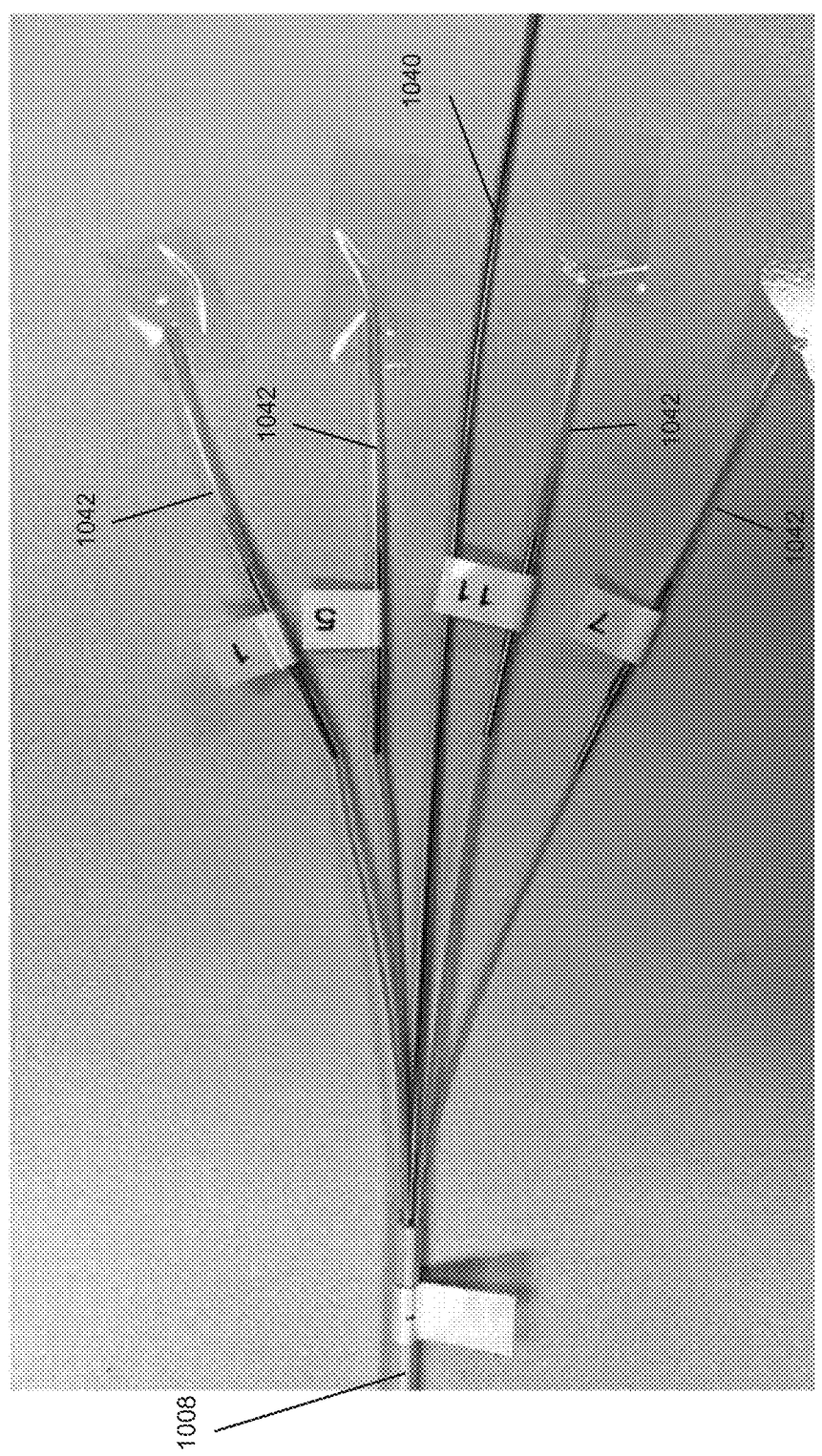
FIG. 52 is a view of an embodiment of a catheter.

FIG. 52 illustrates the distal section of the multi-lumen bridge delivery catheter 1008. The pusher rod 1040 can be for transvalvular implant deployment. The pusher rods 1042 can be for clip deployment. Each pusher rod 1042 can push a clip toward the transvalvular implant. In some embodiments, the pusher rods can be strengthened. More column strength can be provided by adding an Ultem® sleeve to inside or outside of push tube. Ultem® is a high strength plastic material. The coating or sleeve can enhance the ability of the pusher rod 1040, 1042 to apply a force to the transvalvular implant and/or clip.

Figure 53:
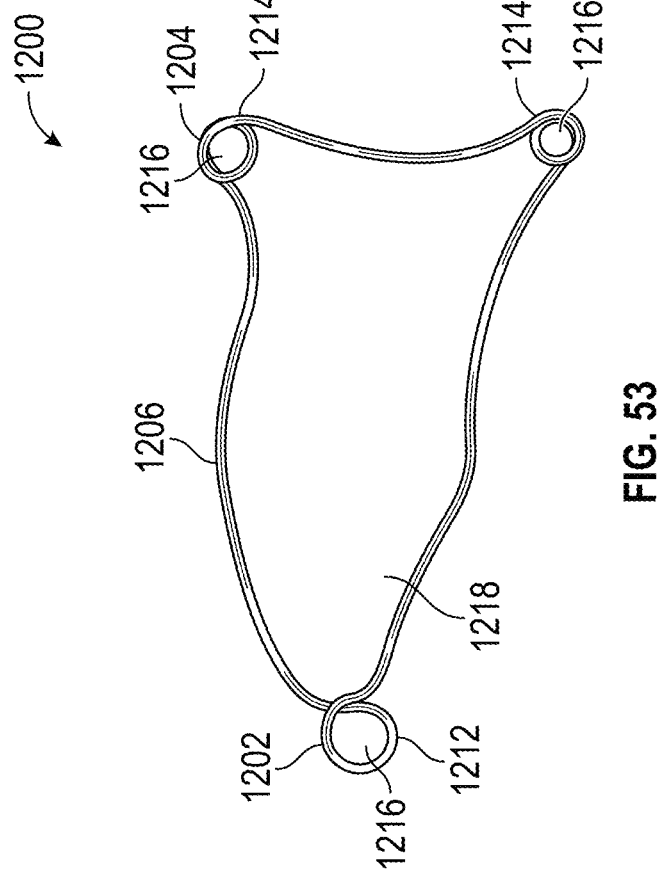
FIG. 53 is a view of an embodiment of a transvalvular implant.

FIG. 53 illustrate an embodiment of a transvalvular implant 1200. The transvalvular implant 1200 can have any feature of any implant describe herein. The transvalvular implant 1200 can include a first end 1202 and a second end 1204. In some embodiments, the first end 1202 is an anterior end. In some embodiments, the second end 1204 is a posterior end. The transvalvular implant 1200 can include a central portion 1206. The transvalvular implant 1200 can include a first anchoring portion 1212 and a second anchoring portion 1214. The transvalvular implant 1200 can have eyelets 1216. The transvalvular implant 1200 can have a central opening 1218. The central opening 1218 can allows catheters, tools, or other devices to pass through the central opening 1218.

The transvalvular implant 1200 can include a total of three eyelets. The first anchoring portion 1212 can include a central eyelet 1216. The second anchoring portion 1214 can include a pair of eyelets 1216. The transvalvular implant 1200 can be asymmetrical. The transvalvular implant 1200 comprises an elongate flexible wire formed into a shaped pattern. The transvalvular implant 1200 can be formed from a single length of wire. The transvalvular implant 1200 can be formed from several lengths of wire. The wire may extend from the first end 1202 to the second end 1204. The wire may form a complete coil to enclose the one or more eyelets 1216. The transvalvular implant 1200 can form a continuous shape. The transvalvular implant 1200 can form a closed shape.

The wire can form coil or eyelet 1216 of the first anchoring portion 1212, extend along the side of the implant forming a generally tapered shape near the central portion 1206, form a first coil or eyelet 1216 of the second anchoring portion 1214, form a second coil or eyelet 1216 of the second anchoring portion 1214, extend along the side of the implant forming a generally tapered shape near the central portion 1206, and connect with the coil or eyelet 1216 of the first anchoring portion 1212. The starting point and the ending point of the transvalvular implant 1200 can be connected. The transvalvular implant 1200 can be generally triangular.

The first anchoring portion 1212 can include a single anchor location. The first anchoring portion 1212 can include a single eyelet. The single eyelet can be centrally located. The first anchoring portion 1212 can be configured to be positioned anteriorly. The second anchoring portion 1214 can include two anchor locations. The second anchoring portion 1214 can include a pair of eyelets. The second anchoring portion 1214 can be configured to be positioned posteriorly. The transvalvular implant 1200 can be implanted with a bifid catheter to deliver two anchors. The catheter can have a bifid partial template as a facilitating tool. The transvalvular implant 1200 can have a template to facilitate placement of the anchors associated with the second anchoring portion 1214. The transvalvular implant 1200 can have a template to facilitate placement of the anchors associated with the first anchoring portion 1212 and the second anchoring portion 1214. The transvalvular implant 1200 can facilitate easier anchor implantation. The transvalvular implant 1200 can facilitate easier implant delivery. The transvalvular implant 1200 can reduce the number of anchors delivered. The transvalvular implant 1200 can include a larger central opening 1218. The opening 1218 can facilitate future catheter intervention. The opening 1218 can allow passage of clips, such as clips to secure the leaflets. The opening 1218 can allow passage of a catheter system. The opening 1218 can allow passage for systems and/or tools for transcatheter mitral valve repair. The opening 1218 can be enlarged. The opening 1218 can be triangular. The transvalvular implant 1200 can be utilized with three instead of four anchors. In some embodiments, the three anchors can simplify the procedure and reduce the overall procedural time. In some embodiments, the transvalvular implant 1200 can also make future transcatheter intervention easier.

Figure 54:
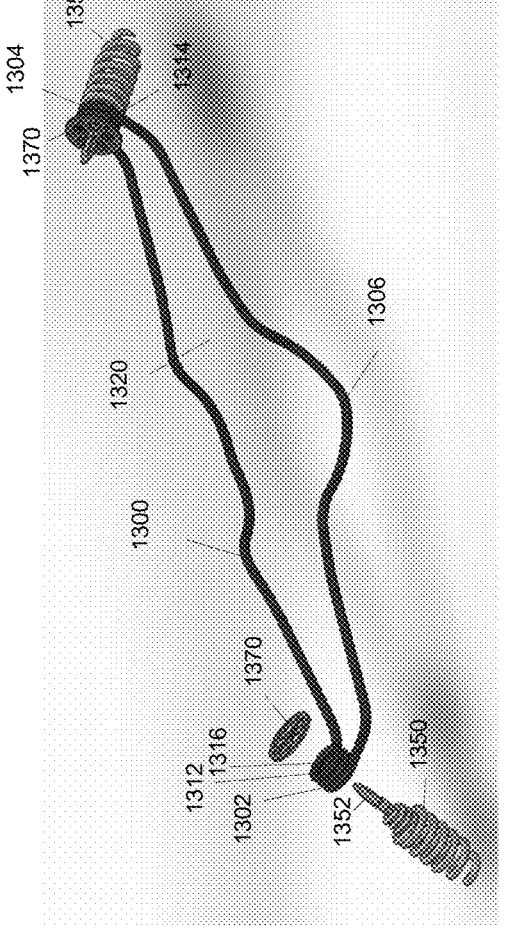
FIG. 54 is a view of an embodiment of a transvalvular implant.

FIG. 54 is a view of an embodiment of a transvalvular implant 1300. The transvalvular implant 1300 can include any feature described herein. The transvalvular implant 1300 can be used in any method. The transvalvular implant 1300 can be deployed in any orientation described herein. The transvalvular implant 1300 can be used in the mitral valve. The transvalvular implant 1300 can be used in the tricuspid valve.

In some embodiments, the transvalvular implant 1300 comprises an elongate structure. The elongate structure can include a longitudinal axis between two anchoring sites. The elongate structure can be greater in length than in width. The transvalvular implant 1300 can be curved. The transvalvular implant 1300 can curve relative to the annulus. The transvalvular implant 1300 can be displaced from a plane. In some embodiments, the transvalvular implant 1300 curves upward. In some embodiments, the transvalvular implant 1300 curves downward.

The transvalvular implant 1300 can include a first end 1302 and a second end 1304. The second end 1304 can be opposite the first end 1302. The first end 1302 and the second end 1304 can be diametrically opposed. The first end 1302 and the second end 1304 can be axially aligned. The first end 1302 and the second end 1304 can be the same or similar. The first end 1302 and the second end 1304 can be identical. The first end 1302 and the second end 1304 can be different. In some embodiments, the first end 1302 has different features than the second end 1304. The first end 1302 and the second end 1304 can have different dimensions. The first end 1302 and the second end 1304 can have different eyelet configurations. The first end 1302 and the second end 1304 can have different attachment structures. Features described in relation to the first end 1302 can apply to features of the second end 1304.

The transvalvular implant 1300 can have a length between the first end 1302 and the second end 1304. The length can be configured to span the valve. The length can be configured to allow anchoring at specific locations on the annulus. The transvalvular implant 1300 can have a length between the first end 1302 and the second end 1304 that is capable of extending across one or more edges formed by leaflets. The transvalvular implant 1200 can include a central portion 1306. The central portion 1306 can be located between the first end 1302 and the second end 1304. The central portion 1306 can include one radius of curvature. The central portion 1306 can include two or more radii of curvature.

The transvalvular implant 1300 can be symmetrical. The transvalvular implant 1300 can include one plane of symmetry. The transvalvular implant 1300 can include two planes of symmetry. The transvalvular implant 1300 can include zero planes of symmetry. The transvalvular implant 1300 can be symmetrical about the central portion 1306. The transvalvular implant 1300 can be symmetrical widthwise. The transvalvular implant 1300 can be symmetrical lengthwise.

The transvalvular implant 1300 can include a lower surface disposed toward the annulus and an upper surface disposed away from the annulus. The central portion 1306 can include a leaflet contact surface. The leaflet contact surface can be curved along the longitudinal axis. The leaflet contact surface can be configured to contact one or more leaflets, as described herein. In other embodiments, the leaflet contact surface can have a different shape and profile. The leaflet contact surface can be concave. The leaflet contact surface can be straight. The leaflet contact surface can be a combination of convex, concave and/or straight segments. The leaflet contact surface can include two concave or straight portions joined together at an apex.

The transvalvular implant 1300 can have a substantially minimum width at the first end 1302. The transvalvular implant 1300 can have a substantially minimum width at the second end 1304. The transvalvular implant 1300 can have a substantially maximum width at the central portion 1306. The transvalvular implant 1300 can have a substantially maximum width near a midpoint of the central portion 1306. The transvalvular implant 1300 can taper along a portion of the length of the transvalvular implant 1300. The transvalvular implant 1300 can taper from the minimum width at the ends 1302, 1304 to the maximum width at the central portion 1306. The transvalvular implant 1300 can form a generally diamond shape. The transvalvular implant 1300 can form a generally parallelogram shape. The transvalvular implant 1300 can form a generally rectangular shape. The transvalvular implant 1300 can form a generally rhombus shape. The sides of the transvalvular implant 1300 can include an indent toward the first end 1302. The sides of the transvalvular implant 1300 can include in an indent toward the second end 1304. The sides of the transvalvular implant 100 can form a generally V shape. The sides of the transvalvular implant 100 can be pinched toward the ends 1302, 1304.

The transvalvular implant 1300 can include a first anchoring portion 1312. The transvalvular implant 1300 can include a second anchoring portion 1314. The first anchoring portion 1312 can be near the first end 1302. The second anchoring portion 1314 can be near the second end 1304. In some embodiments, the first end 1302 can include the first anchoring portion 1312 and the second end 1304 can include the second anchoring portion 1314.

The first anchoring portion 1312 can include one or more eyelets. The first anchoring portion 1312 can include a first eyelet 1316. The first anchoring portion 1312 can include only one eyelet 1316. The first anchoring portion 1312 can include a single eyelet 1316. The second anchoring portion 1314 can include one or more eyelets. The second anchoring portion 1314 can include a second eyelet 1318. The second anchoring portion 1314 can include only one eyelet 1318. The second anchoring portion 1314 can include a single eyelet 1318.

The first eyelet 1316 of the first anchoring portion 1312 and the second eyelet 1318 of the second anchoring portion 1316 can be aligned. The first eyelet 1316 of the first anchoring portion 1312 and the second eyelet 1318 of the second anchoring portion 1316 can be offset. The first eyelet 1316 of the first anchoring portion 1312 and the second eyelet 1318 of the second anchoring portion 1316 can be spaced apart.

The eyelets 1316, 1318 can be for accepting at least a portion of anchors 1350. The eyelets 1316, 1318 can be for accepting tethers 1354 that extend from a portion of the anchors 1350, as described herein. The eyelets 1316, 1318 can be for accepting a central post 1352 of the anchors 1350, as described herein. The eyelets 1316, 1318 can be for accepting any device that allow the transvalvular implant 1300 to be secured to the annulus. In some embodiments, the anchors 1350 are implanted before the transvalvular implant 1300 is positioned relative to the annulus. The eyelets 1316, 1318 can serve as guides as the transvalvular implant 1300 is lowered toward the annulus. The eyelets 1316, 1318 can receive the central post 1352. The eyelets 1316, 1318 can receive the tether 1354. The transvalvular implant 1300 can slide along the guide tether 1354 that extends through the eyelets 1316, 1318. Alternatively, in other embodiments the anchoring portions 1312 and 1314 can have other means for securing the transvalvular implant 1300 to the annulus.

The transvalvular implant 1300 can have a central opening 1320. The central opening 1320 can be enclosed by the transvalvular implant 1300. The central opening 1320 can have a length and width. The transvalvular implant 1300 can become wider toward the center or midpoint. In some embodiments, the width of the central opening 1320 extends along the majority of the length of the transvalvular implant 1300. In some embodiments, the length of the central opening 1320 extends along the majority of the width of the transvalvular implant 1300. The area of the central opening 1320 can be maximized.

The central opening 1320 can be any shape. The central opening 1320 can be diamond shaped. The central opening 1320 can be rhombus shaped. The central opening 1320 can be any generally elongate shape. The central opening 1320 can be open to allow blood to flow through. The central opening 1320 can be open to allow tools or other implants to be passed through. The central opening 1320 can be separate and distinct from the eyelets 1316, 1318 of the anchoring portions 1312, 1314. The central opening 1320 can be enclosed. The eyelets 1316, 1318 can be enclosed. The central opening 1320 can be uncoated. The central opening 1320 can be open along the entire length or a portion thereof. The central opening 1320 can be open along the entire width or a portion thereof. The transvalvular implant 1300 does not obstruct the flow of blood through the central opening 1320. The outline of the transvalvular implant 1300 can form the central opening 1320. The central portion 1306 can include the central opening 1320.

The central portion 1306 can have a variety of shapes. For example, the shape of the central portion 1306 can be substantially diamond shaped, rectangular, rhombus, parallelogram, rectangular, square, circular, oblong, or any other elongate shape. The central portion 1306 can have a three dimensional curved shaped. The edges of the transvalvular implant 1300 can be rounded or otherwise configured so that the transvalvular implant 1300 presents an atraumatic surface to the valve leaflets. In some embodiments, the shape can be oriented in a particular fashion to enhance performance of the transvalvular implant 1300. The transvalvular implant 1300 can include generally two shaped ends 1302, 1304. The ends 1302, 1304 have a relatively smaller surface area while a larger surface area is towards the central portion 1306. This configuration allows a larger surface area for the central opening 1320 to allow blood to flow therethrough. This configuration allows a larger opening 1320 to be in the direction of flow. This configuration can be a streamlined shape that provides less resistance to blood flow. Decreasing the resistance to blood flow is desirable because it can reduce turbulence and reduce the impedance of the transvalvular implant 1300 on the filling of the left ventricle. The transvalvular implant 1300 can have any shape that provides a central opening 1320 that reduces the resistance to blood flow.

The dimensions of the transvalvular implant 1300 will vary, depending upon the specific configuration of the transvalvular implant 1300 as well as the intended patient. In some embodiments, the transvalvular implant 1300 will have an axial length from first end 1302 to second end 1304 within the range of from about 20 mm to about 40 mm. In some embodiments, the transvalvular implant 1300 will have a width near the central portion 1306 within the range of from about 5 mm to about 15 mm. The width of the transvalvular implant 1300 in the central portion 1306 may be varied depending upon the desired performance, as will be discussed herein. The central portion 1306 can be large enough to minimize the risk of erosion resulting from repeated contact between the closed leaflets and the transvalvular implant 1300. The central portion 1306 including the central opening 1320 is designed to minimize flow turbulence and flow obstruction.

The central portion 1306 of the transvalvular implant 1300 can be greater in width, measured perpendicular to blood flow than the first and second anchoring portions 1312 and 1314. By enlarging the central portion 1306 and thus the opening 1320, the resistance to blood flow can be reduced. In some embodiments, enlarging the central portion 1306 increases the surface area of the leaflet contact surface that supports the valve leaflets.

In some embodiments, the enlarged central portion 1306 is separated from the first anchoring portion 1312 and the second anchoring portion 1314 by a first shoulder 1322 and a second shoulder 1324. The first shoulder 1322 can change the curvature. The first shoulder 1322 can be an inflection point. The second shoulder 1324 can change the curvature. The second shoulder 1324 can be an inflection point. The transvalvular implant 1300 can include one or more curved segments. The transvalvular implant 1300 can include concave segments and convex segments. The transvalvular implant 1300 can be convex near the ends 1302, 1304. The transvalvular implant 1300 can be concave near the shoulders 1322, 1324. The transvalvular implant 1300 can be convex near the central portion 1306.

In some embodiments, the length of the central portion 1306 can be the majority of the length of the transvalvular implant 1300. In some embodiments, the length of the central portion 1306 can be a portion of the length of the transvalvular implant 1300. In some embodiments, the length of the central portion 1306 may be greater than 50%, and in some embodiments greater than 75% of the overall length of the transvalvular implant 1300. The length of the central portion 1306, between first shoulder 1322 and second shoulder 1324, can be less than about 50% of the overall length of the transvalvular implant 1300. The length of the central portion 1306, between first shoulder 1322 and second shoulder 1324, can be less than about 30% of the overall length of the transvalvular implant 1300. The length of the central portion 1306, between first shoulder 1322 and second shoulder 1324, can be less than about 10% of the overall length of the transvalvular implant 1300. The length of the central portion 1306 can be designed to minimize the obstruction in the center of the flow path. The transvalvular implant 1300 can present a wider transverse surface for supporting the leaflets when the valve is closed. In some embodiments, the central portion 1306 can be generally convex in the direction of the ventricle. In some embodiments, the central portion 1306 can be generally concave.

The transvalvular implant 1300 can be formed from a single length of wire. The single length of wire can form a loop. The single length of wire can be welded at the ends. The transvalvular implant 1300 can be formed from several lengths of wire. The several lengths of wires can have different diameters. The several lengths of wires can have different lengths. The several lengths of wires can have different materials. The several lengths of wires can have different functions. The several lengths of wires can be welded at the ends.

The transvalvular implant 1300 can be formed from a continuous wire. The transvalvular implant 1300 can be formed from separate pieces of wire. The transvalvular implant 1300 can be formed from flexible material. In some embodiments, the bend angles and orientation of the material can be altered by the user to accommodate the desired axes of compression. In some embodiments, the bend angles and orientation of the material cannot be readily altered. In some embodiments, the bend angles and orientation are formed in a shape memory material. In some embodiments, the bend angles and orientation are biased toward a memory shape.

The transvalvular implant 1300 can be formed from a biocompatible material. The transvalvular implant 1300 can be formed from any material described herein. The transvalvular implant 1300 can be formed shape memory material. The transvalvular implant 1300 can recover the original shape. The transvalvular implant 1300 can comprise shape memory metal or polymer. In some embodiments, a portion of the transvalvular implant 1300 comprises a coating. In some embodiments, the transvalvular implant 1300 is uncoated. In some embodiments, at least the central opening 1320 of the transvalvular implant 1300 is uncoated. In some embodiments, the wire of the transvalvular implant 1300 is encased with a material.

The transvalvular implant 1300 can include a shaped body. The transvalvular implant 1300 can include one or more curved segments. The transvalvular implant 1300 can include an elongate flexible material formed into a diamond shaped pattern. The transvalvular implant 1300 can include four legs forming the diamond shape. The transvalvular implant 1300 can include open spaces between the legs. The transvalvular implant 1300 can include an outline of the diamond shaped pattern. The transvalvular implant 1300 can include the central portion 1306 formed such that the central portion 1306 bows or inclines in the direction of the ventricle to achieve early closure. The material may extend to form the first end 1302 and the second end 1304. The material may form a coil to enclose the eyelet 1316 of the first anchoring portion 1312. The material may form a coil to enclose the eyelet 1318 of the second anchoring portion 1314. The material may form the single eyelet 1316 of the first anchoring portion 1312. The material may form the single eyelet 1318 of the second anchoring portion 1314. The material may enclose the central opening 1320. The material may enclose a single central opening 1320.

Figure 57:
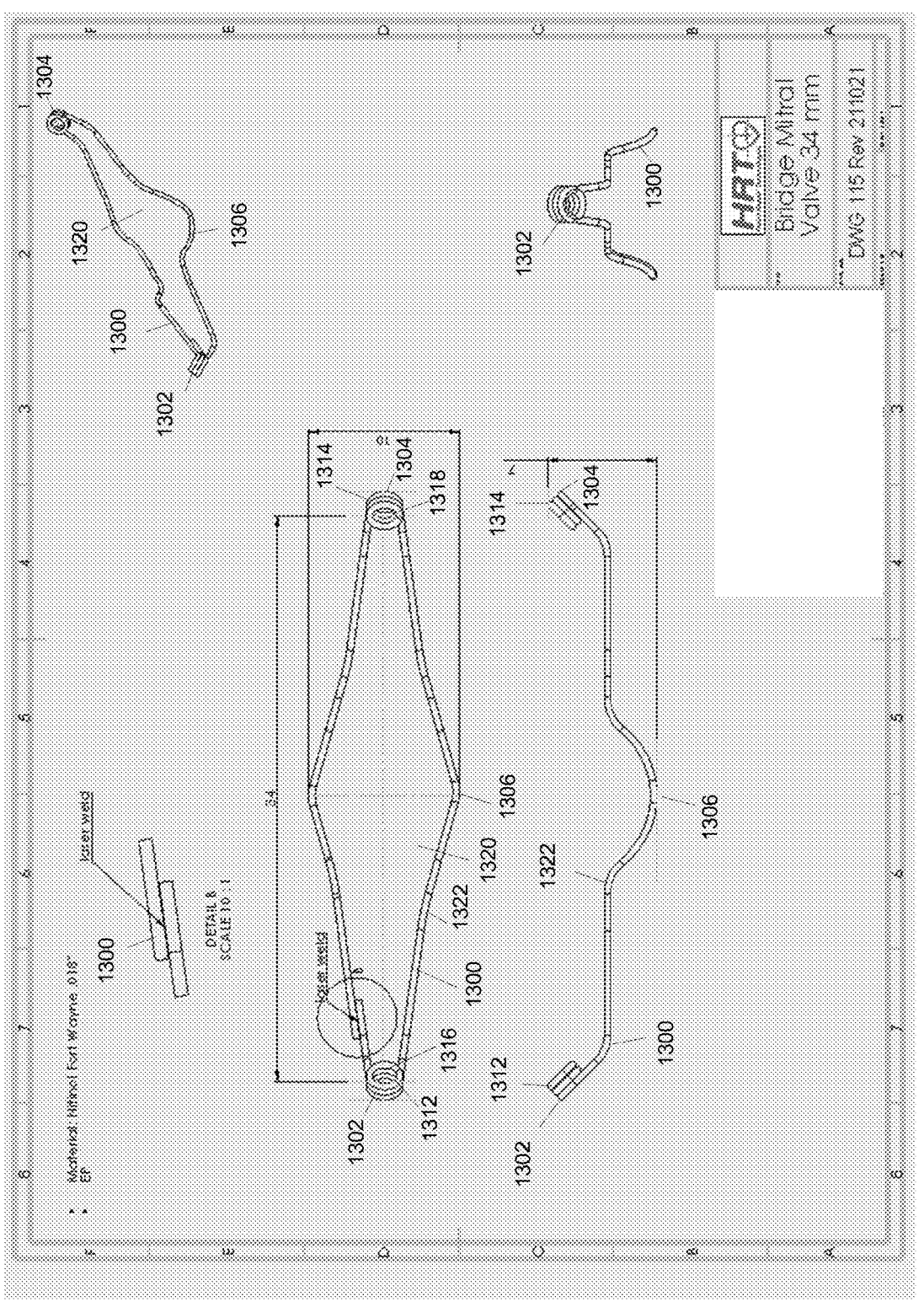
FIG. 57 is a view of an embodiment of a transvalvular implant.

The transvalvular implant 1300 can form a continuous shape as shown in FIG. 57. The material can be Nitinol. The material can be in the form of a wire. The material can have a diameter or cross-section of 0.02", 0.04", 0.06", 0.08", 0.10", 0.12", 0.14", 0.16", 0.18", 0.20", 0.22", 0.24", 0.26", 0.28", 0.30", 0.32", 0.34", 0.36", about 0.18", or any range of two of the foregoing values. The ends of the transvalvular implant 1300 can be laser welded. The width of the transvalvular implant 1300 can be 2 mm, 4 mm, 6 mm, 8 mm, 10 mm, 12 mm, 14 mm, 16 mm, 18 mm, 20 mm, about 10 mm, or any range of two of the foregoing values. The length of the transvalvular implant 1300 can be 20 mm, 22 mm, 24 mm, 26 mm, 28 mm, 30 mm, 32 mm, 34 mm, 36 mm, 38 mm, 40 mm, 42 mm, 44 mm, 46 mm, 48 mm, 50 mm, about 34 mm, or any range of two of the foregoing values. The length can be at least two times greater than the width. The length can be at least three times greater than the width. The height of the transvalvular implant 1300 can be less than 1 mm, 1 mm, 3 mm, 5 mm, 7 mm, 9 mm, 11 mm, 13 mm, 15 mm, 17 mm, 19 mm, about 7 mm, or any range of two of the foregoing values. The curve of the central portion 1306 can form the height. The height can extend downward from the plane of the annulus. The width can be greater than the height. The width and the height can be the same or similar.

The material can extend from a starting point. The starting point can be along the length of the transvalvular implant 1300. The starting point can be offset from the first end 1302. The material can extend from the starting point to the first end 1302. The material can form an coil or eyelet 1316 of the first anchoring portion 1312. The material can form one or more coils. The material can form can form three coils. The material can form coils to provide strength to the eyelet 1316. The material can form coils to prevent deformation of the eyelet 1316. The material can form coils to reinforce the eyelet 1316.

The material extends along the side of the implant forming a first leg to the central portion 1306. The first leg can include a first curve. The first leg can taper outward. The first leg can include a straight segment. The first leg can include a complex curve. The first leg can includes a curve with two radii of curvature. The first leg can extend to the midpoint of the transvalvular implant 1300. The first leg can form the first shoulder 1322. The first leg can form at least a portion of the central portion 1306.

The material extend along the side of the implant forming a second leg from the central portion 1306. The second leg can form at least a portion of the central portion 1306. The second leg can include a complex curve. The second leg can includes a curve with two radii of curvature. The second leg can extend from the midpoint of the transvalvular implant 1300. The second leg can form the second shoulder 1324. The second leg can include a straight segment. The second leg can include a second curve. The second leg can taper inward. The second leg can extend to the second end 1304. The material can form an coil or eyelet 1318 of the second anchoring portion 1314. The material can form one or more coils. The material can form can form three coils. The material can form coils to provide strength to the eyelet 1318. The material can form coils to prevent deformation of the eyelet 1318. The material can form coils to reinforce the eyelet 1318.

The material extend along the side of the implant forming a third leg to the central portion 1306. The third leg can include a third curve. The third leg can taper outward. The third leg can include a straight segment. The third leg can include a complex curve. The third leg can includes a curve with two radii of curvature. The third leg can extend to the midpoint of the transvalvular implant 1300. The third leg form the second shoulder 1324. The third leg can form at least a portion of the central portion 1306.

The material extend along the side of the implant forming a fourth leg from the central portion 1306. The fourth leg can form at least a portion of the central portion 1306. The fourth leg can include a complex curve. The fourth leg can includes a curve with two radii of curvature. The fourth leg can extend from the midpoint of the transvalvular implant 1300. The fourth leg can form the first shoulder 1323. The fourth leg can include a straight segment. The fourth leg can extend to the starting point. The fourth leg can include a laser weld. The fourth leg can form a continuous shape.

The transvalvular implant 1300 can be pinched in shape near the first end 1302. The transvalvular implant 1300 can be pinched in shape near the second end 1304. The transvalvular implant 1300 can include a small footprint near the eyelets 1316, 1318. The transvalvular implant 1300 can be enlarged near the central portion 1306. The transvalvular implant 1300 can include a large footprint near the central portion 1306. The transvalvular implant 1300 can include one or more segments that extend between the ends 1302, 1304. The one or more segments can be curved. The one or more segments can be straight. The one or more segments can be bowed inward. The one or more segments can be bowed outward.

The transvalvular implant 1300 can form an outlined shape. The transvalvular implant 1300 can include two legs connected to the first anchoring portion 1312 separated by a tapered outward shape. The transvalvular implant 1300 can include two legs connected to the second anchoring portion 1314 separated by a tapered outward shape. The transvalvular implant 1300 can include legs connected to the first anchoring portion 1312 and legs connected to the second anchoring portion 1314 pinched inward near the ends 1302, 1304. The transvalvular implant 1300 can include a continuous outline. The transvalvular implant 1300 can include a diamond shaped enclosed opening 1320. The transvalvular implant 100 can include one or more coils that form each eyelet 1316, 1318. The transvalvular implant 1300 can form a closed shape. The transvalvular implant 1300 can connect the starting point and the ending point.

The transvalvular implant 1300 can provide a relatively large support footprint against the valve leaflets, while optimizing the area of open space to permit maximum blood flow therethrough. The transvalvular implant 1300 can be made of any of a variety of flexible materials, including various polymers described elsewhere herein as well as titanium, titanium alloy, Nitinol, stainless steel, elgiloy, MP35N, or other metals known in the art. The material of the transvalvular implant 1300 can be treated or coated. The transvalvular implant 1300 can be encapsulated with silicone or another appropriate material, in order to eliminate untoward effects such as thrombosis or corrosion. The transvalvular implant 1300 can be uncoated.

The transvalvular implant 1300 an be made of single wire. The transvalvular implant 1300 can be free of any material obstructing the central opening 1320. The central opening 1320 can be at or near the center of the implant. The central opening 1320 can be completely open, allowing blood to flow through the implant. The transvalvular implant 1300 can allow for future transcatheter intervention with other transcatheter devices through the opening 1320. The opening 1320 can allow access to the valve. The transvalvular implant 1300 can include attachment points. The transvalvular implant 1300 can include a single eyelet 1316, 1318 at each end 1302, 1304. The transvalvular implant 1300 can include the arcuate central portion 1306. The transvalvular implant 1030 can be curved downward into left ventricle cavity or into left atrium. The transvalvular implant 1300 can from an arch. The transvalvular implant 1300 can form a mitral arch. The transvalvular implant 1300 can form a tricuspid arch. The transvalvular implant 1300 can form a mitral straddle. The transvalvular implant 1300 can form a tricuspid straddle. The transvalvular implant 100 can straddle the valve.

FIG. 54 illustrates a complete bridge system. The complete bridge system can include transvalvular implant 1300. The transvalvular implant 1300 can be a single eyelet bridge. The transvalvular implant 1300 can be a single eyelet mitral bride. The transvalvular implant 1300 can be a single eyelet tricuspid bride. The transvalvular implant 1300 can include the first eyelet 1316 near the first end 1302. The transvalvular implant 1300 can include the second eyelet 1318 near the second end. Each side of the transvalvular implant 1300 can include one eyelet. The transvalvular implant 1300 can include a total of two eyelets 1316, 1318. The transvalvular implant 1300 can include one or more angled eyelets. The eyelets 1316, 1318 can be rounded. The eyelets 1316, 1318 can be circular. The eyelets 1316, 1318 can be formed from coils. The eyelets 1316, 1318 can be diametrically opposed. The transvalvular implant 1300 can include one plane of symmetry. The transvalvular implant 1300 can include two planes of symmetry.

The eyelets 1316, 1318 can include angled eyelets. The angled eyelets 1316, 1318 can be at 45 degrees. The angled eyelets 1316, 1318 can be at other angles, such as 5 degrees, 10 degrees, 15 degrees, 20 degrees, 25 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, or any range of two of the foregoing values. The anchors 1350 can be inserted at an angle. The central posts 1352 of the anchor 1350 can be angled. The central post 1352 receives a single eyelet 1316, 1318. The clips 1380 are locking discs on the central posts 1352. The complete bridge system can include angled anchor posts 1352. The complete bridge system can include a single eyelet bridge. The complete bridge system can include 45 degree eyelets 1316, 1318. The complete bridge system can include a single eyelet 1316, 1318 to engage on the threads and post of the anchor 1350. The complete bridge system can include locking disc clips 1370 on the anchor posts 1352.

Figure 55:
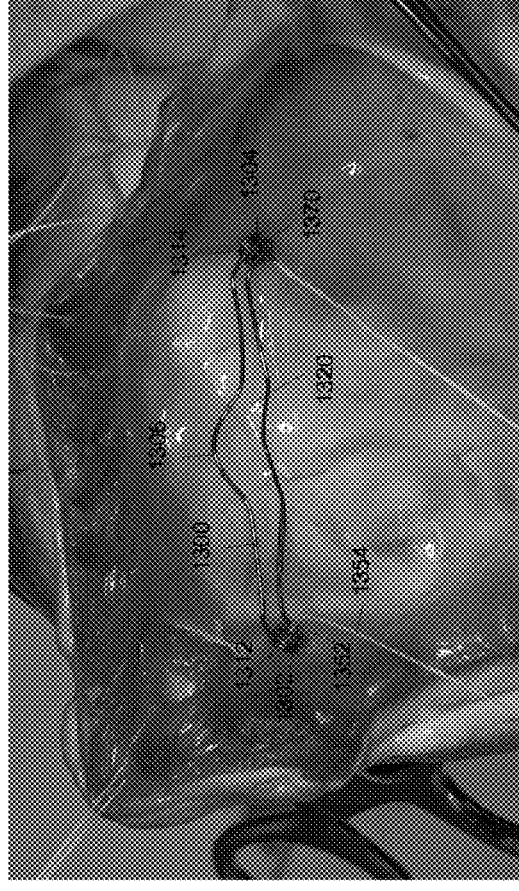
FIG. 55 is a view of an embodiment of a transvalvular implant deployed.
Figure 56A:
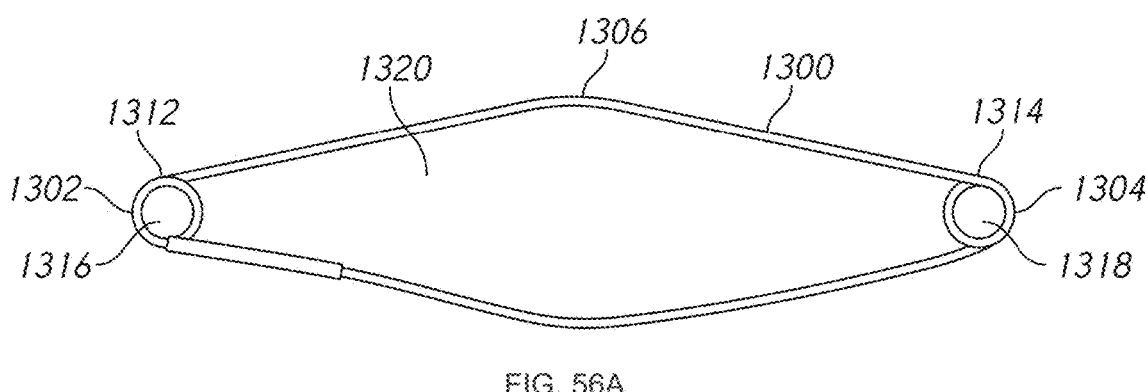
FIGS. 56A-56D are views of embodiments of a transvalvular implant.
Figure 56B:
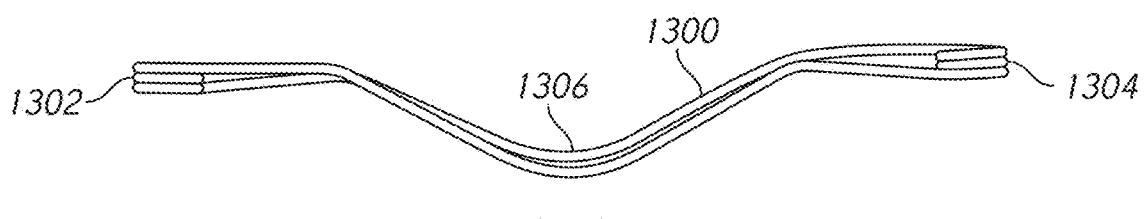

The transvalvular implant 1300 can be positioned relative to the anatomy. FIG. 55 illustrates the transvalvular implant 1300 in a pig heart on the tricuspid annulus. The transvalvular implant 1300 can include a simplified two eyelet design. The eyelets 1316, 1318 can be in a horizontal plane, as shown in FIGS. 56A-56B. The eyelets 1316, 1318 of the anchoring portions 1312, 1314 can be generally axially aligned. The eyelets 1316, 1318 of the anchoring portions 1312, 1314 can lie on a single plane. The eyelets 1316, 1318 of the anchoring portions 1312, 1314 can be flat. The transvalvular implant 1300 can span the valve.

Figure 56C:
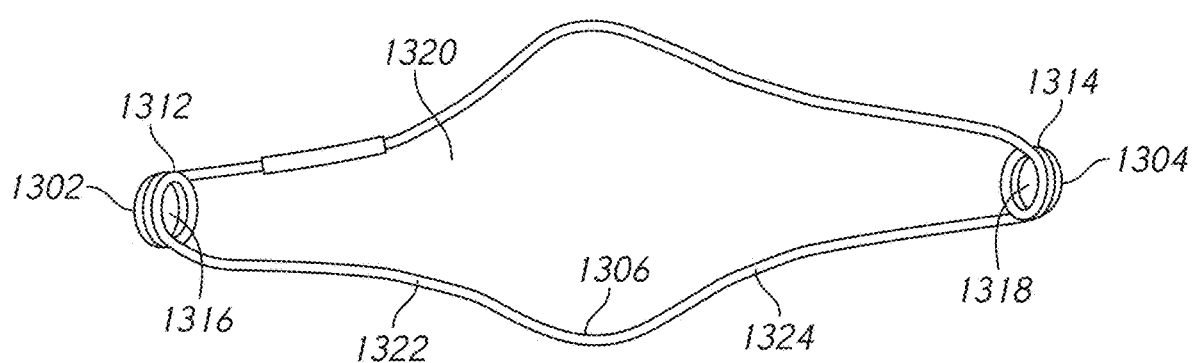
Figure 56D:
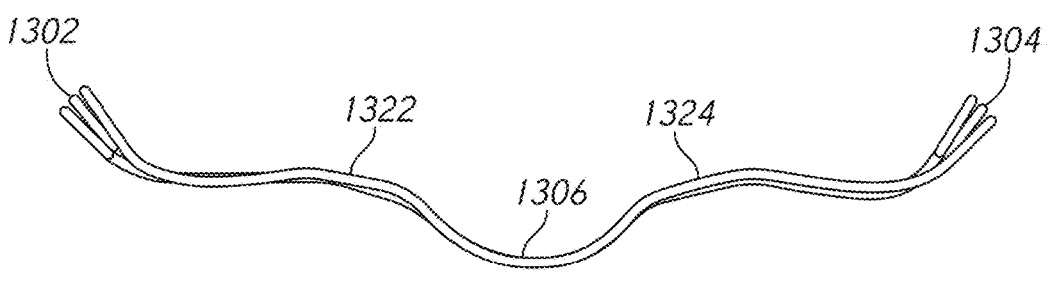

The eyelets 1316, 1318 can be angled relative to a horizontal plane, as shown in FIGS. 56C-56D. The eyelets 1316, 1318 can be at a 45 degree angle to a horizontal plane. The eyelets 1316, 1318 can lie on skewed planes. The eyelets 1316, 1318 can lie on intersecting planes. The eyelets 1316, 1318 can lie on different planes. In some embodiments, the transvalvular implant 1300 can flex to accommodate different angles of the eyelets 1316, 1318. The central portion 1306 can flex to increase the angle of the eyelets 1316, 1318. The central portion 1306 can flex to decrease the angle of the eyelets 1316, 1318. The transvalvular implant 1300 can be angled to engage the saddle shaped annulus of the valve. The transvalvular implant 1300 is angled engage the angled anchor posts 1352. The anchors 1350 can be implanted at an angle. The central posts 1352 can extend at an angle when implanted. The transvalvular implant 1300 can include eyelets 1316, 1318 that mirror then angle of the central post 1352 when implanted. In some embodiments, the transvalvular implant 1300 can allow for changes in the eyelet angle. In some embodiments, the user can bend the transvalvular implant 1300 to change the angle. The transvalvular implant 1300 can include eyelets at angles relative to the horizontal plane. The transvalvular implant 1300 can include eyelets at angles relative to the plane of the annulus. The angle can be 30 degrees, 35 degrees, 40 degrees, 45 degrees, 50 degrees, 55 degrees, 60 degrees, or any range of two of the foregoing values. In some embodiments, the angle is approximately 45 degrees. The transvalvular implant 1300 can include a bridge design with angled eyelets 1316, 1318. The transvalvular implant 1300 can include single eyelets. The transvalvular implant 1300 can include angled eyelets.

The transvalvular implant 1300 can be used in combination with the anchors 1350. FIGS. 54 and 55 illustrate the anchor 1350 with the transvalvular implant 1300. The system can include a cap 1370. The cap 1370 can be any cap described herein. The cap 1370 can be a push-on cap. The cap 1370 can slide relative to the central post 1352 of the anchor 1350. The cap 1370 can slide along the suture 1354. The cap 1370 can be rounded. The cap 1370 can match the shape of the eyelet 1316, 1318. The cap 1370 can be larger in cross-section or diameter than the eyelet 1316, 1318. The cap 1370 can rest against the eyelet 1316, 1318. The cap 1370 can push the transvalvular implant 1300 toward the anchor 1350. The cap 1370 can push the transvalvular implant 1300 along the central post 1352. The cap 1370 can function as a locking clip to hold the transvalvular implant 1300 in position relative to the anchor 1350. The cap 1370 can form a friction fit with the central post 1352 of the anchor 1350. The cap 1370 can be pushed downward on the central post 1352 until a gap between the transvalvular implant 1300 and the coil of the anchor 1350 is reduced. In some embodiments, the cap 1370 does not form a frictional fit with the suture 1354. In some embodiments, the suture 1354 can be cut to release the annular anchor 1350 after the cap 1370 is locked. In some embodiments, the anchor 1350 is not reversible after release of the suture 1354. In some embodiments, the cap 1370 can include a pattern to enhance the locking, such as the patterns shown in FIG. 43A-43C. The cap 1370 can remain in place after the transvalvular implant 1300 is deployed. The cap 1370 can securely lock the transvalvular implant 1300 in position relative to the anchor 1350.

Figure 58:
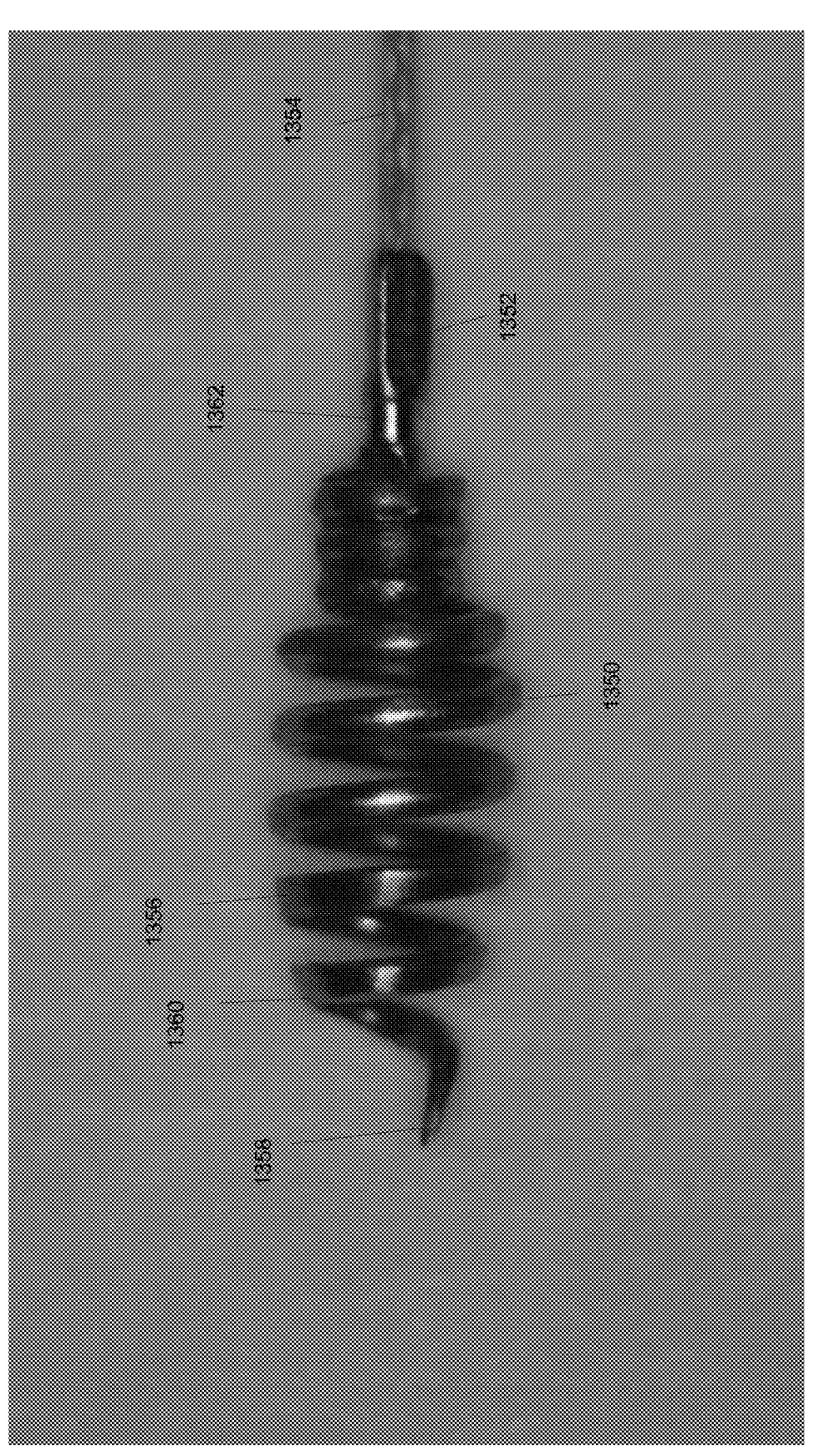
FIG. 58 is a view of an embodiment of an anchor.

FIG. 58 is another view of the anchor 1350. In some embodiments, the anchor 1350 can be coupled to a tether 1354. The tether 1354 can be a monofilament tether. The tether 1354 can be a multifilament tether. The anchor 1350 can have any feature of the anchors described herein. The anchor 1350 can be configured to engage the annulus. The anchor 1350 can include coils 1356. The anchor 1350 can include a central post 1352. The central post 1352 can extend upward. The central post 1352 can be a top portion of the anchor 1350. The coils 1356 can be a bottom portion of the anchor 1350. The coils 1356 can function as a thread. The tether 1354 can be coupled to the central post 1352. The tether 1354 can be crimped to the central post 1352. The central post 1352 can include a tubular structure that surrounds the tether 1354. The anchor 1350 can have a tip 1358. The anchor 1350 can be configured to penetrate the annulus. The anchor 1350 can be configured to be inserted at an angle. The tip 1358 can guide the initial engagement with the annulus. The tip 1358 can be sharpened. The tip 1358 can be a vertical tip. The anchor 1350 can includes sharpened edges 1360. The sharpened edges 1360 can extend from the tip 1358. The sharpened edges 1360 can extend along a portion of the coils 1356. The sharpened edges 1360 can extend along a full revolution of a coil 1356. The sharpened edges 1360 can extend along two revolutions of coils 1356. The sharpened edges 1360 can extend along a portion of the coils 1356. The sharpened edges 1360 can be on the bottom two coils.

The transvalvular implant 1300 can include a simplified two eyelet design. The transvalvular implant 1300 can be used with two anchors. The anchor tip 1358 can be straight. The anchor tip 1358 can be generally vertical. The anchor tip

1358 can be sharp for minimal implantation force. The anchor tip 1358 can include sharp edges. The anchor 1350 can include sharp edges 1360 of the bottom two threads.

In some embodiments, the central post 1352 can be angled with respect to the coils 1356. The central post 1352 can include an angled post. The central post 1352 can be at 45 degrees relative to the coil 1356. The central post 1352 can be at other angles relative to the coil 1356, such as 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, or any range of two of the foregoing values. In some embodiments, the central post 1352 can be coaxial with respect to the coils 1356. The central post 1352 can extend from the annulus at an angle. The central post 1352 can be at 45 degrees relative to the annulus. The central post 1352 can be at other angles relative to the annulus, such as 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, or any range of two of the foregoing values.

The central post 1352 can include a groove 1362. The groove 1362 can be shaped to accommodate the clip 1370. The groove 1362 can allow for better securement of the locking clip 1370. The clip 1370 can be a disc. The groove 1362 can have a height equal to or greater than the height of the of the clip 1370. The groove 1362 and the clip 1370 can form a frictional fit. The groove 1362 can prevent or reduce translation of the clip 1370 relative to the anchor 1350.

Figure 59B:
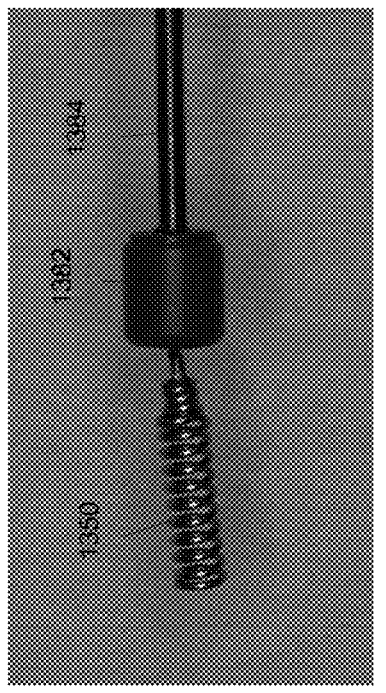
FIGS. 59A-59C are views of an embodiment of a tether cutter.
Figure 59C:
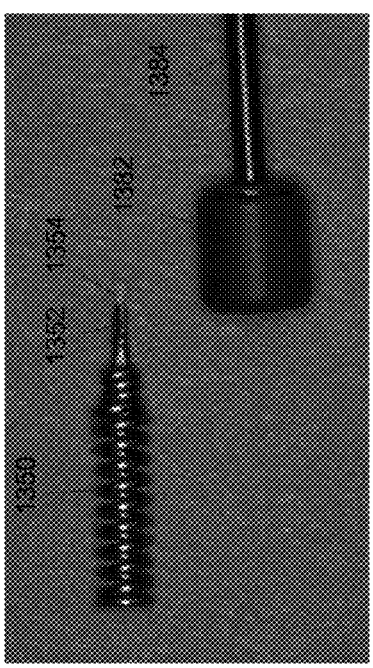
Figure 59A:
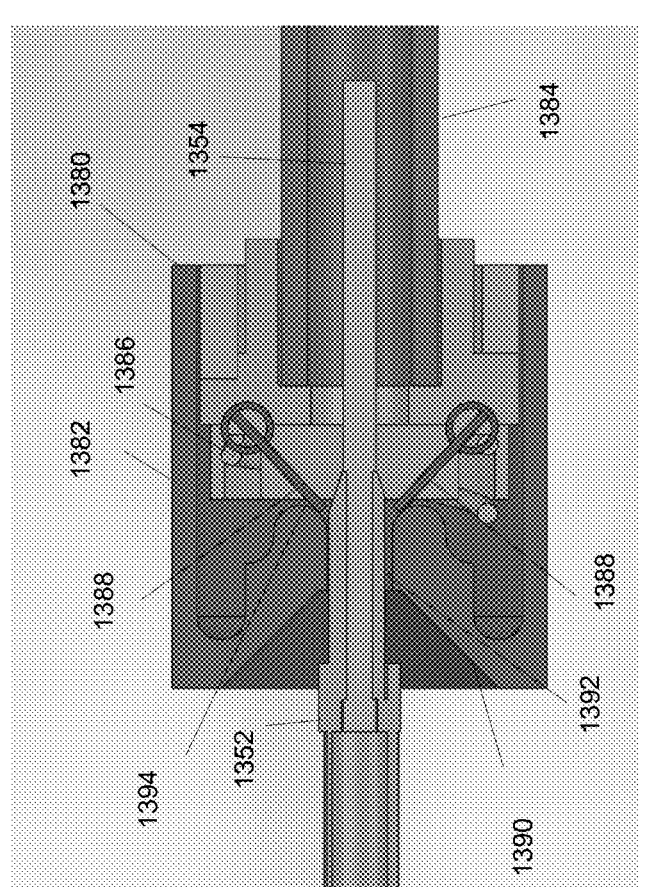

FIGS. 59A-59C are views of an embodiment of a tether cutter 1380. The tether cutter 1380 can include a barrel 1382. The tether cutter 1380 can include a cutter shaft 1384. The tether cutter 1380 can be spring loaded. The spring 1386 can be disposed within the barrel 1382. The spring 1386 can bias the cutter shaft 1384 away from the barrel 1382. The tether cutter 1380 can include one or more cutters 1388. The tether cutter 1380 can include two cutters 1388. The two cutters 1388 can be coupled to the cutter shaft 1384. The movement of the cutter shaft 1384 relative to the barrel 1382 can cause movement of the two cutters 1388. The barrel 1382 can include a conical opening 1390. The barrel 1382 can include a lumen 1392. The barrel 1382 can include one or more stops 1394. The barrel 1382 can include two stops 1394. The two stops 1394 can be shaped surfaces within the barrel 1382.

The tether cutter 1380 can be lowered relative to the anchor 1350. The barrel 1382 can receive the central post 1352. The tether 1354 can extend through barrel 1382. The tether 1354 can extend through the cutter shaft 1384. The tether cutter 1380 can be lowered until the locking clip 1370 engages the conical opening 1390. The central post 1352 can extend through the lumen 1392 of the barrel 1382. The tether cutter 1380 can be loaded with the tether 1354. The tether 1354 can be coupled to the central post 1352 of the anchor 1350.

The cutter shaft 1384 can be moved relative to the barrel 1382. The cutter shaft 1384 can compress the spring 1386. The cutter shaft 1384 can move the two cutters 1388. The cutter shaft 1384 can move the two cutters 1388 toward the two stops 1394. The two stops 1394 can pivot the two cutters 1388. The two stops 1394 can cause the two cutters 1388 to pivot toward the tether 1354. The two cutters 1388 can pivot toward each other. The two cutters 1388 can shear the tether 1354. The two cutters 1388 can cut the tether 1354 at a predetermined tether cut point. The tether cutter 1380 can be withdrawn. The cut end of the tether 1354 can be withdrawn.

The systems and methods can treat mitral valve regurgitation. The systems and methods can treat tricuspid valve regurgitation. In a healthy heart, the blood flows one way from the atrium to the ventricle. The mitral valve closes between the left atrium and the left ventricle. The tricuspid valve closes between the right atrium and the right ventricle. When the mitral and tricuspid valves are not working well, blood leaks back into the upper chambers and into lungs and the rest of the body, causing mitral and tricuspid leaks or regurgitation. Mitral and tricuspid valve regurgitation leads to heart failure. Mitral and tricuspid valve regurgitation can cause weakness, fatigue, shortness of breath, swelling of legs and feet. There is a high morbidity and mortality, with the risks growing as the population ages and increases in cardiovascular disease. There are types of mitral and tricuspid regurgitation. Degenerative mitral regurgitation includes abnormalities in the leaflets, for example mitral valve prolapse. Functional mitral regurgitation includes normal leaflets. Functional mitral regurgitation can include annular dilatation and retracted leaflets. Functional tricuspid regurgitation can include annular dilatation and retracted leaflets. There can be primary tricuspid regurgitation. There can be secondary tricuspid regurgitation. There can be isolated tricuspid regurgitation. The systems and methods can treat degenerative mitral regurgitation, functional mitral regurgitation, and/or functional tricuspid regurgitation. Functional mitral regurgitation and functional tricuspid regurgitation predict poor patient outcomes.

There is a need for intervention in addition to medical therapy. There is a need for achieving at least mild (1+ grade or less) mitral regurgitation or tricuspid regurgitation after treatment. There are at least 250,000 new diagnoses of mitral regurgitation annually, including at least 100,000 in the US and Europe and at least 50,000 in China. These conditional affect 16 million in the US and Europe and 10 million in China. In China, the prevalence of mitral regurgitation for the population over 60 years of age is 13.5%. Only 40,000 patients are treated surgically annually. Less than 3% of patients who could benefit from therapy receive therapy. Without treatment, 5% of patients with severe mitral regurgitation die per year, with a similar prevalence and mortality with tricuspid regurgitation. The systems and methods can treat millions of patients per year, since mitral and tricuspid regurgitation is a large and growing problem.

The fundamental problem in functional mitral and tricuspid regurgitation includes an increased anterior-posterior diameter of the mitral and tricuspid annulus. With functional mitral regurgitation and a diseased mitral valve, the leaflets may not close in the center with a large central orifice causing mitral regurgitation. The mitral valve leaflets do not close along the anterior-posterior diameter. With functional tricuspid regurgitation and a diseased tricuspid valve, the leaflets may not close in the center with a large central orifice causing tricuspid regurgitation. The tricuspid valve leaflets do not close along the anterior-posterior diameter. To achieve excellent clinical outcomes, there is a need for interventional procedures to achieve aggressive and sufficient reduction of the diameter of the central portion of the annulus with sufficient functional mitral regurgitation and function tricuspid regurgitation reduction at least one regurgitant grade and preservation of native annular function, annular saddle shape, and leaflet dynamics The systems and methods described herein can achieve better results than annuloplasty rings or other devices that rely on circumferential cinching. These other devices can have a negative impact on leaflet coaptation geometry. These other devices can stress the leaflet. The systems and methods described herein can achieve better results than edge to edge repair devices. These other devices can lead to recurrence of moderate mitral regurgitation. These other devices can have a high exclusion rate due to anatomical ineligibility. The systems and methods described herein can achieve better results than suturing the leaflets. The systems and methods described herein can achieve better results than a permanent double orifice mitral valve.

The systems and methods can treat mitral and tricuspid regurgitation. The device allows for the valve to respond in native fashion with commissural flexing. The device allows for low filling gradients at rest and exercise preserving the natural saddle shape and leaflet dynamics. The device creates direct SLD reduction and early phase leaflet deep central coaptation of leaflets. The device allows the mitral or tricuspid annulus, beyond the central part, to self-adjusts around the central coaptation. The device can include a transannular bridge for functional mitral regurgitation and functional tricuspid regurgitation. The device can include one or more anchoring pads, The device can include a silicon-nitinol body. The device can have a centered, infra-annular curvature.

The device can include direct annular A-P diameter reduction in contrast to annuloplasty rings or other device. The device can include no circumferential cinching. The device can include no reduction in inter-commissural diameter. The device can preserve leaflet curvature and dynamics. The device can preserve annular saddle shape and function. The device can reduce mitral valve regurgitation from severe to mild/trace in 96% of patients at four years, based on data from 34 patients. Similar results were shown at 12 months. There was low mitral gradients at rest and exercise. The mean gradient at rest can be 2.15 mmHg. The mean gradient at peak exercise can be less than 5 mmHg. The mean gradient at peak systolic pressure can be less than 40 mmHg. Similar results were shown with tricuspid regurgitation. The device can reduce tricuspid valve regurgitation from severe to mild/trace in a surgical feasibility study patients at two years, based on data from 6 patients. Similar results were shown at 18 months. There is low tricuspid gradients at rest and exercise. The mean gradient at peak exercise can be less than 3 mmHg.

The systems and methods can replicate the cornerstone of sound surgical repair. The systems and methods can be customizable, repositionable, and retrievable. The systems and methods can leave options for future transcatheter interventions. The systems and methods can use the trans-femoral vein. The systems and methods can use transseptal access.

The systems and methods can include an echocardiography-assisted, catheterization lab procedure without cardiopulmonary bypass. The systems and methods can include segmented sequential stepwise and controlled implantation of transcatheter implants described herein. The systems and methods can include a three step procedure. The systems and methods can include the ability to test the anchor strength prior to delivering the implant. The systems and methods can include retrievable and repositionable anchors.

The systems and methods can include SLD (A-P diameter) cinching prior to implant selection and loading enabling optimization of implant size selection. The systems and methods can include segmented steps and procedural simplicity enhance the safety of the procedure with potential for generalizable wider adoption. The systems and methods can target a broader patient population when compared to the existing devices in the mitral and tricuspid space.

Figures 60A, 60B, 60C:
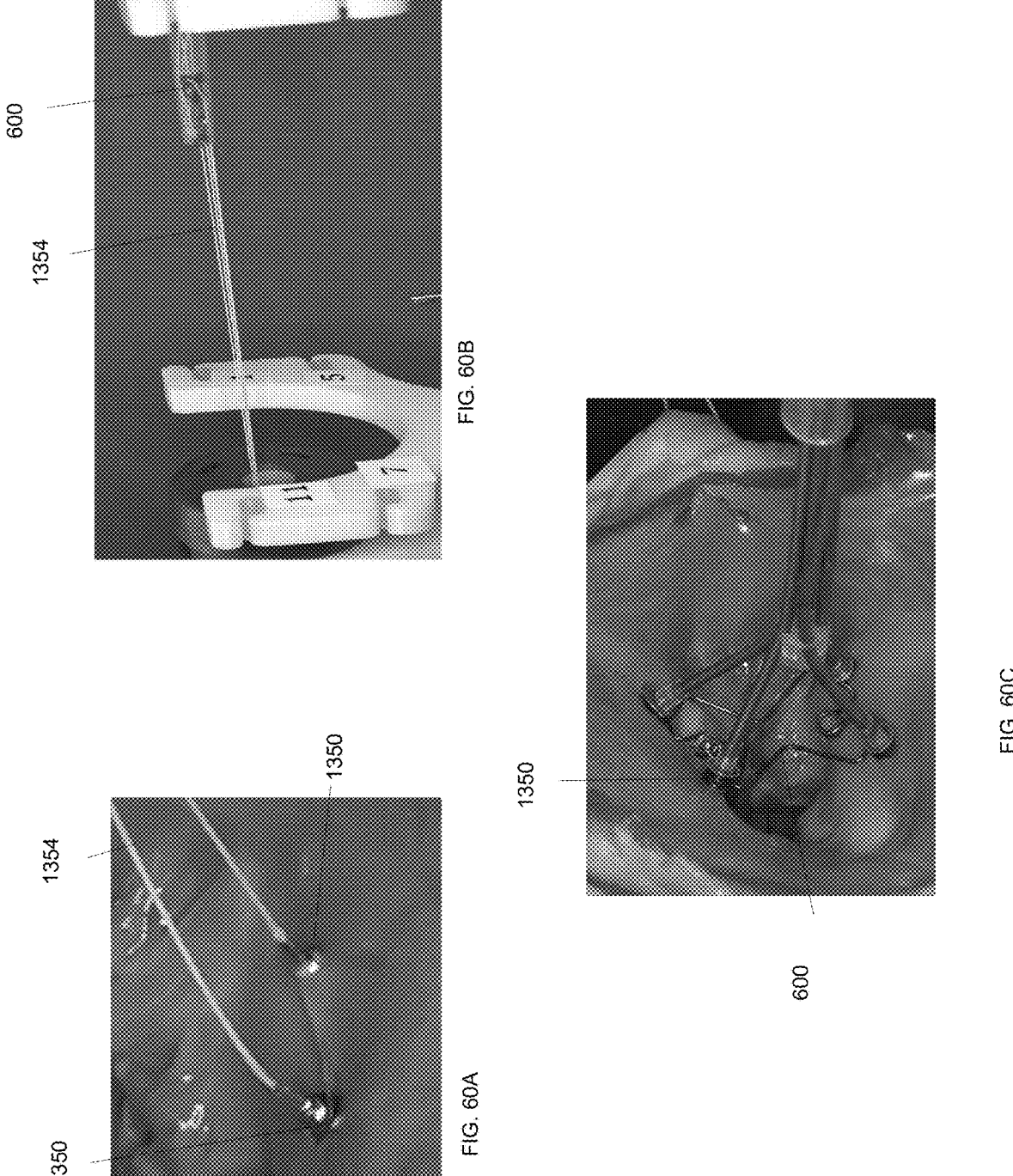
FIGS. 60A-60C are views of methods.

FIG. 60A-60C illustrate methods steps. The systems and methods can include annular anchors implantation, as shown in FIG. 60A. The systems and methods can include deploying two annular anchors 1350 as shown. The anchors 1350 can be located on the anterior annulus. The anchors 1350 can be located on the posterior annulus. The anchors 1350 can be located on the septal annulus. The anchors 1350 can have sutures 1354 extending from the anchors 1350. The systems and methods can include extracorporeal implant loading, as shown in FIG. 60B. The transvalvular implant 600 can be loaded on the sutures 1354 that extend from the annular anchors 1350. The transvalvular implant 600 can be loaded outside of the body of the patient, and slid toward the patient via a delivery catheter. The systems and methods can include implant delivery and annular securement, as shown in FIG. 60C. The transvalvular implant 600 can slide toward the annular anchors 1350. The methods can include any implant described herein. The methods can include any anchor described herein. The methods can include or omit any method step described herein.

Figure 61B:
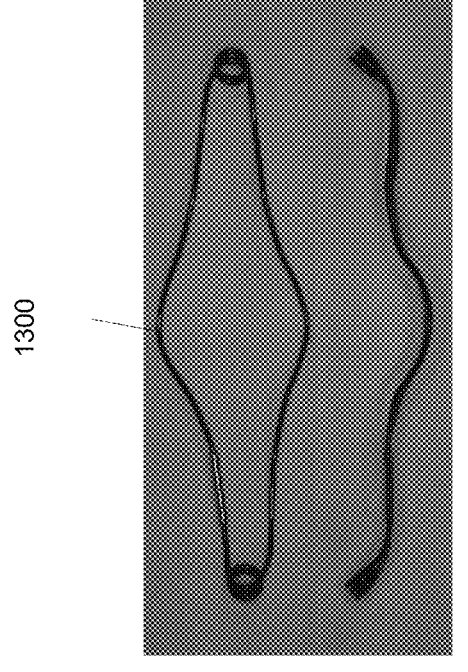
FIGS. 61A-61C are views of systems and system components.
Figure 61C:
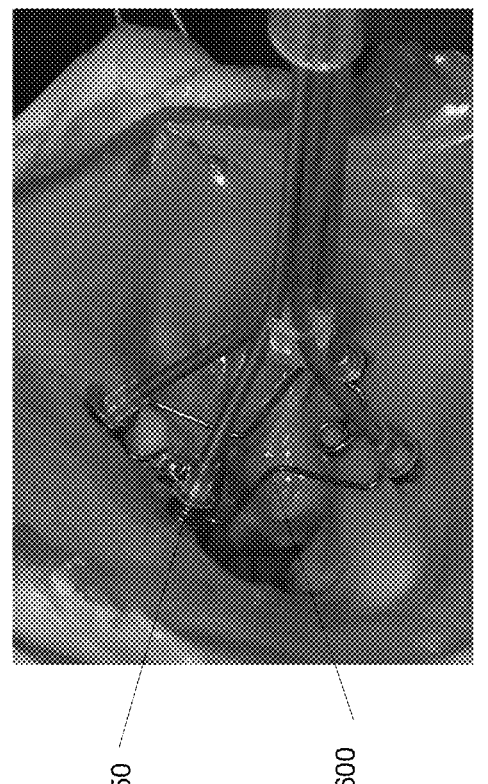
Figure 61A:
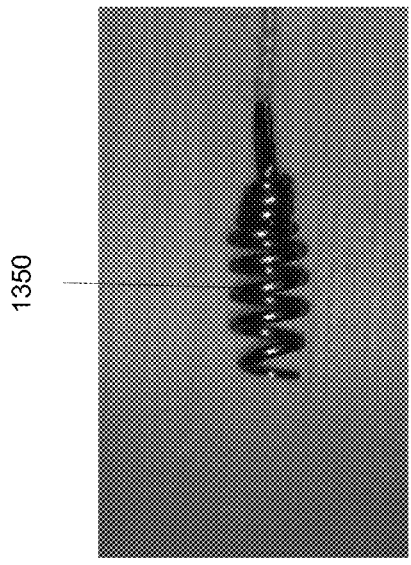

FIG. 61A-61C illustrate the transcatheter mitral and tricuspid repair system. The system can include the anchors 1350. The systems and methods can include any anchor described herein. The system can include the transvalvular implant 1300. The systems and methods can include any implant described herein. The anchors 1350 and the transvalvular implant 1300 can combine into a repair system. The anchors 1350 can combine with any implant described herein, including transvalvular implant 600. The procedure can be echo and fluroscopy driven. The procedure can be trans-femoral with trans-septal access. The annular anchors can be fully retrievable, repositionable, with minimal implantation force. The implant can have a design to achieve the desired form and function. The implant can be easily folded and delivered via catheter. The implant can have an open central area for options for future transcatheter repair or replacement. The implant can be compatible with other repair or replacement devices. The catheter delivery system can include a guide catheter, such as 23 Fr. The catheter delivery system can include a steering catheter, such as 16 Fr. The catheter delivery system can include an anchor delivery catheter, such as 10 Fr. The catheter delivery system can include an implant delivery catheter, such as 16 Fr. The catheter delivery system can be ergonomically easy to use. The catheter delivery system can simplify and reduce procedure times.

Figure 62B:
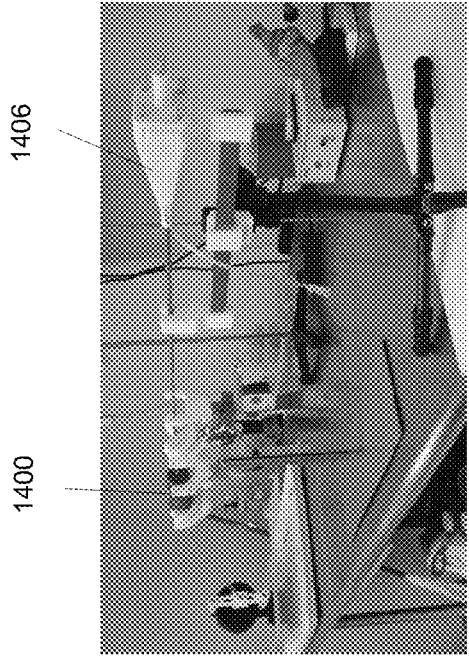
FIGS. 62A-62B are views of a delivery system.
Figure 62A:
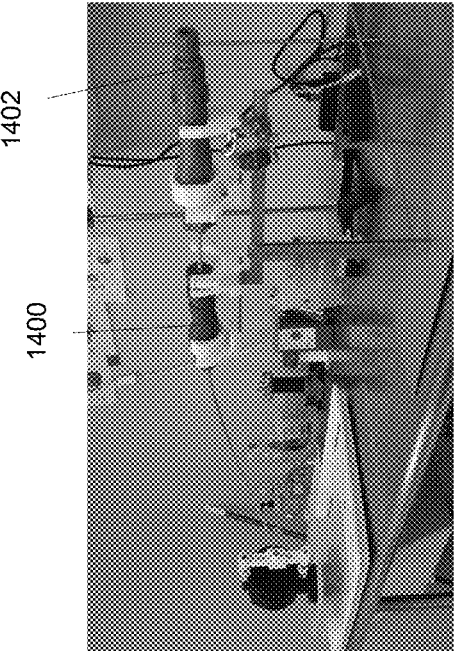

FIG. 62A-62B illustrate the delivery system. FIG. 62A illustrates a guide catheter 1400 and a steering catheter 1402. FIG. 62B illustrates a implant delivery catheter 1402. The delivery system can be comparative in size to other systems. The delivery system can be simpler than other delivery systems.

The systems and methods have been tested in vitro and in pig hearts. The systems and methods have been tested with acute beating heart live animal studies. The systems and methods have shown successful anchoring and implant delivery. The systems and methods have shown good anchor depths and inter-anchor distances. The systems and methods have achieved excellent direct SLD cinching of the annulus with the implanted anchors. The systems and methods have shown high magnitude of mitral regurgitation reduction. The systems and methods have shown evidence of long term left ventricle remodeling. The systems and methods can have synergy with other technology. The systems and methods has optimal results with little or no residual regurgitation after the procedure. The systems and methods have less procedural complexity than other devices and methods.

The systems and methods include validated technology with over sixty surgical patients. The systems and methods can be used for trans-septal treatment of functional mitral regurgitation and function tricuspid regurgitation. The systems and methods can include a simplified implant with a simplified implantation procedure coupled with clinical validation of the concept by the clinical results with the surgical follow up. The systems and methods provide a simple, versatile annular technology with only a limited number of attachment points in contrast to other annuloplasty rings and other devices with complex procedures. The systems and methods conform to patient's specific annular geometry thus applicable to more patients. The systems and methods allow aggressive SLD reduction adaptable to different degrees of leaflet restriction and left ventricle dilatation, thus expanding widely the adoption to many patient population. The systems and methods allow for effective treatment of both functional mitral regurgitation and functional tricuspid regurgitation, with a single transcatheter platform. The systems and methods have standard of care potential for cardiac valve repair.

Figure 63B:
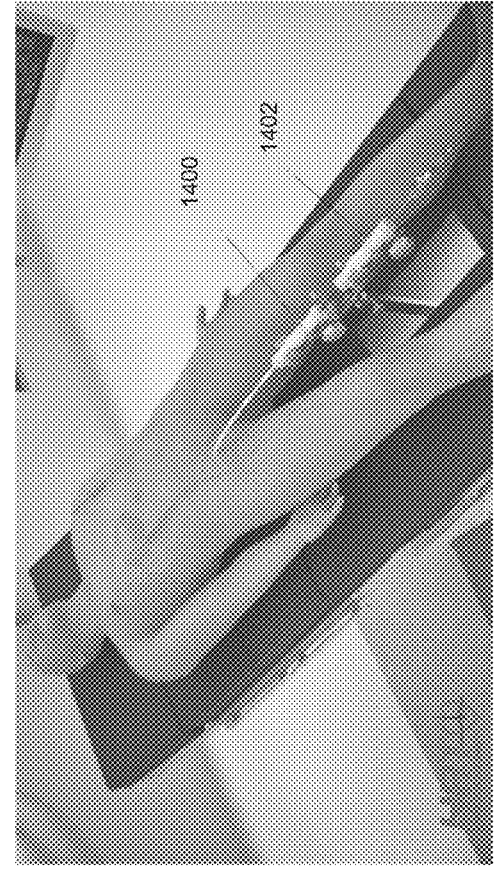
FIGS. 63A-63O are views of methods.
Figure 63A:
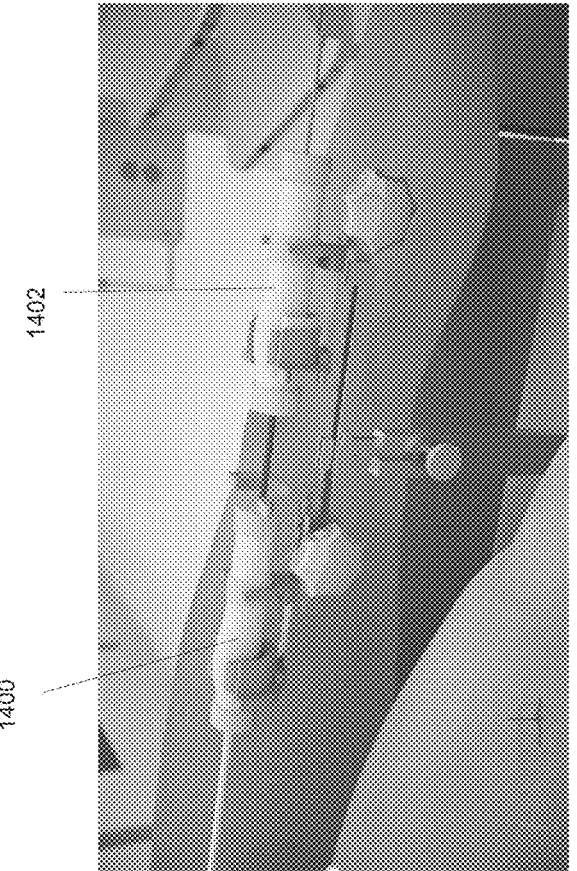

FIGS. 63A-63O are schematic views of methods of use of a transcatheter system, according to some embodiments. The systems and methods can revolutionize the treatment of mitral and tricuspid regurgitation. In a simple procedure, surgeons can treat mitral or tricuspid valve regurgitation in vivo, as an alternative to open heart surgery. FIG. 63A shows the transcatheter system, external to the patient. The catheter delivery system can include the guide catheter 1400. The catheter delivery system can include the steering catheter 1402. The catheter delivery system can include an anchor delivery catheter 1404. The catheter delivery system can include the implant delivery catheter 1406. FIG. 63A shows the guide catheter 1400 and the steering catheter 1402.

Figure 63D:
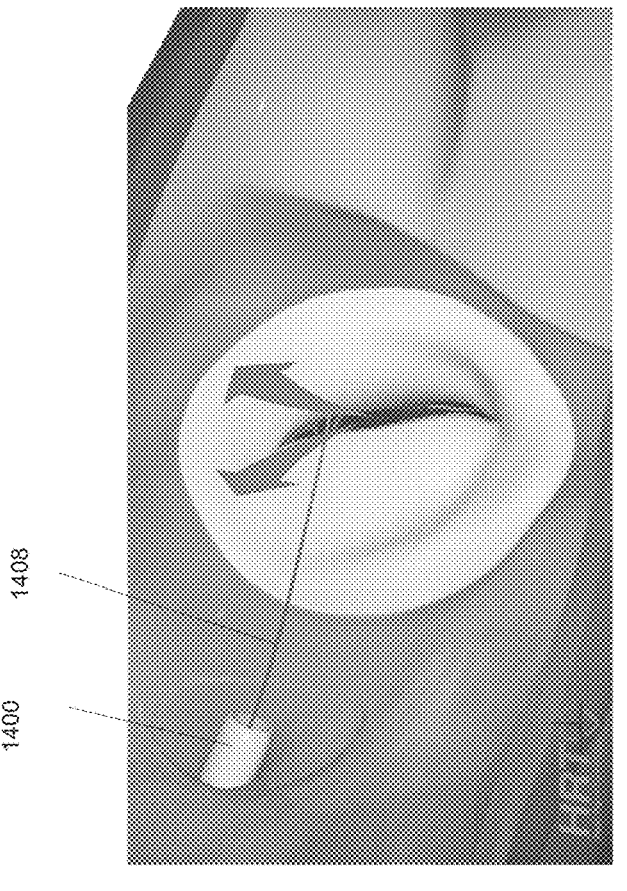
Figure 63C:
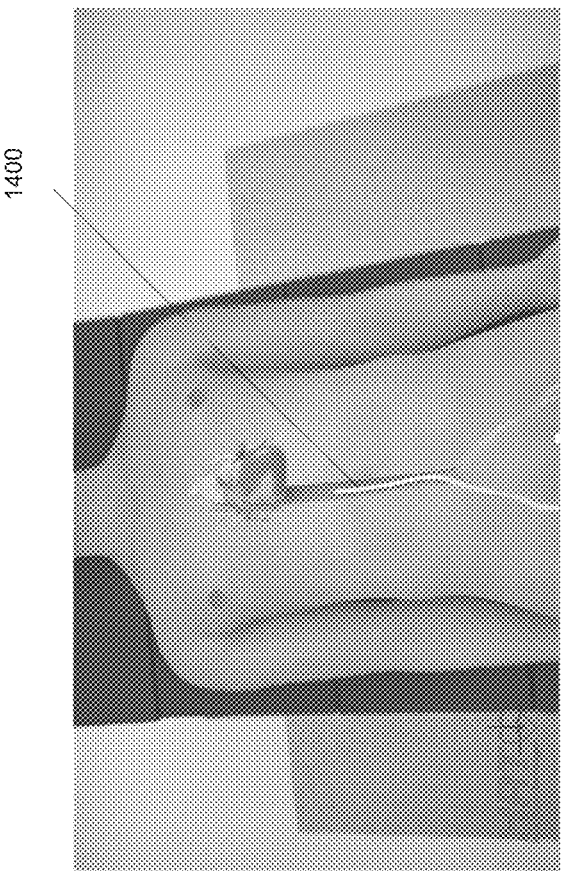

FIG. 63B shows the entry into the patient. FIG. 63B shows the guide catheter 1400 and the steering catheter 1402. FIG. 63C shows the progression of the guide catheter 1400 toward the heart. The catheter system can be introduced via the femoral vein or other access point and delivered to the heart. The catheter system can be delivered using a transseptal puncture. FIG. 63D shows the guide catheter 1400 gaining access to the heart. In some embodiments, a guide wire 1408 can be positioned to the left atrium. The guide catheter 1400 can be navigated into the heart along the guide wire 1408. The guide wire 1408 can span between the right atrium and the left atrium. The guide wire 1408 can extend from the left atrium, through the valve annulus and toward the left ventricle. The guide catheter 1400 can gain access to the mitral valve. The mitral valve can continue to function during the procedure. The heart is not stopped. The catheters of transcatheter system can include any of the features of catheters described herein. While some embodiments are described in the context of transvalvular implant 1300, other implants that span the annulus can be utilized, and the method adapted to other valve annuli including the tricuspid, aortic, and/or pulmonic valve annuli depending on the desired clinical result.

Figures 63E, 63F:
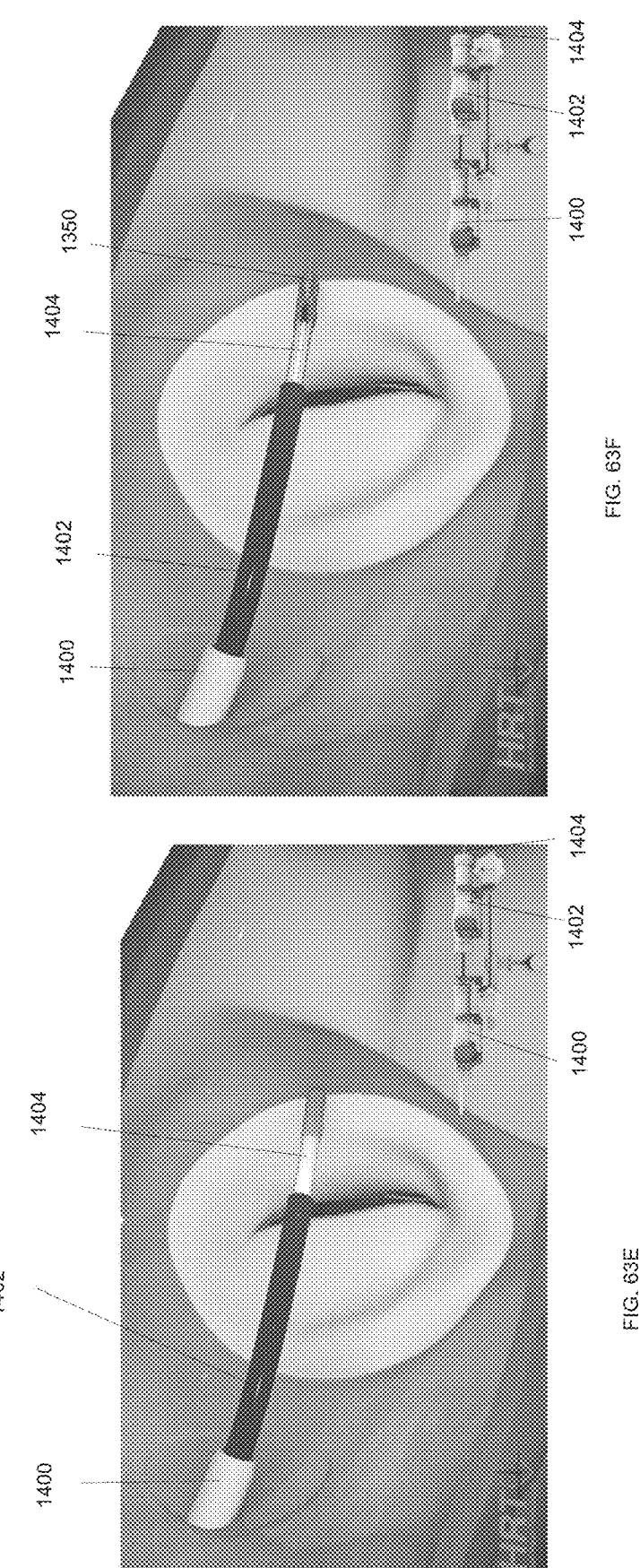

FIG. 63E illustrates the guide catheter 1400, the steering catheter 1402, and the anchor delivery catheter 1404. The guide catheter 1400 can provide a transseptal conduit to, for example, the left atrium. The guide catheter 1400 can be placed in the left atrium through the transseptal access. In some embodiments, the steering catheter 1402 can be utilized after the guide catheter 1400 is placed. The steering catheter 1402 can be positioned relative to the annulus. The steering catheter 1402 can be deployed in the left atrium to direct the system appropriately to the mitral valve annulus.

The steering catheter 1402 can be steered toward the posterior annulus, as shown in FIG. 63E. The anchor delivery catheter 1404 can extend from the steering catheter 1402. The anchor delivery catheter 1404 can telescope within the steering catheter 1402. The steering catheter 1402 can telescope within the guide catheter 1400. The guide catheter 1400, the steering catheter 1402, and the anchor delivery catheter 1404 can be positioned to deliver the first anchor 1350 to the posterior annulus. The first anchor 1350 can be driven into the posterior annulus.

FIG. 63F illustrates the anchor delivery catheter 1404 according to some embodiments. The anchor delivery catheter 1404 can have any features described herein. The anchor delivery catheter 1404 can deliver a single anchor. The anchor delivery catheter 1404 can rotate the first anchor 1350 to drive the anchor into the posterior annulus. The anchor delivery catheter 1404 can rotate relative to the steering catheter 1402. The anchor delivery catheter 1404 can rotate relative to guide catheter 1400.

Figure 63H:
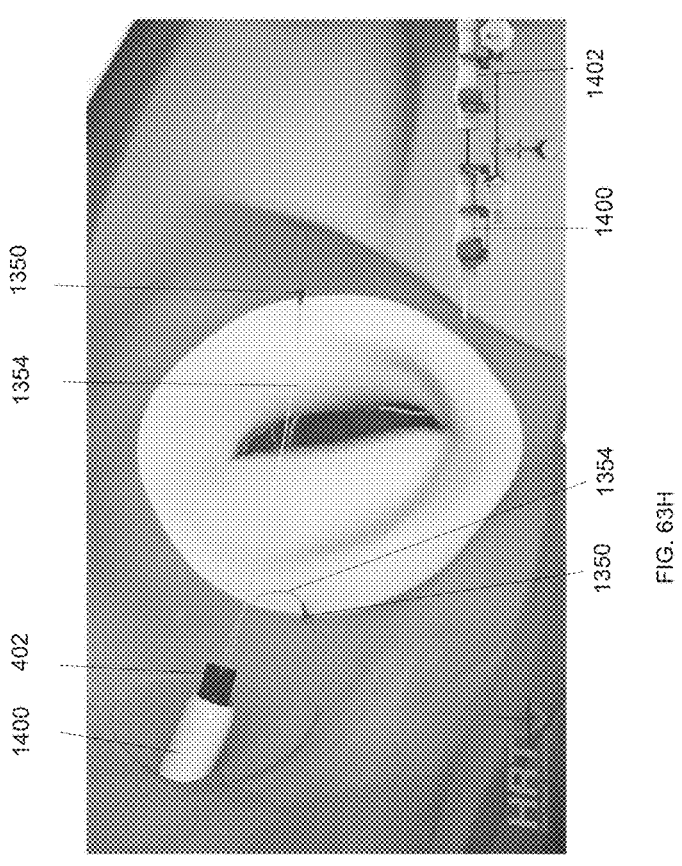
Figure 63G:
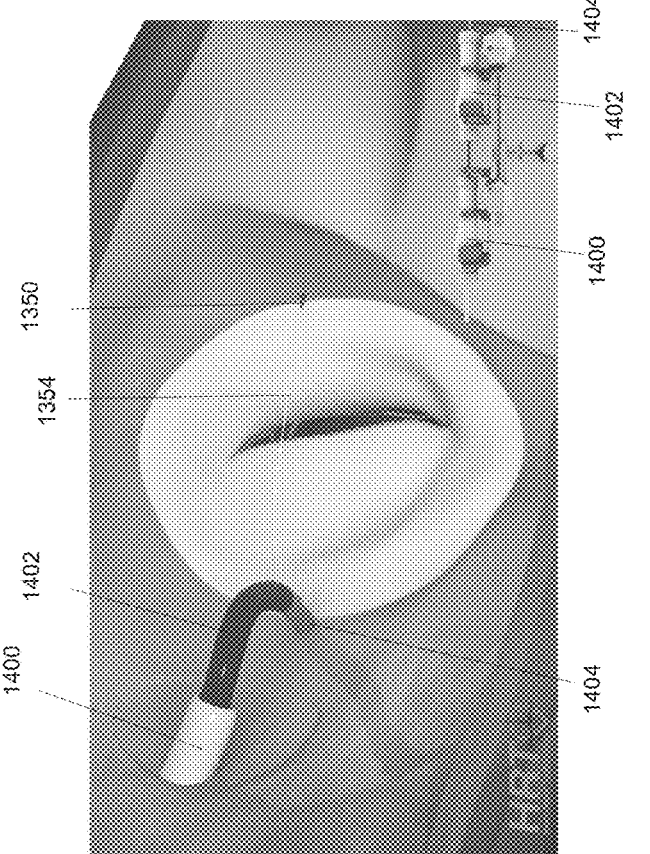

FIG. 63G illustrates the guide catheter 1400, the steering catheter 1402, and the anchor delivery catheter 1404. The first anchor 1350 is secured to the posterior annulus. The first suture 1354 extends from the first anchor 1350. The steering catheter 1402 can be repositioned relative to the anterior annulus. The steering catheter 1402 can be deployed in the left atrium to direct the system appropriately to the anterior annulus. The steering catheter 1402 can be steered toward the anterior annulus, as shown in FIG. 63G. The anchor delivery catheter 1404 can extend from the steering catheter 1402. The anchor delivery catheter 1404 can telescope within the steering catheter 1402. The steering catheter 1402 can telescope within the guide catheter 1400. The guide catheter 1400, the steering catheter 1402, and the anchor delivery catheter 1404 can be positioned to deliver the second anchor 1350 to the anterior annulus. The second anchor 1350 can be driven into the anterior annulus. In other embodiments, the first anchor 1350 can be driven into the posterior annulus and the second anchor 1350 can be driven into the anterior annulus.

FIG. 63H illustrates both anchors 1350. The first anchor 1350 is secured to the posterior annulus. The first suture 1354 extends from the first anchor 1350. The second anchor 1350 is secured to the anterior annulus. The second suture 1354 extends from the second anchor 1350. The anchor delivery catheter 1404 can be retracted. The steering catheter 1402 can be retracted. In some embodiments, the guide catheter 1400 or another cinching catheter can be advanced to cinch the sutures 1354. The transvalvular implant 1300 can be positioned relative to the tails of the sutures 1354 which are external to the patient. Each suture 1354 can extend through a corresponding eyelet of the transvalvular implant 1300. The transvalvular implant 1300 can be compressed within the implant delivery catheter 1406. The transvalvular implant 1300 can engage the sutures 1354 when compressed within the implant delivery catheter 1406.

Figures 63I, 63J:
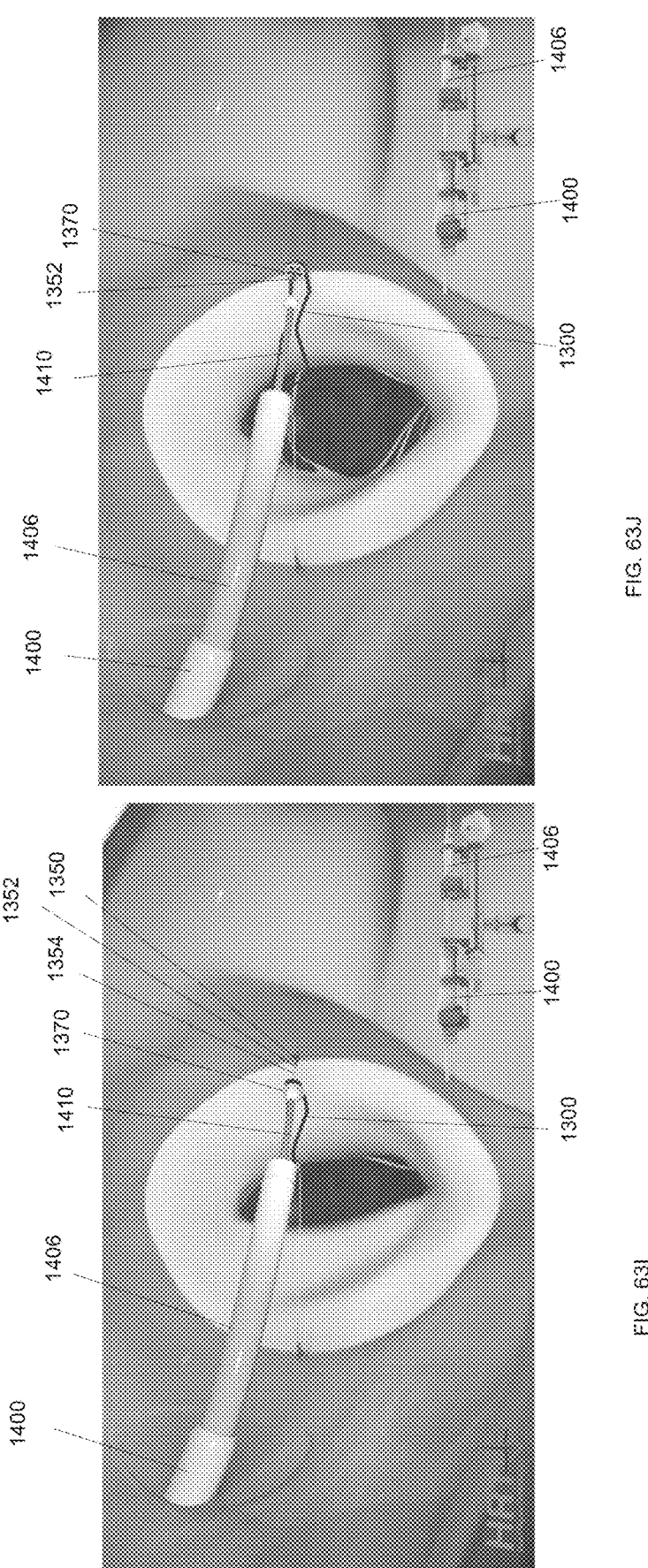

FIG. 63I illustrates the implant delivery catheter 1406. The implant delivery catheter 1406 can extend through the guide catheter 1400. The implant delivery catheter 1406 can include an implant pusher 1410. In some embodiments, the implant pusher 1410 can be releasably secured to the locking disc clip 1370. In some embodiments, the implant pusher 1410 can be releasably secured to the transvalvular implant 1300. In some embodiments, the implant pusher 1410 merely pushes the locking disc clip 1370 and the transvalvular implant 1300. The implant pusher 1410 can slide along the suture 1354 which extends from the anchor 1350. The suture 1354 can guide the transvalvular implant 1300 toward the anchor 1350. The implant pusher 1410 can push the locking disc clip 1370 and the transvalvular implant 1300 toward the anchor 1350. The implant pusher 1410 can push transvalvular implant 1300 over the central post 1352. The implant pusher 1410 can push the locking disc clip 1370 over the central post 1352. The locking disc clip 1370 can engage the groove 1362 of the central post 1352, as shown in FIG. 58. At least a portion of the transvalvular implant 1300 can remain within the implant delivery catheter 1406.

FIG. 63J illustrates the implant delivery catheter 1406. The implant delivery catheter 1406 can be retracted toward the guide catheter 1400. The implant delivery catheter 1406 can be retracted to release the transvalvular implant 1300. The implant pusher 1410 can be retracted. The implant pusher 1410 can retract along the first suture 1354. The locking disc clip 1370 can remain engaged with the groove 1362 of the central post 1352 of the first anchor 1350. The locking disc clip 1370 can retain the transvalvular implant 1300 relative to the first anchor 1350. The transvalvular implant 1300 can be secured to the posterior annulus. At least a portion of the transvalvular implant 1300 can remain within the implant delivery catheter 1406.

Figures 63K, 63L:
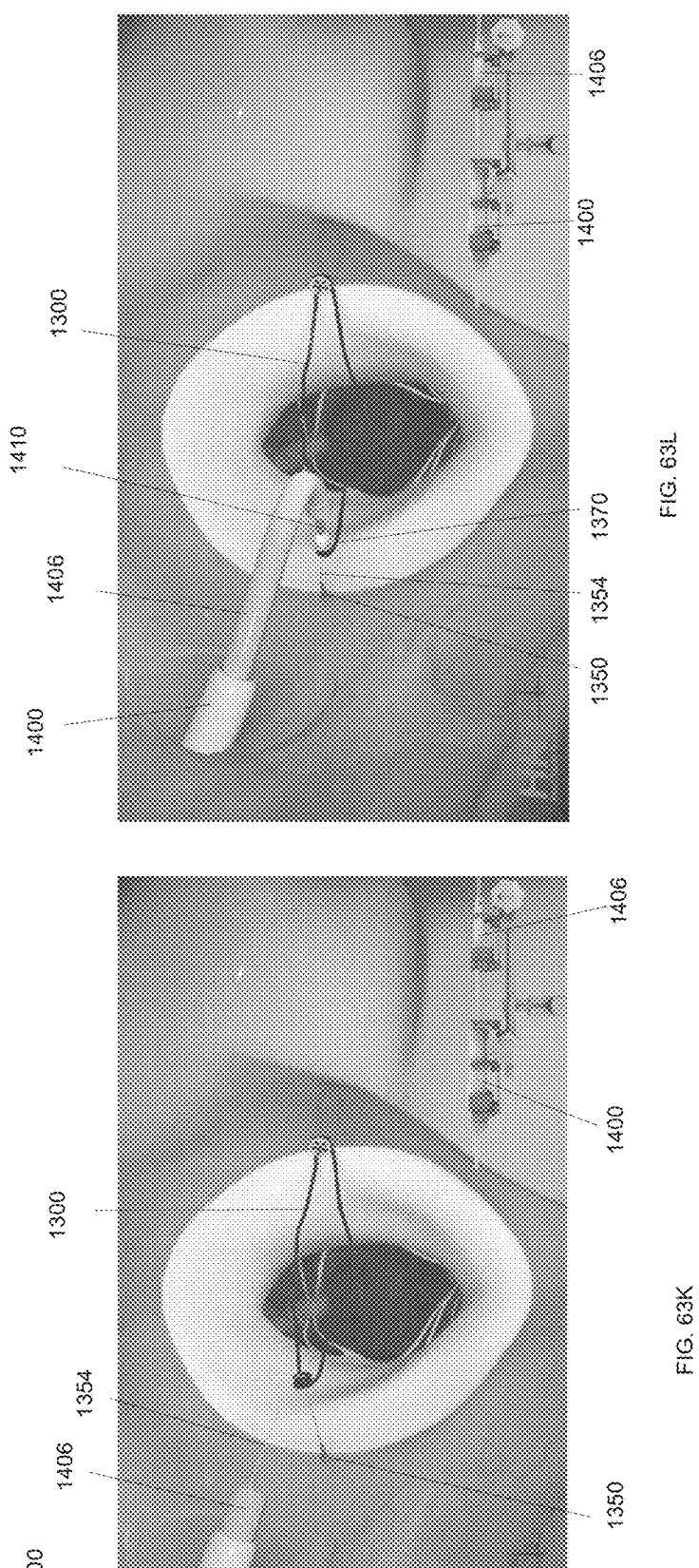

FIG. 63K illustrates the transvalvular implant 1300. The implant delivery catheter 1406 can be retracted toward the guide catheter 1400. The implant delivery catheter 1406 can be retracted to release the transvalvular implant 1300. The transvalvular implant 1300 can be secured to the posterior annulus. The second suture 1354 extends through the eyelet of the transvalvular implant 1300. The transvalvular implant 1300 is not yet secured to the anterior annulus.

FIG. 63L illustrates the implant delivery catheter 1406. The implant delivery catheter 1406 can be steered toward the anterior annulus. In some embodiments, the implant pusher 1410 can be slid along the second suture 1354. In some embodiments, one implant pushers 1410 is utilized for both anchors 1350. In some embodiments, two implant pushers 1410 are utilized, one for each anchor 1350. In some embodiments, the implant pusher 1410 can be releasably secured to the second locking disc clip 1370. In some embodiments, the implant pusher 1410 can be releasably secured to the transvalvular implant 1300. In some embodiments, the implant pusher 1410 merely pushes the second locking disc clip 1370 and the transvalvular implant 1300. The implant pusher 1410 can slide along the second suture 1354 which extends from the second anchor 1350. The second suture 1354 can guide the transvalvular implant 1300 toward the second anchor 1350. The implant pusher 1410 can push the second locking disc clip 1370 and the transvalvular implant 1300 toward the second anchor 1350. The implant pusher 1410 can push the transvalvular implant 1300 over the central post 1352 of the second anchor 1350. The implant pusher 1410 can push the second locking disc clip 1370 over the central post 1352 of the second anchor 1350. The second locking disc clip 1370 can engage the groove 1362 of the central post 1352 of the second anchor 1350.

Figure 63N:
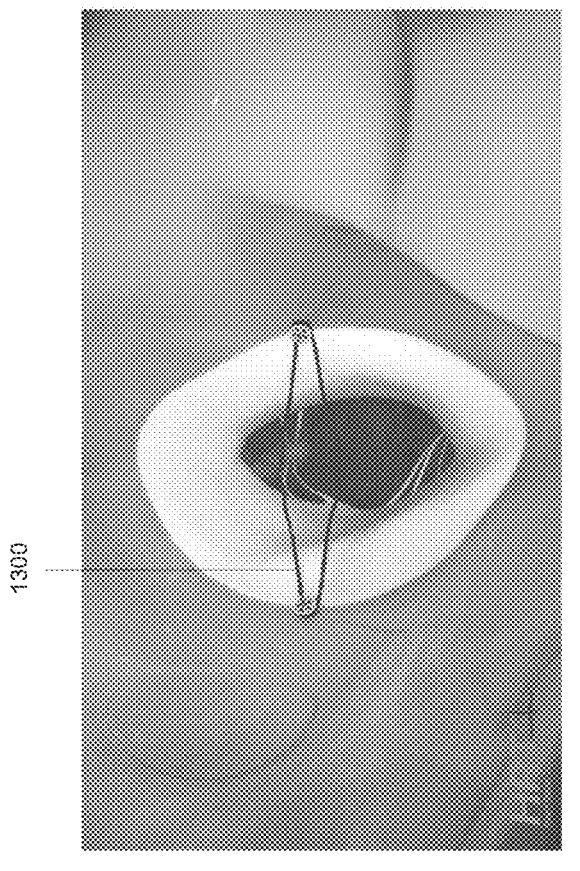
Figure 63M:
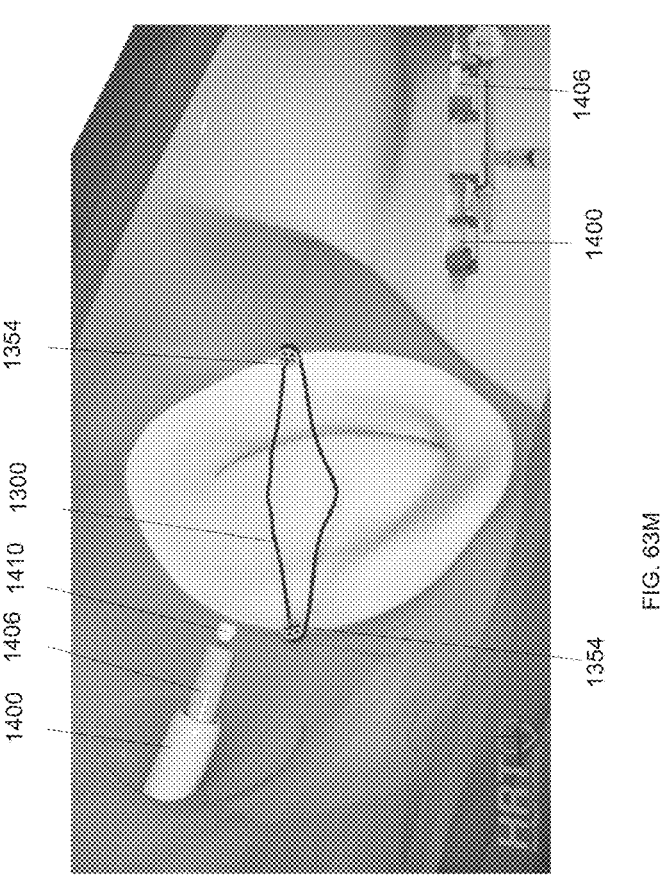
Figure 630:
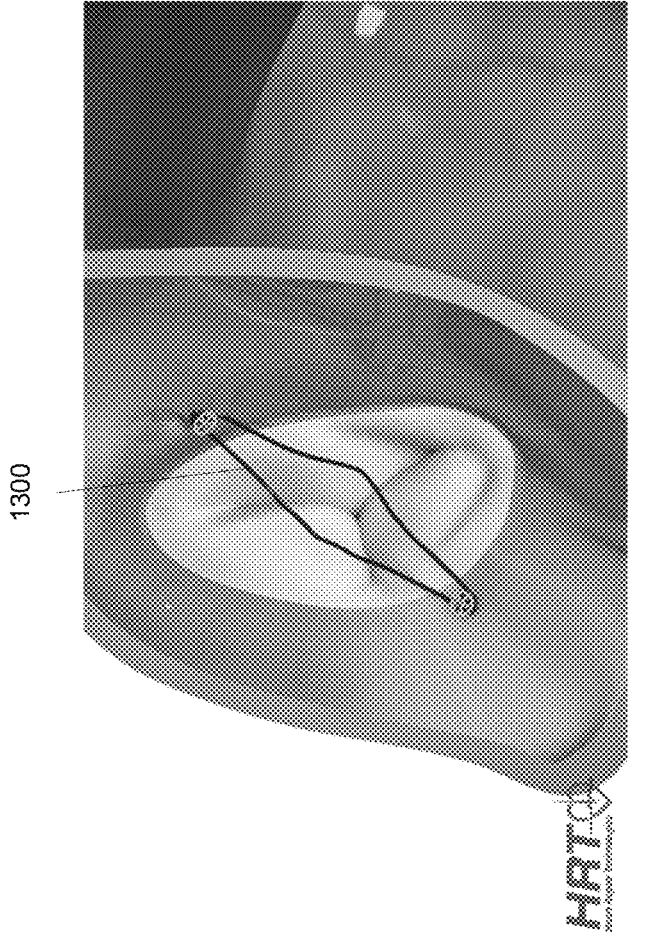

FIG. 63M illustrates the transvalvular implant 1300. The implant delivery catheter 1406 can be retracted toward the guide catheter 1400. The implant pusher 1410 can be retracted. The transvalvular implant 1300 can be secured to both anchors 1350. The valve can normally close. FIG. 63N illustrates the transvalvular implant 1300. The valve can normally open. FIG. 63O illustrates the transvalvular implant 1300 relative to a tricuspid valve. The tricuspid valve can normally open and close. The transvalvular implant 1300 can be placed according to any method described herein. The anchor 1350 can be delivered first.

The transvalvular implant 1300 and the locking clip 1370 can be delivered after the anchors 1350 are secured. There is coupling of the transvalvular implant 1300 on the top of the anchor 1350. The transvalvular implant 1300 is locked in by the locking clip 1370.

In some embodiments, the implant pusher 1410 can provide suture management. Each suture 1354 can extend through a separate implant pusher 1410 such that the sutures 1354 are prevented from tangling or tangling is reduced. In some embodiments, the sutures 1354 can extend through separate eyelets of the transvalvular implant 1300 for suture management.

In some embodiments, the method can include the cinching of the annulus. In some embodiments, with the anchors 1350 in place and the sutures 1354 extending from the anchors 1350, the annulus can be cinched, in other words, the opposing sides of the annulus can be brought closer together along part of the annulus. The cinching can confirm securement of the anchors 1350. The cinching can reduce any slack in the sutures 1354. The cinching can confirm the correct size of the transvalvular implant 1300. The cinching can confirm the desired spacing or length between the pair of anchors 1350 associated with the posterior annulus and the anterior annulus. The length of the transvalvular implant 1300 can be selected to maintain the cinched position of the annulus. In some embodiments, the guide catheter 1400 or another cinching catheter can be brought toward the annulus to cinch the sutures 1354, and thus the anchors 1350. In some embodiments, as the guide catheter 1400 or cinching catheter moves toward the annulus, the sutures 1354 can be moved toward each other. In some embodiments, tension is applied to the sutures 1354 to cinch the sutures 1354. The sutures 1354 can be connected to the annulus via the annular anchors 1350 in order to move the annulus. The cinching can increase the engagement between the posterior and anterior leaflet to enhance coaptation, as described herein. The transvalvular implant 1300 can include any of the features of any implant described herein. The transvalvular implant 1300 can be deployed after the anchors 1350 are deployed. The transvalvular implant 1300 can be guided into place via the sutures 1354 which are permanently attached to the anchors 1350. The transvalvular implant 1300 can include eyelets through which the sutures 1354 can pass. In some embodiments, each eyelet can be designed to accept one suture 1354. The first end of the transvalvular implant 1300 can include one eyelet designed to accept one suture 1354. The transvalvular implant 1300 can be compressed for delivery. FIGS. 63M and 63O illustrates the transvalvular implant 1300 deployed in the mitral valve and the tricuspid valve. The transvalvular implant 1300 can slide along the anchored sutures 1354 toward the annulus. The second end of the transvalvular implant 1300 can include one eyelet designed to accept one suture 1354. The two eyelets can correspond to the two sutures 1354. The two eyelets can provide suture management to prevent the sutures 1354 from being tangled during delivery.

The implant delivery catheter 1406 and the implant pusher 1410 can move the transvalvular implant 1300 toward the annulus. Once positioned, the transvalvular implant 1300 can be used in conjunction with the anchor 1350 to cinch the posterior annulus toward the anterior annulus to facilitate proper leaflet coaptation. The implant pusher 1410 can move locking disc clip 1370 toward the annulus. Each locking disc clip 1370 can slide along the corresponding suture 1354 during delivery. The locking disc clip 1370 can secure the transvalvular implant 1300 to the anchor 1350. The suture 1354 can be threaded through the locking disc clip 1370. The locking disc clip 1370 can allow movement of the locking disc clip 1370 toward the annulus but prevent or limit movement of the locking disc clip 1370 away from the annulus once in the groove 1362 of the anchor 1350. In some embodiments, the transvalvular implant 1300 and the locking disc clip 1370 can be simultaneously delivered. In some embodiments, the transvalvular implant 1300 can be delivered first and the locking disc clip 1370 can be delivered after. In some embodiments, the locking disc clips 1370 can be sequentially delivered.

FIGS. 63M and 63O illustrate the deployed transvalvular implant 1300 according to some embodiments. The transvalvular implant 1300 can be sized to maintain the position of the anchors 1350 and underlying annulus. The transvalvular implant 1300 can be sized to cinch the anchors 1350 and therefore the annulus. In some embodiments, a trimming catheter is provided. The trimming catheter can slide along the suture 1354 toward the annulus. The trimming catheter can trim the suture 1354 above the locking disc clips 1370. In some embodiments, both sutures 1354 can be sequentially trimmed by the trimming catheter. The trimming catheter can allow the suture 1354 to be retrieved by pulling the suture from the body of the patient.

Disclosed herein are methods of percutaneous transcatheter delivery of embodiments of a transvalvular implant, which can also be referred to herein as a transvalvular bridge. The transvalvular implant can be delivered to the valve for repair of regurgitation. The transvalvular implant can be delivered to the mitral valve to repair of mitral regurgitation. The transvalvular implant can be delivered to the tricuspid valve to repair of tricuspid regurgitation.

The systems and methods can include various features or advantages. The systems and methods can replicate an open procedure. The systems and methods can guarantee anchor placement. The systems and methods can show a surgeon the suture count prior to securing the first locking clip The systems and methods can provide positional identification of the anchors relative to the annulus. The systems and methods can be conducted on beating heart. The systems and methods can be echogenic. The systems and methods can prevent or limit occlusions. The systems and methods can prevent or limit leaflet damage. The systems and methods can prevent or limit chordae damage. The systems and methods can allow for complete bail out or reversal until the first locking clip is secured. The systems and methods can allow for complete identification and count of all catheter delivery components and suture-tail cuts. The systems and methods can allow for a low pressure delivery of one or more anchors. The systems and methods can allow for flexible deployment of a retaining system. The systems and methods can allow for percutaneous securement by locking clip. The systems and methods can allow for transseptal delivery. The systems and methods can allow for over the wire delivery. The systems and methods can allow for one catheter placement that enables delivery of two individual anchors. The systems and methods can allow for single anchor delivery which is repeated two times to secure the transvalvular bridge and locking clips with annular anchors. The systems and methods can allow for one or more catheters that secure the transvalvular implant. The transvalvular implant can slide along sutures connected to anchors. The transvalvular implant can reshape the annulus along a diameter. The transvalvular implant can be anchored to the annulus. The transvalvular implant can span the valve orifice.

The methods can include transseptally placing a guide catheter. The methods can include sequentially advancing a steering catheter to the annulus and deliver one or more anchors, e.g., two anchors, three anchors, four anchors, five anchors, six anchors, etc. The methods can include deploying the transvalvular implant along sutures. The methods can include cinching the anchors, sutures, and/or the transvalvular implant. The methods can include deploying the one or more locking clips, e.g., deploying one locking clip for each anchor. The methods can include inserting a trimming catheter. The methods can include cutting the excess suture.

From an end user point, the sutures are pre-assembled to the anchors. In some embodiments, the transvalvular bridge can slide along the sutures once the anchors are placed. The transvalvular implant can include eyelets to receive the sutures. The transvalvular implant can include a pre-shape form to reshape the annulus. The transvalvular implant can be anchored on the annulus. The transvalvular implant can be anchored along an anatomical diameter. The transvalvular implant can be anchored at the anterior annulus. The transvalvular implant can be anchored on the anterior annulus and the posterior annulus. T The transvalvular implant can be anchored at the posterior annulus. The transvalvular implant can be anchored between an anterior annulus and straddling the commissure between the septal annulus and the posterior annulus. The transvalvular implant can be anchored on the posterior annulus beyond the septal-posterior commissure.

In some embodiments, the heart valve is a mitral valve. The transvalvular implant can be used to treat functional mitral regurgitation. The transvalvular implant can reduce the septal lateral diameter of the mitral valve annulus sufficiently to bring the posterior annulus towards the anterior annulus. The transvalvular implant can be used to achieve full closure of mitral valve leaflets during systole, thereby preventing mitral regurgitation. The transvalvular implant can straddle the valve orifice in an annular horizontal plane of the annulus. The transvalvular implant can straddle the mitral valve orifice in an annular horizontal plane in a septal lateral dimension of the mitral annulus. The central portion of the transvalvular implant can be curved towards the left ventricular cavity.

In some embodiments, the heart valve is a tricuspid valve. The transvalvular implant can be used to treat functional tricuspid regurgitation by reducing the anterior-posterior diameter of the tricuspid valve annulus sufficiently to bring the anterior annulus to the septal and/or posterior annulus. The transvalvular implant can be used to achieve full closure of the tricuspid leaflets during systole, thereby preventing tricuspid valve regurgitation. The transvalvular implant can straddle the tricuspid valve orifice in an annular horizontal plane in an anterior-posterior dimension of the tricuspid valve annulus. The central portion of the transvalvular implant can be curved towards the right ventricular cavity.

The systems and methods can related generally to the field of heart valve repair devices, methods, and kits more specifically to trans catheter methods and devices for treatment of valve regurgitation from dilated annulus and/or from deformed and retracted valve leaflets by use of an arching implant which straddles the valve orifice. The systems and methods can related generally to the field of heart valve repair devices, methods, and kits more specifically to trans catheter methods and devices for treatment of mitral valve regurgitation from dilated mitral annulus and/or from deformed and retracted mitral valve leaflets by use of an arching implant which straddles the mitral valve orifice in a septal-lateral dimension. The systems and methods can related generally to the field of heart valve repair devices, methods, and kits more specifically to trans catheter methods and devices for treatment of tricuspid valve regurgitation from dilated tricuspid annulus and/or from deformed and retracted tricuspid valve leaflets by use of an arching implant which straddles the tricuspid valve orifice.

The heart has a total of four valves which allows the blood to flow through the four chambers of the heart in one direction. The mitral valve has two valve leaflets, anterior and posterior. They are attached to the mitral valve annulus. The leaflets are supported by chordae tendinae from their free edges towards the wall of the left ventricle by papillary muscle. Normally when the left ventricle contracts the leaflets close together preventing blood to leak backwards into the left atrium, the upper pumping chamber. Sometimes one or both leaflets do not close properly as a result of alteration in the annular ventricular apparatus and altered ventricular geometry. In ischemic heart failure this can be due to papillary or lateral left ventricle wall muscle dysfunction, and in non-ischemic heart failure it can be ascribed to mitral annular dilatation and chordal tethering, all as a result of dysfunctional remodeling of left ventricle. This causes incomplete leaflet coaptation and allows the blood to leak backwards into the left atrium during left ventricular contraction (systole). This type of mitral regurgitation is commonly referred as functional mitral regurgitation in which the predominant pathophysiology is the increased distance from the anterior to posterior annular dimension, increased septal-lateral diameter.

The main objective of the treatment of functional mitral regurgitation can be to reduce the septal lateral diameter sufficiently to bring the posterior annulus towards the anterior annulus to achieve full closure of leaflets and competent mitral valve during systole preventing mitral regurgitation. The standard treatment for more than three decades has been implantation of an annuloplasty ring on the mitral annulus with circumferential cinching of the entire or part of the annulus to achieve an indirect reduction of septal-lateral diameter of the annulus. This has resulted in only partial success due to limitations of the extent of annular cinching with increasing obstruction to blood flow across the mitral valve (increased mitral Gradient). Alternatively, a mitral valve replacement device can be implanted by replacing the original valve. Both these approaches are very invasive and met with frequent complications. Several less invasive catheter-based treatment and approaches has emerged recently including an edge to edge repair of leaflets, including MitraClip. Notwithstanding the presence of a variety of presently available surgical and trans catheter procedures, there still remains a need for a simple but effective disruptive trans catheter procedure and devices and systems to effectively treat a larger proportion of the patients with functional mitral regurgitation.

The systems and methods can include the implant which can be referred to as an arch or straddle. The implant can straddle the valve orifice in an annular horizontal plane in a septal lateral dimension (from anterior to posterior) of the annulus. The arch refers to a curved body which can be concave either towards the left ventricular cavity or left atrial cavity. The implant can be made of single or plurality of wires. The implant can be made stainless steel or nitinol or any other material. The implant can have four eyelets, two in the front and two in the back part of the frame of the implant. The shape and configurations of the wire form implant can vary to different geometries. The implant can have a feature in the center with a hole created by the configuration of the embodiments. The center hole enables introduction of any other trans catheter device for additional treatment modalities. The wire form can allow the implant to be folded in any dimension to be delivered via a delivery catheter. The implant can be of various sizes in mm length in its longitudinal dimension.

The systems and methods can include anchors. The anchor which can hold the implant onto the annulus can be made of various material, including stainless steel, nitinol, titanium and other compatible material. The anchor can have a configuration of a helical screw. The anchor can have length varying from 8 mm to 4 mm. The anchor can have the last few threads (2-4) sharpened and tapered with tip grind at the outer coil face of helix. The anchor can be coated with silicon or other materials. The anchor can have a straight center pin which fits into the helical screw anchor to stabilize as well facilitate penetration of the annulus during anchor implantation on to the valve annulus. The anchor can have a center post made of hypo tube which is bonded to a quadrangular helix top mount. The quadrangular helix top mount can be machine made to fit tightly into the top of the helical screw anchor. This mount serves as the holding platform for the implant and the locking clip or cap. The top of this anchor post can hold the anchor tether inside the post. The tether can be inserted 4 mm into the anchor post tube. The tether can crimped in place.

Any of a wide variety of specific tissue anchor constructions may be utilized in combination with the transvalvular implant of the present invention. In addition, a variety of features have been described as illustrative in connection with a variety of implementations of the invention. Any of the features described above, may be recombined with any other of the embodiments disclosed herein, without departing from the present invention, as should be apparent to those of skill in the art.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological valve within the body.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "attaching an implant to the mitral valve annulus" includes "instructing the attaching of an implant to the mitral valve annulus." For example, actions such as "attaching a transvalvular bridge to the tricuspid valve annulus" includes "instructing the attaching of a transvalvular bridge to the tricuspid valve annulus." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A transvalvular implant comprising:
an elongate body having a first end, a first anchoring portion located proximate the first end, a second end, a second anchoring portion located proximate the second end, and a central portion connected to the first end and the second end, wherein the central portion comprises an arcuate shape, wherein the elongate body tapers from a minimum width at the first end and second end to a maximum width at the central portion, wherein the elongate body comprises of a generally diamond shape, the elongate body consisting of single length of wire, wherein the elongate body forms a continuous outline wherein a starting point and an ending point of the single length of wire are connected with a weld, wherein the first anchoring portion of the elongate body comprises a first eyelet and the second anchoring portion comprises a second eyelet, wherein the first eyelet comprises stacked coils which enclose a first eyelet opening, wherein the second eyelet comprises stacked coils which enclose a second eyelet opening, wherein the elongate body comprises a central opening, wherein the central opening comprises a generally diamond shape, wherein the transvalvular implant does not obstruct the flow of blood through the central opening;
a first helical anchor comprising a first post, wherein the first post is configured to extend through the first eyelet opening of the first eyelet;
a first locking clip configured to lock with the first post above the elongate body;
a second helical anchor comprising a second post, wherein the second post is configured to extend through the second eyelet opening of the second eyelet; and
a second locking clip configured to lock with the second post above the elongate body.

2. The transvalvular implant of claim 1, wherein the central portion is configured to be displaced transversely from an intraannular plane which includes a valve annulus and is transverse to a direction of blood flow when the elongate body is attached to the valve annulus.

3. The transvalvular implant of claim 1, wherein the first end and the second end are configured to be attached to a mitral valve annulus within an intraannular plane and the central portion is configured to be convex in a direction of outflow to support valve leaflets at a point displaced toward a ventricle from the intraannular plane.

4. The transvalvular implant of claim 1, wherein the first end and the second end are configured to be attached to a tricuspid valve annulus within an intraannular plane and the central portion is configured to be convex.

5. The transvalvular implant of claim 1, wherein the first end and the second end are configured to reside on a generally septal-lateral axis transverse to coaptive edges of valve leaflets when the elongate body is attached to a valve annulus.

6. The transvalvular implant of claim 1, wherein the transvalvular implant is configured for straddling a mitral valve orifice in a septal lateral diameter of a mitral valve annulus.

7. The transvalvular implant of claim 1, wherein the transvalvular implant is configured for the treatment of mitral valve regurgitation caused by dilatation of a mitral valve annulus and deformation of mitral valve leaflets or the treatment of tricuspid valve regurgitation caused by dilatation of a tricuspid valve annulus and deformation of tricuspid valve leaflets.

8. The transvalvular implant of claim 1, wherein a first tether extends from the first post, wherein the first tether is configured to be threaded through the first eyelet opening of the first anchoring portion.

9. The transvalvular implant of claim 1, wherein the elongate body comprises stainless steel or nitinol.

10. The transvalvular implant of claim 1, wherein the elongate body comprises two planes of symmetry.

11. The transvalvular implant of claim 1, wherein transvalvular implant is wider toward a center or midpoint.

12. The transvalvular implant of claim 1, wherein the central opening extends along a majority of a length of the transvalvular implant.

13. The transvalvular implant of claim 1, wherein the central opening is uncoated.

14. The transvalvular implant of claim 1, wherein the central opening is enclosed by the elongate body.

15. The transvalvular implant of claim 1, wherein the central opening is uncovered.

16. The transvalvular implant of claim 8, wherein the first locking clip is configured to slide along the first tether to the first post.

17. The transvalvular implant of claim 8, wherein a second tether extends from the second post, wherein the second tether is configured to be threaded through the second eyelet opening of the second eyelet of the second anchoring portion.

18. The transvalvular implant of claim 1, wherein the first eyelet comprises three stacked coils.

19. The transvalvular implant of claim 1, wherein the first locking clip forms a friction fit with the first post of the first helical anchor.

20. The transvalvular implant of claim 1, wherein the first post comprises a groove shaped to accommodate the first locking clip.

* * * * *